United States Patent
Allgeier et al.

(10) Patent No.: US 8,716,296 B2
(45) Date of Patent: May 6, 2014

(54) INHIBITORS OF PROTEIN KINASES

(75) Inventors: Hans Allgeier, Lörrach-Haagen (DE); Martin Augustin, Seefeld-Hechendorf (DE); Anke Müller, Germering (DE); Lutz Zeitlmann, München (DE); Andreas Marquardt, Planegg (DE); Michael A. Pleiss, Sunnyvale, CA (US); Ulrich Heiser, Halle/Saale (DE); André Johannes Niestroj, Sennewitz (DE)

(73) Assignee: Ingenium Pharmaceuticals GmbH, Martinsried (DE)

( * ) Notice: Subject to any disclaimer, the term of this patent is extended or adjusted under 35 U.S.C. 154(b) by 663 days.

(21) Appl. No.: 12/226,286

(22) PCT Filed: Oct. 13, 2008

(86) PCT No.: PCT/EP2008/063715
§ 371 (c)(1),
(2), (4) Date: Jun. 9, 2010

(87) PCT Pub. No.: WO2009/047359
PCT Pub. Date: Apr. 16, 2009

(65) Prior Publication Data
US 2010/0249149 A1   Sep. 30, 2010

Related U.S. Application Data

(60) Provisional application No. 60/998,821, filed on Oct. 12, 2007.

(51) Int. Cl.
*A01N 43/54*   (2006.01)
*C07D 401/00*   (2006.01)

(52) U.S. Cl.
USPC .......................................... 514/256; 544/329

(58) Field of Classification Search
None
See application file for complete search history.

(56) References Cited

FOREIGN PATENT DOCUMENTS

| | | |
|---|---|---|
| EP | 1679309 | 7/2006 |
| FR | 2878247 | 5/2006 |
| WO | WO 01/62233 | 8/2001 |
| WO | WO 02/074742 | 9/2002 |
| WO | WO 02/081445 | 10/2002 |
| WO | WO 02/094825 | 11/2002 |
| WO | WO 02/100401 | 12/2002 |
| WO | WO 2004/084824 | 10/2004 |
| WO | WO 2005/005438 | 1/2005 |
| WO | WO 2005/012262 | 2/2005 |
| WO | WO 2005/012298 | 2/2005 |
| WO | WO 2005/026129 | 3/2005 |
| WO | WO 2005/027902 | 3/2005 |
| WO | WO 2005/103022 | 11/2005 |
| WO | WO 2006/125616 | 11/2006 |

OTHER PUBLICATIONS

Bredereck et al. Formamide reactions. VIII. A new pyrimidine synthesis, 1957, Tech. Hochschule, Stuttgart, Germany, Chemische Berichte, 90, 942-52.*
Osborne et al. The chemistry of triazine derivatives. II. The acylation of 2,4,6-trimethyl-s-triazine to triazinyl ketones and their facile isomerization to acetamidopyrimidines, Journal of Heterocyclic Chemistry (1964), 1(3), 145-50.*
Sedova et al. 6-Aminopyrimidine 1-oxides. Acylation and methylation, Khimiya Geterotsiklicheskikh Soedinenii (1986), (11), 1528-34.*
Barboric M. et al., NF-kappaB Binds P-TEFb to Stimulate Transcriptional Elongation by RNA Polymerase II, Molecular Cell, 2001, vol. 8, 327-337.
Besson J.M., The neurobiology of pain,The Lancet, 1999, vol. 353, 9164, 1610-1615.
Bredereck H et al., Chemische Berichte, 1957, vol. 90, pp. 942-952.
Brower, New paths to pain relief, Nat Biotechnol, 2000, vol. 18(4), 387-391.
Bundgaard H., "Design of Prodrugs" ed. 1985.
Dai Y and Grant S, Current Opinion in Pharmacology 2003, vol. 3(4), pp. 362-370.
Decosterd I, Woolf CJ, Pain, 2000, vol. 87, 149-158.
Falco G.D. et al., CDK9, a member of the cdc2-like family of kinases, binds to gp130, the receptor of the IL-6 family of cytokines, Oncogene, 2002, vol. 21, 49, 7464-7470.
Feldmann and Maini, NatMed 2003, 9(10), pp. 1245-1251.
Filgueira De Azevedo W Jr et al., Molecular model of cyclin-dependent kinase 5 complexed with roscovitine, Biochem Biophys Res Commun 2002, 293(1), pp. 279-284.
Firestein, 2003 Nature 423, pp. 356-361.
Han et al., 2003 Autoimmunity, 28, pp. 197-208.
Huwe et al., Angew. Chem. Int. Ed. Engl. 2003, 42(19), pp. 2122-2138.
Kingery WS et al.; Pain Nov. 1997, 73(2), pp. 123-139.
Koltzenburg M, Neural mechanisms of cutaneous nociceptive pain, Clin J Pain, 2000, vol. 16, 3131-138.
Lee K.M. et al., Spinal NfκB activation induces COX-2 upregulation and contributes to inflammatory pain hypersensitivity, European Journal of Neuroscience, 2004, vol. 19, 3375-3381.
Liu H., Herrmann C., Differential Localization and Expression of the CDK9 42k and 55k Isoforms, J Cell Physiol, 2005, vol. 203, 251-260.
MacLachlan TK et al., J Cell Biochem, 1998, 71 467-478.
Protective Groups in Organic Chemistry, ed. JFW MCOMIE, Plenum Press, 1973.

(Continued)

Primary Examiner — Jeffrey H Murray
Assistant Examiner — Oluwafemi Masha
(74) Attorney, Agent, or Firm — Olson & Cepuritis, Ltd.

(57) ABSTRACT

Compounds of general formula (I):

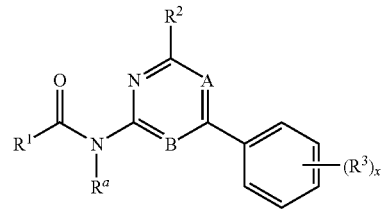

Formula (I)

are useful as inhibitors of cyclin dependent kinases such as CDK9.

29 Claims, 5 Drawing Sheets

(56) References Cited

OTHER PUBLICATIONS

Meijer L, LeClerc S., Leost M., Properties and potential applications of chemical inhibitors of cyclin-dependent kinases, Pharmacol Ther, 1999, vol. 82, issue 2-3, 279-284.
Morgan DO et al., Ann. Red. Cell Dev. Biol. 1997, 13, pp. 261-291.
Muijlwijk-Koezen van J et al., J Med Chem, vol. 44, No. 5, Mar. 2001, pp. 749-762.
Nasmyth K et al., Science 1996, vol. 274, pp. 1643-1677.
O'Hare et al., Pharmacol. Ther 2002, 93, pp. 135-143.
Osborne DR et al., J Heteroc Chem, 1964, vol. 1, pp. 145-150.
Osborne DR et al., J Organic Chem, 1963, 28(19), pp. 2933-2934.
Sausville EA, Trends Mol Med 2002, 8, pp. S32-S27.
Sedova VF et al., Chem of Hetreroc Comp, vo. 22, No. 11, 1986, pp. 1236-1241.
Wang D et al., Inhibition of human immunodeficiency virus type 1 transcription by chemical cyclin-dependent kinase inhibitors, J. Virol., 2001, vol. 75, 7266-7279.
West et al., 2001, Journal of Virology 75(18), pp. 8524-8537.
Zhou M. et al., Coordination of transcription factor phosphorylation and histone methylation by the P-TEFb Kinase during human immunodeficiency virus type I transcription, J. Virol, 2004, vol. 78, 24, pp. 13522-13533.

* cited by examiner

US 8,716,296 B2

INHIBITORS OF PROTEIN KINASES

CROSS-REFERENCE TO RELATED APPLICATIONS

This application is a U.S. National Stage of PCT/EP2008/063715, filed Oct. 13, 2008, and claims benefit of U.S. Provisional Patent Application No. 60/998,821, filed Oct. 12, 2007, each of which is incorporated herein by reference in its entirety.

FIELD OF THE INVENTION

The present invention relates to inhibitors of cyclin-dependent kinases and therapeutic applications thereof. Furthermore, the invention relates to methods of preventing and/or treating any type of pain, inflammatory disorders, immunological diseases, proliferative diseases, infectious diseases, cardiovascular diseases and neurodegenerative diseases comprising the administration of an effective amount of at least one inhibitor of cyclin-dependent kinases.

BACKGROUND OF THE INVENTION

Cyclin-dependent protein kinases ("CDKs"), constitute a family of well-conserved enzymes that play multiple roles within the cell, such as cell cycle regulation and transcriptional control (Science 1996, Vol. 274:1643-1677; Ann. Rev. Cell Dev. Biol., 1997, 13:261-291.

Some members of the family, such as CDK1, 2, 3, 4, and 6 regulate the transition between different phases of the cell cycle, such as the progression from a quiescent stage in G1 (the gap between mitosis and the onset of DNA replication for a new round of cell division) to S (the period of active DNA synthesis), or the progression from G2 to M phase, in which active mitosis and cell division occur. Other members of this family of proteins, including CDK7, 8, and 9 regulate key points in the transcription cycle, whereas CDK5 plays a role in neuronal and secretory cell function.

CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific portions of the cell cycle.

CDK9 in association with its cyclin partners (cyclin T1, T2a, T2b, or K) constitutes the catalytic component of the positive P-TEFb protein kinase complex that functions during the elongation phase of transcription by phosphorylating the carboxyl-terminal domain (CTD) of the largest subunit of RNA polymerase II. P-TEFb acts in concert with positive transcription factor NfkB as well as negative transcription factors, thus overcoming a block of transcriptional elongation (Liu and Herrmann 2005).

It is known that cell-cycle dysregulation, which is one of the cardinal characteristics of neoplastic cells, is closely associated with genetic alteration and deregulation of CDKs and their regulators, suggesting that inhibitors of CDKs may be useful as therapeutics for proliferative diseases, such as cancer. Thus, small molecule inhibitors targeting CDKs have been the focus of extensive interest in cancer therapy (Current Opinion in Pharmacology, 2003(3): 362-370). The ability of inhibiting cell cycle progression suggests a general role for small molecule inhibitors of CDKs as therapeutics for proliferative diseases, such as cancer. While inhibition of cell cycle-related CDKs is clearly relevant in oncology applications, this may not be the case for the inhibition of RNA polymerase-regulating CDKs. Recently, inhibition of CDK9/cyclin T function was linked to prevention of HIV replication and the discovery of new CDK biology thus continues to open up new therapeutic indications for CDK inhibitors (Sausville, E. A. Trends Molec. Med. 2002, 8, S32-S37), such as, for example, viral infections (WO 02/100401). CDK inhibitors could conceivably also be used to treat other conditions such as immunological diseases and neurodegenerative diseases, amongst others.

More than 50 pharmacological CDK inhibitors have been described, some of which have potent antitumor activity (Current Opinion in Pharmacology, 2003(3): 362-370). A comprehensive review about the known CDK inhibitors may be found in Angew. Chem. Int. Ed. Engl. 2003, 42(19):2122-2138.

The use of 2-anilino-4-phenylpyrimidine derivatives as cyclin-dependent kinase inhibitors for the treatment of e.g. cancer has been reported in WO 2005/012262. Furthermore, 2-pyridinylamino-4-thiazolyl-pyrimidine derivatives for the treatment of cancer etc. have been described in WO 2005/012298. The use of 4,5-dihydro-thiazolo, oxazolo and imidazolo[4,5-h]quinazolin-8-ylamines as protein kinase inhibitors is known from WO 2005/005438. Furthermore, indolinone derivatives and indirubin derivatives, which are useful as cyclin-dependent kinase inhibitors have been disclosed in WO 02/081445 and WO 02/074742. Additionally, CDK inhibitors for various therapeutic applications have been described in WO2005/026129.

Known CDK inhibitors may be classified according to their ability to inhibit CDKs in general or according to their selectivity for a specific CDK. Flavopiridol, for example, acts as a "pan" CDK antagonist and is not particularly selective for a specific CDK (Current Opinion in Pharmacology, 2003(3): 362-370). Purine-based CDK inhibitors, such as olomoucine, roscovitine, purvanolols and CGP74514A are known to exhibit a greater selectivity for CDKs 1, 2 and 5, but show no inhibitory activity against CDKs 4 and 6 (Current Opinion in Pharmacology, 2003(3): 362-370). Furthermore, it has been demonstrated that purine-based CDK inhibitors such as roscovitine can exert anti-apoptotic effects in the nervous system (Pharmacol Ther 2002, 93:135-143) or prevent neuronal death in neurodegenerative diseases, such as Alzheimers's disease (Biochem Biophys Res Commun 2002 (297):1154-1158; Trends Pharmacol Sci 2002 (23):417-425).

Given the tremendous potential of targeting CDKs for the therapy of conditions such as proliferative, immunological, infectious, cardiovascular and neurodegenerative diseases, the development of small molecules as selective inhibitors of particular CDKs constitutes a desirable goal.

The present invention provides novel small molecule inhibitors of cyclin-dependent kinases such as CDK9. Suitably, said small molecule inhibitors show selectivity in inhibiting a particular CDK, in particular CDK9. Said small molecule inhibitors may have a therapeutic utility for the treatment of conditions such as proliferative, immunological, neurodegenerative, infectious and cardiovascular diseases. Furthermore, the small molecule inhibitors of the present invention have surprisingly been shown to exert a beneficial effect in the treatment of inflammatory diseases and pain.

Current treatments for inflammatory diseases and any type of pain are only partially effective, and many also cause debilitating or dangerous side effects. For example, many of the traditional analgesics used to treat severe pain induce debilitating side effects such as nausea, dizziness, constipation, respiratory depression, and cognitive dysfunction (Brower, 2000).

Although there is already a broad panel of approved pain medications like non-narcotic analgesics, opioid analgesics, calcium channel blockers, muscle relaxants, and systemic corticosteroids available, said treatments remain merely empirical and, while they may relieve the symptoms of pain, they do not lead to complete relief in most cases. This is also due to fact that the mechanisms underlying the development of the different types of pain are still only poorly understood. Researchers are only just beginning to appreciate the complexity and diversity of the signaling systems used to relay nerve impulses for each type of pain.

Generally, pain is defined as an unpleasant sensory and emotional experience associated with actual or potential tissue damage, or described in terms of such damage, according to the International Association for the Study of Pain (IASP). Specifically, pain may occur as acute or chronic pain.

Acute pain occurs for brief periods of time, typically less than 1 month and is associated with temporary disorders. It is a natural body response to let the host be aware of physiological or biochemical alteration that could result in further damage within a short period of time. It is felt when noxious stimuli activate high threshold mechanical and/or thermal nociceptors in peripheral nerve endings and the evoked action potentials in thinly myelinated (Aδ) and/or unmyelinated (C) afferent fibres reach a conscious brain. Said noxious stimuli may be provided by injury, surgery, illness, trauma or painful medical procedures. Acute pain usually disappears when the underlying cause has been treated or has healed. Unrelieved acute pain, however, may lead to chronic pain problems that may result in long hospital stays, rehospitalizations, visits to outpatient clinics and emergency departments, and increased health care costs.

In contrast to acute pain, chronic pain persists long after the initial injury has healed and often spreads to other parts of the body, with diverse pathological and psychiatric consequences. Chronic somatic pain results from inflammatory responses to trauma in peripheral tissues (e.g., nerve entrapment, surgical procedures, cancer, or arthritis), which leads to oversensitization of nociceptors and intense searing pain responses to normally non-noxious stimuli (hyperalgesia). Chronic pain is continuous and recurrent and its intensity will vary from mild to severe disabling pain that may significantly reduce quality of life.

Chronic pain is currently treated with conventional analgesics such as NSAIDs (ibuprofen, naproxen), Cox-2 inhibitors (celecoxib, valdecoxib, rofecoxib) and opiates (codeine, morphine, thebain, papaverin, noscapin). For a significant number of patients however, these drugs provide insufficient pain relief.

Another subtype of pain, inflammatory pain, can occur as acute as well as chronic pain. Inflammatory pain is mediated by noxious stimuli like e.g. inflammatory mediators (e.g. cytokines, such as TNF α, prostaglandins, substance P, bradykinin, purines, histamine, and serotonin), which are released following tissue injury, disease, or inflammation and other noxious stimuli (e.g. thermal, mechanical, or chemical stimuli). In addition, cytokines and growth factors can influence neuronal phenotype and function (Besson 1999). These mediators are detected by nociceptors (sensory receptors) that are distributed throughout the periphery of the tissue. Said nociceptors are sensitive to noxious stimuli (e.g. mechanical, thermal, or chemical), which would damage tissue if prolonged (Koltzenburg 2000). A special class of so called C-nociceptors represent a class of "silent" nociceptors that do not respond to any level of mechanical or thermal stimuli but are activated in presence of inflammation only.

Current approaches for the treatment of especially inflammatory pain aim at cytokine inhibition (e.g. IL1β) and suppression of pro-inflammatory TNFα. Current approved anti-cytokine/antiTNFalpha treatments are based on chimeric antibodies such as Infliximab and Etanercept which reduce TNFα circulation in the bloodstream. TNFα is one of the most important inflammatory mediators that induces synthesis of important enzymes such as COX-2, MMP, iNOS, cPLa$_2$ and others. The main drawbacks of these "biologicals", however, reside in their immunogenic potential with attendant loss of efficacy and their kinetics that lead to a more or less digital all-or-nothing reduction of circulating TNFα. The latter can result in severe immune suppressive side effects.

A distinct form of chronic pain, neuropathic (or neurogenic) pain, arises as a result of peripheral or central nerve dysfunction and includes a variety of conditions that differ in etiology as well as location. Generally, the causes of neuropathic pain are diverse, but share the common symptom of damage to the peripheral nerves or components of central pathways. The causative factors might be metabolic, viral or mechanical nerve lesion. Neuropathic pain is believed to be sustained by aberrant somatosensory processes in the peripheral nervous system, the CNS, or both. Neuropathic pain is not directly linked to stimulation of nociceptors, but instead, is thought to arise e.g. from oversensitization of glutamate receptors on postsynaptic neurons in the gray matter (dorsal horn) of the spinal cord.

Neuropathic pain is associated with conditions such as nerve degeneration in diabetes and postherpetic neuralgia (shingles). Neuropathic pain conditions are the consequence of a number of diseases and conditions, including diabetes, AIDS, multiple sclerosis, stump and phantom pain after amputation, cancer-related neuropathy, postherpetic neuralgia, traumatic nerve injury, ischemic neuropathy, nerve compression, stroke, spinal cord injury.

Management of neuropathic pain remains a major clinical challenge, partly due to an inadequate understanding of the mechanisms involved in the development and maintenance of neuropathic pain. Many existing analgesics are ineffective in treating neuropathic pain and most of current narcotic and non-narcotic drugs do not control the pain. Current clinical practice includes the use of a number of drug classes for the management of neuropathic pain, for example anticonvulsants, tricyclic antidepressants, and systemic local anaesthetics. However, the usual outcome of such treatment is partial or unsatisfactory pain relief, and in some cases the adverse effects of these drugs outweigh their clinical usefulness. Classic analgesics are widely believed to be poorly effective or ineffective in the treatment of neuropathic pain. Few clinical studies on the use of non steroidal anti-inflammatory drugs (NSAIDs) or opiates in the treatment of neuropathic pain have been conducted, but in those which have, the results appear to indicate that NSAIDs are poorly effective or ineffective and opiates only work at high doses. A review analysing the controlled clinical data for peripheral neuropathic pain (PNP) (Pain, November, 1997 73(2), 123-39) reported that NSAIDs were probably ineffective as analgesics for PNP and that there was no long-term data supporting the analgesic effectiveness of any drug.

Available analgesic drugs often produce insufficient pain relief. Although tricyclic antidepressants and some antiepileptic drugs, for example gabapentin, lamotrigine and carbamazepine, are efficient in some patients, there remains a large unmet need for efficient drugs for the treatment of these conditions.

In conclusion, there is a high unmet need for safe and effective methods of treatment of inflammatory diseases and pain treatment, in particular of chronic inflammatory and neuropathic pain.

DEFINITIONS

Throughout the description and the claims the expression "alkyl", unless specifically limited, denotes a $C_{1-12}$ alkyl group, suitably a $C_{1-6}$ alkyl group, e.g. $C_{1-4}$ alkyl group. Alkyl groups may be straight chain or branched. Suitable alkyl groups include, for example, methyl, ethyl, propyl (e.g. n-propyl and isopropyl), butyl (e.g n-butyl, iso-butyl, sec-butyl and tert-butyl), pentyl (e.g. n-pentyl), hexyl (e.g. n-hexyl), heptyl (e.g. n-heptyl) and octyl (e.g. n-octyl). The expression "alk", for example in the expressions "alkoxy", "haloalkyl" and "thioalkyl" should be interpreted in accordance with the definition of "alkyl". Exemplary alkoxy groups include methoxy, ethoxy, propoxy (e.g. n-propoxy), butoxy (e.g. n-butoxy), pentoxy (e.g. n-pentoxy), hexoxy (e.g. n-hexoxy), heptoxy (e.g. n-heptoxy) and octoxy (e.g. n-octoxy). Exemplary thioalkyl groups include methylthio-. Exemplary haloalkyl groups include fluoroalkyl e.g. $CF_3$.

The expression "alkenyl", unless specifically limited, denotes a $C_{2-12}$ alkenyl group, suitably a $C_{2-6}$ alkenyl group, e.g. a $C_{2-4}$ alkenyl group, which contains at least one double bond at any desired location and which does not contain any triple bonds. Alkenyl groups may be straight chain or branched. Exemplary alkenyl groups including one double bond include propenyl and butenyl. Exemplary alkenyl groups including two double bonds include pentadienyl, e.g. (1E,3E)-pentadienyl.

The expression "alkynyl", unless specifically limited, denotes a $C_{2-12}$ alkynyl group, suitably a $C_{2-6}$ alkynyl group, e.g. a $C_{2-4}$ alkynyl group, which contains at least one triple bond at any desired location and may or may not also contain one or more double bonds. Alkynyl groups may be straight chain or branched. Exemplary alkynyl groups include propynyl and butynyl.

The expression "alkylene" denotes a chain of formula —$(CH_2)_n$— wherein n is an integer e.g. 1-5, unless specifically limited.

The expression "cycloalkyl", unless specifically limited, denotes a $C_{3-10}$ cycloalkyl group (i.e. 3 to 10 ring carbon atoms), more suitably a $C_{3-8}$ cycloalkyl group, e.g. a $C_{3-6}$ cycloalkyl group. Exemplary cycloalkyl groups include cyclopropyl, cyclobutyl, cyclopentyl, cyclohexyl, cycloheptyl and cyclooctyl. A most suitable number of ring carbon atoms is three to six.

The expression "cycloalkenyl", unless specifically limited, denotes a $C_{5-10}$ cycloalkenyl group (i.e. 5 to 10 ring carbon atoms), more suitably a $C_{5-8}$ cycloalkenyl group e.g. a $C_{5-6}$ cycloalkenyl group. Exemplary cycloalkenyl groups include cyclopentenyl, cyclohexenyl, cycloheptenyl and cyclooctenyl. A most suitable number of ring carbon atoms is five to six.

The expression "carbocyclyl", unless specifically limited, denotes any ring system in which all the ring atoms are carbon and which contains between three and twelve ring carbon atoms, suitably between three and ten carbon atoms and more suitably between three and eight carbon atoms. Carbocyclyl groups may be saturated or partially unsaturated, but do not include aromatic rings or non-aromatic rings fused to aromatic rings. Examples of carbocyclyl groups include monocyclic, bicyclic, and tricyclic ring systems, in particular monocyclic and bicyclic ring systems. Other carbocylcyl groups include bridged ring systems (e.g. bicyclo[2.2.1]heptenyl). A specific example of a carbocyclyl group is a cycloalkyl group. A further example of a carbocyclyl group is a cycloalkenyl group.

The expression "heterocyclyl", unless specifically limited, refers to a carbocyclyl group wherein one or more (e.g. 1, 2 or 3) ring atoms are replaced by heteroatoms selected from N, S and O. A specific example of a heterocyclyl group is a cycloalkyl group (e.g. cyclopentyl or more particularly cyclohexyl) wherein one or more (e.g. 1, 2 or 3, particularly 1 or 2, especially 1) ring atoms are replaced by heteroatoms selected from N, S or O (in particular N or O). Exemplary heterocyclyl groups containing one hetero atom include pyrrolidine, tetrahydrofuran and piperidine, and exemplary heterocyclyl groups containing two hetero atoms include morpholine and piperazine. A further specific example of a heterocyclyl group is a cycloalkenyl group (e.g. a cyclohexenyl group) wherein one or more (e.g. 1, 2 or 3, particularly 1 or 2, especially 1) ring atoms are replaced by heteroatoms selected from N, S and O (in particular N or O). An example of such a group is dihydropyranyl (e.g. 3,4-dihydro-2H-pyran-2-yl-).

The expression "aryl", unless specifically limited, denotes a $C_{6-12}$ aryl group, suitably a $C_{6-10}$ aryl group, more suitably a $C_{6-8}$ aryl group. Aryl groups will contain at least one aromatic ring (e.g. one, two or three rings) but may also contain additional rings which are non-aromatic. An example of a typical aryl group with one aromatic ring is phenyl. An example of a typical aryl group with two aromatic rings is naphthyl. Phenyl fused to $C_{5-8}$ carbocyclyl (suitably $C_{5-6}$ carbocyclyl) (e.g. indane) is also an example of aryl.

The expression "heteroaryl", unless specifically limited, denotes an aryl residue, wherein one or more (e.g. 1, 2, 3, or 4, suitably 1, 2 or 3) ring atoms are replaced by heteroatoms selected from N, S and O, or else a 5-membered aromatic ring containing one or more (e.g. 1, 2, 3, or 4, suitably 1, 2 or 3) ring atoms selected from N, S and O. Exemplary monocyclic heteroaryl groups having one heteroatom include: five membered rings (e.g. pyrrole, furan, thiophene); and six membered rings (e.g. pyridine, such as pyridin-2-yl, pyridin-3-yl and pyridin-4-yl). Exemplary monocyclic heteroaryl groups having two heteroatoms include: five membered rings (e.g. pyrazole, oxazole, isoxazole, thiazole, isothiazole, imidazole, such as imidazol-1-yl, imidazol-2-yl imidazol-4-yl); six membered rings (e.g. pyridazine, pyrimidine, pyrazine). Exemplary monocyclic heteroaryl groups having three heteroatoms include: 1,2,3-triazole and 1,2,4-triazole. Exemplary monocyclic heteroaryl groups having four heteroatoms include tetrazole. Exemplary bicyclic heteroaryl groups include: indole (e.g. indol-6-yl), benzofuran, benzthiophene, quinoline, isoquinoline, indazole, benzimidazole, benzthiazole, quinazoline and purine. Phenyl fused to heterocyclyl (e.g. benzo-1,3-dioxol-5-yl, 2,3-dihydro-benzo1,4dioxin-6-yl) is also an example of heteroaryl. Suitably the heteroatom or heteroatoms are members of the aromatic ring.

The expression "-alkylcarbocyclyl", unless specifically limited, denotes a carbocyclyl residue which is connected via an alkylene moiety e.g. a $C_{1-4}$ alkylene moiety.

The expression "-alkylheterocyclyl", unless specifically limited, denotes a heterocyclyl residue which is connected via an alkylene moiety e.g. a $C_{1-4}$ alkylene moiety.

The expression "-alkylaryl", unless specifically limited, denotes an aryl residue which is connected via an alkylene moiety e.g. a $C_{1-4}$ alkylene moiety.

The expression "-alkylheteroaryl", unless specifically limited, denotes a heteroaryl residue which is connected via an alkylene moiety e.g. a $C_{1-4}$ alkylene moiety.

The term "halogen" or "halo" comprises fluorine (F), chlorine (Cl) and bromine (Br).

The term "amino" refers to the group —NH$_2$.

Stereoisomers:

All possible stereoisomers of the claimed compounds are included in the present invention.

Where the compounds according to this invention have at least one chiral centre, they may accordingly exist as enantiomers. Where the compounds possess two or more chiral centres, they may additionally exist as diastereomers. It is to be understood that all such isomers and mixtures thereof are encompassed within the scope of the present invention.

Preparation and Isolation of Stereoisomers:

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Pharmaceutically Acceptable Salts:

In view of the close relationship between the free compounds and the compounds in the form of their salts or solvates, whenever a compound is referred to in this context, a corresponding salt, solvate or polymorph is also intended, provided such is possible or appropriate under the circumstances.

Solvates

Some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

Salts and solvates of the compounds of formula (I) and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds and their pharmaceutically acceptable salts and solvates.

Suitable salts according to the invention include those formed with both organic and inorganic acids or bases. Pharmaceutically acceptable acid addition salts include those formed from hydrochloric, hydrobromic, sulfuric, nitric, citric, tartaric, phosphoric, lactic, pyruvic, acetic, trifluoroacetic, triphenylacetic, sulfamic, sulfanilic, succinic, oxalic, fumaric, maleic, malic, mandelic, glutamic, aspartic, oxaloacetic, methanesulfonic, ethanesulfonic, arylsulfonic (for example p-toluenesulfonic, benzenesulfonic, naphthalenesulfonic or naphthalenedisulfonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic), isethionic acids, perchloric, propionic, glycolic, hydroxyethanesulfonic, pamoic, cyclohexanesulfamic, saccharinic and trifluoroacetic acid, particularly hydrochloric. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

All pharmaceutically acceptable acid addition salt forms of the compounds of the present invention are intended to be embraced by the scope of this invention.

Polymorph Crystal Forms:

Furthermore, some of the crystalline forms of the compounds may exist as polymorphs and as such are intended to be included in the present invention.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985.

Protective Groups:

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, fully incorporated herein by reference. The protecting groups may be removed at a convenient subsequent stage using methods known from the art.

As used herein, the term "composition" is intended to encompass a product comprising the claimed compounds in therapeutically effective amounts, as well as any product which results, directly or indirectly, from combinations of the claimed compounds.

SUMMARY OF THE INVENTION

The present invention is directed to inhibitors of cyclin-dependent kinases and to methods and compositions for treating and/or preventing any type of pain, inflammatory disorders, immunological diseases, proliferative diseases, infectious diseases, cardiovascular diseases and neurodegenerative diseases comprising: administering an effective amount of at least one inhibitor of a cyclin-dependent kinase (cdk, CDK) to a subject in need thereof.

According to the invention, there is provided an inhibitor compound, which is a compound according to the general Formula I:

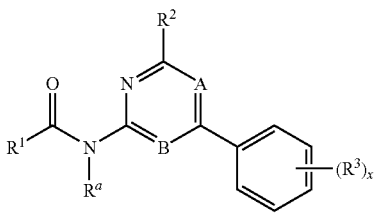

Formula (I)

or a pharmaceutically acceptable salt, solvate or polymorph thereof, including all tautomers and stereoisomers thereof wherein:

A is N and B is CH, C($C_{1-4}$alkyl) or C($NH_2$),
or A is CH, C($C_{1-4}$alkyl) or C($NH_2$) and B is N;
$R^a$ is H or methyl;
$R^1$ is selected from the group consisting of:
  $C_{1-8}$ alkyl;
  —$NR^6R^7$;
  $C_{1-6}$ alkyl-$NR^6R^7$;
  $R^{20}$;
  —$C_{1-6}$ alkyl-$R^{20}$;
  —$C_{1-6}$ alkyl-C(O)$OR^4$;
  $C_{1-6}$alkyl-C(O)$R^4$;
  —$NR^{10}$—($C_{1-6}$alkyl)-$NR^6R^7$;
  —$NR^{10}$—($C_{1-6}$alkyl)-$R^{20}$;
  —$NR^{10}$—($C_{1-6}$alkyl)-C(O)$OR^4$;
  —$NR^{10}R^{20}$;
  O—($C_{1-6}$ alkyl)-$NR^6R^7$;
  —O—($C_{1-6}$alkyl)-$R^{20}$;
  —O—($C_{1-6}$alkyl)-C(O)$OR^4$;
  —$OR^{20}$;
  $C_{1-6}$ alkyl-$OR^{20}$;
  $C_{1-6}$ alkyl-$SR^{20}$;
  $C_1$-$C_6$ alkyl-$NR^{10}R^{20}$;
  ($C_{1-6}$ alkyl)-O—($C_{1-6}$ alkyl)-$R^{20}$;
  ($C_{1-6}$ alkyl)-S—($C_{1-6}$ alkyl)-$R^{20}$;
  C(O)$R^{20}$;

where alkyl moieties may be straight or branched and may be substituted by one or more substituents chosen from halo, methoxy, ethoxy $NR^6R^7$ or a nitrogen-containing heterocyclic ring;

$R^4$ represents H or $C_{1-4}$-alkyl;
$R^6$ and $R^7$ are each independently selected from the group consisting of H, $C_{1-6}$ alkyl, hydroxy-$C_{2-6}$alkyl-;
$R^{10}$ represents H or $C_{1-4}$alkyl;
$R^{20}$ is selected from aryl, heteroaryl, carbocyclyl and heterocyclyl and may be substituted by one or more substituents selected from:
  $C_{1-6}$alkyl, $C_{2-6}$alkenyl, $C_{2-6}$alkynyl any of which may be substituted by one or more halo or OH substituents;
  $R^{21}$, —$C_{1-4}$ alkyl-$R^{21}$; $OR^{21}$, O($C_{1-4}$ alkyl)$R^{21}$, $SR^{21}$, $SOR^{21}$, $SO_2R^{21}$, C(O)$R^{21}$, $C_{1-4}$ alkyl-$OR^{21}$,
  —O($C_{2-6}$alkenyl), —O($C_{2-6}$alkynyl), any of which may be substituted by one or more halo or OH substituents;
  $OR^{22}$, —$SR^{22}$, —$SOR^{22}$, —$SO_2R^{22}$, —C(O)$R^{22}$, —C(O)$OR^{22}$, —$C_{1-4}$ alkyl-O—$R^{22}$, —$C_{1-4}$ alkyl-O—$C_{1-4}$ alkyl-O—$R^{22}$, $C_{1-4}$alkyl-C(O)$R^{22}$, —$C_{1-4}$alkyl-C(O)$R^{22}$, $NR^{11}$C(O)$OR^{22}$, $NR^{11}$C(O)$R^{22}$, —$SO_2$—$NR^{11}R^{12}$, —C(O)—$NR^{11}R^{12}$, —$C_{1-4}$alkyl-C(O)—$NR^{11}R^{12}$, —NH—$SO_2R^{15}$, —N($C_{1-4}$alkyl)-$SO_2R^{15}$, —($C_{1-4}$alkyl)$NR^{11}R^{12}$, $NR^{11}R^{12}$, —($C_{1-6}$alkyl) $NR^{11}R^{12}$, nitro, halogen, cyano and hydroxyl; and when $R^{20}$ is carbocyclyl or heterocyclyl or an aromatic group in which an aromatic ring is fused to a non-aromatic ring, $R^{20}$ may additionally be substituted by oxo;

$R^{21}$ is is selected from aryl, heteroaryl, carbocyclyl and heterocyclyl and may be substituted by one or more substituents as defined below;
when $R^{21}$ is an aryl or heteroaryl group, it may be substituted by one or more substituents selected from: wherein phenyl is optionally substituted by methyl, methoxy, halogen, halomethyl fluoromethoxy or trifluoromethoxy
when $R^{21}$ is a carbocyclic or heterocyclic group it may be substituted by one or more substituents selected from methyl, oxo or halogen;
$R^{22}$ is hydrogen or $C_{1-6}$ alkyl optionally substituted by halo or hydroxyl;
$R^{11}$ and $R^{12}$ each independently represent a substituent selected from H or $C_{1-4}$ alkyl or $R^{11}$ and $R^{12}$ are joined such that together they form a 3-8 membered non-aromatic ring;
$R^{15}$ represents H or $C_{1-4}$alkyl;
$R^2$ represents H, $C_{1-6}$alkyl or $NH_2$;
each $R^3$ independently represents a substituent, selected from the group consisting of $C_{1-6}$alkyl, $C_{2-6}$alkenyl, $C_{2-6}$alkynyl, $C_{1-6}$haloalkyl, $C_{3-8}$cycloalkyl (optionally substituted by methyl, oxo or halogen), phenyl (optionally substituted by methyl, methoxy, halogen, halomethyl fluoromethoxy or trifluoromethoxy), —$C_{1-6}$alkyl-OH, —$C_{1-4}$alkylphenyl (optionally substituted by methyl, methoxy, halogen, halomethyl fluoromethoxy or trifluoromethoxy), $C_{1-6}$alkenyloxy, $C_{3-6}$alkynyloxy-, $C_{1-6}$haloalkoxy-, —O—$C_{3-8}$ cycloalkyl, —O—$C_{1-4}$alkyl-$C_{3-8}$cycloalkyl, —O-phenyl (optionally substituted by methyl, methoxy, halogen, halomethyl fluoromethoxy or trifluoromethoxy), —O—$C_{1-4}$alkylphenyl (optionally substituted by methyl, methoxy, halogen, halomethyl fluoromethoxy or trifluoromethoxy), —S($C_{1-6}$alkyl), —SO ($C_{1-6}$alkyl), —$SO_2C_{1-6}$alkyl, —$SO_2C_{3-8}$cycloalkyl, —$SO_2$—$NR^{31}R^{32}$, —C(O)$C_{1-6}$alkyl, —C(O)$C_{3-8}$cycloalkyl, —C(O)OH, —C(O)O$C_{1-6}$alkyl, —C(O)—$NR^{31}R^{32}$, —$C_{1-4}$ alkyl-O—$C_{1-4}$alkyl, $C_{1-4}$alkyl-O—$C_{1-4}$alkyl-OH, —$C_{1-4}$ alkyl-O—$C_{1-4}$alkyl-O—$C_{1-4}$ alkyl, $C_{1-4}$ alkyl-O—$C_{3-7}$cycloalkyl, —$C_{1-4}$alkyl-C(O)$C_{1-6}$alkyl, —$C_{1-4}$alkyl-C(O)OH, —$C_{1-4}$alkyl-C(O)O$C_{1-4}$ alkyl, —$C_{1-4}$alkyl-C(O)—$NR^{31}R^{32}$, —NH—$SO_2R^{33}$, —N($C_{1-4}$alkyl)-$SO_2R^{33}$, —($C_{1-4}$alkyl) $NR^{31}R^{32}$, —$NR^{31}R^{32}$, —($C_{1-8}$alkyl)$NR^{31}R^{32}$, nitro, halogen, cyano, hydroxyl;
$R^{31}$ and $R^{32}$ each independently represent a substituent selected from H, $C_{1-4}$ alkyl or $C_{1-4}$haloalkyl or $R^{31}$ and $R^{32}$ are joined such that together they form a 3-8 membered non-aromatic ring;
$R^{33}$ represents H or $C_{1-4}$alkyl;
x represents the number of independently selected $R^3$ substituents on the phenyl ring, in the range 0-4.

Some compounds similar to those of general formula (I) are known from the prior art. For example, from EP 1 679 309 (Ono Pharmaceutical), which concerns anti-stress drugs as well as indications such as Parkinson's, schizophrenia, myocardial infarction. EP 1 679 309 discloses some compounds which are similar to compounds of the present invention; however, these compounds differ from the more suitable compounds of the present invention in which A represents N and B represents CH or C($C_{1-4}$alkyl) as they are of a configuration where the atom corresponding to A of the present invention represents CH and the atom corresponding to B of the present invention represents N.

WO 2004/084824 (Merck) concerns biaryl substituted 6-membered heterocycles as sodium channel blockers. Indications include chronic and neuropathic pain and other conditions including CNS disorders. WO 2004/084824 discloses compounds which are similar to the more suitable compounds of the present invention but discloses no means of synthesising compounds wherein A represents N and B represents CH or C(C$_{1-4}$ alkyl).

WO 2002/094825 (Banyu Pharmaceutical) concerns NPY agonists and indications include circulatory diseases, central diseases, metabolic diseases, sexual and reproductive dysfunction, digestive diseases, respiratory diseases etc. The compounds disclosed in this document differ from those of the present invention in that WO 2002/094825 concerns compounds in which R$^1$ (as defined by the present application) is a three ring system comprising a piperidine ring linked to a terminal bicyclic ring via a Spiro ring junction.

WO 2005/103022 (Transtech Pharma) concerns substituted thiazole and pyrimidine derivatives as melancortin receptor modulators. Indications include cancer include cardiovascular diseases. WO 2005/103022 discloses some compounds which are similar to compounds of the present invention; however, these compounds differ from the more suitable compounds of the present invention in that these compounds have A represents CH and B represents N (as defined by the present application), whereas the more suitable compounds of the present invention have A represents N and B represents CH or C(C$_{1-4}$alkyl).

FR 2878247 (Galderma Research & Development) concerns novel compounds that modulate peroxisome proliferator-activated receptor type of subtype gamma receptors and use thereof in cosmetic or pharmaceutical compositions. The indications are mostly skin disorders but also include disorders related to lipid metabolism, such as obesity, and inflammatory conditions, such as arthritis, and cancer. The examples disclosed by FR 2878247 which are most similar to the compounds of the present application differ from the more suitable compounds of the present invention in that these compounds have A represents CH and B represents N (as defined by the present application), whereas the more suitable compounds of the present invention have A represents N and B represents CH or C(C$_{1-4}$alkyl).

WO 2001/62233 (F Hoffmann La Roche) concerns adenosine receptor modulators. Indications include inter alia Alzheimer's, Parkinson's, schizophrenia and pain. WO 2001/62233 discloses some compounds which are similar to compounds of the present invention; however, these compounds differ from the more suitable compounds of the present invention in that these compounds have A represents CH and B represents N (as defined by the present application), whereas the more suitable compounds of the present invention have A represents N and B represents CH or C(C$_{1-4}$alkyl).

In one aspect of the invention, in the compound of general formula (I):
A is N and B is CH, C(C$_{1-4}$alkyl) or C(NH$_2$), or A is CH, C(C$_{1-4}$alkyl) or C(NH$_2$) and B is N;
R$^1$ is selected from the group consisting of:
C$_{1-8}$alkyl;
C$_{1-8}$haloalkyl;

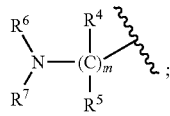

aryl;
heteroaryl;
C$_{3-12}$ carbocyclyl;
heterocyclyl;
—C$_{1-6}$alkyl-aryl;
—C$_{1-6}$alkyl-heteroaryl;
—C$_{1-6}$alkyl-carbocyclyl;
—C$_{1-6}$alkyl-heterocyclyl;
—C$_{1-6}$alkyl-C(O)OH;
—C$_{1-6}$alkyl-C(O)OC$_{1-4}$alkyl;

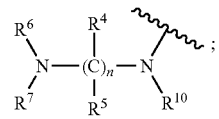

—NR$^{10}$C$_{1-6}$alkyl-aryl;
—NR$^{10}$C$_{1-6}$alkyl-heteroaryl;
—NR$^{10}$C$_{1-6}$alkyl-carbocyclyl;
—NR$^{10}$C$_{1-6}$alkyl-heterocyclyl;
—NR$^{10}$C$_{1-6}$alkyl-C(O)OH;
—NR$^{10}$C$_{1-6}$alkyl-C(O)OC$_{1-4}$alkyl;
—NR$^{10}$aryl;
—NR$^{10}$heteroaryl;
—NR$^{10}$carbocyclyl;
—NR$^{10}$heterocyclyl;

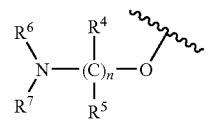

—OC$_{1-6}$alkyl-aryl;
—OC$_{1-6}$alkyl-heteroaryl;
—OC$_{1-6}$alkyl-carbocyclyl;
—OC$_{1-6}$alkyl-heterocycly1;
—OC$_{1-6}$alkyl-C(O)OH;
—OC$_{1-6}$alkyl-C(O)OC$_{1-4}$alkyl;
—Oaryl;
—Oheteroaryl;
—Ocarbocyclyl; and
—Oheterocyclyl;
wherein any of the aforesaid aryl and heteroaryl may optionally be substituted by one or more groups independently selected from the group consisting of C$_{1-6}$alkyl, C$_{2-6}$ alkenyl, C$_{2-6}$alkynyl, C$_{1-6}$haloalkyl, C$_{3-8}$cycloalkyl (optionally substituted by methyl, oxo or halogen), phenyl (optionally substituted by methyl, methoxy, halogen, halomethyl fluoromethoxy or trifluoromethoxy)-C$_{1-6}$alkyl-OH, —C$_{1-4}$ alkylphenyl (wherein phenyl is optionally substituted by methyl, methoxy, halogen, halomethyl fluoromethoxy or trifluoromethoxy), C$_{1-6}$alkoxy-, C$_{1-6}$ lkenyloxy, C$_{3-6}$alkynyloxy-, C$_{1-6}$haloalkoxy-, —O—C$_{3-8}$cycloalkyl, —O—C$_{1-4}$alkyl-C$_{3-8}$ cycloalkyl, —O-phenyl (optionally substituted by methyl, methoxy, halogen, halomethyl fluoromethoxy or trifluoromethoxy), —O—C$_{1-4}$ alkylphenyl (optionally substituted by methyl, methoxy, halogen, halomethyl fluoromethoxy or trifluoromethoxy), —S(C$_{1-6}$alkyl), —SO(C$_{1-6}$alkyl), —SO$_2$C$_{1-6}$alkyl, —SO$_2$C$_{3-8}$cycloalkyl, —SO$_2$—NR$^{11}$R$^{12}$, —C(O)C$_{1-6}$alkyl, —C(O)C$_{3-8}$cycloalkyl, —C(O)OH, —C(O)OC$_{1-6}$alkyl, —C(O)—NR$^{11}$R$^{12}$, —C$_{1-4}$alkyl-O—C$_{1-4}$alkyl, —C$_{1-4}$alkyl-O—C$_{1-4}$alkyl-OH, —C$_{1-4}$ alkyl-O—C$_{1-4}$ alkyl-O—C$_{1-4}$alkyl, —C$_{1-4}$ alkyl-O—C$_{3-7}$cycloalkyl, —C$_{1-4}$alkyl-C(O)C$_{1-6}$alkyl, —C$_{1-4}$ alkyl-C(O)OH, —C$_{1-4}$alkyl-C(O)OC$_{1-4}$alkyl, —C$_{1-4}$alkyl-C(O)—NR$^{11}$R$^{12}$, —NH—SO$_2$R$^{15}$, —N(C$_{1-4}$ alkyl)-SO$_2$R$^{15}$, —(C$_{1-4}$alkyl)NR$^{11}$R$^{12}$, NR$^{11}$R$^{12}$, —(C$_{1-6}$alkyl)NR$^{11}$R$^{12}$, nitro, halogen, cyano and hydroxyl; and wherein any of the aforesaid carbocyclyl and heterocyclyl may optionally be substituted by one or more groups independently selected from the group consisting of C$_{1-6}$ alkyl, C$_{2-6}$alkenyl, C$_{2-6}$alkynyl, C$_{1-6}$haloalkyl, C$_{3-8}$cycloalkyl (optionally substituted by methyl, oxo or halogen), phenyl (optionally substituted by methyl, methoxy, halogen, halomethyl fluoromethoxy or trifluoromethoxy), —C$_{1-6}$alkyl-OH, —C$_{1-4}$ alkylphenyl (wherein phenyl is optionally substituted by methyl, methoxy, halogen, halomethyl fluoromethoxy or trifluoromethoxy), C$_{1-6}$alkoxy-, C$_{1-6}$ alkenyloxy, C$_{3-6}$alkynyloxy-, C$_{1-6}$haloalkoxy-, —O—C$_{3-8}$cycloalkyl, —O—C$_{1-4}$alkyl-C$_{3-8}$ cycloalkyl, —O-phenyl (optionally substituted by methyl, methoxy, halogen, halomethyl fluoromethoxy or trifluoromethoxy), —O—C$_{1-4}$ alkylphenyl (optionally substituted by methyl, methoxy, halogen, halomethyl fluoromethoxy or trifluoromethoxy), —S(C$_{1-6}$alkyl), —SO(C$_{1-6}$alkyl), —SO$_2$C$_{1-6}$alkyl, —SO$_2$C$_{3-8}$cycloalkyl, —SO$_2$—NR$^{11}$R$^{12}$, —C(O)C$_{1-6}$alkyl, —C(O)C$_{3-8}$cycloalkyl, —C(O)OH, —C(O)OC$_{1-6}$alkyl, —C(O)—NR$^{11}$R$^{12}$, —C$_{1-4}$alkyl-O—C$_{1-4}$alkyl, —C$_{1-4}$alkyl-O—C$_{1-4}$alkyl-OH, —C$_{1-4}$ alkyl-O—C$_{1-4}$ alkyl-O—C$_{1-4}$alkyl, —C$_{1-4}$ alkyl-O—C$_{3-7}$cycloalkyl, —C$_{1-4}$alkyl-C(O)C$_{1-6}$alkyl, —C$_{1-4}$ alkyl-C(O)OH, —C$_{1-4}$alkyl-C(O)OC$_{1-4}$alkyl, —C$_{1-4}$alkyl-C(O)—NR$^{11}$R$^{12}$, —NH—SO$_2$R$^{15}$, —N(C$_{1-4}$ alkyl)-SO$_2$R$^{15}$, —(C$_{1-4}$alkyl)NR$^{11}$R$^{12}$, —NR$^{11}$R$^{12}$, —(C$_{1-6}$alkyl)NR$^{11}$R$^{12}$, nitro, halogen cyano, hydroxyl and oxo;

R$^2$ represents H, C$_{1-6}$alkyl or NH$_2$;

R$^3$ represents a substituent, selected from the group consisting of C$_{1-6}$alkyl, C$_{2-6}$alkenyl, C$_{2-6}$alkynyl, C$_{1-6}$haloalkyl, C$_{3-8}$cycloalkyl (optionally substituted by methyl, oxo or halogen), phenyl (optionally substituted by methyl, methoxy, halogen, halomethyl fluoromethoxy or trifluoromethoxy), —C$_{1-6}$alkyl-OH, —C$_{1-4}$alkylphenyl (optionally substituted by methyl, methoxy, halogen, halomethyl fluoromethoxy or trifluoromethoxy), C$_{1-6}$alkoxy-, C$_{1-6}$alkenyloxy, C$_{3-6}$alkynyloxy-, C$_{1-6}$haloalkoxy-, —O—C$_{3-8}$cycloalkyl, —O—C$_{1-4}$alkyl-C$_{3-8}$cycloalkyl, —O-phenyl (optionally substituted by methyl, methoxy, halogen, halomethyl fluoromethoxy or trifluoromethoxy), —O—C$_{1-4}$ alkylphenyl (optionally substituted by methyl, methoxy, halogen, halomethyl fluoromethoxy or trifluoromethoxy), —S(C$_{1-6}$alkyl), —SO(C$_{1-6}$alkyl), —SO$_2$C$_{1-6}$alkyl, —SO$_2$C$_{3-8}$cycloalkyl, —SO$_2$—NR$^{31}$R$^{32}$, —C(O)C$_{1-6}$alkyl, —C(O)C$_{3-8}$cycloalkyl, —C(O)OH, —C(O)OC$_{1-6}$alkyl, —C(O)—NR$^{31}$R$^{32}$, —C$_{1-4}$alkyl-O—C$_{1-4}$alkyl, —C$_{1-4}$alkyl-O—C$_{1-4}$ alkyl-OH, —C$_{1-4}$alkyl-O—C$_{1-4}$alkyl-O—C$_{1-4}$alkyl, —C$_{1-4}$ alkyl-O—C$_{3-7}$cycloalkyl, —C$_{1-4}$alkyl-C(O)C$_{1-6}$ alkyl, —C$_{1-4}$alkyl-C(O)OH, —C$_{1-4}$alkyl-C(O)OC$_{1-4}$alkyl, —C$_{1-4}$alkyl-C(O)—NR$^{31}$R$^{32}$, —NH—SO$_2$R$^{33}$, —N(C$_{1-4}$alkyl)-SO$_2$R$^{33}$, —(C$_{1-4}$alkyl)NR$^{31}$R$^{32}$, —NR$^{31}$R$^{32}$, —(C$_{1-6}$ alkyl)NR$^{31}$R$^{32}$, nitro, halogen, cyano, hydroxyl;

R$^4$ and R$^5$ independently represent H or C$_{1-4}$-alkyl;

R$^6$ and R$^7$ are each independently selected from the group consisting of H, C$_{1-6}$alkyl, hydroxy-C$_{2-6}$alkyl-;

R$^{10}$ represents H or C$_{1-4}$alkyl;

R$^{11}$ and R$^{12}$ each independently represent a substituent selected from H or C$_{1-4}$alkyl or R$^{11}$ and R$^{12}$ are joined such that together they form a 3-8 membered non-aromatic ring;

R$^{15}$ represents H or C$_{1-4}$alkyl;

R$^{31}$ and R$^{32}$ each independently represent a substituent selected from H, C$_{1-4}$alkyl or C$_{1-4}$ alkyl or R$^{31}$ and R$^{32}$ are joined such that together they form a 3-8 membered non-aromatic ring;

R$^{33}$ represents H or C$_{1-4}$alkyl, x represents the number of independently selected R$^3$ substituents on the phenyl ring, in the range 0-4;

m represents an integer 1-4; and n represents an integer 2-4.

DETAILED DESCRIPTION OF THE INVENTION

In the compounds of general formula (I), it is often the case that A is N and B is CH, C(C$_{1-4}$ alkyl) or C(NH$_2$) and such compounds themselves form a separate aspect of the invention.

In suitable compounds of the present application, independently or in any combination:

R$^a$ is hydrogen;

B is CH or C$_{1-4}$ alkyl;

R$^2$ is hydrogen or C$_{1-4}$ alkyl,

R$^3$ is halogen, C$_{1-6}$alkoxy, —O—C$_{1-4}$alkylphenyl (e.g. —O-benzyl) or —O—C$_{1-4}$alkyl-C$_{3-8}$ cycloalkyl; and x is 1 or 2.

In still more suitable compounds of general formula (I) independently or in any combination, B is CH;

R$^2$ is hydrogen or methyl, especially hydrogen; and

R$^3$ is halogen, methoxy, ethoxy, isopropyloxy, benzyloxy or —OCH$_2$cyclopropyl.

When x is 1, R$^3$ most suitably represents C$_{1-6}$alkoxy, —O—C$_{1-4}$alkylphenyl or —O—C$_{1-4}$alkyl-C$_{3-8}$cycloalkyl, typically a methoxy or ethoxy group, particularly methoxy.

When x is 2, one of the R$^3$ groups may be a methoxy, ethoxy, -isopropyloxy, benzyloxy or (1-cyclopropyl)methoxy, more typically a methoxy or ethoxy group, and most suitably a methoxy group, and the other R$^3$ group is typically halo, especially fluoro.

When R$^3$ is C$_{1-6}$alkoxy, —O—C$_{1-4}$alkylphenyl or —O—C$_{1-4}$alkyl-C$_{3-8}$cycloalkyl it is preferably a substituents at the 2-position of the phenyl ring. When R$^3$ represents halogen, halogen is suitably a substituent at the 3, 4 or 5-position of the phenyl ring.

Examples of suitable R$^1$ groups in the compounds of general formula (I) include:

—C$_1$-C$_6$ alkyl;

—R$^{20}$;

—C(O)R$^{20}$;

—C$_1$-C$_6$ alkyl-R$^{20}$, wherein the alkyl group is optionally substituted with halo, methoxy, ethoxy, —NR$^6$R$^7$ or a nitrogen-containing heterocyclyl ring;

—C$_1$-C$_6$ alkyl-OR$^{20}$;

—(C$_1$-C$_6$ alkyl)-O—(C$_1$-C$_6$ alkyl)-R$^{20}$;

—C$_1$-C$_6$ alkyl-NR$^{10}$R$^{20}$;

—C$_1$-C$_6$ alkyl-SR$^{20}$;

—NR$^{10}$R$^{20}$;

—NR$^6$R$^7$;

—NR$^{10}$—(C$_1$-C$_6$ alkyl)-NR$^6$R$^7$ or

—NR$^{10}$—(C$_1$-C$_6$ alkyl)-C(O)OH;

wherein $R^6$, $R^7$, $R^{10}$ and $R^{20}$ are as defined above.

When $R^1$ represents —$C_1$-$C_6$ alkyl, a specific example is tert-butyl.

When $R^1$ represents $R^{20}$ or $NR^{10}R^{20}$, $R^{20}$ may be any substituted or unsubstituted carbocyclyl, heterocyclyl, aryl or heteroaryl group. In the case where $R^1$ is a substituted carbocyclyl group, the substitutent may, in some particularly suitable compounds, be on the same atom which links the carbocyclyl group to the remainder of the molecule.

In the case where $R^1$ represents $C(O)R^{20}$, $R^{20}$ is typically an aryl or heteroaryl group, which may be unsubstituted or substituted as defined above, or a heterocyclyl group. Suitably, $R^{20}$ is phenyl or a 6-membered heterocyclyl group such as piperidinyl.

Similarly, when $R^1$ represents $C_1$-$C_6$ alkyl-$R^{20}$, $R^{20}$ is also suitably an aryl, heteroaryl or heterocyclyl group, optionally substituted as set out above.

In compounds where $R^1$ represents $C_1$-$C_6$ alkyl-$OR^{20}$, —($C_1$-$C_6$ alkyl)-O—($C_1$-$C_6$ alkyl)-$R^{20}$, $C_1$-$C_6$ alkyl-$NR^{10}R^{20}$ or $C_1$-$C_6$ alkyl-$SR^{20}$, $R^{20}$ is usually an aryl or heteroaryl group optionally substituted as set out above.

When $R^{20}$ represents heterocyclyl, $R^{20}$ is suitably a 5- or 6-membered heterocyclyl ring containing one or two heteroatoms independently selected from oxygen, sulfur or nitrogen. Some suitable heterocyclyl rings contain one nitrogen, sulfur or oxagen atom. Alternative suitable heterocyclyl rings contain one or two nitrogen atoms, with heterocyclyl rings containing a single nitrogen atom being particularly suitable. Examples of specific heterocyclyl $R^{20}$ moieties include piperidinyl, for example piperidin-3-yl- and piperidin-4-yl-, pyrrolidinyl, tetrahydropyranyl and tetrahydrothiopyranyl. The heterocyclyl ring may be unsubstituted or substituted by any of the substituents for heterocyclyl previously described but suitably by one or more substituents, for example one, two, three or four substituents. The substituents may be independently selected from oxo, —$C_{1-4}$alkyl, —$C_{1-4}$alkyl-O—$C_{1-4}$alkyl, —$C(O)C_{1-4}$alkyl, —$C(O)OC_{1-4}$alkyl, halogen and —$C_{1-4}$alkyl$R^{21}$, with specific examples of these substituents being fluoro, oxo, methyl, ethyl, isopropyl, isobutyl, —$(CH_2)_2$—O—$CH_3$, —$(CH_2)_3$—O—$CH_3$, —$C(O)O$-$^t$butyl, —$CH_2$-phenyl).

When $R^{20}$ represents carbocyclyl, it is typically a cycloalkyl group for example cyclopropyl, cyclobutyl, cyclopentyl and cyclohexyl, particularly cyclohexyl. The carbocyclyl ring may be unsubstituted or substituted by any of the substituents for carbocyclyl previously described but most suitably by one or more —$C_{1-8}$alkyl, oxo, —$NH_2$, —NHC(O)$C_{1-4}$alkyl, —NHC(O)O$C_{1-4}$alkyl, —$C(O)NH_2$, optionally substituted aryl or heteroaryl groups.

More suitably, the carbocyclyl ring may be unsubstituted or substituted with one or more substituents chosen from —$NH_2$; —NHC(O)$C_{1-4}$alkyl; —NHC(O)O$C_{1-4}$alkyl; —$C(O)NH_2$, optionally substituted phenyl, for example 4-chlorophenyl or 4-methoxyphenyl; or optionally substituted pyridyl, for example 4-pyridyl.

When $R^{20}$ represents aryl, examples of aryl include naphthyl and phenyl, particularly phenyl, optionally substituted with one or more substituents. Typical substituents for these aryl groups include —NH—$SO_2C_{1-4}$alkyl, $C_{1-4}$ alkyl, —O($C_{1-4}$ alkyl), —$NHR^{12}$, where $R^{12}$ is as defined above, aryl, heteroaryl, nitro and halo. Particulary suitable substituents include fluoro, chloro, methyl, methoxy, ethoxy, —$NH_2$, —NH—$SO_2CH_3$, —$CH_2C(O)OH$, heteroaryl and nitro. An example of a heteroaryl substituents for $R^{20}$ is tetrazolyl.

In compounds of general formula (I), when $R^{20}$ represents a heteroaryl moiety, it is typically either a monocyclic or bicyclic heteroaryl group. Generally, monocyclic heteroaryl groups $R^{20}$ comprise 5- or 6-membered ring systems, while bicyclic groups comprise a 5- or 6-membered ring fused to a further 5- or 6-membered ring. Bicyclic groups include phenyl fused to unsaturated heterocyclyl rings and heteroaryl moieties fused to unsaturated rings optionally containing one or more further heteroatoms.

Suitable substituents for these heteroaryl groups are as set out above but examples of substituents in particularly suitable compounds include include $C_{1-4}$alkyl, especially methyl or ethyl; halo, for example fluoro, chloro or bromo; or —($C_1$-$C_4$ alkyl)-O—$R^{21}$ or $R^{21}$, where $R^{21}$ is unsubstituted phenyl or heteroaryl, especially unsubstituted heteroaryl Particularly suitable monocyclic heteroaryl groups $R^{20}$ include:

6-membered heteroaryl rings containing one or two nitrogen atoms, for example pyridine and pyrimidine);

five-membered heteroaryl ring containing one to four heteroatoms, for example thiophene, furan pyrrole, pyrazole, triazole, tetrazole, isoxazole, oxazole, thiazole and imidazole.

Particularly suitable bicyclic heteroaryl groups $R^{20}$ include azaindolizine, quinoline, isoquinoline and partially saturated derivatives thereof, for example dihydroquinolinone, tetrahydroquinoline and pyridyl fused to a 5-membered carbocyclyl group. In addition to the substituents listed above, these partially saturated bicyclic groups may optionally be substituted by oxo.

When $R^1$ is —$NR^6R^7$; or —$NR^{10}$—($C_1$-$C_6$ alkyl)-$NR^6R^7$, it is generally the case that $R^7$ are each independently hydrogen or $C_1$-$C_4$ alkyl, more especially hydrogen or methyl. Specific examples of $R^1$ groups of this type are $NH_2$ and $NR^{10}(CH_2)_2N(CH_3)_2$.

When $R^1$ is —$C_1$-$C_6$ alkyl-$NR^{10}R^{20}$; —$NR^{10}R^{20}$; —$NR^{10}$—($C_1$-$C_6$ alkyl)-$NR^6R^7$ or —$NR^{10}$—($C_{1-6}$ alkyl)-C(O)OH; it is generally the case that $R^{10}$ is hydrogen or methyl, but more especially hydrogen.

Examples of specific Compounds of the invention are set out in Tables 1 and 2.

TABLE 1

| Examples | Structure | Formula | Mol.-Weight |
|---|---|---|---|
| 1 | 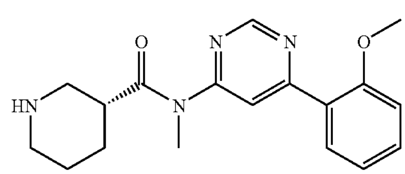 [SMILES: COc1ccccc1-c1cc(N(C)C(=O)[C@@H]2CCCNC2)ncn1] | C18H22N4O2 | 326.393 |

TABLE 1-continued

| Examples | Structure | Formula | Mol.-Weight |
|---|---|---|---|
| 2 | TFA | C17H19FN4O2 | 330.357 |
| 3 | TFA | C17H19FN4O2 | 330.357 |
| 4 | TFA | C18H22N4O3 | 342.392 |
| 5 | enantiomeric pure | C17H18N4O3 | 326.35 |
| 6 | enantiomeric pure | C17H18N4O3 | 326.35 |
| 7 | 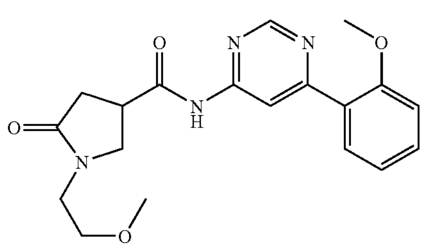 | C19H22N4O4 | 370.402 |
| 8 | 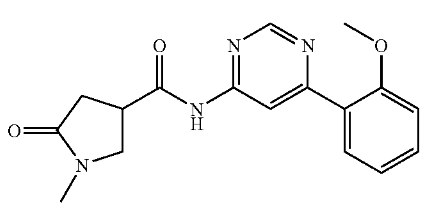 | C17H18N4O3 | 326.35 |

TABLE 1-continued

| Examples | Structure | Formula | Mol.-Weight |
|---|---|---|---|
| 9 | 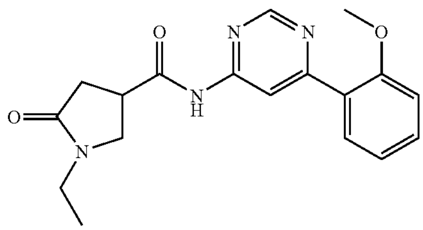 [SMILES: CCN1CC(C(=O)Nc2cc(-c3ccccc3OC)ncn2)CC1=O] | C18H20N4O3 | 340.376 |
| 10 | 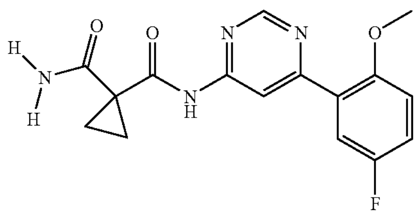 [SMILES: COc1ccc(F)cc1-c1cc(NC(=O)C2(C(N)=O)CC2)ncn1] | C16H15FN4O3 | 330.314 |
| 11 | 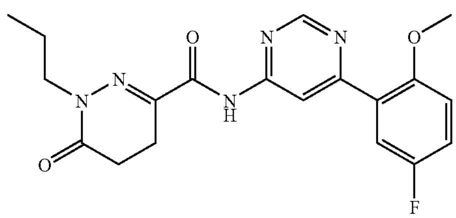 [SMILES: CCCN1N=C(C(=O)Nc2cc(-c3cc(F)ccc3OC)ncn2)CCC1=O] | C19H20FN5O3 | 385.392 |
| 12 | 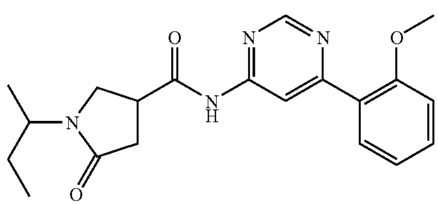 [SMILES: CCC(C)N1CC(C(=O)Nc2cc(-c3ccccc3OC)ncn2)CC1=O] | C20H24N4O3 | 368.43 |
| 13 | 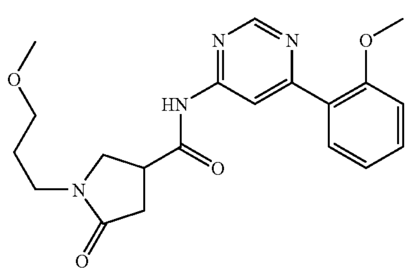 [SMILES: COCCCN1CC(C(=O)Nc2cc(-c3ccccc3OC)ncn2)CC1=O] | C20H24N4O4 | 384.429 |
| 14 | 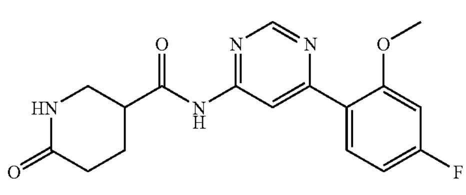 [SMILES: COc1cc(F)ccc1-c1cc(NC(=O)C2CCC(=O)NC2)ncn1] | C17H17FN4O3 | 344.34 |
| 15 | 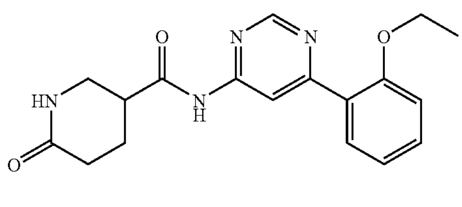 [SMILES: CCOc1ccccc1-c1cc(NC(=O)C2CCC(=O)NC2)ncn1] | C18H20N4O3 | 340.376 |

TABLE 1-continued

| Examples | Structure | Formula | Mol.-Weight |
|---|---|---|---|
| 16 | 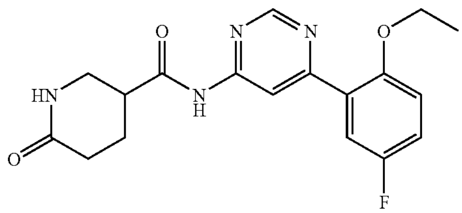 [SMILES: CCOc1ccc(F)cc1-c1cc(NC(=O)C2CCC(=O)NC2)ncn1] | C18H19FN4O3 | 358.367 |
| 17 | 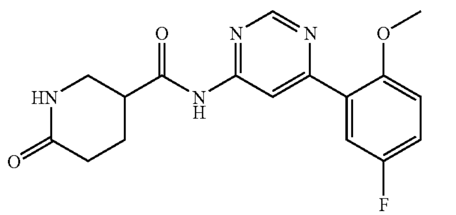 [SMILES: COc1ccc(F)cc1-c1cc(NC(=O)C2CCC(=O)NC2)ncn1] | C17H17FN4O3 | 344.34 |
| 18 | 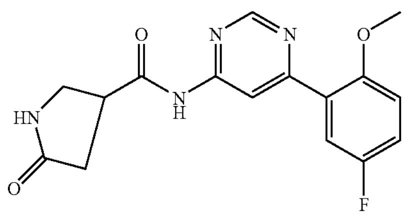 [SMILES: COc1ccc(F)cc1-c1cc(NC(=O)C2CNC(=O)C2)ncn1] | C16H15FN4O3 | 330.314 |
| 19 | 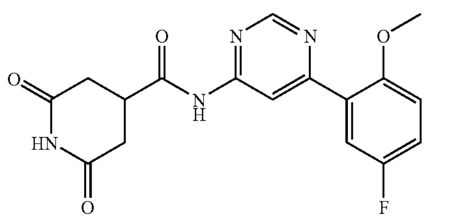 [SMILES: COc1ccc(F)cc1-c1cc(NC(=O)C2CC(=O)NC(=O)C2)ncn1] | C17H15FN4O4 | 358.324 |
| 20 | 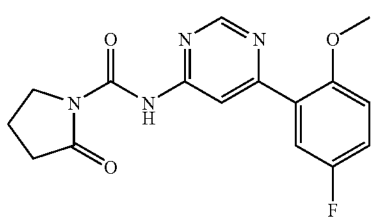 [SMILES: COc1ccc(F)cc1-c1cc(NC(=O)N2CCCC2=O)ncn1] | C16H15FN4O3 | 330.314 |
| 21 | 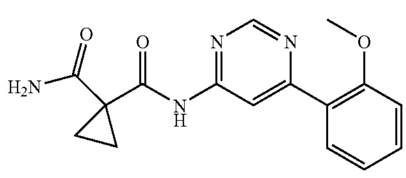 [SMILES: COc1ccccc1-c1cc(NC(=O)C2(C(N)=O)CC2)ncn1] | C16H16N4O3 | 312.323 |
| 22 | 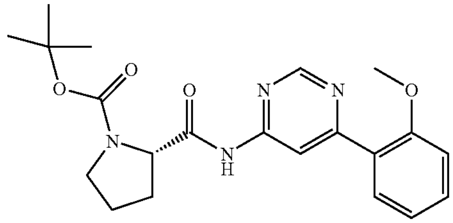 [SMILES: COc1ccccc1-c1cc(NC(=O)[C@@H]2CCCN2C(=O)OC(C)(C)C)ncn1] | C21H26N4O4 | 398.456 |

TABLE 1-continued

| Examples | Structure | Formula | Mol.-Weight |
|---|---|---|---|
| 23 | 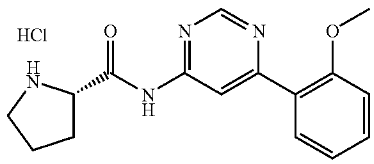 [SMILES: COc1ccccc1-c1cc(NC(=O)[C@@H]2CCCN2)ncn1 ; Cl] | C16H18N4O2 | 298.34 |
| 24 | 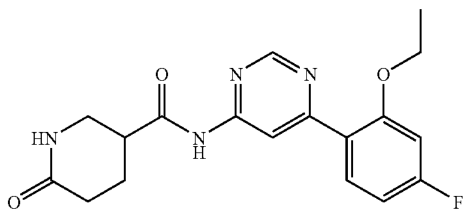 [SMILES: CCOc1cc(F)ccc1-c1cc(NC(=O)C2CCC(=O)NC2)ncn1] | C18H19FN4O3 | 358.367 |
| 25 | 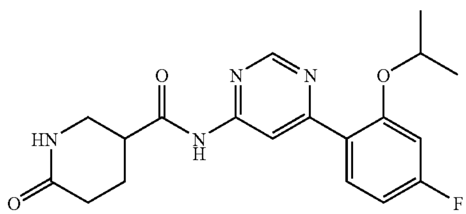 [SMILES: CC(C)Oc1cc(F)ccc1-c1cc(NC(=O)C2CCC(=O)NC2)ncn1] | C19H21FN4O3 | 372.393 |
| 26 | 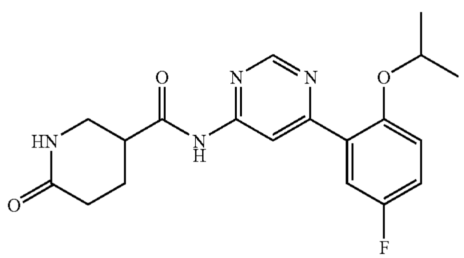 [SMILES: CC(C)Oc1ccc(F)cc1-c1cc(NC(=O)C2CCC(=O)NC2)ncn1] | C19H21FN4O3 | 372.393 |
| 27 | 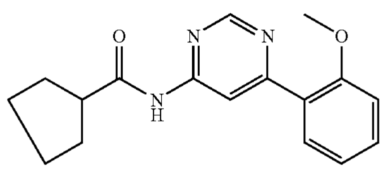 [SMILES: COc1ccccc1-c1cc(NC(=O)C2CCCC2)ncn1] | C17H19N3O2 | 297.352 |
| 28 | 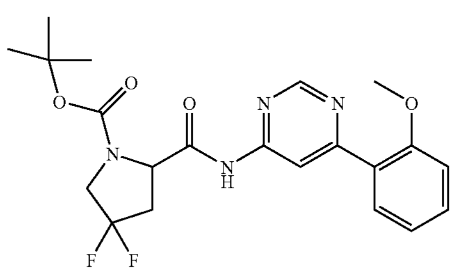 [SMILES: COc1ccccc1-c1cc(NC(=O)C2CC(F)(F)CN2C(=O)OC(C)(C)C)ncn1] | C21H24F2N4O4 | 434.436 |
| 29 | 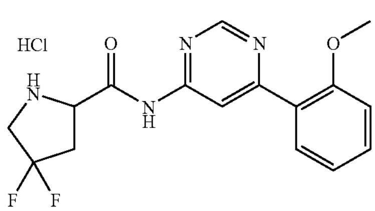 [SMILES: COc1ccccc1-c1cc(NC(=O)C2CC(F)(F)CN2)ncn1 ; Cl] | C16H16F2N4O2 | 334.321 |

TABLE 1-continued
| Examples | Structure | Formula | Mol.-Weight |
|---|---|---|---|
| 30 | 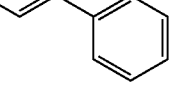 | C18H22N4O2 | 326.393 |
| 31 | 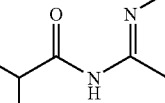 | C18H22N4O2 | 326.393 |
| 32 | 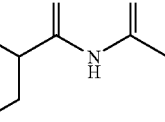 | C23H30N4O4 | 426.509 |
| 33 | 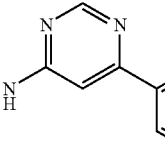 | C23H30N4O4 | 426.509 |
| 34 | 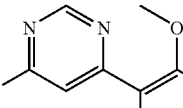 | C18H22N4O2 | 326.393 |
| 35 | 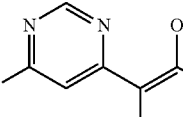 | C21H25FN4O4 | 416.446 |
| 36 | 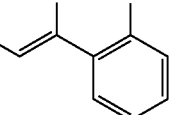 | C16H17FN4O2 | 316.33 |
| 37 | 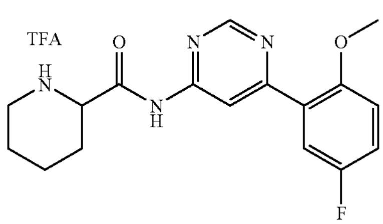 | C17H19FN4O2 | 330.357 |

TABLE 1-continued

| Examples | Structure | Formula | Mol.-Weight |
|---|---|---|---|
| 38 | 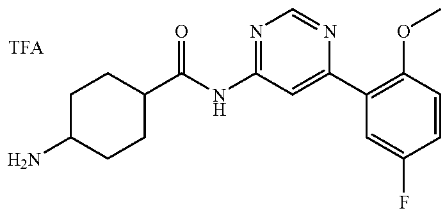 [SMILES: COc1ccc(F)cc1-c1cc(NC(=O)C2CCC(N)CC2)ncn1] | C18H21FN4O2 | 344.383 |
| 39 | 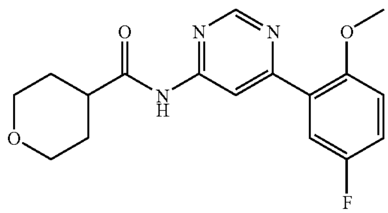 [SMILES: COc1ccc(F)cc1-c1cc(NC(=O)C2CCOCC2)ncn1] | C17H18FN3O3 | 331.342 |
| 40 | 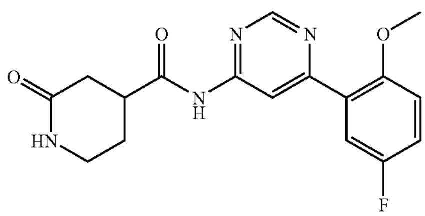 [SMILES: COc1ccc(F)cc1-c1cc(NC(=O)C2CCNC(=O)C2)ncn1] | C17H17FN4O3 | 344.34 |
| 41 | 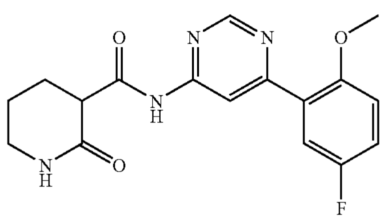 [SMILES: COc1ccc(F)cc1-c1cc(NC(=O)C2CCCNC2=O)ncn1] | C17H17FN4O3 | 344.34 |
| 42 | 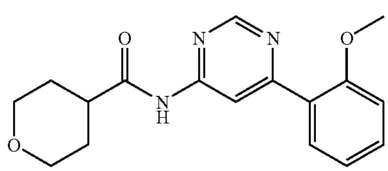 [SMILES: COc1ccccc1-c1cc(NC(=O)C2CCOCC2)ncn1] | C17H19N3O3 | 313.351 |
| 43 | 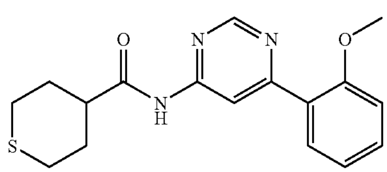 [SMILES: COc1ccccc1-c1cc(NC(=O)C2CCSCC2)ncn1] | C17H19N3O2S | 329.417 |
| 44 | 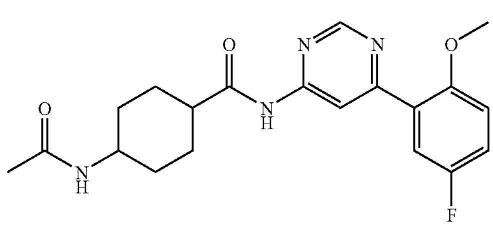 [SMILES: COc1ccc(F)cc1-c1cc(NC(=O)C2CCC(NC(C)=O)CC2)ncn1] | C20H23FN4O3 | 386.42 |

TABLE 1-continued

| Examples | Structure | Formula | Mol.-Weight |
|---|---|---|---|
| 45 | 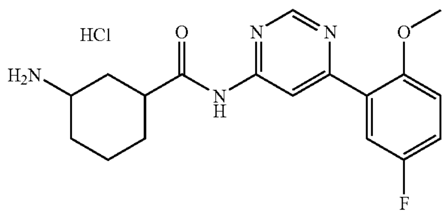 [SMILES: COc1ccc(F)cc1-c1cc(NC(=O)C2CCCC(N)C2)ncn1 ; Cl] | C18H21FN4O2 | 344.383 |
| 46 | 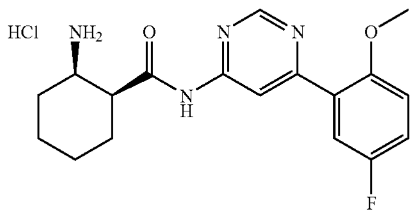 [SMILES: Cl ; COc1ccc(F)cc1-c1cc(NC(=O)[C@H]2CCCC[C@H]2N)ncn1] | C18H21FN4O2 | 344.383 |
| 47 | 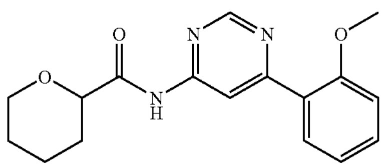 | C17H19N3O3 | 313.351 |
| 48 | 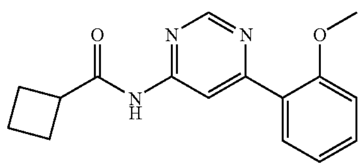 [SMILES: COc1ccccc1-c1cc(NC(=O)C2CCC2)ncn1] | C16H17N3O2 | 283.325 |
| 49 | 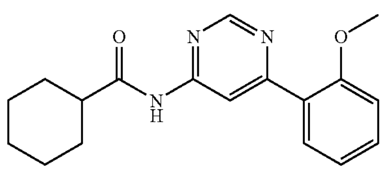 | C18H21N3O2 | 311.378 |
| 50 | 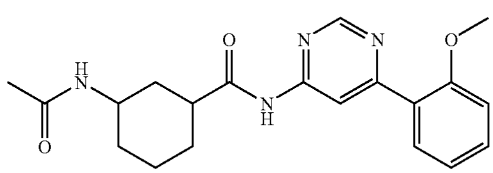 [SMILES: COc1ccccc1-c1cc(NC(=O)C2CCCC(NC(C)=O)C2)ncn1] | C20H24N4O3 | 368.43 |
| 51 | 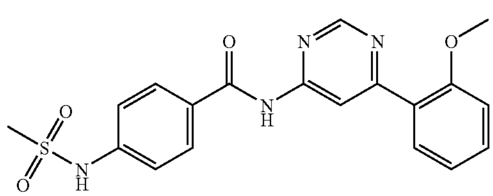 | C19H18N4O4S | 398.436 |
| 52 | 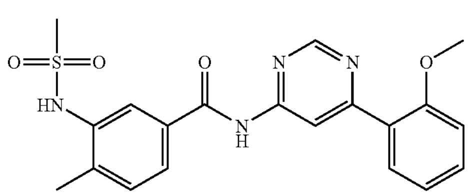 [SMILES: COc1ccccc1-c1cc(NC(=O)c2ccc(C)c(NS(C)(=O)=O)c2)ncn1] | C20H20N4O4S | 412.462 |

TABLE 1-continued

| Examples | Structure | Formula | Mol.-Weight |
|---|---|---|---|
| 53 | 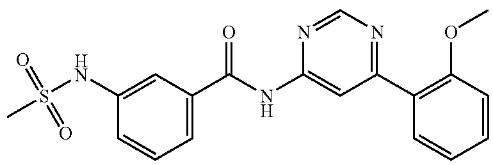 | C19H18N4O4S | 398.436 |
| 54 | 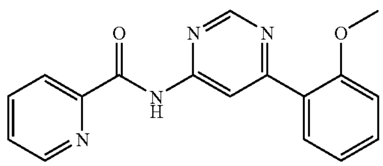 [SMILES: COc1ccccc1-c1cc(NC(=O)c2ccccn2)ncn1] | C17H14N4O2 | 306.319 |
| 55 | 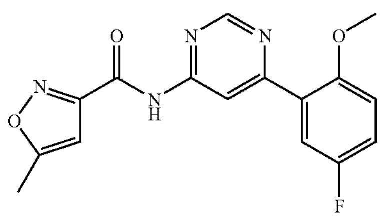 [SMILES: COc1ccc(F)cc1-c1cc(NC(=O)c2cc(C)on2)ncn1] | C16H13FN4O3 | 328.298 |
| 56 | 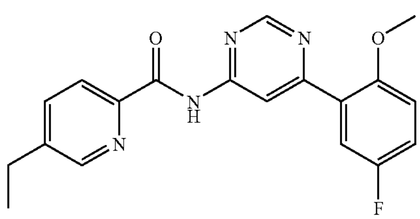 [SMILES: CCc1ccc(C(=O)Nc2cc(-c3cc(F)ccc3OC)ncn2)nc1] | C19H17FN4O2 | 352.362 |
| 57 | 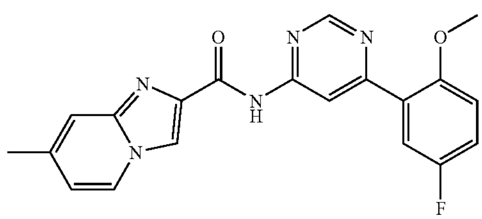 | C20H16FN5O2 | 377.372 |
| 58 | 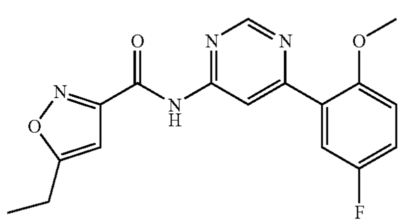 [SMILES: CCc1cc(C(=O)Nc2cc(-c3cc(F)ccc3OC)ncn2)no1] | C17H15FN4O3 | 342.324 |
| 59 | 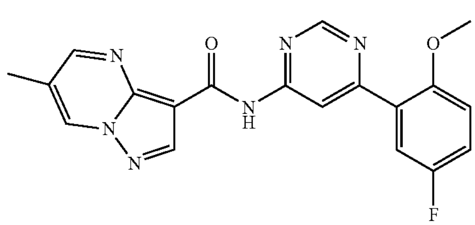 | C19H15FN6O2 | 378.36 |

TABLE 1-continued

| Examples | Structure | Formula | Mol.-Weight |
|---|---|---|---|
| 60 | 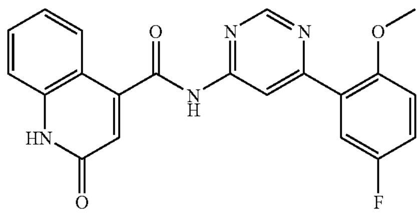 [SMILES: COc1ccc(F)cc1-c1cc(NC(=O)c2cc(=O)[nH]c3ccccc23)ncn1] | C21H15FN4O3 | 390.367 |
| 61 | 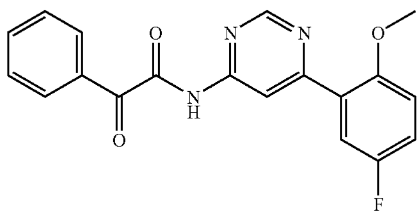 [SMILES: COc1ccc(F)cc1-c1cc(NC(=O)C(=O)c2ccccc2)ncn1] | C19H14FN3O3 | 351.331 |
| 62 | 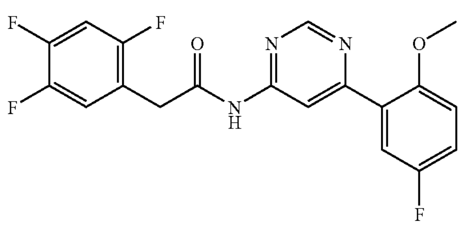 [SMILES: COc1ccc(F)cc1-c1cc(NC(=O)Cc2cc(F)c(F)cc2F)ncn1] | C19H13F4N3O2 | 391.319 |
| 63 | 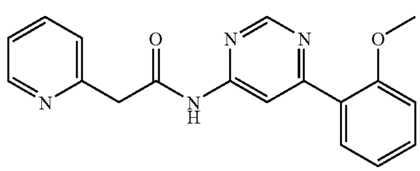 [SMILES: COc1ccccc1-c1cc(NC(=O)Cc2ccccn2)ncn1] | C18H16N4O2 | 320.345 |
| 64 | 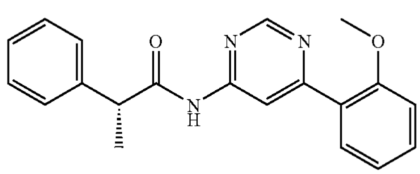 [SMILES: COc1ccccc1-c1cc(NC(=O)[C@H](C)c2ccccc2)ncn1] | C20H19N3O2 | 333.384 |
| 65 | 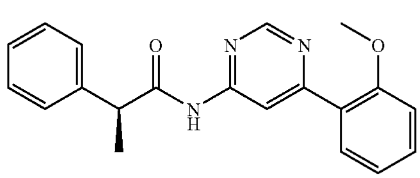 [SMILES: COc1ccccc1-c1cc(NC(=O)[C@@H](C)c2ccccc2)ncn1] | C20H19N3O2 | 333.384 |
| 66 | 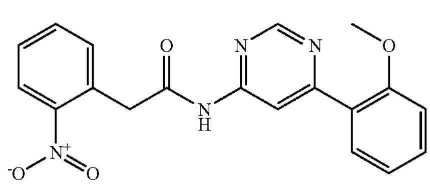 | C19H16N4O4 | 364.355 |

TABLE 1-continued

| Examples | Structure | Formula | Mol.-Weight |
|---|---|---|---|
| 67 | 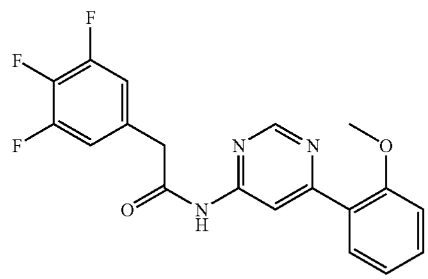 [SMILES: COc1ccccc1-c1cc(NC(=O)Cc2cc(F)c(F)c(F)c2)ncn1] | C19H14F3N3O2 | 373.329 |
| 68 | 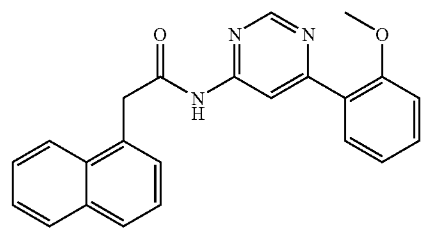 [SMILES: COc1ccccc1-c1cc(NC(=O)Cc2cccc3ccccc23)ncn1] | C23H19N3O2 | 369.416 |
| 69 | 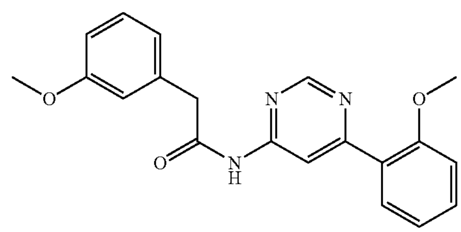 | C20H19N3O3 | 349.383 |
| 70 | 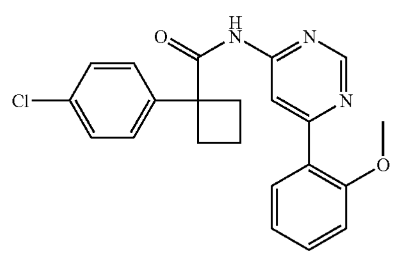 [SMILES: COc1ccccc1-c1cc(NC(=O)C2(c3ccc(Cl)cc3)CCC2)ncn1] | C22H20ClN3O2 | 393.866 |
| 71 | 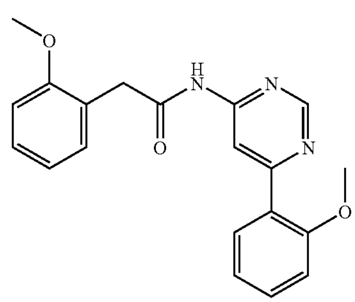 [SMILES: COc1ccccc1CC(=O)Nc1cc(-c2ccccc2OC)ncn1] | C20H19N3O3 | 349.383 |
| 72 | 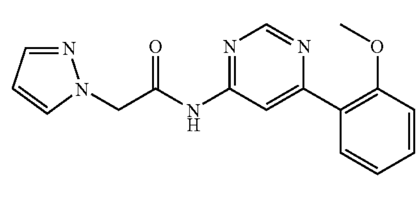 [SMILES: COc1ccccc1-c1cc(NC(=O)Cn2cccn2)ncn1] | C16H15N5O2 | 309.323 |

TABLE 1-continued

| Examples | Structure | Formula | Mol.-Weight |
|---|---|---|---|
| 73 | 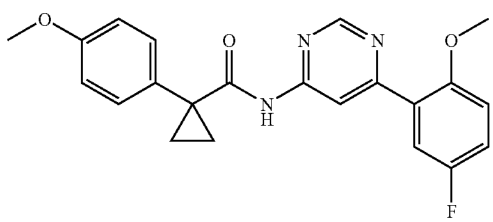 | C22H20FN3O3 | 393.411 |
| 74 | 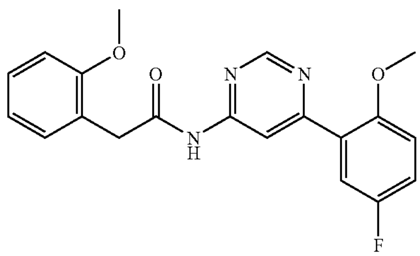 [SMILES: COc1ccccc1CC(=O)Nc1cc(-c2cc(F)ccc2OC)ncn1] | C20H18FN3O3 | 367.374 |
| 75 | 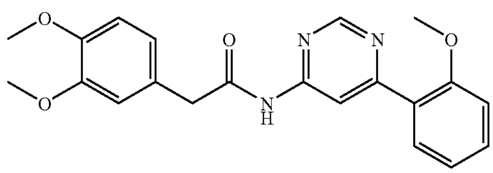 [SMILES: COc1ccc(CC(=O)Nc2cc(-c3ccccc3OC)ncn2)cc1OC] | C21H21N3O4 | 379.409 |
| 76 | 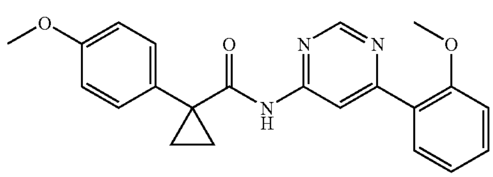 [SMILES: COc1ccc(C2(C(=O)Nc3cc(-c4ccccc4OC)ncn3)CC2)cc1] | C22H21N3O3 | 375.42 |
| 77 | 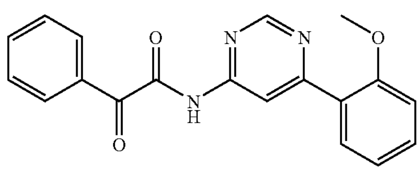 [SMILES: COc1ccccc1-c1cc(NC(=O)C(=O)c2ccccc2)ncn1] | C19H15N3O3 | 333.341 |
| 78 | 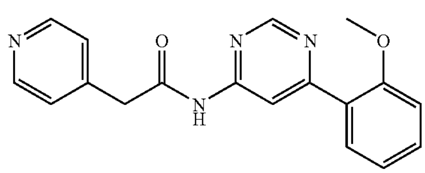 [SMILES: COc1ccccc1-c1cc(NC(=O)Cc2ccncc2)ncn1] | C18H16N4O2 | 320.345 |
| 79 | 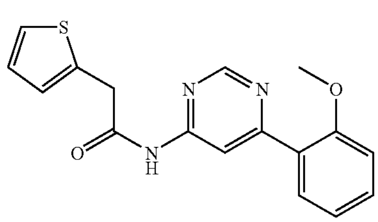 [SMILES: COc1ccccc1-c1cc(NC(=O)Cc2cccs2)ncn1] | C17H15N3O2S | 325.385 |
| 80 | 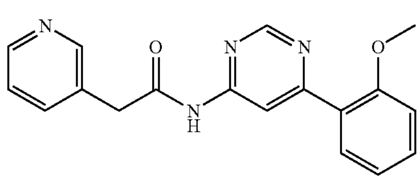 [SMILES: COc1ccccc1-c1cc(NC(=O)Cc2cccnc2)ncn1] | C18H16N4O2 | 320.345 |

TABLE 1-continued

| Examples | Structure | Formula | Mol.-Weight |
|---|---|---|---|
| 81 | 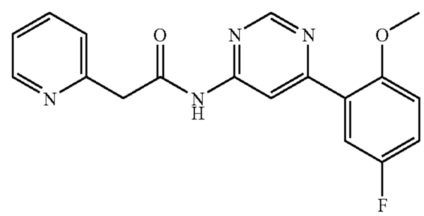 [SMILES: COc1ccc(F)cc1-c1cc(NC(=O)Cc2ccccn2)ncn1] | C18H15FN4O2 | 338.336 |
| 82 | 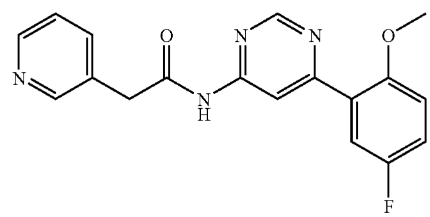 | C18H15FN4O2 | 338.336 |
| 83 | 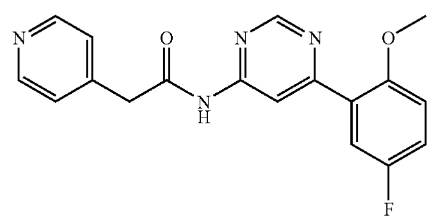 | C18H15FN4O2 | 338.336 |
| 84 | 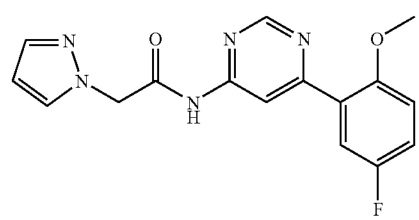 [SMILES: COc1ccc(F)cc1-c1cc(NC(=O)Cn2cccn2)ncn1] | C16H14FN5O2 | 327.313 |
| 85 | 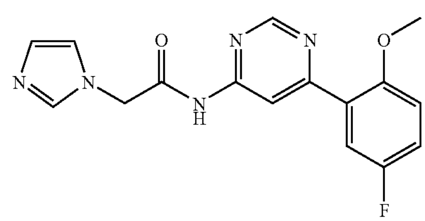 [SMILES: COc1ccc(F)cc1-c1cc(NC(=O)Cn2ccnc2)ncn1] | C16H14FN5O2 | 327.313 |
| 86 | 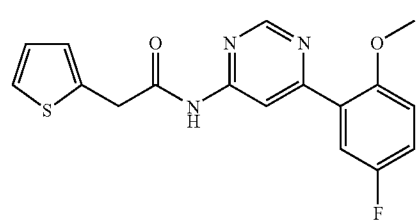 [SMILES: COc1ccc(F)cc1-c1cc(NC(=O)Cc2cccs2)ncn1] | C17H14FN3O2S | 343.375 |
| 87 | 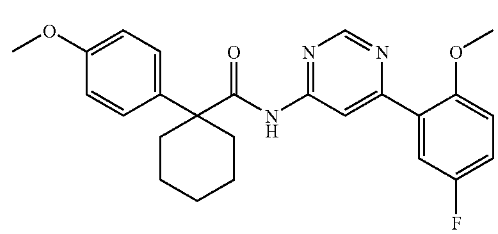 | C25H26FN3O3 | 435.491 |

TABLE 1-continued

| Examples | Structure | Formula | Mol.-Weight |
|---|---|---|---|
| 88 | 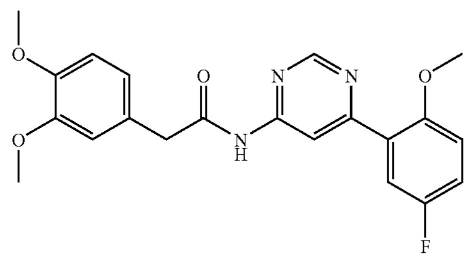 [SMILES: COc1ccc(CC(=O)Nc2cc(-c3cc(F)ccc3OC)ncn2)cc1OC] | C21H20FN3O4 | 397.4 |
| 89 | 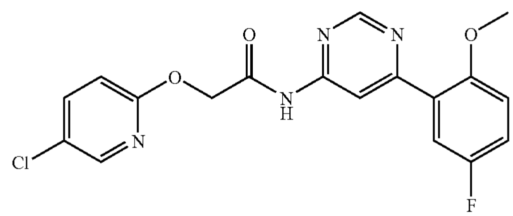 [SMILES: COc1ccc(F)cc1-c1cc(NC(=O)COc2ccc(Cl)cn2)ncn1] | C18H14ClFN4O3 | 388.78 |
| 90 | 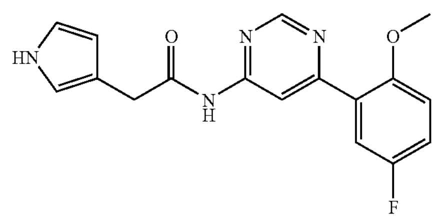 [SMILES: COc1ccc(F)cc1-c1cc(NC(=O)Cc2cc[nH]c2)ncn1] | C17H15FN4O2 | 326.325 |
| 91 | 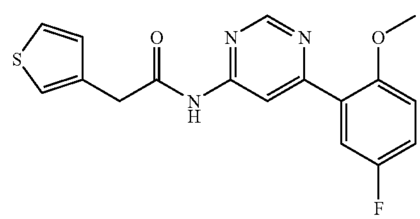 [SMILES: COc1ccc(F)cc1-c1cc(NC(=O)Cc2ccsc2)ncn1] | C17H14FN3O2S | 343.375 |
| 92 | 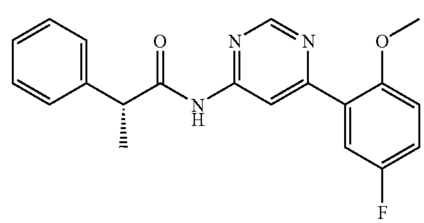 [SMILES: COc1ccc(F)cc1-c1cc(NC(=O)[C@H](C)c2ccccc2)ncn1] | C20H18FN3O2 | 351.374 |
| 93 | 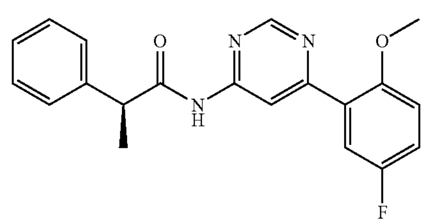 [SMILES: COc1ccc(F)cc1-c1cc(NC(=O)[C@@H](C)c2ccccc2)ncn1] | C20H18FN3O2 | 351.374 |
| 94 | 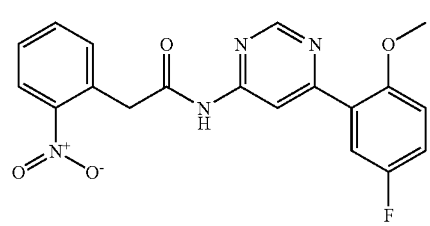 [SMILES: COc1ccc(F)cc1-c1cc(NC(=O)Cc2ccccc2[N+](=O)[O-])ncn1] | C19H15FN4O4 | 382.345 |

TABLE 1-continued

| Examples | Structure | Formula | Mol.-Weight |
|---|---|---|---|
| 95 | 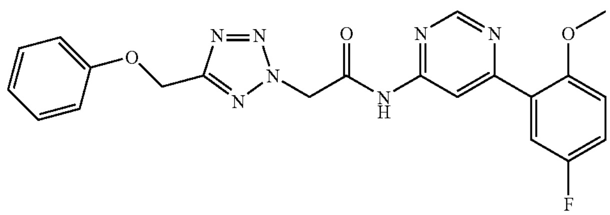 [SMILES: COc1ccc(F)cc1-c1cc(NC(=O)Cn2nnc(COc3ccccc3)n2)ncn1] | C21H18FN7O3 | 435.411 |
| 96 | 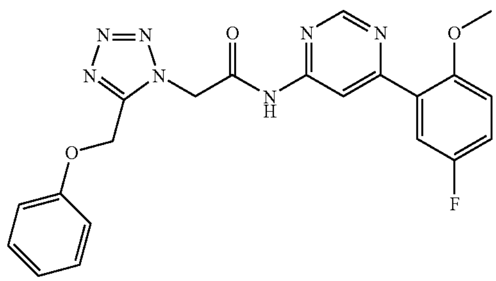 [SMILES: COc1ccc(F)cc1-c1cc(NC(=O)Cn2nnnc2COc2ccccc2)ncn1] | C21H18FN7O3 | 435.411 |
| 97 | 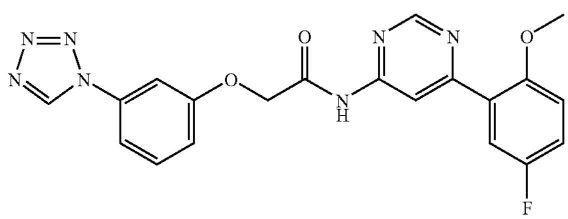 [SMILES: COc1ccc(F)cc1-c1cc(NC(=O)COc2cccc(-n3cnnn3)c2)ncn1] | C20H16FN7O3 | 421.385 |
| 98 | 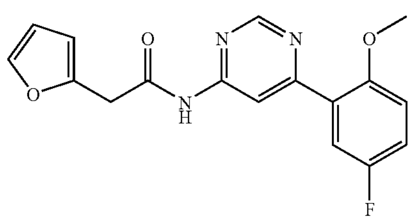 | C17H14FN3O3 | 327.31 |
| 99 | 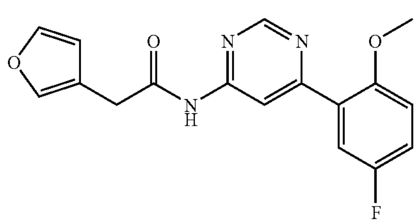 [SMILES: COc1ccc(F)cc1-c1cc(NC(=O)Cc2ccoc2)ncn1] | C17H14FN3O3 | 327.31 |
| 100 | 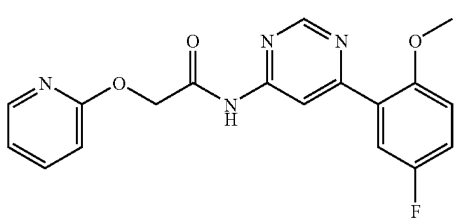 [SMILES: COc1ccc(F)cc1-c1cc(NC(=O)COc2ccccn2)ncn1] | C18H15FN4O3 | 354.335 |

TABLE 1-continued

| Examples | Structure | Formula | Mol.-Weight |
|---|---|---|---|
| 101 | 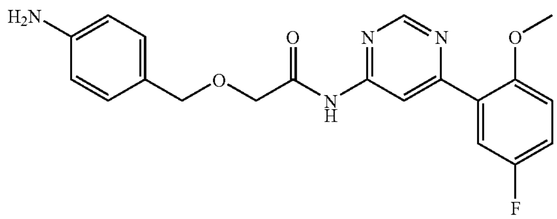 [SMILES: COc1ccc(F)cc1-c1cc(NC(=O)COCc2ccc(N)cc2)ncn1] | C20H19FN4O3 | 382.388 |
| 102 | 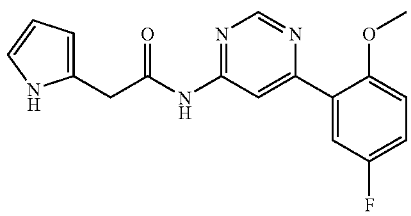 | C17H15FN4O2 | 326.325 |
| 103 | 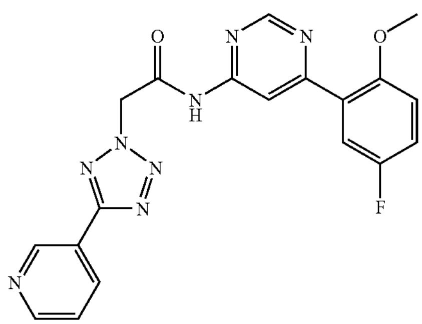 [SMILES: COc1ccc(F)cc1-c1cc(NC(=O)Cn2nnc(-c3cccnc3)n2)ncn1] | C19H15FN8O2 | 406.373 |
| 104 | 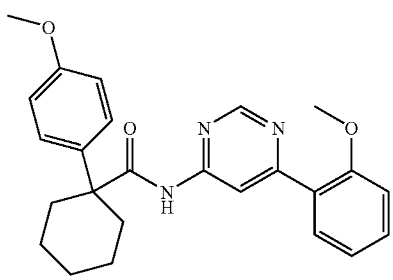 [SMILES: COc1ccc(C2(C(=O)Nc3cc(-c4ccccc4OC)ncn3)CCCCC2)cc1] | C25H27N3O3 | 417.5 |
| 105 | 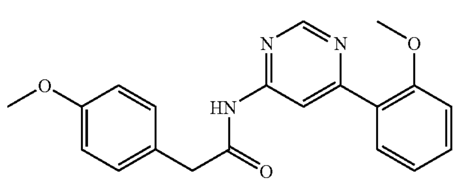 [SMILES: COc1ccc(CC(=O)Nc2cc(-c3ccccc3OC)ncn2)cc1] | C20H19N3O3 | 349.383 |
| 106 | 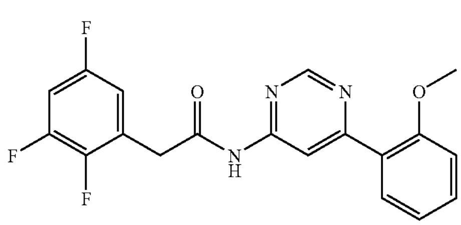 [SMILES: COc1ccccc1-c1cc(NC(=O)Cc2cc(F)cc(F)c2F)ncn1] | C19H14F3N3O2 | 373.329 |

TABLE 1-continued

| Examples | Structure | Formula | Mol.-Weight |
|---|---|---|---|
| 107 | 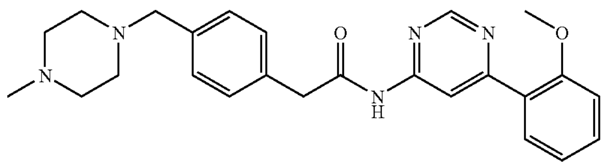 [SMILES: COc1ccccc1-c1cc(NC(=O)Cc2ccc(CN3CCN(C)CC3)cc2)ncn1] | C25H29N5O2 | 431.53 |
| 108 | 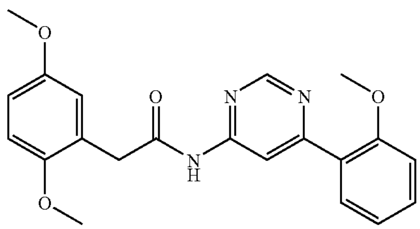 [SMILES: COc1ccc(OC)c(CC(=O)Nc2cc(-c3ccccc3OC)ncn2)c1] | C21H21N3O4 | 379.409 |
| 109 | 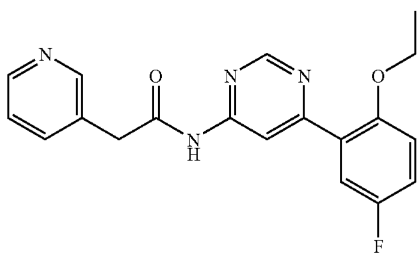 [SMILES: CCOc1ccc(F)cc1-c1cc(NC(=O)Cc2cccnc2)ncn1] | C19H17FN4O2 | 352.362 |
| 110 | 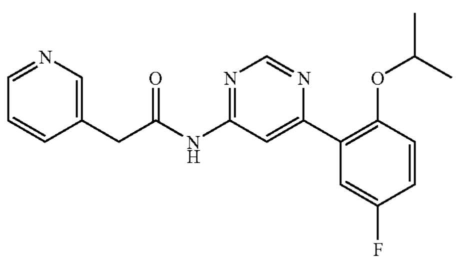 [SMILES: CC(C)Oc1ccc(F)cc1-c1cc(NC(=O)Cc2cccnc2)ncn1] | C20H19FN4O2 | 366.389 |
| 111 | 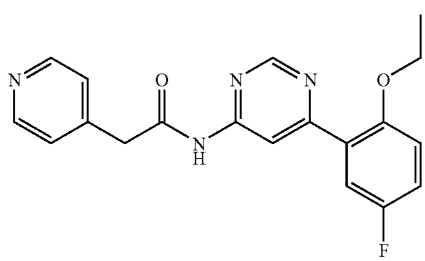 [SMILES: CCOc1ccc(F)cc1-c1cc(NC(=O)Cc2ccncc2)ncn1] | C19H17FN4O2 | 352.362 |
| 112 | 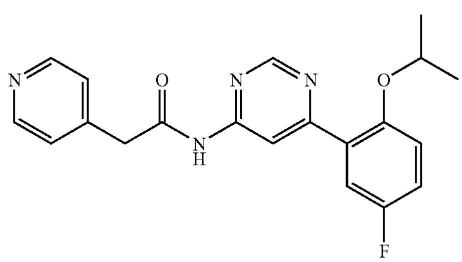 [SMILES: CC(C)Oc1ccc(F)cc1-c1cc(NC(=O)Cc2ccncc2)ncn1] | C20H19FN4O2 | 366.389 |

TABLE 1-continued

| Examples | Structure | Formula | Mol.-Weight |
|---|---|---|---|
| 113 | 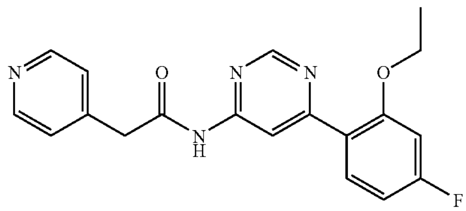 [SMILES: CCOc1cc(F)ccc1-c1cc(NC(=O)Cc2ccncc2)ncn1] | C19H17FN4O2 | 352.362 |
| 114 | HCl | C19H17FN4O2 | 352.362 |
| 115 | 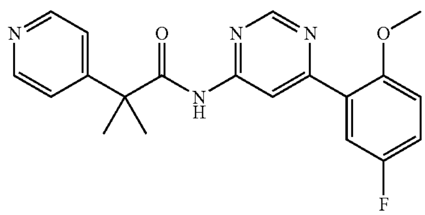 | C20H19FN4O2 | 366.389 |
| 116 | HCl | C18H15FN4O2 | 338.336 |
| 117 | 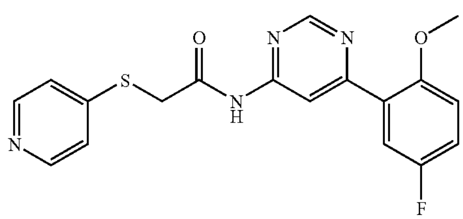 [SMILES: COc1ccc(F)cc1-c1cc(NC(=O)CSc2ccncc2)ncn1] | C18H15FN4O2S | 370.401 |
| 118 | 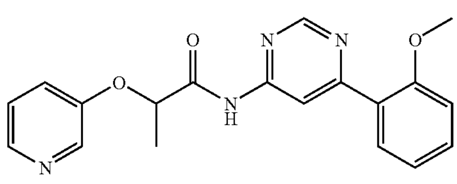 [SMILES: COc1ccccc1-c1cc(NC(=O)C(C)Oc2cccnc2)ncn1] | C19H18N4O3 | 350.371 |
| 119 | HCl | C20H19FN4O2 | 366.389 |

TABLE 1-continued

| Examples | Structure | Formula | Mol.-Weight |
|---|---|---|---|
| 120 | 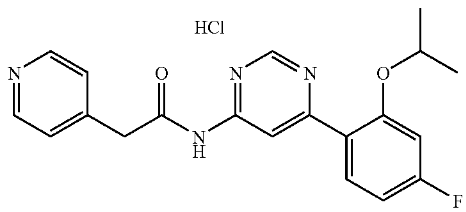 [SMILES: CC(C)Oc1cc(F)ccc1-c1cc(NC(=O)Cc2ccncc2)ncn1 ; Cl] | C20H19FN4O2 | 366.389 |
| 121 | 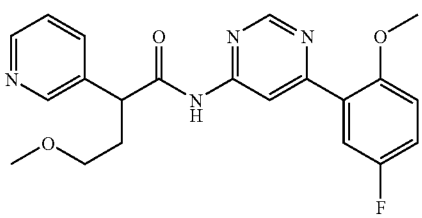 [SMILES: COCCC(C(=O)Nc1cc(-c2cc(F)ccc2OC)ncn1)c1cccnc1] | C21H21FN4O3 | 396.415 |
| 122 | 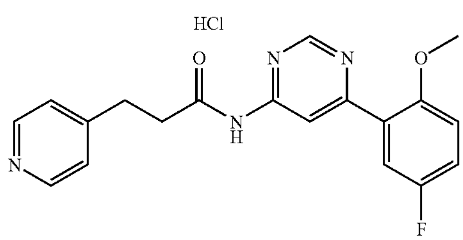 [SMILES: Cl ; COc1ccc(F)cc1-c1cc(NC(=O)CCc2ccncc2)ncn1] | C19H17FN4O2 | 352.362 |
| 123 | 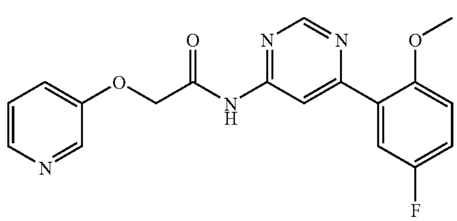 [SMILES: COc1ccc(F)cc1-c1cc(NC(=O)COc2cccnc2)ncn1] | C18H15FN4O3 | 354.335 |
| 124 | 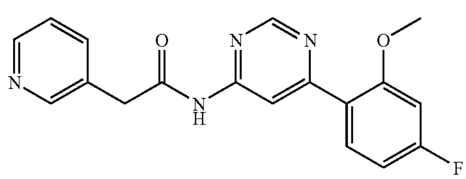 [SMILES: COc1cc(F)ccc1-c1cc(NC(=O)Cc2cccnc2)ncn1] | C18H15FN4O2 | 338.336 |
| 125 | 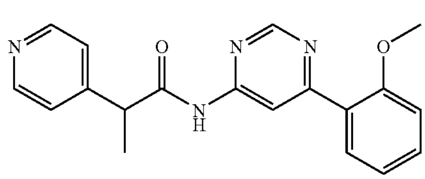 [SMILES: COc1ccccc1-c1cc(NC(=O)C(C)c2ccncc2)ncn1] | C19H18N4O2 | 334.372 |
| 126 | 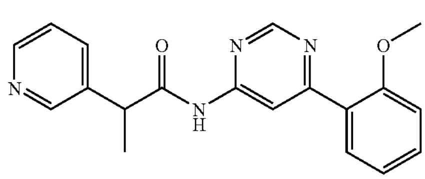 | C19H18N4O2 | 334.372 |

TABLE 1-continued
| Examples | Structure | Formula | Mol.-Weight |
|---|---|---|---|
| 127 | 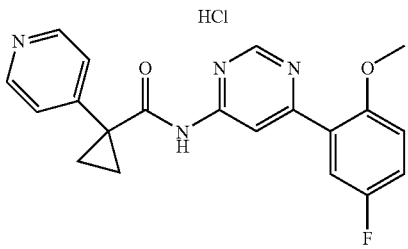 [SMILES: Cl ; COc1ccc(F)cc1-c1cc(NC(=O)C2(c3ccncc3)CC2)ncn1] HCl | C20H17FN4O2 | 364.373 |
| 128 | 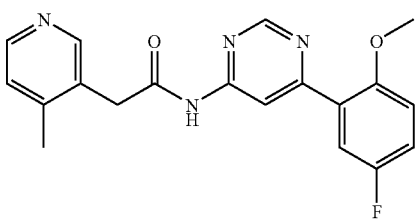 [SMILES: COc1ccc(F)cc1-c1cc(NC(=O)Cc2cnccc2C)ncn1] | C19H17FN4O2 | 352.362 |
| 129 | 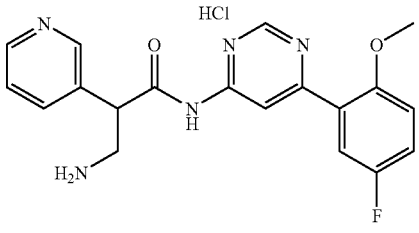 [SMILES: Cl ; COc1ccc(F)cc1-c1cc(NC(=O)C(CN)c2cccnc2)ncn1] HCl | C19H18FN5O2 | 367.377 |
| 130 | 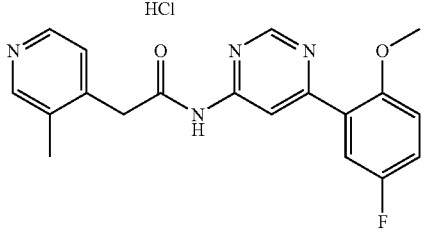 [SMILES: Cl ; COc1ccc(F)cc1-c1cc(NC(=O)Cc2ccncc2C)ncn1] HCl | C19H17FN4O2 | 352.362 |
| 131 | 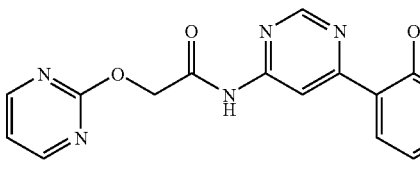 | C17H15N5O3 | 337.333 |
| 132 | 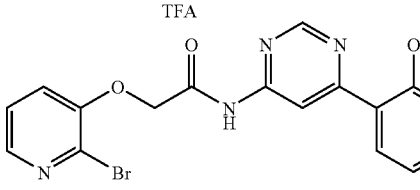 TFA | C18H15BrN4O3 | 415.241 |
| 133 | 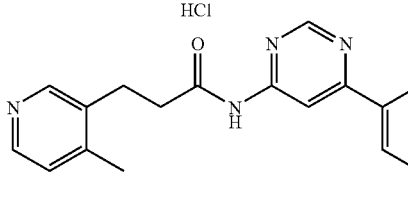 HCl | C20H19FN4O2 | 366.389 |

TABLE 1-continued

| Examples | Structure | Formula | Mol.-Weight |
|---|---|---|---|
| 134 | HCl | C20H17FN4O2 | 364.373 |
| 135 | 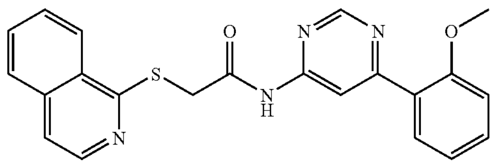 | C22H18N4O2S | 402.469 |
| 136 | HCl | C18H16FN5O2 | 353.35 |
| 137 | TFA | C22H23FN6O2 | 422.455 |
| 138 | 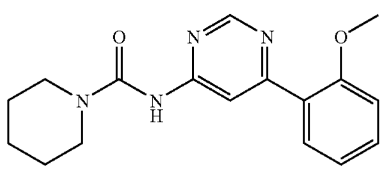 [SMILES: COc1ccccc1-c1cc(NC(=O)N2CCCCC2)ncn1] | C17H20N4O2 | 312.366 |
| 139 | TFA | C16H19N5O2 | 313.354 |
| 140 | HCl | C18H22FN5O2 | 359.398 |

TABLE 1-continued

| Examples | Structure | Formula | Mol.-Weight |
|---|---|---|---|
| 141 | 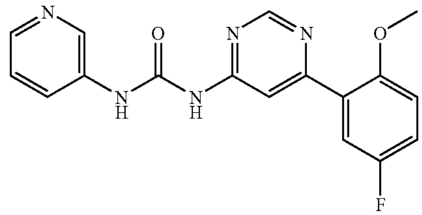 | C17H14FN5O2 | 339.324 |
| 142 | 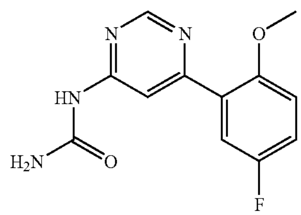 [SMILES: COc1ccc(F)cc1-c1cc(NC(N)=O)ncn1] | C12H11FN4O2 | 262.24 |
| 143 | 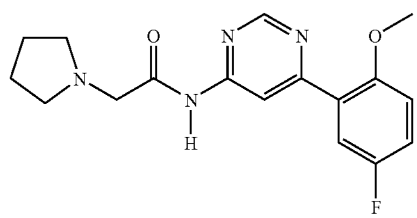 [SMILES: COc1ccc(F)cc1-c1cc(NC(=O)CN2CCCC2)ncn1] | C17H19FN4O2 | 330.357 |
| 144 | 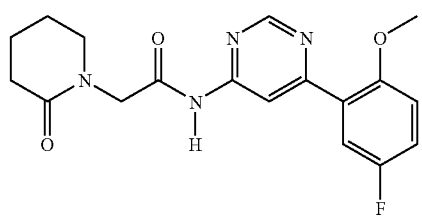 [SMILES: COc1ccc(F)cc1-c1cc(NC(=O)CN2CCCCC2=O)ncn1] | C18H19FN4O3 | 358.367 |
| 145 | 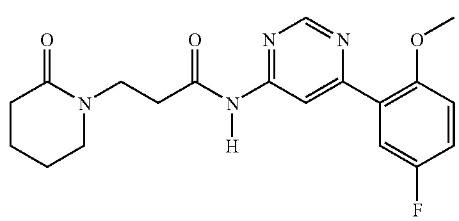 [SMILES: COc1ccc(F)cc1-c1cc(NC(=O)CCN2CCCCC2=O)ncn1] | C19H21FN4O3 | 372.393 |
| 146 | 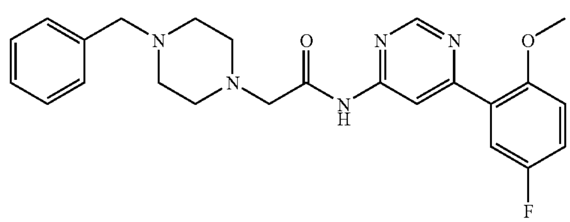 [SMILES: COc1ccc(F)cc1-c1cc(NC(=O)CN2CCN(Cc3ccccc3)CC2)ncn1] | C24H26FN5O2 | 435.494 |
| 147 | 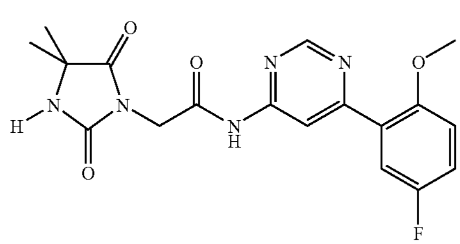 [SMILES: COc1ccc(F)cc1-c1cc(NC(=O)CN2C(=O)NC(C)(C)C2=O)ncn1] | C18H18FN5O4 | 387.365 |

TABLE 1-continued

| Examples | Structure | Formula | Mol.-Weight |
|---|---|---|---|
| 148 | 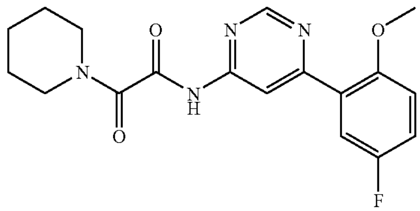 [SMILES: COc1ccc(F)cc1-c1cc(NC(=O)C(=O)N2CCCCC2)ncn1] | C18H19FN4O3 | 358.367 |
| 149 | 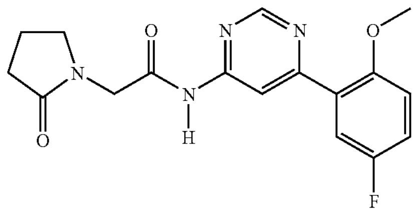 [SMILES: COc1ccc(F)cc1-c1cc(NC(=O)CN2CCCC2=O)ncn1] | C17H17FN4O3 | 344.34 |
| 150 | 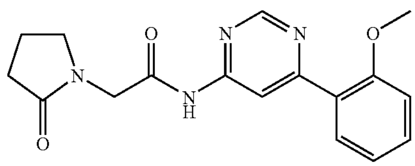 [SMILES: COc1ccccc1-c1cc(NC(=O)CN2CCCC2=O)ncn1] | C17H18N4O3 | 326.35 |
| 151 | 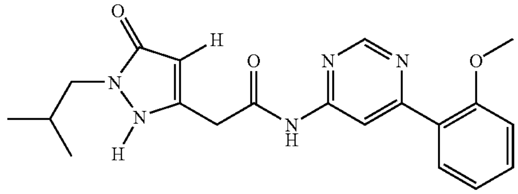 [SMILES: COc1ccccc1-c1cc(NC(=O)Cc2cc(=O)n(CC(C)C)[nH]2)ncn1] | C20H23N5O3 | 381.428 |
| 152 | 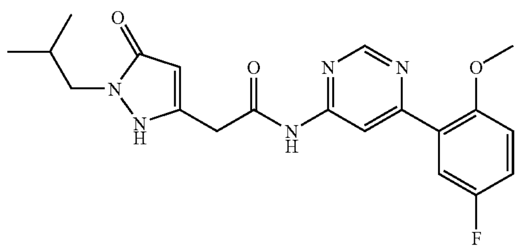 [SMILES: COc1ccc(F)cc1-c1cc(NC(=O)Cc2cc(=O)n(CC(C)C)[nH]2)ncn1] | C20H22FN5O3 | 399.419 |
| 153 | HCl | C18H21FN4O2 | 344.383 |
| 154 | 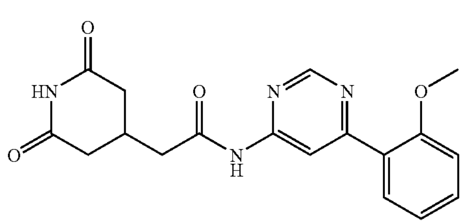 [SMILES: COc1ccccc1-c1cc(NC(=O)CC2CC(=O)NC(=O)C2)ncn1] | C18H18N4O4 | 354.36 |

TABLE 1-continued

| Examples | Structure | Formula | Mol.-Weight |
|---|---|---|---|
| 155 | 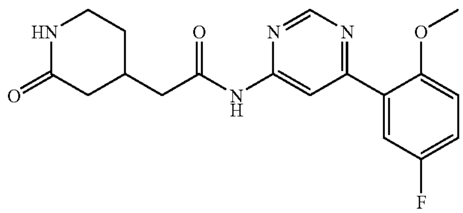 [SMILES: COc1ccc(F)cc1-c1cc(NC(=O)CC2CCNC(=O)C2)ncn1] | C18H19FN4O3 | 358.367 |
| 156 | 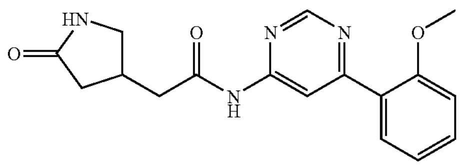 [SMILES: COc1ccccc1-c1cc(NC(=O)CC2CNC(=O)C2)ncn1] | C17H18N4O3 | 326.35 |

TABLE 2

| Compound No. | Structure and IUPAC name | MS m/z | MeltPoint Celsius |
|---|---|---|---|
| 1A | Piperidine-4-carboxylic acid [6-(2-ethoxy-phenyl)-pyrimidin-4-yl]-amide | 327.1, 339.1 (M + 1) | |
| 2A | 1-Methyl-piperidine-4-carboxylic acid [6-(2-ethoxy-phenyl)-pyrimidin-4-yl]-amide | 341 (M + 1) | 65-67 |
| 3A | 1-Ethyl-piperidine-4-carboxylic acid [6-(2-ethoxy-phenyl)-pyrimidin-4-yl]-amide | 355 (M + 1) | 137-139 |
| 4A | 1-Isopropyl-piperidine-4-carboxylic acid [6-(2-ethoxy-phenyl)-pyrimidin-4-yl]-amide | 369 (M + 1) | 173-175 |

TABLE 2-continued

| Compound No. | Structure and IUPAC name | MS m/z | MeltPoint Celsius |
|---|---|---|---|
| 5A | 1-Benzyl-piperidine-4-carboxylic acid [6-(2-ethoxy-phenyl)-pyrimidin-4-yl]-amide | 417 (M + 1) | |
| 6A | Piperidine-4-carboxylic acid [6-(2-methoxy-phenyl)-pyrimidin-4-yl]-amide | 313 (M + 1) | 279-280 |
| 7A | Piperidine-4-carboxylic acid [6-(2-isopropoxy-phenyl)-pyrimidin-4-yl]-amide | 341 (M + 1) | |
| 8A | Piperidine-4-carboxylic acid [6-(2-cyclopropylmethoxy-phenyl)-pyrimidin-4-yl]-amide | 353 (M + 1) | |
| 9A | Piperidine-4-carboxylic acid [6-(2-benzyloxy-phenyl)-pyrimidin-4-yl]-amide | 389 (M + 1) | 224-227 |
| 10A | Piperidine-4-carboxylic acid [6-(4-fluoro-2-methoxy-phenyl)-pyrimidin-4-yl]-amide | 331 (M + 1) | |

TABLE 2-continued

| Compound No. | Structure and IUPAC name | MS m/z | MeltPoint Celsius |
|---|---|---|---|
| 11A | Piperidine-4-carboxylic acid [6-(5-fluoro-2-methoxy-phenyl)-pyrimidin-4-yl]-amide | 331 (M + 1) | |
| 12A | Piperidine-4-carboxylic acid [6-(2-fluoro-6-methoxy-phenyl)-pyrimidin-4-yl]-amide | 331 (M + 1) | 140-143 |
| 13A | 1-Acetyl-piperidine-4-carboxylic acid [6-(2-ethoxy-phenyl)-pyrimidin-4-yl]-amide | 369 (M + 1), 391 (M + Na) | 171-173 |
| 14A | Piperidine-4-carboxylic acid [6-(2-methoxy-phenyl)-pyrimidin-4-yl]-amide hydrochloride | 313 (M + 1) | 214-217 |
| 15A | Piperidine-4-carboxylic acid [6-(2-methoxy-phenyl)-pyrimidin-4-yl]-amide mesylate | 313 (M + 1) | 268-270 |

TABLE 2-continued

| Compound No. | Structure and IUPAC name | MS m/z | MeltPoint Celsius |
|---|---|---|---|
| 16A | 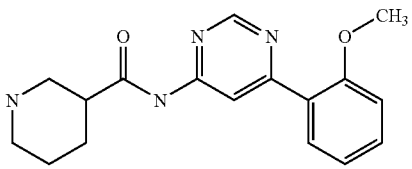<br>Piperidine-3-carboxylic acid [6-(2-methoxy-phenyl)-pyrimidin-4-yl]-amide | 313 (M + 1) | |
| 17A | 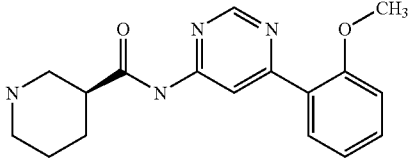 [SMILES: COc1ccccc1-c1cc(NC(=O)[C@H]2CCCNC2)ncn1]<br>(S)-Piperidine-3-carboxylic acid [6-(2-methoxy-phenyl)-pyrimidin-4-yl]-amide | 312.9 | 163-165 |
| 18A | <br>(R)-Piperidine-3-carboxylic acid [6-(2-methoxy-phenyl)-pyrimidin-4-yl]-amide | 312.9 | 210-213 |
| 19A | 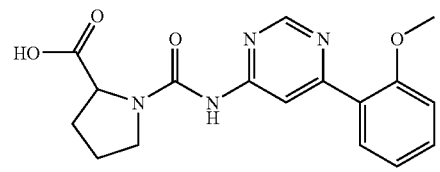 [SMILES: COc1ccccc1-c1cc(NC(=O)N2CCCC2C(=O)O)ncn1]<br>1-[6-(2-Methoxy-phenyl)-pyrimidin-4-ylcarbamoyl]-pyrrolidine-2-carboxylic acid | 343 (M + 1) | |
| 20A | 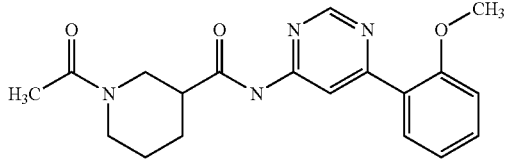 [SMILES: COc1ccccc1-c1cc(NC(=O)C2CCCN(C(C)=O)C2)ncn1]<br>1-Acetyl-piperidine-3-carboxylic acid [6-(2-methoxy-phenyl)-pyrimidin-4-yl]-amide | 356.1, 377 (M + 1) | |
| 21A | 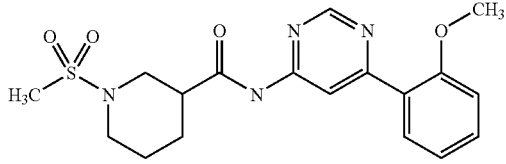<br>1-Methanesulfonyl-piperidine-3-carboxylic acid [6-(2-methoxy-phenyl)-pyrimidin-4-yl]-amide | 391 (M + 1) | |

TABLE 2-continued

| Compound No. | Structure and IUPAC name | MS m/z | MeltPoint Celsius |
|---|---|---|---|
| 22A | Piperidine-3-carboxylic acid [6-(2-methoxy-phenyl)-2-methyl-pyrimidin-4-yl]-amide | 327 (M + 1) | 229-230 |
| 23A | HCl<br>1-[6-(2-Methoxy-phenyl)-pyrimidin-4-yl]-3-piperidin-3-yl-urea hydrochloride | 328 (M + 1) | |
| 24A | HCl<br>1-[6-(2-Methoxy-phenyl)-pyrimidin-4-yl]-3-piperidin-4-yl-urea hydrochloride | 328 (M + 1) | |
| 25A | N-[6-(2-Methoxy-phenyl)-pyrimidin-4-yl]-2,2-dimethyl-propionamide | 286.4 (M + 1) | |
| 26A | N-[6-(2-Methoxy-phenyl)-pyrimidin-4-yl]-2-phenyl-acetamide | 320.5 (M + 1) | |
| 27A | N-[6-(2-Methoxy-phenyl)-pyrimidin-4-yl]-benzamide | 306.2 (M + 1) | |

TABLE 2-continued

| Compound No. | Structure and IUPAC name | MS m/z | MeltPoint Celsius |
|---|---|---|---|
| 28A | 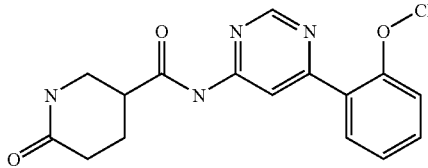<br>6-Oxo-piperidine-3-carboxylic acid [6-(2-methoxy-phenyl)-pyrimidin-4-yl]-amide | 327.1 (M + 1) | |
| 29A | 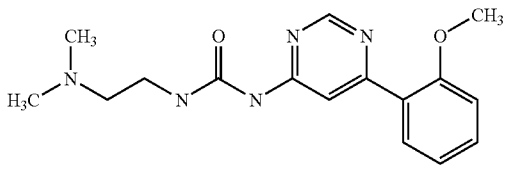<br>1-(2-Dimethylamino-ethyl)-3-[6-(2-methoxy-phenyl)-pyrimidin-4-yl]-urea | 316.2 (M + 1) | |
| 30A | 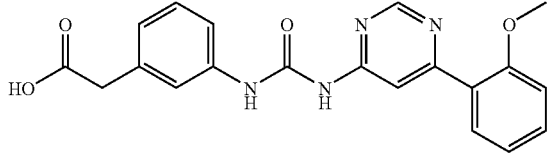 [SMILES: COc1ccccc1-c1cc(NC(=O)Nc2cccc(CC(=O)O)c2)ncn1]<br>(3-{3-[6-(2-methoxy-phenyl)-pyrimidin-4-yl]-ureido}-phenyl)-acetic acid | 379 (M + 1) | |
| 31A | 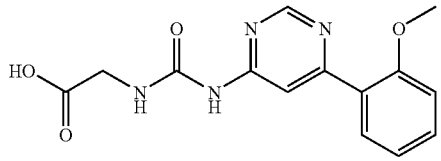<br>{3-[6-(2-methoxy-phenyl)-pyrimidin-4-yl]-ureido}-acetic acid | 303 (M + 1) | |
| 32A | 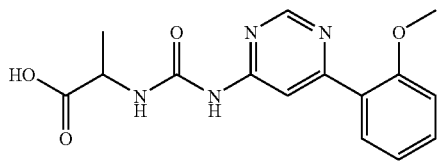 [SMILES: COc1ccccc1-c1cc(NC(=O)NC(C)C(=O)O)ncn1]<br>2-{3-[6-(2-methoxy-phenyl)-pyrimidin-4-yl]-ureido}-propionic acid | 317 (M + 1) | |
| 33A | 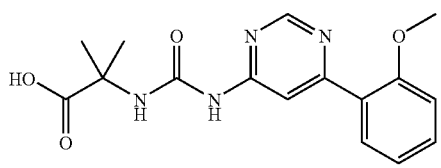<br>2-{3-[6-(2-methoxy-phenyl)-pyrimidin-4-yl]-ureido}-2-methyl-propionic acid | 331 (M + 1) | |

TABLE 2-continued

| Compound No. | Structure and IUPAC name | MS m/z | MeltPoint Celsius |
|---|---|---|---|
| 34A | 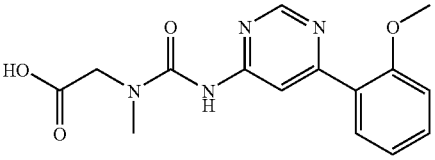 [SMILES: COc1ccccc1-c1cc(NC(=O)N(C)CC(=O)O)ncn1]<br>{3-[6-(2-methoxy-phenyl)-pyrimidin-4-yl]-1-methyl-ureido}-acetic acid | 317 (M + 1) | |

Processes

The present invention provides a process for preparation of a compound of formula (I) as defined above or a protected derivative thereof, which comprises
(a) converting one compound of formula (I) to another compound of formula (I).

In step (a), exemplary conversion reactions include
alkylation reactions such as N-alkylation reactions (e.g. conversion of the group $R^1$=piperidine to $R^1$=N-methyl-piperidine)
acylation (e.g. when $R^1$ represents piperidine: conversion of the NH group of piperidine to $NC(O)CH_3$)
removal of a protecting group (e.g. to give compounds of general formula (I) wherein $R^1$ is piperidinyl from a compound of general formula (I) wherein $R^1$ is piperidine and wherein the nitrogen of piperidine is protected by Boc e.g. by use of TFA)
ester hydrolysis (e.g. conversion of an ethyl ester to give the corresponding acid, such as conversion of $R^1$ represents $NHC(Me)_2C(O)OEt$ to $R^1$ represents $NHC(Me)_2C(O)OH$)
when $R^{20}$ represents phenyl: reduction of an $-NH_2$ substituent on $R^{20}$ to an $-NO_2$ substituent on $R^{20}$ by hydrogen in the presence of raney nickel
by coupling of an amine group with methanesulfonyl chloride
wherein a compound of formula (I) has $R^1$ is $-C_{1-4}$alkyl-O—$R^{20}$ or $R^1$ is $-C_{1-4}$alkyl-NH—$R^{20}$:
an exemplary conversion reaction from $R^1$=—$C_{1-4}$alkyl-$L_5$ to $R_1$=—$C_{1-4}$alkyl—O—$R^{20}$ or $R^1$=—$C_{1-4}$alkyl NH—$R^{20}$ may involve reacting a compound of formula (I) in which $R^1$ is —$C_{1-4}$alkyl-$L_5$, wherein $L_5$ represents a suitable leaving group (e.g. chloro), with a compound of formula:
$R^{20}$—OH or $R^{20}$—$NH_2$ optionally in the presence of a base.

Alternatively the present invention provides a process for preparation of a compound of formula (I) or a protected derivative thereof, which comprises
(b) reacting a compound of formula A

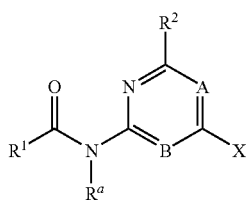

Formula A wherein A, B, $R^1$, $R^a$ and $R^2$ are as defined in general formula (I) and X is a suitable substituent for a cross coupling reaction, or a protected derivative thereof with a compound of formula B

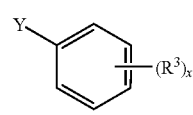

Formula B wherein $R^3$ and x are as defined in general formula (I) and Y is a suitable substituent for a cross coupling reaction, or a protected derivative thereof;
wherein X and Y represent suitable substituents for a cross-coupling reaction and are chosen to react with one another.

In step (b), exemplary cross coupling reactions include Suzuki coupling reactions. For example, X may represent halogen (e.g. Cl) and Y may represent a boronic acid or boronic ester group (e.g. $B(OH)_2$). Typical Suzuki coupling conditions are reaction of a boronic acid with the corresponding chloro coupling partner in the presence of triphenylphosphine in saturated sodium carbonate solution and 1,4-dioxane with palladium(II) acetate as the catalyst, heating at reflux.

Compounds of formula A may be synthesised from compounds of formula C

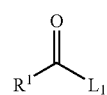

Formula C wherein $R^1$ is as defined in general formula (I) and $L_1$ is a leaving group; and compounds of formula D

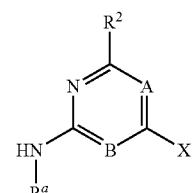

Formula D wherein A, B, $R^a$ and $R^2$ are as defined for general formula (I) and X is defined as for Formula A above.

The reaction of a compound of formula C with a compound of formula D is suitably carried out in an organic solvent (e.g. dicloromethane). The reaction is suitably carried out at elevated temperature.

In step (b), exemplary $L_1$ substituents include halogen (e.g. Cl). When $L_1$ is chloro, a compound of formula C may be prepared from the corresponding carboxylic acid by reaction with thionyl chloride.

Compounds of general formulae C and D are known and are readily available or may be synthesised by known methods.

Alternatively the present invention provides a process for preparation of a compound of formula (I) or a protected derivative thereof, which comprises:

(c) reacting a compound of formula E

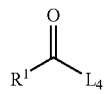

Formula E or a protected derivative thereof
wherein $R^1$ is as defined for general formula (I) and $L_4$ represents a suitable leaving group;
with a compound of formula F

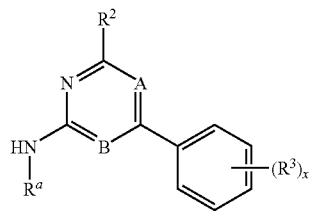

Formula F wherein $R^a$, $R^2$, $R^3$, x, A and B are as defined in general formula (I), or a protected derivative thereof In step (c), exemplary $L_4$ substituents include halogen (e.g. Cl) and $OC(O)OC_{1-4}$alkyl (e.g. OC(O)Oisobutyl).

When $L_4$ represents chloro, the reaction of a compound of formula E with a compound of formula F may suitably be carried out in an organic solvent (e.g. dichloromethane). The reaction may suitably be carried out in the presence of a nucleophilic catalyst (e.g. dimethylaminopyridine).

When $L_4$ represents $OC(O)OC_{1-4}$alkyl, the reaction the reaction of a compound of formula E with a compound of formula F may suitably be carried out in an organic solvent (e.g. tetrahydrofuran).

Compounds of formula E wherein $L_4$ represents OC(O) $OC_{1-4}$alkyl may be synthesised by reaction of the corresponding carboxylic acid with an alkylchloroformate. The reaction may suitably be carried out in an organic solvent (e.g. tetrahydrofuran). The reaction may suitably be carried out in the presence of a further reagent such as N-methyl-morpholine. Such compounds of formula E wherein $L_4$ represents OC(O) $OC_{1-4}$ alkyl may be prepared in situ.

Compounds of formula E wherein $L_4$ is chloro may be prepared from the corresponding carboxylic acid by reaction with thionyl chloride and may optionally be prepared in situ.

Other compounds of formula E are readily available or may be synthesised by known methods.

Compounds of formula F may be synthesised from compounds of formula B as defined above and compounds of formula D as defined above by a cross coupling reaction (e.g. by a Suzuki reaction) similar to that described for the reaction between compounds of formulae A and B.

Alternatively the present invention provides a process for preparation of a compound of formula (I) or a protected derivative thereof, which comprises (d) preparing a compound of formula (I), in which $R^1$ is a moiety which connects to the main carbonyl of formula (I) via a nitrogen atom (e.g. $R^1$=—$NR^{10}$—($C_{1-6}$alkyl)-$R^{20}$ or —$NR^{10}R^{10}$ or nitrogen-containing heterocyclyl wherein $R^1$ connects to the main carbonyl of formula (I) via a nitrogen atom of the heterocyclyl ring), by a process comprising reaction of the corresponding amine or a protected derivative thereof with a compound of formula G

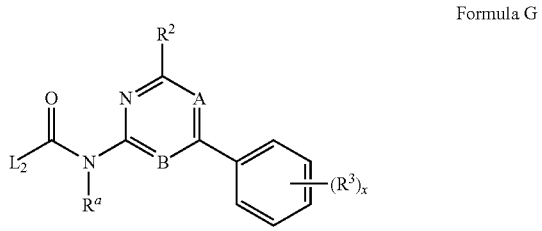

Formula G wherein $R^a$, $R^2$, $R^3$, x, A and B are as defined for general formula (I) and $L_2$ represents a suitable leaving group;
or a protected derivative thereof.

In step (d), exemplary $L_2$ substituents include OPh or $OC_{1-4}$alkyl.

The reaction may suitably be carried out in a non-polar organic solvent (e.g. toluene).

The reaction may suitably be carried out at elevated temperature, preferably under microwave conditions.

Compounds of formula G may be synthesised from compounds of formula F as defined above and compounds of formula H

Formula H wherein $L_3$ represents a suitable leaving group (e.g. Cl) and $L_2$ is defined as above for formula G.

Suitable reaction conditions include reaction of phenyl chloroformate (compound of formula N) with a compound of formula F in the presence of a base (e.g. DIPEA) in an organic solvent (e.g. dichloromethane).

Compounds of Formula H are well known and are readily available or may be prepared by known methods from readily available starting materials.

Alternatively the present invention provides a process for preparation of a compound of formula (I) or a protected derivative thereof, which comprises (e) reacting a compound of formula F as defined above or a protected derivative thereof with a compound of formula J

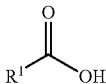

Formula J wherein $R^1$ is as defined for general formula (I);

in the presence of a suitable coupling agent such as HATU or HBTU. The reaction is suitably carried out at elevated temperature. The reaction may suitably be carried out in an organic solvent (such as dichloromethane or acetonitrile) and may suitably be carried out in the presence of a base (such as DIPEA).

Compounds of Formula J are well known and are readily available or may be prepared by known methods from readily available starting materials.

Alternatively the present invention provides a process for preparation of a compound of formula (I) or a protected derivative thereof, which comprises (f) reacting a compound of formula K

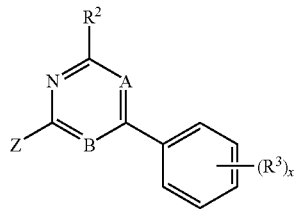

Formula K wherein $R^2$, $R^3$, x, A and B are as defined for general formula (I) and Z represents a suitable substituent for a cross-coupling reaction (e.g. chloro) with a compound of formula L

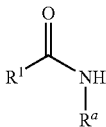

Formula L wherein $R^1$ and $R^a$ are as defined for general formula (I);

under suitable conditions for coupling reaction, such as a Buchwald type coupling reaction, such as in the presence of a suitable catalyst and a base (e.g. in the presence of $Pd(PPh_3)_4$, Xantophos and caesium carbonate).

Compounds of Formulae K and L are well known and are readily available or may be prepared by known methods from readily available starting materials. For example, compounds of Formula K may be prepared by a cross coupling reaction (e.g. by a Suzuki coupling reaction).

Alternatively the present invention provides a process for preparation of a compound of formula (I) or a protected derivative thereof, which comprises (g) preparing a compound of formula (I), in which $R^1$ is —$NHR^{20}$ or —NH—($C_{1-6}$alkyl)-$R^{20}$ by reacting a compound of formula F as defined above with a compound of formula:

$R^{20}N=C=O$ or $R^{20}$—($C_{1-6}$ alkyl)-N=C=O wherein $R^{20}$ is as defined for general formula (I), for example $R^{20}$ represents a heteroaryl group such as pyridine.

The reaction is suitably carried out in the presence of a base (such as triethylamine).

Certain intermediate compounds are new and are claimed as an aspect of the invention.

In a preferred embodiment of this invention, the cyclin-dependent kinase inhibitor according to Formula I inhibits a CDK selected from the group consisting of CDK1, CDK2, CDK3, CDK4, CDK5, CDK6, CDK7, CDK8, CDK9, CDK10, CDK11, CrkRS (Crk7, CDC2-related protein kinase 7), CDKL1 (cyclin-dependent kinase-like 1); KKIALRE, CDKL2 (cyclin-dependent kinase-like 2), KKIAMRE, CDKL3 (cyclin-dependent kinase-like 3), NKIAMRE, CDKL4, similar to cyclin-dependent kinase-like 1, CDC2L1 (cell division cycle 2-like 1), PITSLRE B, CDC2L1 (cell division cycle 2-like 1), PITSLRE A, CDC2L5 (cell division cycle 2-like 5), PCTK1 (PCTAIRE protein kinase 1), PCTK2 (PCTAIRE protein kinase 2), PCTK3 (PCTAIRE protein kinase 3) or PFTK1 (PFTAIRE protein kinase 1).

The inhibitor may also inhibit more than one cyclin-dependent kinase selected from the above-recited group.

In a particular preferred embodiment of this invention, the compound according to Formula I inhibits CDK9.

In a further embodiment of this invention, the compound according to Formula I selectively inhibits one or more CDKs without having a substantial inhibitory effect on other enzymes or proteins.

In a preferred embodiment, such inhibitory compounds display an increased selectivity for a particular CDK. "Increased selectivity" as used herein means that the inhibitory compound is at least 10-100 times more selective for a particular CDK selected from the group of CDKs as recited herein, supra. In a preferred embodiment of the present invention, the inhibitory compound is 20-90 times more selective for a particular CDK. In a particular preferred embodiment, the inhibitory compound is 30-80 times more selective for a particular CDK.

In a particular preferred embodiment, the compound according to Formula I displays an increased selectivity for CDK9 than for other CDKs.

As used herein, the term "inhibiting" or "inhibition" refers to the ability of a compound to downregulate, decrease, reduce, suppress, inactivate, or inhibit at least partially the cellular function of a cyclin-dependent kinase, i.e. its activity or the expression of the cyclin-dependent kinase.

Furthermore, the term "cyclin-dependent kinase inhibitor" refers to any compound or group of compounds that is capable of downregulating, decreasing, suppressing or otherwise regulating the amount and/or activity of a cyclin-dependent kinase. Inhibition of said kinases can be achieved by any of a variety of mechanisms known in the art, including, but not limited to binding directly to the kinase polypeptide, denaturing or otherwise inactivating the kinase, or inhibiting the expression of the gene (e.g., transcription to mRNA, translation to a nascent polypeptide, and/or final polypeptide modifications to a mature protein), which encodes the kinase. Furthermore, a cyclin-dependent kinase inhibitor may also interfere with expression, modification, regulation or activation of a molecule acting downstream of a CDK in a CDK-dependent pathway. Generally, kinase inhibitors may be proteins, polypeptides, nucleic acids, small molecules, or other chemical moieties. Specifically, kinase inhibitors also include monoclonal or polyclonal antibodies directed against cyclin-dependent kinases. In a preferred embodiment, the cyclin-dependent kinase inhibitor is selected from the compounds as represented by Formula I as disclosed herein.

Therapeutic Use

The compounds of Formula I are inhibitors of cyclin-dependent kinases. Thus, they are expected to have the ability to arrest, or to recover control of the cell cycle in abnormally dividing cells. Consequently, it is suggested that the compounds according to Formula I will prove useful in treating and/or preventing proliferative disorders such as cancers. It is known that CDKs play a role in apoptosis, proliferation, differentiation and transcription and therefore, the compounds according to Formula I may also be useful in the treatment of diseases other than proliferative diseases, such as infectious diseases, immunological diseases, neurodegenerative diseases and cardiovascular diseases.

Furthermore, the compounds according to Formula I also display an unexpected antinociceptive and anti-inflammatory effect.

Thus, in a preferred embodiment, the compounds of Formula I may be used in methods and/or pharmaceutical compositions for the treatment of any type of pain, including chronic pain, neuropathic and/or inflammatory pain.

In a further preferred embodiment, the compounds of Formula I may be used in methods and/or pharmaceutical compositions for the treatment of inflammatory disorders.

In a particular preferred embodiment, the compounds of Formula I for use in the treatment of pain or in the treatment of inflammatory disorders display an increased selectivity for CDK9 than for other CDKs.

Pain

As can be seen from the Examples, administration of CDK inhibitors according to Formula I to mice suffering from nerve lesion results in a hypoalgesic effect, in particular in murine models of inflammatory and neuropathic pain.

The discovery that inhibition of a cyclin-dependent kinase is involved in mediating a hypoalgesic effect was unexpected.

Thus, in a preferred embodiment, this invention relates to a method of treating any type of pain comprising administering an effective amount of an inhibitor of cyclin-dependent kinase according to Formula I. Specifically, the compounds of Formula I may be used for the treatment of chronic, neuropathic and/or inflammatory pain. In a particular preferred embodiment, the compounds of Formula I for use in the treatment of any type of pain display an increased selectivity for CDK9 than for other CDKs.

The role of CDK9 in the development of pain could be based on the following mechanism of action: Both cyclin T1 and CDK9 stimulate the basal promoter activity of TNFα. TNFα is a pro-inflammatory cytokine and pain mediator that controls expression of inflammatory genetic networks. For mediation of cellular TNF receptor responses, the nuclear factor-κB (NFκB) pathway is crucial. TNFα triggers its recruitment to cytokine genes while NfκB interacts with p-TEFb complex for stimulation of gene transcription (Barboric M et al., 2001).

Additionally, it has been shown that CDK9 is a binding partner of TRAF2, a member of the TNFα receptor complex (MacLachlan et al, 1998), while GP130, a subunit of the pro-inflammatory IL6 receptor complex has recently been identified as another potential binding partner of CDK9 (Falco et al, 2002). As a key player in TNFα and interleukin signaling as well as in NfκB mediated expression of several genes (e.g. cytokines as pain mediators), CDK9 can thus be considered as a central target for the treatment of any type of pain, such as inflammatory pain (see FIG. 2).

For the treatment of neuropathic pain, pharmacological action has to take place beyond the blood-brain-barrier (BBB) in the central nervous system (CNS). Microglial cells as the principal immune cells in the CNS, for example, release, upon activation, a variety of noxious factors such as cytokines (TNFα, IL1β, IL6) and other pro-inflammatory molecules (Huwe 2003). Microglia are activated by stimulation of TNFα receptor or Toll-like receptor and signal is mediated via Iκ kinase (IKK) and NfκB leading to transcriptional activation of the cytokines described above. Microglial contribution has been discussed as instrumental in chronic CNS diseases and may contribute to pain perception (Watkins et al, 2003).

Recently it has been shown that the transcription factor NfκB regulates expression of Cyclooxygenase-2 (COX-2) via Interleukin 1β (IL1β) in the spinal cord (Lee et al. 2004). As the major contributor to elevation of spinal prostaglandin E2, the pain mediator COX-2 is already known as a target for a variety of anti-nociceptive/anti-inflammatory drugs. NfκB inhibitors have proven their ability to significantly reduce COX-2 levels and mechanical allodynia as well as thermal hyperalgesia in animal models.

In contrast to COX-2, inhibition of CDK9 action would lead to suppression of a variety of pain mediators instead of just a single one. Thus, anti-nociceptive action of CDK9 inhibitors may be superior compared to, e.g. COX-2 inhibitors.

Due to its relevance for NfκB mediated gene transcription, the inhibitory interaction with CDK9 may therefore be a reasonable approach not only for the treatment of acute inflammatory pain, but also for the treatment of chronic pain.

The term "pain" as used herein generally relates to any type of pain and broadly encompasses types of pain such as acute pain, chronic pain, inflammatory and neuropathic pain. In a preferred embodiment of the present invention, "pain" comprises neuropathic pain and associated conditions. The pain may be chronic, allodynia (the perception of pain from a normally innocuous stimulus), hyperalgesia (an exaggerated response to any given pain stimulus) and an expansion of the receptive field (i.e. the area that is "painful" when a stimulus is applied), phantom pain or inflammatory pain.

Acute pain types comprise, but are not limited to pain associated with tissue damage, postoperative pain, pain after trauma, pain caused by burns, pain caused by local or systemic infection, visceral pain associated with diseases comprising: pancreatits, intestinal cystitis, dysmenorrhea, Irritable bowel syndrome, Crohn's disease, ureteral colic and myocardial infarction.

Furthermore, the term "pain" comprises pain associated with CNS disorders comprising: multiple sclerosis, spinal cord injury, traumatic brain injury, Parkinson's disease and stroke.

In a preferred embodiment, "pain" relates to chronic pain types comprising headache (for example migraine disorders, episodic and chronic tension-type headache, tension-type like headache, cluster headache, and chronic paroxysmal hemicrania), low back pain, cancer pain, osteoarthritis pain and neuropathic pain, but is not limited thereto. Inflammatory pain (pain in response to tissue injury and the resulting inflammatory process) as defined herein relates to inflammatory pain associated with diseases comprising connective tissue diseases, rheumatoid arthritis, systemic lupus erythematosus, multiple sclerosis and arthritis, but is not limited thereto.

Neuropathic pain (pain resulting from damage to the peripheral nerves or to the central nervous system itself) includes conditions comprising, but not limited to metabolic neuropathies (e.g., diabetic neuropathy), post-herpetic neuralgia, trigeminal neuralgia, cranial neuralgia, post-stroke neuropathic pain, multiple sclerosis-associated neuropathic pain, HIV/AIDS-associated neuropathic pain, cancer-associated neuropathic pain, carpal tunnel-associated neuropathic pain, spinal cord injury-associated neuropathic pain, complex regional pain syndrome, fibromyalgia-associated neuropathic pain, reflex sympathic dystrophy, phantom limb syndrome or peripheral nerve or spinal cord trauma, nerve transection including surgery, limb amputation and stump pain, pain caused by the side effects of anti-cancer and anti-AIDS therapies, post-surgical neuropathic pain, neuropathy-associated pain such as in idiopathic or post-traumatic neuropathy and mononeuritis, and neuropathic pain caused by connective tissue disease such as rheumatoid arthritis, Wallenberg's syndrome, systemic lupus erythematosus, multiple sclerosis, or polyarteritis nodosa. The neuropathy can be classified as radiculopathy, mononeuropathy, mononeuropathy multiplex, polyneuropathy or plexopathy.

The term "allodynia" denotes pain arising from stimuli which are not normally painful. Allodynic pain may occur other than in the area stimulated.

The term "hyperalgesia" denotes an increased sensitivity to a painful stimulus.

The term "hypoalgesia" denotes a decreased sensitivity to a painful stimulus.

Inflammatory Diseases

Surprisingly, it could be shown that the CDK inhibiting compounds according to Formula I as disclosed herein exert an anti-inflammatory effect in in vitro and in vivo inflammatory assays.

Thus, in a preferred embodiment, this invention relates to a method of treating inflammatory diseases comprising administering an effective amount of an inhibitor of cyclin-dependent kinase according to Formula I. In a particular preferred embodiment, the compounds of Formula I for use in the treatment of inflammatory diseases display an increased selectivity for CDK9 than for other CDKs.

The role of CDK9 in the development of inflammatory diseases could be based on the following mechanism of action: inflammatory diseases such as rheumatoid arthritis (RA); atherosclerosis; asthma; inflammatory bowel disease, systemic lupus erythematosus and several other autoimmune diseases are mediated by tumor necrosis factor α (TNFα), a key regulator of inflammatory and tissue obstructive pathways in said diseases. It is known that the TNFα signal is mediated via several transducers such as IκB Kinase (IKK), which phosphorylates the IκB protein which dissociates from NfκB upon its phosphorylation. Dissociated NfκB, a positive regulator of cytokine transcription, translocates into the cell nucleus where it binds to its recognition sites.

Activated NfκB has been found in the synovium of RA patients [Han et al.; 2003, Autoimmunity, 28, 197-208]. It regulates pro-inflammatory genes such as TNFα, IL-6, IL-8, NOS and COX2. Targeting NfκB and its upstream signalling partner IKK has already proven to be an efficient therapeutic strategy in many animal models of arthritis [Firestein, 2003, Nature 423, 356-361].

Bound NfκB associates with a coactivator complex containing histone acetyltransferases (CBP, p300, p/CAF, SRC-1, and SRC-1-related proteins) that recruits and activates CDK9 which catalyzes the phosphorylation of the CTD of RNA Pol II [West et al.; 2001, Journal of Virology 75(18), 8524-8537]. Resulting hyperphosphorylation of the RNA Pol II CTD leads to transcriptional activation of pro-inflammatory cytokines such as IL-1β, IL-6 and IL-8 that are also known as being regulated by TNFα.

Several studies showed that TNFα is a 'master regulator' of an autologous signalling cascade that regulates pro-inflammatory cytokine expression. To interrupt this pro-inflammatory cascade, specific antibodies (Abs) can be used successfully to block the TNFα signal. Anti-TNFα treatment of RA with Abs has already proven its therapeutic efficacy in several clinical studies and FDA approved drugs such as Infliximab and Etanercept have entered the market [Feldmann and Maini, NatMed, 2003, 9 (10); 356-61]. However, disadvantages of Ab based therapies include their immunogenic potential, attendant loss of efficacy during progressive treatment and high treatment costs. Additionally, the Ab kinetics permits a more or less all-or-nothing reduction of circulating TNFα. As a result, physiologic functions of the immune response are also suppressed [Laufer et al., Inflammation and Rheumatic Diseases, 2003; Thieme, pp. 104-5].

Therapeutic interventions into the TNFα-mediated signalling cascade.with kinase inhibitors aiming at targets such as p38 MAPK or IKK have shown severe adverse effects—in most cases due to a lack of specificity against the respective target. In contrast thereto, CDK specific inhibitors according to Formula I as presented herein may intervene at the very bottom end of the TNFα signalling pathways reducing the interaction with physiological functions. Additionally, said compounds will allow interruption of the autologous TNFα mediated inflammatory network by avoidance of adverse effects via superior specificity. Therefore, treatment with CDK specific inhibitors of Formula I constitutes a promising strategy for the treatment of inflammatory and autoimmune diseases.

Thus, the compounds according to Formula I as presented herein may be used for the treatment and/or prevention of inflammatory diseases.

The term "inflammatory diseases" as used herein relates to diseases triggered by cellular or non-cellular mediators of the immune system or tissues causing the inflammation of body tissues and subsequently producing an acute or chronic inflammatory condition.

Examples for such inflammatory diseases are hypersensitivity reactions of type I-IV, for example but not limited to hypersensitivity diseases of the lung including asthma, atopic diseases, allergic rhinitis or conjunctivitis, angioedema of the lids, hereditary angioedema, antireceptor hypersensitivity reactions and autoimmune diseases, Hashimoto's thyroiditis, systemic lupus erythematosus, Goodpasture's syndrome, pemphigus, myasthenia gravis, Grave's and Raynaud's disease, type B insulin-resistant diabetes, rheumatoid arthritis, psoriasis, Crohn's disease, scleroderma, mixed connective tissue disease, polymyositis, sarcoidosis, Wegener's granulomatosis, glomerulonephritis, acute or chronic host versus graft reactions.

Furthermore, the term "inflammatory diseases" includes but is not limited to abdominal cavity inflammation, dermatitis, gastrointestinal inflammation (including inflammatory bowel disease, ulcerative colitis), fibrosis, ocular and orbital inflammation, dry eye disease and severe dry eye disease resulting from Sjörgen's syndrome, mastitis, otitis, mouth inflammation, musculoskeletal system inflammation (including gout, osteoarthritis), inflammatory diseases of the central nervous system (including multiple sclerosis, bacterial meningitis, meningitis), genitourinary tract inflammation (incl prostatitis, glomerulonephritis), cardiovascular inflammation (including atherosclerosis, heart failure), respiratory tract inflammation (including chronic bronchitis, chronic obstructive pulmonary disease), thyroiditis, diabetes mellitus, osteitis, myositis, multiple organ failure (including sepsis), polymyositis and psoriatic arthritis.

Immunological Diseases

The compounds according to Formula I are also envisaged to be useful in the treatment and/or prevention of immunological diseases, such as, for example, autoimmune diseases.

Accordingly, the present invention provides a method for the treatment and/or prevention of immunological diseases comprising the administration of an effective amount of at least one CDK inhibitor according to Formula I to a subject in need thereof.

The term "immunological diseases" as used herein relates to diseases including but not limited to allergy, asthma, graft-versus-host disease, immune deficiencies and autoimmune diseases.

Specifically, immunological diseases include diabetes, rheumatic diseases, AIDS, chronic granulomatosis disease, rejection of transplanted organs and tissues, rhinitis, chronic obstructive pulmonary diseases, osteoporosis, ulcerative colitis, Crohn's disease, sinusitis, lupus erythematosus, psoriasis, multiple sclerosis, myasthenia gravis, alopecia, recurrent infections, atopic dermatitis, eczema and severe anaphylactic reactions, but are not limited thereto. Furthermore, "immunological diseases" also include allergies such as contact allergies, food allergies or drug allergies.

Proliferative Diseases

The compounds of Formula I are inhibitors of cyclin-dependent kinases, which represent key molecules involved in regulation of the cell cycle. Cell-cycle disregulation is one of the cardinal characteristics of neoplastic cells. Thus, said compounds are expected to prove useful in arresting or recovering control of the cell cycle in abnormally dividing cells. It is thus expected that the compounds according to Formula I are useful in the treatment and/or prevention of proliferative diseases such as cancer.

Accordingly, the invention provides a method for the treatment and/or prevention of proliferative diseases comprising administering an effective amount of at least one inhibitor of a cyclin-dependent kinase according to Formula I.

As used herein, the term "proliferative disease" relates to cancer disorders, including, but not limited to benign neoplasms, dysplasias, hyperplasias as well as neoplasms showing metastatic growth or any other transformations.

The term "cancer" includes but is not limited to benign and malign neoplasia like carcinoma, sarcoma, carcinosarcoma, cancers of the blood-forming tissues, tumors of nerve tissues including the brain and cancer of skin cells.

Examples of cancers which may be treated include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumor of myeloid lineage, for example acute and chronicmyelogenous leukemias, myelodysplastic syndrome, or promyelocytic leukemia; thyroid follicular cancer; a tumour of mesenchymal origin, for example fibrosarcoma or habdomyosarcoma,; a tumor of the central or peripheral nervous system, for example astrocytoma, neuroblastoma, glioma or schwannoma; melanoma; seminoma; teratocarcinoma; osteosarcoma; xenoderoma pigmentoum; keratoctanthoma; thyroid follicular cancer; Kaposi's sarcoma, astrocytoma, basal cell carcinoma, small intestine cancer, small intestinal tumors, gastrointestinal tumors, glioblastomas, liposarcoma, germ cell tumor, head and neck tumors (tumors of the ear, nose and throat area), cancer of the mouth, throat, larynx, and the esophagus, cancer of the bone and its supportive and connective tissues like malignant or benign bone tumour, e.g. malignant osteogenic sarcoma, benign osteoma, cartilage tumors; like malignant chondrosarcoma or benign chondroma, osteosarcomas; tumors of the urinary bladder and the internal and external organs and structures of the urogenital system of male and female, soft tissue tumors, soft tissue sarcoma, Wilm's tumor or cancers of the endocrine and exocrine glands like e.g. thyroid, parathyroid, pituitary, adrenal glands, salivary glands.

Infectious Diseases

Furthermore, the invention relates to a method of treating and/or preventing infectious diseases comprising administering an effective amount of at least one inhibitor of a cyclin-dependent kinase according to Formula I.

It is known that certain host cell CDKs are involved in viral replication, i.e. CDK2, CDK7, CDK8 and CDK9 (J. Virol. 2001; 75: 7266-7279). Specifically, the role of CDK9 kinase activity in regulation of HIV-1 transcription elongation and histone methylation has been described (J. Virol 2004, 78(24):13522-13533.

In a preferred embodiment, the invention thus relates to a method of treating and/or preventing infectious diseases comprising administering an effective amount of at least one inhibitor of a cyclin-dependent kinase according to Formula I, wherein said compound displays an increased selectivity for CDK9 than for other CDKs.

The term "infectious diseases" as used herein comprises infections caused by pathogens such as viruses, bacteria, fungi and/or parasites.

Virus-induced infectious diseases include diseases caused by infection with retroviruses, human endogenous retroviruses, hepadnaviruses, herpesviruses, flaviviruses, adenoviruses, togaviruses and poxviruses. Specifically, infectious diseases are caused by viruses comprising, but not limited to viruses such as HIV-1, HIV-2, HTLV-I and HTLV-II, hepadnaviruses such as HBV, herpesviruses such as Herpes simplex virus I (HSV I), herpes simplex virus 11 (HSV II), Epstein-Barr virus (EBV), varicella zoster virus (VZV), human cytomegalovirus (HCMV) or human herpesvirus 8 (HHV-8), flaviviruses such as HCV, West nile or Yellow Fever virus, human papilloma virus, poxviruses, Sindbis virus or adenoviruses.

Examples of infectious diseases include, but are not limited to AIDS, borreliosis, botulism, diarrhea, BSE (Bovine Spongiform Encephalopathy), chikungunya, cholera, CJD (Creutzfeldt-Jakob Disease), conjunctivitis, cytomegalovirus cnfection, dengue/dengue Fever, encephalitis, eastern equine encephalitis, western equine encephalitis, Epstein-Barr Virus Infection, Escherichia coli Infection, foodborne infection, foot and mouth disease, fungal dermatitis, gastroenteritis, Helicobacter pylori Infection, Hepatitis (HCV, HBV), Herpes Zoster (Shingles), HIV Infection, Influenza, malaria, measles, meningitis, meningoencephalitis, molluscum contagiosum, mosquito-borne Diseases, Parvovirus Infection, plague, PCP (*Pneumocystis carinii* Pneumonia), polio, primary gastroenteritis, Q Fever, Rabies, Respiratory Syncytial Virus (RSV) Infection, rheumatic fever, rhinitis, Rift Valley Fever, Rotavirus Infection, salmonellosis, salmonella enteritidis, scabies, shigellosis, smallpox, streptococcal infection, tetanus, Toxic Shock Syndrome, tuberculosis, ulcers (peptic ulcer disease), hemorrhagic fever, variola, warts, West Nile Virus Infection (West Nile Encephalitis), whooping cough, yellow fever.

Cardiovascular Diseases

Furthermore, the invention relates to the treatment and/or prevention of cardiovascular diseases comprising administering an effective amount of at least one inhibitor of a cyclin-dependent kinase according to Formula I.

It has been reported that the field of cardiovascular diseases constitutes a possible clinical application for CDK inhibitors (Pharmacol Ther 1999, 82(2-3):279-284). Furthermore, it is known that inhibition of the cyclin T/CDK9 complex and more specifically, inhibition of CDK9 may play a beneficial role in the treatment of cardiovascular diseases such as heart failure (WO2005/027902).

Thus, in a preferred embodiment, the invention relates to a method of treating and/or preventing cardiovascular diseases comprising administering an effective amount of at least one inhibitor of a cyclin-dependent kinase according to Formula I, wherein said compound displays an increased selectivity for CDK9 than for other CDKs.

The term "cardiovascular diseases" includes but is not limited to disorders of the heart and the vascular system like congestive heart failure, myocardial infarction, ischemic diseases of the heart, such as stable angina, unstable angina and asymptomatic ischemia, all kinds of atrial and ventricular arrhythmias, hypertensive vascular diseases, peripheral vascular diseases, coronary heart disease and atherosclerosis. Furthermore, as used herein, the term includes, but is not limited to adult congenital heart disease, aneurysm, angina pectoris, angioneurotic edema, aortic valve stenosis, aortic aneurysm, aortic regurgitation, arrhythmogenic right ventricular dysplasia, arteriovenous malformations, atrial fibrillation, Behcet syndrome, bradycardia, cardiomegaly, cardiomyopathies such as congestive, hypertrophic and restrictive cardiomyopathy, carotid stenosis, cerebral hemorrhage, Churg-Strauss syndrome, cholesterol embolism, bacterial endocarditis, fibromuscular dysplasia, congestive heart failure, heart valve diseases such as incompetent valves or stenosed valves, heart attack, epidural or subdural hematoma, von Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, mitral valve prolapse, long QT syndrome mitral valve prolapse, myocardial ischemia, myocarditis, disorders of the pericardium, pericarditis, peripheral vascular diseases, phlebitis, polyarteritis nodosa, pulmonary atresia, Raynaud disease, restenosis, rheumatic heart disease, Sneddon syndrome, stenosis, superior vena cava syndrome, syndrome X, tachycardia, hereditary hemorrhagic telangiectasia, telangiectasis, temporal arteritis, thromboangiitis obliterans, thrombosis, thromboembolism, varicose veins, vascular diseases, vasculitis, vasospasm, ventricular fibrillation, Williams syndrome, peripheral vascular disease, varicose veins and leg ulcers, deep vein thrombosis and Wolff-Parkinson-White syndrome.

Furthermore, the term cardiovascular diseases includes diseases resulting from congenital defects, genetic defects, environmental influences (i.e., dietary influences, lifestyle, stress, etc.), and other defects or influences.

Neurodegenerative Diseases

CDK inhibitors have been described to exert neuroprotective effects. Specifically, it has been reported that CDK inhibitors prevent neuronal death in neurodegenerative diseases such as Alzheimer's disease (Biochem Biophys Res Commun 2002 (297):1154-1158; Trends Pharmacol Sci 2002 (23):417-425; Pharmacol Ther 1999, 82(2-3):279-284).

Thus, the compounds according to Formula I, which are CDK inhibitors, are expected to provide beneficial effects in the therapeutic management of neurodegenerative diseases.

Accordingly, the invention relates a method of treating and/or preventing neurodegenerative diseases comprising administering an effective amount of at least one inhibitor of a cyclin-dependent kinase according to Formula I.

The term "neurodegenerative diseases" as used herein includes disorders of the central nervous system as well as disorders of the peripheral nervous system, including, but not limited to brain injuries, cerebrovascular diseases and their consequences, Parkinson's disease, corticobasal degeneration, motor neuron disease, dementia, including ALS, multiple sclerosis, traumatic brain injury, stroke, post-stroke, post-traumatic brain injury, and small-vessel cerebrovascular disease, dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld-Jakob dementia, HIV dementia, schizophrenia with dementia, Korsakoffs psychosis and AIDS-related dementia.

Similarly, cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities are also considered to be neurodegenerative disorders.

Specifically, the present invention relates to a method for treating the above-referenced types of pain and associated conditions and inflammatory disorders, immunological diseases, proliferative diseases, infectious diseases, cardiovascular diseases and neurodegenerative diseases, wherein the term "treating" comprises the prevention, amelioration or treating of pain and associated conditions and inflammatory disorders, immunological diseases, proliferative diseases, infectious diseases, cardiovascular diseases and neurodegenerative diseases.

In a further aspect of the invention, therefore, there is provided a compound of general formula (I) for use in medicine, particularly in the treatment or prevention of diseases and conditions mediated by the activity of cyclin dependent kinases, especially CDK9.

There is further provided the use of a compound of general formula (I) in the preparation of an agent for the treatment or prevention of diseases and conditions mediated by the activity of cyclin dependent kinases, especially CDK9.

Furthermore, the invention provides a method for the treatment or prevention of diseases and conditions mediated by the activity of cyclin dependent kinases, especially CDK9, the method comprising administering to a patient in need of such treatment an effective amount of a compound of general formula (I).

As set out above, the conditions mediated by the activity of cyclin dependent kinases include pain, inflammatory disorders, proliferative diseases, immunological diseases, infectious diseases, cardiovascular diseases and neurodegenerative diseases.

Specific disorders and diseases falling into these categories are discussed in detail above.

Pharmaceutical Compositions

Preferred embodiments of the present invention include the administration of compositions comprising at least one cyclin-dependent kinase inhibitor according to Formula I as an active ingredient together with at least one pharmaceutically acceptable (i.e. non-toxic) carrier, excipient and/or diluent. Such a compositions comprise a further aspect of the invention.

Suitably, the composition comprises at least one cyclin-dependent kinase inhibitor according to Formula I as an active ingredient, wherein said at least one cyclin-dependent kinase inhibitor has an increased selectivity for CDK9 than for other CDKs.

Furthermore, the invention also comprises compositions combining at least two inhibitors of CDK and/or pharmaceutically acceptable salts thereof. Said at least two inhibitors may inhibit the same cyclin-dependent kinase or may also inhibit different types of cylin-dependent kinases, e.g. one inhibitor in the composition may inhibit CDK9 while the other inhibitor is capable of inhibiting CDK2, for example.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluene sulfonic acid, salicylic acid, methanesulfonic acid, oxalic acid, succinic acid, citric acid, malic acid, lactic acid, fumaric acid, and the like.

Having regard to pain treatment, an individual pain medication often provides only partially effective pain alleviation because it interferes with just one pain-transducing pathway out of many. Thus, it is also intended to administer CDK inhibitors according to Formula I in combination with a pain-reducing (analgesic) agent that acts at a different point in the pain perception process.

An "analgesic agent" comprises a molecule or combination of molecules that causes a reduction in pain perception. An analgesic agent employs a mechanism of action other than inhibition of CDK.

One class of analgesics, such as nonsteroidal anti-inflammatory drugs (NSAIDs), down-regulates the chemical messengers of the stimuli that are detected by the nociceptors and another class of drugs, such as opioids, alters the processing of nociceptive information in the CNS. Other analgesics are local anesthetics, anticonvulsants and antidepressants such as tricyclic antidepressants. Administering one or more classes of drug in addition to CDK inhibitors can provide more effective amelioration of pain.

Preferred NSAIDs for use in the methods and compositions of the present invention are aspirin, acetaminophen, ibuprofen, and indomethacin. Furthermore, cyclooxygenase-2 (COX-2) inhibitors, such as specific COX-2 inhibitors (e.g. celecoxib, COX189, and rofecoxib) may also be used as an analgesic agent in the methods or compositions of the present invention.

Preferred tricyclic antidepressants are selected from the group consisting of Clomipramine, Amoxapine, Nortriptyline, Amitriptyline, Imipramine, Desipramine, Doxepin, Trimipramine, Protriptylin, and Imipramine pamoate.

Furthermore, the use of anticonvulsants (e.g. gabapentin), GABAB agonists (e.g. L-baclofen), opioids, vanniloid receptor antagonists and cannabinoid (CB) receptor agonists, e.g. CB1 receptor agonists as analgesic is also preferred in the methods and compositions in the present invention.

In preparing cyclin-dependent kinase inhibitor compositions of this invention, one can follow the standard recommendations of well-known pharmaceutical sources such as Remington: The Science and Practice of Pharmacy, 19$^{th}$ ed. (Mack Publishing, 1995).

The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, wherein said preparations in addition to typical vehicles and/or diluents contain at least one inhibitor according to the present invention and/or a pharmaceutical acceptable salt thereof as active ingredient.

The pharmaceutical compositions according to the present invention containing at least one inhibitor according to the present invention and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like.

Moreover, suitable binders, lubricants, disintegrating agents and coloring agents may also be incorporated into the tablet or capsule. Powders and tablets may contain about 5 to about 95% by weight of a cyclin-dependent kinase inhibitor according to the Formula I as recited herein or analogues thereof or the respective pharmaceutical active salt as active ingredient.

Suitable binders include without limitation, starch, gelatin, natural sugars such as glucose or betalactose, corn sweeteners, natural and synthetic gums such as acacia, tragacanth or sodium oleate, sodium alginate, carboxymethylcellulose, polyethylene glycol and waxes. Among suitable lubricants there may be mentioned boric acid, sodium stearate, magnesium stearate, sodium benzoate, sodium acetate, sodium chloride, and the like.

Suitable disintegrants include starch, methylcellulose, agar, bentonite, xanthan gum, guar gum, and the like.

Sweetening and flavoring agents as well as preservatives may also be included, where appropriate. The disintegrants, diluents, lubricants, binders etc. are discussed in more detail below.

Soluble polymers as targetable drug carriers can include polyvinylpyrrolidone, pyran copolymer, polyhydroxypropylmethacrylamidephenol, polyhydroxyethylaspartamidephenol, or polyethyleneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Moreover, the pharmaceutical compositions of the present invention may be formulated in sustained release form to provide the rate controlled release of any one or more of the components or active ingredients to optimise the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration.

Aerosol preparations suitable for inhalation may include solutions and solids in powder form, which may be present in combination with a pharmaceutically acceptable carrier such as an inert, compressed gas, e.g. nitrogen.

For preparing suppositories, a low melting wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted, shortly before use, to liquid form preparations for either oral or parenteral administration. Such liquid forms include solutions, suspensions, and emulsions.

The compounds according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g.

of methylcellulose, polyvinyl alcohols, or denatured gelatins or starch for holding or containing compositions comprising the active ingredient(s). Capsules with hard shells are typically made of blended or relatively high gel strength gelatins from bones or pork skin. The capsule itself may contain small amounts of dyes, opaquing agents, plasticisers and/or preservatives. Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix.

Powders for constitution comprise powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75% by weight, and more suitably from about 30 to about 60% by weight.

The term disintegrants refers to materials added to the composition to support disintegration and release of the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium-croscaramellose, alginates such as alginic acid and sodium alginate, clays such as bentonites, and effervescent mixtures. The amount of disintegrant in the composition may range from about 2 to about 20% by weight of the composition, more suitably from about 5 to about 10% by weight.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20% by weight of the composition, suitably from about 3 to about 10% by weight, and more suitably from about 3 to about 6% by weight.

Lubricants refer to a class of substances which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5% by weight of the composition, suitably from about 0.5 to about 2% by weight, and more suitably from about 0.3 to about 1.5% by weight of the composition.

Glidents are materials that prevent baking of the components of the pharmaceutical composition together and improve the flow characteristics of granulate so that flow is smooth and uniform. Suitable glidents include silicon dioxide and talc.

The amount of glident in the composition may range from about 0.1 to about 5% by weight of the final composition, suitably from about 0.5 to about 2% by weight.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5% by weight of the composition, suitably from about 0.1 to about 1% by weight.

The present invention relates to the administration of compositions containing as active ingredient a cyclin-dependent kinase inhibitor to a subject in need thereof for the treatment of any type of pain, inflammatory disorders, immunological diseases, proliferative diseases, cardiovascular diseases or neurodegenerative diseases.

"A subject in need thereof" comprises an animal, suitably a mammal, and most suitably a human, expected to experience any type of pain, inflammatory disorders, immunological diseases, proliferative diseases, cardiovascular diseases or neurodegenerative diseases in the near future or which has ongoing experience of said conditions. For example, such animal or human may have a ongoing condition that is causing pain currently and is likely to continue to cause pain, or the animal or human has been, is or will be enduring a procedure or event that usually has painful consequences. Chronic painful conditions such as diabetic neuropathic hyperalgesia and collagen vascular diseases are examples of the first type; dental work, particularly in an area of inflammation or nerve damage, and toxin exposure (including exposure to chemotherapeutic agents) are examples of the latter type.

In order to achieve the desired therapeutic effect, the respective cyclin-dependent kinase inhibitor has to be administered in a therapeutically effective amount.

The term "therapeutically effective amount" is used to indicate an amount of an active compound, or pharmaceutical agent, that elicits the biological or medicinal response indicated. This response may occur in a tissue, system, animal or human that is being sought by a researcher, veterinarian, medical doctor or other clinician, and includes alleviation of the symptoms of the disease being treated. In the context of the present invention, a therapeutically effective amount comprises, e.g., an amount that reduces pain, in particular inflammatory or neuropathic pain. Specifically, a therapeutically effective amount denotes an amount which exerts a hypoalgesic effect in the subject to be treated.

Such effective amount will vary from subject to subject depending on the subject's normal sensitivity to, e.g., pain, its height, weight, age, and health, the source of the pain, the mode of administering the inhibitor of CDKs, the particular inhibitor administered, and other factors. As a result, it is advisable to empirically determine an effective amount for a particular subject under a particular set of circumstances.

The invention will now be described in greater detail with reference to the Examples and to the drawings wherein:

FIG. 1 schematically depicts the spared nerve injury model (SNI model, as developed by Decosterd and Woolf (2000), which is characterized by ligation and section of two branches of the sciatic nerve (namely tibial and common peroneal nerves) leaving the sural nerve intact.

FIG. 2 schematically depicts a possible role of CDK9 as a target in the development of pain.

FIG. 4A shows the results of TNFα-measurements in LPS-induced THP-1 macrophages.

FIG. 4B shows the results of IL-6 measurements in LPS-induced THP-1 macrophages.

GENERAL METHODS FOR THE PREPARATION OF THE COMPOUNDS

Figure 1:
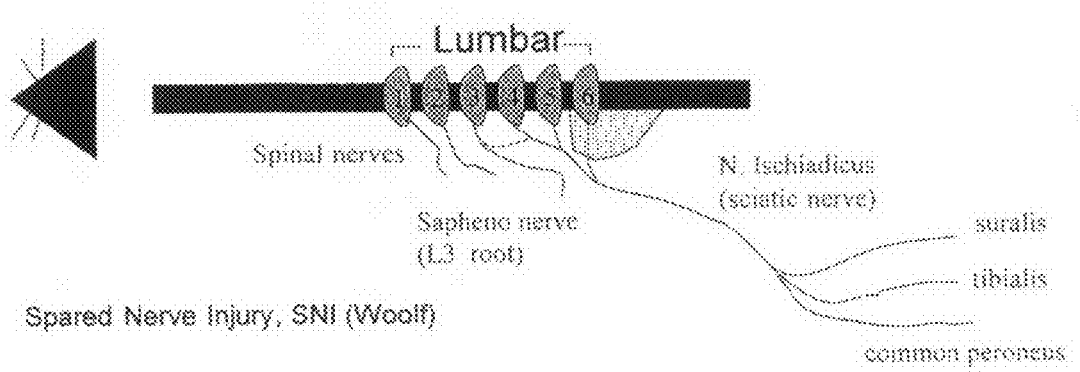

All reagents were purchased from ACROS Organics, Aldrich, Lancaster, Maybridge and Boron Molecular.

The LC/MS analyses for the compounds were done at Surveyor MSQ (Thermo Finnigan, USA) with APCI ionization.

The $^1$H NMR spectra were recorded on <<MERCURY plus 400 MHz>> spectrometer (Varian). Chemical shift values are given in ppm relative to tetramethylsilane (TMS), with the residual solvent proton resonance as internal standard. Melting points were determined on Sanyo Gallenkamp apparatus.

Analytical Methods

NMR spectra were performed on a Bruker AM 400 spectrometer or on a Varian 400 MHz Mercury Plus spectrometer. The following abbreviations are used: s (singlet), d (doublet), dd (doublet of doublets), t (triplet), and m (multiplet). ESI-MS: Mass spectra were taken with an MDS Sciex API 365 mass spectrometer equipped with an Ionspray™ interface (MDS Sciex; Thorn Hill, ON, Canada). The instrument settings, data acquisition and processing were controlled by the Applied Biosystems (Foster City, Calif., USA) Analyst™ software for Windows NT™. 50-100 scans were performed by the positive ionization Q1 scan mode to accumulate the peaks. Sample solutions were diluted with 50% methanol in 0.5% formic acid to reach concentrations about 10 µg/ml. Each sample solution was introduced directly by a microsyringe (1 ml) through an infusion pump (Havard Apparatus 22; Havard Instruments; Holliston, Mass., USA) and fused silica capillary tubing at a rate of 20 ul/min. Thin layer chromatography (TLC) was done using Macherey Nagel Polygram® SIL G/UV$_{245}$. Visualisation was accomplished by means of UV light at 254 nm, followed by dyeing with potassium permanganate or ninhydrin. Solvents were distilled prior to use. All commercially available reagents were used without further purification. Analytical HPLC was performed using a Merck-Hitachi device: AcN-water (flow rate: 1 ml min$^{-1}$), column: LiChrosphere 5 um RP18e, 125×4.0 mm (Merck), pump: L-7100 Merck-Hitachi was used. Gradient A, B and C were used for the detection of the purified compounds in the examples. Characterisation of gradient A: starting from AcN-water (5/95) at t=0 min to AcN-water (50/50) within 15 min, to AcN-water (95/5) after additional 5 min, remaining for additional 3 min at AcN-water (95/5); characterisation of gradient B: starting from AcN-water (5/95) at t=0 min to AcN-water (60/40) within 15 min, to AcN-water (95/5) after additional 5 min, remaining for additional 10 min at AcN-water (95/5); characterisation of gradient C: starting from AcN-water (20/80) at t=0 min to AcN-water (95/5) within 30 min. Preparative HPLC was performed using a Merck-Hitachi device: AcN-water (flow rate: 6 ml/min), column: LUNA C18(2) 100A, 250×21.2 mm, 10µ (Merck), interface: D-7000, UV-VIS Detector: L-7420, pump: L-6250 Merck-Hitachi was used.

Table 1 Examples

Methods and Preparation of the Starting Materials

Preparation of
6-(2-methoxyphenyl)pyrimidin-4-amine, General
Procedure for Preparation of pyrimidines of Class A

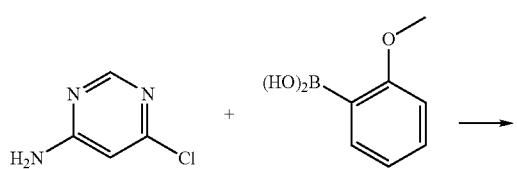

To a solution of 2-methoxyphenylboronic acid (20.0 g, 155 mmol) in 500 ml of 1,4-dioxane was added 200 ml of saturated aqueous sodium carbonate solution. Argon gas was purged for 30 min at room temperature. 4-Amino-6-chloropyrimidine (28.1 g, 186 mmol) and tetrakistriphenylphosphinepalladium (9.00 g, 77.5 mmol) were added to reaction mixture simultaneously and argon gas was bubbled for another 40 min The reaction mixture was heated to reflux for 16 h, TLC confirms completion of reaction and the mixture was concentrated under reduced pressure. The residue was partitioned between DCM and water. The organic layer was separated, washed with brine, water, dried ($Na_2SO_4$) and concentrated. The obtained crude residue purified through silica gel column chromatography eluting with 15% ethyl acetate in DCM to provide 6-(2-methoxyphenyl)pyrimidin-4-amine (18.0 g, 58%). $^1$H-NMR: (DMSO-$d_6$) δ=8.17 (1H, s), 7.71 (1H, d), 7.41 (1H, t), 6.96-7.06 (2H, m), 6.95 (1H, s), 3.98 (3H, s); MS (m/z)=202.1 (M+H).

Preparation of 2-chloro-N-(6-(5-fluoro-2-methoxyphenyl)-pyrimidin-4-yl)acetamide, General Procedure for Preparation of pyrimidines of Class B

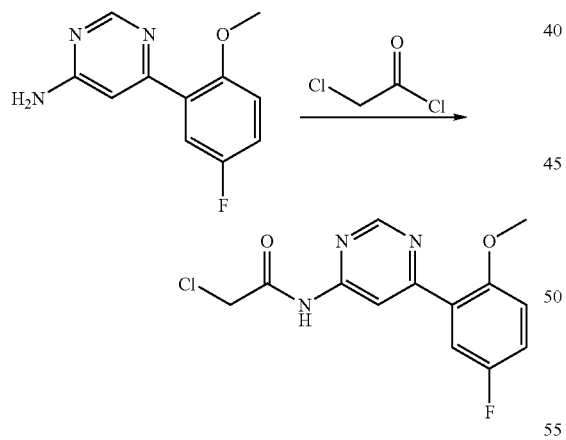

Chloro acetyl chloride (2.30 g, 1.62 ml, 20.4 mmol) was added slowly to a suspension of 6-(5-fluoro-2-methoxyphenyl)pyrimidin-4-amine (3.00 g, 13.7 mmol) in chloroform (15 ml) at room temperature. NEt$_3$ (2.80 g, 3.87 ml, 27.5 mmol) was added to the reaction mixture and stirred for 24 h. On completion of reaction, the volatile components were evaporated. The residue was purified by flash column chromatography over silica gel (200-400 mesh) using methanol (0-10%) in chloroform and dried to afford 2.20 g (54.4%) of the desired compound. $^1$H-NMR (400 MHz, DMSO-$d_6$): δ=11.27 (s, 1H), 8.97 (s, 1H), 8.75 (s, 1H), 7.75 (dd, 1H), 7.38 (m, 1H), 7.24 (m, 2H), 4.43 (s, 2H), 3.86 (s, 3H); ms (m/z): 296 (M+H); HPLC purity: 98.3%.

Preparation of 4-chloro-6-(2-methoxyphenyl)pyrimidine, General Procedure for Preparation of pyrimidines of Class C

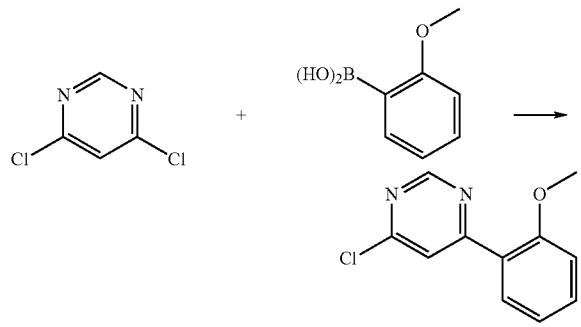

To a solution of 2-Methoxyphenyl boronic acid (10.0 g, 66.1 mmol) in THF (100 ml) and water (40 ml) 4,6 dichloropyrimidine (10.1 g, 67.8 mmol) was added. Palladium diacetate (750 mg, 3.30 mmol) and PPh$_3$ (1.76 g, 6.70 mmol) and sodium carbonate (21.3 g, 201 mmol) were added to reaction mixture at 0° C. The reaction mixture was stirred at room temperature overnight, reaction monitor by TLC. After completion of reaction, the reaction mixture was concentrated under reduced pressure. The residue was extracted with ethyl acetate and water. The organic layer was separated, washed with brine, dried (Na$_2$SO$_4$) and concentrated. The obtained crude residue purified through silica gel column chromatography eluting with 30% ethyl acetate in hexane to provide compound 9.0 g (61.9%) of the expected product.

Methods

Method 1: (Via Acid Chloride)

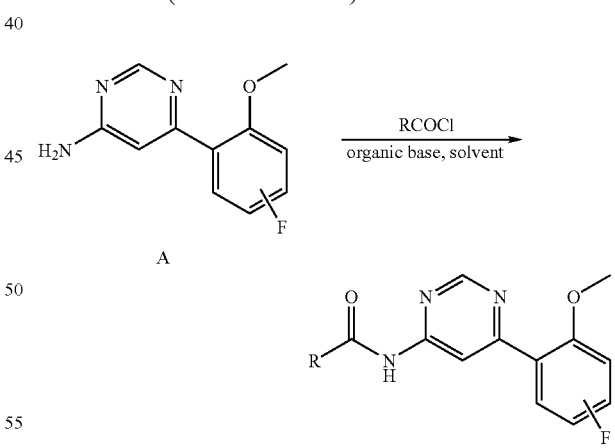

Thionyl chloride (2 eq) was added dropwise to a cooled mixture of an carboxylic acid RCOOH (1 eq) and 2 drops of dry DMF in dry DCM and stirred at room temperature (or heated at reflux) for 1-2 h. The volatiles were evaporated and the residual acid chloride dissolved in dry DCM/AcN. In another flask was taken a mixture of amine A (1 eq) and NEt$_3$ (3-4 eq) in dry DCM/AcN and the solution of acid chloride added dropwise at room temperature. The reaction mixture was stirred for 1-2 h and quenched into excess of sodium bicarbonate solution. The organic layer was separated and the aqueous layer extracted with DCM. The combined organic layers were washed successively with water and brine, dried (Na$_2$SO$_4$) and concentrated in vacuo to a crude residue. The residue was subjected to either preparative TLC/HPLC to isolate the pure compound.

Method 2: (Via HATU/HBTU Coupling)

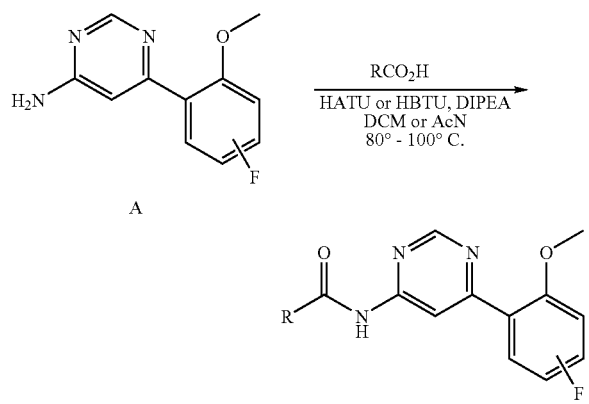

DIPEA (2 eq) was added to a solution of an carboxylic acid RCOOH (1 eq) in DCM or AcN and stirred for 15-20 min in a sealed tube. HATU or HBTU (1 eq) was added and the mixture was purged with argon for 10 min. The reaction mass was stirred at room temperature till a clear solution ensued. Amine A (1 eq) was added, the mixture purged again for 10 min and then heated at 80-100° C. in sealed tube for 2-18 h. The reaction mixture was cooled and worked up as in method 1. Purification by preparative TLC/HPLC afforded the pure compounds.

Method 3: (Via Chloroacetyl Derivative B)

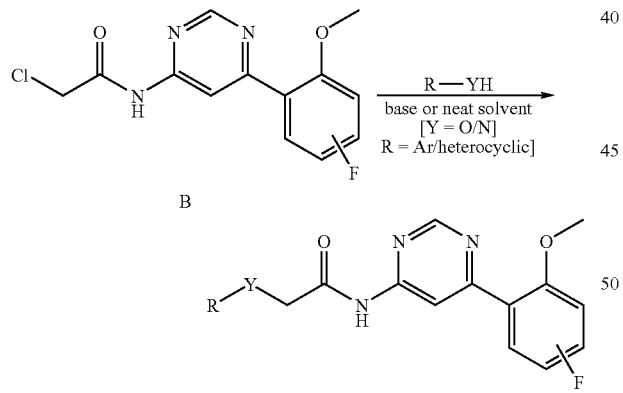

Amine/hydroxyl derivative R—YH (Y=O/N; 2 eq) [neat or with 2 eq of potassium carbonate] was taken in dry AcN/DMF and stirred for 0.5 h. A solution of the chloroacetyl derivative B (1 eq) in dry AcN/DMF was added and the whole mixture stirred at room temperature (or at 80-85° C.) for 2-8 h. The reaction mixture was diluted with excess water and extracted with ethyl acetate. The organic layer was then successively washed with water, brine, dried (Na$_2$SO$_4$) and concentrated to dryness in vacuo. The residue so obtained was subjected to preparative TLC/HPLC to afford the pure compounds.

Method 4: (Via Buchwald Type Reaction on Amides)

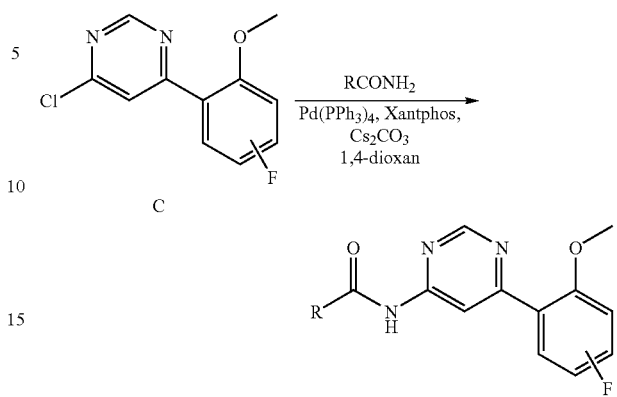

Tetrakis(triphenylphosphine)palladium (0) (5 mol %) was added to a mixture of amide RCONH$_2$ (1 eq) and C (1 eq) in dry 1,4-dioxane in a dry sealed tube and purged with argon for 15 min. Cesium carbonate (2 eq) and Xantphos (10 mol %) were added and the whole mass purged again with argon for 15 min and sealed. The reaction mixture was then heated at 120° C. for 3-6 h, before cooling to room temperature. It was then poured into excess water and extracted with ethyl acetate. The organic layer was washed with water, brine, dried (Na$_2$SO$_4$) and concentrated to dryness in vacuo. The residue so obtained was subjected to preparative TLC/HPLC to afford the pure compounds.

Method 5: (Via Suzuki-Coupling with the Organoboronic Acid and the Corresponding Chloro Pyrimidine)

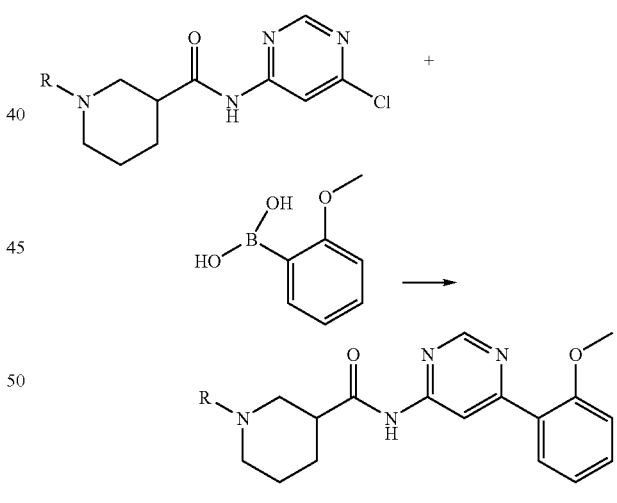

To a solution of the boronic acid (1.25 mmol) in a mixture of THF and water (6 ml, 1:1), 6-chloro-pyrimidin-4-ylcarbamoyl-piperidine (1.0 mmol) was added at 0° C., followed by palladium acetate (2.1 mmol), PPh$_3$ (2.1 mmol) and a saturated solution of sodium carbonate (2 ml). The reaction mixture was stirred at room temperature for 30 h and then filtered through a celite bed which was washed with ethyl acetate. The aqueous layer was extracted with ethyl acetate, the organic layers were combined, washed with brine, dried (Na$_2$SO$_4$) and evaporated under reduced pressure. The crude product was purified by column chromatography, using hexane/ethyl acetate as eluent, to provide the pure product.

Method 6: (Via Deprotection by Palladium Hydroxide Under Hydrogen Atmosphere)

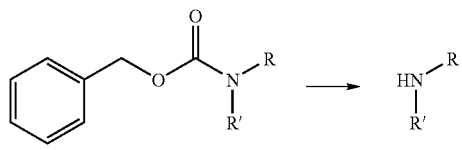

To a solution of the Cbz-protected compound (15 mmol) in 50 ml of methanol was added 20% palladium hydroxide (1.5 g) under an atmosphere of nitrogen and the mixture was stirred at room temperature under an atmosphere of hydrogen for 8 h. The reaction mixture was filtered through celite and the solvent was evaporated. The obtained mixture was taken in diethyl ether, stirred, filtered, washed with diethyl ether and dried under vacuum to obtain the crude product, which was purified by preparative TLC/HPLC.

Method 7: (Via Deprotection Under Acid Conditions by Means of HCl)

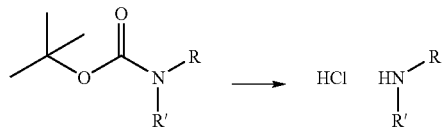

To a solution of the Boc-protected compound (1 mmol) in 20 ml of 1,4-dioxane was added a solution of HCl in 1,4-dioxane (4 M, 20 ml) at room temperature and the mixture was stirred for 3 h. After this the solvent was evaporated to give the crude amine hydrochloride salt, which was purified by preparative TLC/HPLC.

Method 8: (Via Mixed Anhydride)

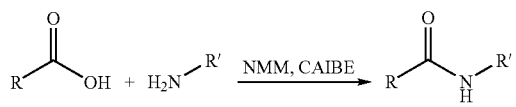

NMM (131 mg, 143 µl, 1.3 mmol) was added to a stirred and cooled solution (−15° C.) of the carbonic acid (1.3 mmol) in dry THF (4 ml). CAIBE (178 mg, 170 µl, 1.3 mmol) was added dropwise. After stirring for 15 min, appropriate amine (1.3 mmol) in dry THF (2 ml) was added and the mixture was stirred 14 h, during which time it was allowed to warm to room temperature. The solvent was evaporated in vacuo and the obtained residue was dissolved in ethyl acetate (10 ml), washed with 1N HCl, water, aqueous NaHCO$_3$, water and brine (5 ml per washing step) and dried over Na$_2$SO$_4$. After filtration the solvent was evaporated under reduced pressure. The crude compound was purified by a suitable chromatographic method.

Method 9: (Via Deprotection Under, Acid Conditions by Means of TFA)

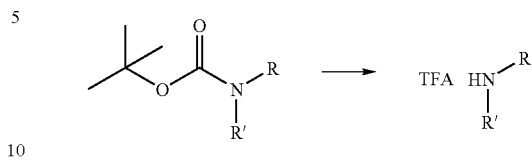

To a solution of the Boc-protected compound (0.1 mmol) in a small amount of DCM was added a mixture of TFA/DCM (4 ml, 1:1). This solution was stirred for 2 h at room temperature before the solvents were removed under reduced pressure. The resulted residue was purified by preparative TLC/HPLC.

Method 10: (Via Hydrogenation by Means of Raney Ni)

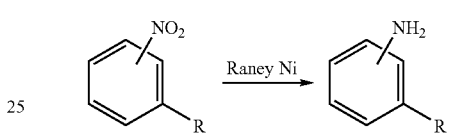

To a solution of the Nitro-derivative (2 mmol) in 10 ml of methanol was added Raney-Nickel (0.2 g) under an atmosphere of nitrogen and the mixture was stirred at room temperature under an atmosphere of hydrogen for 8 h. The reaction mixture was filtered through celite and the solvent was evaporated. The obtained mixture was taken in diethyl ether, stirred, filtered, washed with diethyl ether and dried under vacuum to obtain the crude product, which was purified by preparative TLC/HPLC.

Method 11: (Via Coupling with Methanesulfonyl Chloride)

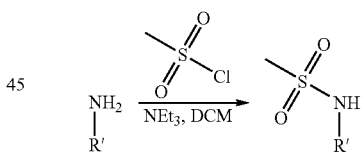

To a solution of the amine (1 mmol) and NEt$_3$ (2 mmol) in DCM (10 ml) was added methanesulfonyl chloride (1.05 mmol) at 0° C. After stirring for additional 0.5 h the reaction mixture was diluted with ethyl acetate (10 ml), washed with water and brine (5 ml per washing step) and dried over Na$_2$SO$_4$. After filtration the solvent was evaporated under reduced pressure. The crude compound was purified by a suitable chromatographic method.

Method 12: (Via Reaction of an Isocyanate with an Amine)

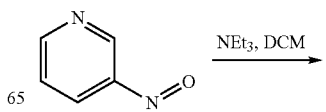

-continued

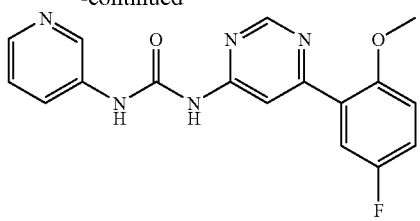

To a solution of an isocyanate (1 mmol) in toluene (10 ml) was added a solution of the amine (1 mmol) in toluene (2 ml) at 0° C. The resulting mixture was heated in a sealed tube at 130-140° C. for 36 h. The reaction mixture was diluted with ethyl acetate (10 ml), washed with water and brine (5 ml per washing step) and dried over $Na_2SO_4$. After filtration the solvent was evaporated under reduced pressure. The crude compound was purified by a suitable chromatographic method.

Synthesis of the Examples

Example 1

(3R)—N-(6-(2-methoxyphenyl)pyrimidin-4-yl)-N-methylpiperidine-3-carboxamide

Preparation of the precursor (R)-benzyl 3-(6-(2-methoxyphenyl)pyrimidin-4-ylcarbamoyl)piperidine-1-carboxylate To a solution of 6-(2-methoxyphenyl)pyrimidin-4-amine (5.80 g, 28.8 mmol) in 60 ml of DCM was added 4-dimethylaminopyridine (4.16 g, 34.0 mmol) followed by N-Cbz nipecotinic acid chloride (8.00 g, 28.4 mmol) [prepared from N-Cbz nipecotinic acid and oxalyl chloride] dropwise at room temperature. The reaction mixture stirred for 2 h and washed with water. The organic layer was separated, dried ($Na_2SO_4$) and concentrated. The obtained crude residue was passed through pad of silica gel eluting with 25% ethyl acetate in hexane to provide (R)-benzyl 3-(6-(2-methoxyphenyl)pyrimidin-4-yl-carbamoyl)piperidine-1-carboxylate (8.5 g, yield: 67%).
$^1$H-NMR: ($CDCl_3$) δ=8.95 (1H, s), 8.78 (1H, s), 8.20 (1H, bs), 7.91 (1H, dd), 7.45-7.35 (5H, m), 7.16-7.00 (2H, m), 5.20 (2H, s), 4.40-4.26 (1H, m), 4.18-4.02 (1H, m), 3.98 (3H, s), 3.41-3.17 (2H, m), 3.08-2.92 (1H, m), 2.60-2.41 (1H, m), 2.18-1.55 (4H, m); MS (m/z)=407.1.

Preparation of Example 1

To a solution of (R)-benzyl 3-(6-(2-methoxyphenyl)pyrimidin-4-yl-carbamoyl)piperidine-1-carboxylate (7.0 g) in 50 ml of methanol was added 10% palladium hydroxide (1.5 g) under an atmosphere of nitrogen and the mixture was stirred at room temperature under an atmosphere of hydrogen for 8 h. The reaction mixture was filtered through celite and the solvent was evaporated. The obtained mixture was taken in diethyl ether, stirred, filtered, washed with diethyl ether and dried under vacuum to obtain Example 1 as a white solid (3.5 g, yield: 72%).
$^1$H-NMR: (DMSO-$d_6$) δ=11.10 (1H, s), 8.95 (1H, s), 8.67 (1H, s), 7.84 (1H, d, J=10 Hz), 7.48 (1H, dd), 7.20-7.04 (2H, m), 3.98 (3H, s), 3.06-2.56 (5H, m), 1.96-1.32 (4H, m); MS (m/z)=312.9 (M+H); mp: 210-213° C.; Analytical purity: 95.5%; Chiral purity [R=91.62% and S=8.37%].

Example 2

N-(6-(5-fluoro-2-methoxyphenyl)pyrimidin-4-yl)piperidine-3-carboxamide*TFA

Preparation of the precursor 3-[6-(5-fluoro-2-methoxy-phenyl)-pyrimidin-4-ylcarbamoyl]-piperidine-1-carboxylic acid benzyl ester To a solution of 5-fluoro-2-methoxyphenyl boronic acid (0.20 g, 1.1 mmol) in a mixture of THF and water (6 ml, 1:1), benzyl 3-(6-chloropyrimidin-4-ylcarbamoyl)piperidine-1-carboxylate (0.35 g, 1.0 mmol) was added at 0° C. followed by palladium acetate (12 mg, 0.054 mmol), $PPh_3$ (31 mg, 0.12 mmol) and saturated solution of sodium carbonate (2 ml). The reaction mixture was stirred at room temperature for 30 h and then filtered through a celite bed which was washed with ethyl acetate. The aqueous layer was extracted with ethyl acetate, the organic layers were combined, washed with brine, dried and evaporated under reduced pressure. The crude product was purified by column chromatography, using hexane/ethyl acetate (4:1) as eluent, to provide 0.31 g (yield: 53.8%) of 3-[6-(5-fluoro-2-methoxy-phenyl)-pyrimidin-4-ylcarbamoyl]-piperidine-1-carboxylic acid benzyl ester Preparation of Example 2

A mixture of 3-[6-(5-fluoro-2-methoxy-phenyl)-pyrimidin-4-ylcarbamoyl]-piperidine-1-carboxylic acid benzyl ester (0.25 g, 0.5 mmol), methanol (7 ml) and 20% palladium hydroxide (0.12 g, 50% w/w) was stirred overnight under an atmosphere of hydrogen. Then it was filtered through a celite bed which was washed with methanol. The filtrates were evaporated under reduced pressure and purified by column chromatography to give 0.125 g of the desired product along with a nonseparable impurity. Further purification by preparative HPLC gave 2 mg (yield: 0.8%) of N-(6-(5-fluoro-2-methoxyphenyl)pyrimidin-4-yl)piperidine-3-carboxamide as TFA salt.
$^1$H NMR (400 MHz, DMSO-$d_6$ and $D_2O$): δ 1.6-1.7 (m, 2H), 1.75-1.9 (m, 1H), 2-2.1 (m, 1H), 2.8-3.0 (m, 2H), 3.0-3.1 (m, 1H), 3.15-3.2 (m, 1H), 3.3-3.35 (m, 1H), 3.8 (s, 3H), 7.1-7.2 (m, 1H), 7.35-7.4 (m, 1H), 7.6-7.7 (m, 1H), 8.8 (s, 1H), 8.9 (s, 1H); MS (m/z): 331 (M+H).

Example 3

N-(6-(2-fluoro-6-methoxyphenyl)pyrimidin-4-yl)piperidine-3-carboxamide*TFA

Preparation of the precursor 3-[6-(2-fluoro-6-methoxy-phenyl)-pyrimidin-4-ylcarbamoyl]-piperidine-1-carboxylic acid benzyl ester To a solution of 2-fluoro-6-methoxyphenyl boronic acid (0.20 g, 1.1 mmol) in a mixture of THF and water (6 ml, 1:1), 3-(6-chloro-pyrimidin-4-ylcarbamoyl)-piperidine-1-carboxylic acid benzyl ester (0.35 g, 0.93 mmol) was added at 0° C. followed by palladium acetate (12 mg, 54 µmol), $PPh_3$ (31 mg, 0.12 mmol) and saturated solution of sodium carbonate (2 ml). The reaction mixture was stirred at room temperature for 30 h and then filtered through a celite bed which was washed with ethyl acetate. The aqueous layer was extracted with ethyl acetate, the organic layers were combined, washed with brine, dried and evaporated under reduced pressure. The crude product was purified by column chromatography, using hexane/ethyl acetate (4:1) as eluent, to provide 0.31 g (yield:

66.7%) of 3-[6-(2-fluoro-6-methoxy-phenyl)-pyrimidin-4-ylcarbamoyl]-piperidine-1-carboxylic acid benzyl ester.

Preparation of Example 3

A mixture of 3-[6-(2-fluoro-6-methoxy-phenyl)-pyrimidin-4-ylcarbamoyl]-piperidine-1-carboxylic acid benzyl ester (0.3 g, 0.6 mmol), methanol (7 ml) and 20% palladium hydroxide (0.12 g, 50% w/w) was stirred overnight under an atmosphere of hydrogen. Then it was filtered through a celite bed which was washed with methanol. The filtrates were evaporated under reduced pressure and purified by column chromatography to give 0.2 g (93.8% yield) of the desired product along with a nonseparable impurity. Further purification by preparative HPLC gave 2 mg (yield: 0.9%) of N-(6-(2-fluoro-6-methoxyphenyl)pyrimidin-4-yl)piperidine-3-carboxamide as TFA salt.

$^1$H NMR (400 MHz, DMSO-$d_6$ and $D_2O$): δ=1.6-1.7 (m, 2H), 1.75-1.8 (m, 2H), 2-2.1 (m, 2H), 3.0-3.2 (m, 2H), 3.3-3.35 (m, 1H), 3.6 (s, 3H), 6.8-6.9 (m, 1H), 6.95-7.0 (m, 1H), 7.4-7.5 (m, 1H), 8.1 (s, 1H), 8.9 (s, 1H); MS (m/z): 331 (M+H).

Example 4

N-(6-(2,6-dimethoxyphenyl)pyrimidin-4-yl)piperidine-3-carboxamide*TFA

Preparation of the Precursor 3-[6-(2,6-dimethoxy-phenyl)-pyrimidin-4-ylcarbamoyl]-piperidine-1-carboxylic acid benzyl ester To a solution of 2,6-dimethoxyphenyl boronic acid (0.60 g, 3.3 mmol) in a mixture of dimethoxyethane/water (8 ml, 3:1), 3-(6-chloro-pyrimidin-4-ylcarbamoyl)-piperidine-1-carboxylic acid benzyl ester (0.82 g, 2.2 mmol) was added followed by tetrakis(triphenylphospine) palladium(0) (0.15 g, 0.13 mmol) and saturated solution of potassium carbonate (2 ml). The reaction mixture was heated at 90° C. for 2 h, then it was cooled to room temperature and filtered through a celite bed which was washed with ethyl acetate. The aqueous layer was extracted with ethyl acetate, the organic layers were combined, washed with brine, dried ($Na_2SO_4$) and evaporated under reduced pressure. The crude product was purified by column chromatography, using hexane/ethyl acetate (4:1) as eluent, to provide 0.80 g (yield: 53%) of 3-[6-(2,6-dimethoxy-phenyl)-pyrimidin-4-ylcarbamoyl]-piperidine-1-carboxylic acid benzyl ester.

Preparation of Example 4

Method: 6, Yield: 0.2%.

A mixture of 3-[6-(2,6-dimethoxy-phenyl)-pyrimidin-4-ylcarbamoyl]-piperidine-1-carboxylic acid benzyl ester (800 mg, 1.68 mmol), methanol (7 ml) and 20% palladium hydroxide (400 mg, 50% w/w) was stirred overnight under an atmosphere of hydrogen. Then it was filtered through a celite bed which was washed with methanol. The filtrates were evaporated under reduced pressure and purified by column chromatography to give 120 mg of the desired product along with a nonseparable impurity. Further purification by preparative HPLC gave 2 mg of piperidine-3-carboxylic acid [6-(2,6-dimethoxy-phenyl)-pyrimidin-4-yl]-amide as TFA salt.

$^1$H NMR (400 MHz, DMSO-$d_6$ and $D_2O$): δ 1.6-1.7 (m, 2H), 1.75-1.9 (m, 1H), 2-2.1 (m, 1H), 2.8-3.0 (m, 2H), 3.0-3.1 (m, 1H), 3.15-3.2 (m, 1H), 3.3-3.35 (m, 1H), 3.6 (s, 6H), 6.8 (d, 2H), 7.35-7.5 (m, 1H), 7.9 (s, 1H), 8.9 (s, 1H); MS (m/z): 342 (M+H).

Examples 5 and 6

N-(6-(2-methoxyphenyl)pyrimidin-4-yl)-6-oxopiperidine-3-carboxamide, Preparation of the Racemic Mixture To a solution of 6-oxo-piperidine 3-carboxylic acid (0.21 g, 1.5 mmol) in dry DMF (10 ml) was added HBTU (1.13 g, 2.98 mmol), and DIPEA (0.30 g, 0.39 ml, 2.3 mmol) under ice cooled condition, then it was allowed to stir at room temperature for 45 min. To this reaction mixture was added the amine A (0.30 g, 1.5 mmol) in dry DMF dropwise under ice cooled condition. The reaction mixture was then heated for 4 h at 120° C. After the completion of reaction it was cooled, DMF was evaporated completely and then it was dissolved in ethyl acetate (30 ml), and was washed with water (2×15 ml), and then with brine, dried ($Na_2SO_4$), evaporated under reduced pressure. Final purification was done by column chromatography using flash silica gel (10% methanol/DCM) provided 78 mg (yield: 17%) of the desired product.

Separation of the Racemic Mixture of N-(6-(2-methoxyphenyl)pyrimidin-4-yl)-6-oxopiperidine-3-carboxamide to the Examples 5 and 6

Examples 5 and 6 were separated into the enantiomers by purification with chiral HPLC starting from 82.5 mg of the racemate yielding 40 mg of each enantiomer, utilizing the methods:

Preparative methode: Column: 250×50 mm CHIRAL-PAK® AD-H 5 μm; Mobile phase: heptane/ethanol/diethylamine: 70/30/0.1; Flow rate: 120 ml/min; Detection: UV 325 nm; Temperature: 25° C.;

Analytical methode: Column: 250×4.6 mm CHIRAL-PAK® IB 5 μm; Mobile phase: heptane/ethanol/diethylamine: 70/30/0.1; Flow rate: 1 ml/min; Detection: DAD 280 nm; Temperature: 30° C.

Example 5

$^1$H NMR (400 MHz, $CD_3OD$): δ=2.02-2.08 (m, 1H), 2.12-2.20 (m, 1H), 2.40-2.48 (m, 2H), 2.92-3.02 (m, 1H), 3.46-3.54 (m, 2H), 3.90 (s, 3H), 7.07 (t, 1H), 7.15 (d, 1H), 7.47 (t, 1H), 7.77 (d, 1H), 8.66 (s, 1H), 8.84 (s, 1H); MS (m/z): 327 (M+H); HPLC (λ=280 nm, [Analytical methode]): rt 14.1 min (99.3%); mp: 205-208° C.; Spec. opt. rot.: 41.08.

Example 6

$^1$H NMR (400 MHz, $CD_3OD$): δ=2.02-2.08 (m, 1H), 2.12-2.20 (m, 1H), 2.40-2.48 (m, 2H), 2.92-3.02 (m, 1H), 3.46-3.54 (m, 2H), 3.90 (s, 3H), 7.07 (t, 1H), 7.15 (d, 1H), 7.47 (t, 1H), 7.77 (d, 1H), 8.66 (s, 1H), 8.84 (s, 1H); MS (m/z): 327 (M+H); HPLC (λ=280 nm, [Analytical methode]): rt 18.5 min (99.0%); mp: 203-207° C.; Spec. opt. rot.: −40.67.

Example 7

N-(6-(2-methoxyphenyl)pyrimidin-4-yl)-2-(pyridin-4-yl)acetamide

Example 7 was synthesized according to Method 4 in a yield of 41%, purified by flash column chromatography over silica gel (200-400 mesh) using methanol (0-10%) in chloroform.

¹H NMR (400 MHz, CD₃OD): δ=2.69-2.73 (m, 2H), 3.31 (s, 3H), 3.43-3.49 (m, 3H), 3.50-3.53 (m, 2H), 3.75 (dd, 1H), 3.82 (t, 1H), 3.91 (s, 3H), 7.10 (td, 1H), 7.17 (d, 1H), 7.49-7.54 (m, 1H), 7.74 (dd, 1H), 8.70 (d, 1H), 8.89 (d, 1H); MS (m/z): 371 (M+H); HPLC (λ=214 nm, [A]): rt 12.0 min (99%).

Example 8

N-(6-(2-methoxyphenyl)pyrimidin-4-yl)-1-methyl-5-oxopyrrolidine-3-carboxamide

Example 8 was synthesized according to Method 4 in a yield of 51%, purified by flash column chromatography over silica gel (200-400 mesh) using methanol (0-10%) in chloroform.

¹H NMR (400 MHz, CD₃OD): δ=2.70 (d, 2H, CH—CH₂), 2.82 (s, 3H, CH₃), 3.45-3.53 (m, 1H, CH—CH₂), 3.65-3.74 (m, 2H, CH₂), 3.90 (s, 3H, O—CH₃), 7.10 (t, ³J=7.5 Hz, 1H, Methoxy-Ar), 7.18 (d, ³J=8.3 Hz, 1H, Methoxy-Ar), 7.49-7.54 (m, 1H, Methoxy-Ar), 7.75 (dd, ³J=7.9 Hz, ⁴J=1.6 Hz, 1H, Methoxy-Ar), 8.70 (d, ⁵J=0.8 Hz, 1H, Pyrimidin-Ar), 8.89 (s, br., 1H, Pyrimidin-Ar); MS (m/z): 327 (M+H); HPLC (λ=214 nm, [A]): rt 11.3 min (98%).

Example 9

1-ethyl-N-(6-(2-methoxyphenyl)pyrimidin-4-yl)-5-oxopyrrolidine-3-carboxamide

Example 9 was synthesized according to Method 4 in a yield of 56.7%, purified by flash column chromatography over silica gel (200-400 mesh) using methanol (0-10%) in chloroform.

¹H NMR (400 MHz, CD₃OD): δ=1.10-1.15 (m, 3H, CH₂—CH₃), 2.71 (d, ³J=7.9 Hz, 2H, CH₂—CH₃), 3.30-3.33 (m, 2H, CH₂—CH), 3.42-3.52 (m, 1H, CH₂—CH), 3.66-3.76 (m, 2H, CH₂—CH), 3.90 (d, 3H, O—CH₃), 7.07-7.12 (m, 1H, Methoxy-Ar), 7.19 (d, ³J=8.3 Hz, 1H, Methoxy-Ar), 7.49-7.54 (m, 1H, Methoxy-Ar), 7.74 (dd, ³J=7.9 Hz, ⁴J=1.7 Hz, 1H, Methoxy-Ar), 8.70 (d, ⁵J=1.2 Hz, 1H, Pyrimidin-Ar), 8.90 (d, ⁵J=1.2 Hz, 1H, Pyrimidin-Ar); MS (m/z): 341 (M+H); HPLC (λ=214 nm, [A]): rt 12.4 min (99%).

Example 10

N-(6-(5-fluoro-2-methoxyphenyl)pyrimidin-4-yl)cyclopropane-1,1-dicarboxamide

Example 10 was synthesized according to Method 4, purified by preparative HPLC using Sunfire C18 column (250×50 mm; 10μ) Mobile phase: 0.1% formic acid (aq): AcN (50:50) and flow rate: 118 ml/min, λ=210 nm.

¹H NMR (400 MHz, DMSO-d₆): δ=12.58 (s, 1H), 8.93 (s, 1H), 8.72 (s, 1H), 7.73-7.70 (dd, 1H), 7.52 (s, br., 1H), 7.35-7.32 (m, 2H), 7.24-7.20 (m, 1H), 3.86 (s, 3H), 1.56 (d, 4H); MS (m/z): 331 (M+H); HPLC (λ=214 nm, [A]): it 13.5 min (100%); mp: 190° C.

Example 11

N-(6-(5-fluoro-2-methoxyphenyl)pyrimidin-4-yl)-1,4,5,6-tetrahydro-6-oxo-1-propylpyridazine-3-carboxamide Example 11 was synthesized according to Method 4, purified by preparative HPLC using Zodiacsil 120-5-C18 column (250×32 mm; 10μ), Mobile phase: 0.01M NH₄OAc (aq): AcN (35:65) and flow rate: 4 ml/min.

¹H NMR (400 MHz, CDCl₃): δ=9.41 (s, 1H), 8.96 (s, 1H), 8.88 (s, 1H), 7.78-7.75 (dd, 1H), 7.16-7.11 (m, 1H), 6.99-6.95 (m, 1H), 3.93 (s, 3H), 3.83 (t, 2H), 2.97 (t, 2H), 2.60 (t, 2H), 1.78-1.70 (m, 2H), 0.96 (t, 3H); MS (m/z): 386 (M+H); HPLC (λ=214 nm, [A]): rt 19.0 min (100%); mp: 200° C.

Example 12

1-sec-butyl-N-(6-(2-methoxyphenyl)pyrimidin-4-yl)-5-oxopyrrolidine-3-carboxamide Example 12 was synthesized according to Method 4 in a yield of 36.2%, purified by flash column chromatography over silica gel (200-400 mesh) using methanol (0-10%) in chloroform.

NMR (400 MHz, CD₃OD): δ=0.86 (td, ³J=7.5 Hz, ⁴J=2.1 Hz, 3H, CH₂—CH₃), 1.15 (d, ³J=6.6 Hz, 3H, CH—CH₃), 1.48-1.59 (m, 2H, CH₂—CH₃), 2.71-2.75 (m, 2H, CH—CH₂—C(O)), 3.42-3.52 (m, 1H, CH—C(O)), 3.55-3.70 (m, 2H, N—CH₂), 3.91 (d, 3H, O—CH₃), 3.99-4.06 (m, 1H, CH—N), 7.10 (td, ³J=7.5 Hz, ⁴J=0.8 Hz, 1H, Methoxy-Ar), 7.18 (d, ³J=8.3 Hz, 1H, Methoxy-Ar), 7.49-7.54 (m, 1H, Methoxy-Ar), 7.75 (dd, ³J=7.9 Hz, ⁴J=1.7 Hz, 1H, Methoxy-Ar), 8.70 (s, 1H, Pyrimidin-Ar), 8.90 (s, 1H, Pyrimidin-Ar); MS (m/z): 369 (M+H); HPLC (λ=214 nm, [A]): rt 13.2 min (100%).

Example 13

N-(6-(2-methoxyphenyl)pyrimidin-4-yl)-1-(3-methoxypropyl)-5-oxopyrrolidine-3-carboxamide Example 13 was synthesized according to Method 4 in a yield of 44.3%, purified by flash column chromatography over silica gel (200-400 mesh) using methanol (0-10%) in chloroform.

¹H NMR (400 MHz, CD₃OD): δ=1.79 (qu, ³J=6.6 Hz, 2H, CH₂—Ch—CH₂), 2.68-2.72 (m, 2H, CH₂), 3.29 (s, 3H, CH₃), 3.31-3.50 (m, 5H, CH₂), 3.65-3.75 (m, 2H, CH₂), 3.88 (s, 3H, O—CH₃), 7.05 (t, ³J=7.5 Hz, 1H, Methoxy-Ar), 7.13 (d, ³J=8.3 Hz, 1H, Methoxy-Ar), 7.42-7.48 (m, 1H, Methoxy-Ar), 7.75 (dd, ³J=7.9 Hz, ⁴J=2.1 Hz, 1H, Methoxy-Ar), 8.66 (s, 1H, Pyrimidin-Ar), 8.82 (s, 1H, Pyrimidin-Ar); MS (m/z): 385 (M+H); HPLC (λ=214 nm, [A]): rt 11.1 min (96.2%).

Example 14

N-(6-(4-fluoro-2-methoxyphenyl)pyrimidin-4-yl)-6-oxopiperidine-3-carboxamide

Example 14 was synthesized according to Method 2 in a yield of 47.6%, purified by flash column chromatography over silica gel (200-400 mesh) using methanol (0-10%) in chloroform, followed by preparative HPLC using LUNA C18 (2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

MS (m/z): 345 (M+H); HPLC (λ=214 nm, [A]): rt 9.7 min (100%); mp: 148° C.

Example 15

N-(6-(2-ethoxyphenyl)pyrimidin-4-yl)-6-oxopiperidine-3-carboxamide

Example 15 was synthesized according to Method 2 in a yield of 5.2%, purified by flash column chromatography over silica gel (200-400 mesh) using methanol (0-10%) in chloroform, followed by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

MS (m/z): 341 (M+H); HPLC (λ=214 nm, [B]): rt 11.2 min (99.7%); mp: 117° C.

Example 16

N-(6-(2-ethoxy-5-fluorophenyl)pyrimidin-4-yl)-6-oxopiperidine-3-carboxamide

Example 16 was synthesized according to Method 2 in a yield of 4.1%, purified by flash column chromatography over silica gel (200-400 mesh) using methanol (0-10%) in chloroform, followed by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

MS (m/z): 359 (M+H); HPLC (λ=214 nm, [B]): rt 11.3 min (95.2%); mp: 208° C.

Example 17

N-(6-(5-fluoro-2-methoxyphenyl)pyrimidin-4-yl)-6-oxopiperidine-3-carboxamide Example 17 was synthesized according to Method 2 in a yield of 5.5%, purified by preparative HPLC using Zodiacsil 120-5-C18 column (250×32 mm; 10μ), Mobile phase: 0.01M NH$_4$OAc (aq): AcN (35:65) and flow rate: 48 ml/min.

$^1$H NMR (400 MHz, DMSO-d$_6$): δ=11.06 (s, 1H), 8.94 (s, 1H), 8.76 (s, 1H), 7.72-7.69 (dd, 1H), 7.50 (s, 1H), 7.36-7.32 (m, 1H), 7.25-7.21 (m, 1H), 3.87 (s, 3H), 3.27 (merged with solvent, ~2H), 2.98-2.96 (m, 1H), 2.24-2.18 (m, 2H), 2.01 (m, 1H), 1.89 (m, 1H); MS (m/z): 345 (M+H); HPLC (λ=214 nm, [A]): rt 11.4 min (97%); mp: 245° C.

Example 18

N-(6-(5-fluoro-2-methoxyphenyl)pyrimidin-4-yl)-5-oxopyrrolidine-3-carboxamide Example 18 was synthesized according to Method 2 in a yield of 11.7%, purified by preparative TLC using silica gel (GF254) and eluting with 5% MeOH in chloroform.

$^1$H NMR (400 MHz, CD$_3$OD): δ=8.86 (s, 1H), 8.78 (s, 1H), 7.65-7.62 (dd, 1H), 7.24-7.14 (m, 2H), 3.91 (s, 3H), 3.72-3.56 (m, 4H), 2.72-2.58 (m, 3H); MS (m/z): 331 (M+H); HPLC (λ=214 nm, [A]): rt 10.9 min (100%); mp: 222° C.

Example 19

N-(6-(5-fluoro-2-methoxyphenyl)pyrimidin-4-yl)-2,6-dioxopiperidine-4-carboxamide Example 19 was synthesized according to Method 2 in a yield of 3.5%, purified initially by flash column chromatography over silica gel (100-200 mesh) using 0-4% MeOH in chloroform and further by preparative HPLC using Kromasil C18 (250×30 mm; 10μ) column. Mobile phase: 0.01M NH$_4$OAc in AcN: AcN(70:30) and flow rate: 42 ml/min λ=210 nm.

$^1$H NMR (400 MHz, DMSO-d$_6$): δ=11.12 (s, 1H), 10.78 (s, 1H), 8.95 (s, 1H), 8.70 (s, 1H), 7.71-7.68 (dd, 1H), 7.37-7.32 (m, 1H), 7.24-7.20 (m, 1H), 3.86 (s, 3H), 3.36-3.33 (m, 1H), 2.79-2.64 (m, 4H); 359 MS (m/z): (M+H); HPLC (λ=214 nm, [A]): rt 12.0 min (96%); mp: 160° C.

Example 20

N-(6-(5-fluoro-2-methoxyphenyl)pyrimidin-4-yl)-2-oxopyrrolidine-1-carboxamide Example 20 was synthesized according to Method 4 in a yield of 12.4%, purified by flash column chromatography over silica gel (100-200 mesh) using 0-20% ethyl acetate in petroleum ether.

$^1$H NMR (400 MHz, CDCl$_3$): δ=9.07 (s, 1H), 9.1 (s, 1H), 7.77-7.74 (dd, 1H), 7.15-7.10 (m, 1H), 6.98-6.95 (m, 1H), 4.15 (t, 2H), 3.93 (s, 3H), 2.71 (t, 2H), 2.23-2.17 (m, 2H); MS (m/z): 288 (M+H); HPLC (λ=214 nm, [A]): rt min (100%); mp: 137° C.

Example 21

N-(6-(5-fluoro-2-methoxyphenyl)pyrimidin-4-yl) cyclopropane-1,1-dicarboxamide Example 21 was synthesized according to Method 2 in a yield of 7.3%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

$^1$H NMR (400 MHz, DMSO-d$_6$): δ=1.52-1.56 (m, 4H, CH$_2$), 3.84 (s, 3H, CH$_3$), 7.06-7.10 (m, 1H, Methoxy-Ar), 7.18 (d, $^3$J=7.9 Hz, 1H, Methoxy-Ar), 7.34 (s, br., 1H, HN), 7.45-7.52 (m, 1H, Methoxy-Ar), 7.87 (dd, $^3$J=7.5 Hz, $^4$J=1.7 Hz, 1H, Methoxy-Ar), 8.63 (d, $^5$J=1.2 Hz, 1H, Pyrimidin-Ar), 8.90 (d, $^5$J=1.2 Hz, 1H, Pyrimidin-Ar); MS (m/z): 313 (M+H); HPLC (λ=214 nm, [C]): rt 6.8 min (90%).

Example 22

(S)-tert-butyl 2-(6-(2-methoxyphenyl)pyrimidin-4-ylcarbamoyl)pyrrolidine-1-carboxylate Example 22 was synthesized according to Method 4 in a yield of 55.8%, purified by flash column chromatography over silica gel (200-400 mesh) using methanol (0-10%) in chloroform.

$^1$H NMR (400 MHz, CDCl$_3$): δ=1.47 (s, 9H, tert.-Bu), 1.89-1.96 (m, 2H, CH$_2$), 2.16-2.32 (m, 1H, CH$_2$), 2.34-2.49 (m, 1H, CH$_2$), 3.34-3.58 (m, 2H, CH$_2$), 3.91 (s, 3H, CH$_3$), 4.44-4.51 (m, 1H, CH—CH$_2$), 6.99 (d, $^3$J=8.3 Hz, 1H, Methoxy-Ar), 7.05 (t, $^3$J=7.5 Hz, 1H, Methoxy-Ar), 7.38-7.43 (m, 1H, Methoxy-Ar), 7.89 (s, br., 1H, Methoxy-Ar), 8.73 (s, br., 1H, Pyrimidin-Ar), 9.10 (d, $^5$J=1.2 Hz, 1H, Pyrimidin-Ar); 399 MS (m/z): (M+H); HPLC (λ=214 nm, [C]): rt 13.1 min (100%).

Example 23

(2S)—N-(6-(2-methoxyphenyl)pyrimidin-4-yl)pyrrolidine-2-carboxamide*HCl

Example 23 was synthesized according to Method 7 in a yield of 95%, purified by washing with ethyl ether.

$^1$H NMR (400 MHz, CD$_3$OD): δ=2.08-2.14 (m, 2H, CH$_2$), 2.14-2.25 (m, 1H, CH$_2$), 2.53-2.63 (m, 1H, CH$_2$), 3.38-3.52 (m, 2H, CH$_2$), 3.95 (s, 3H, CH$_3$), 4.62 (dd, $^3$J=8.7 Hz, $^3$J=6.6 Hz, 1H, CH—CH$_2$), 7.19 (td, $^3$J=7.5 Hz, $^4$J=0.8 Hz, 1H, Methoxy-Ar), 7.27 (d, $^3$J=8.3 Hz, 1H, Methoxy-Ar), 7.62-

7.67 (m, 1H, Methoxy-Ar), 7.75 (dd, $^3J$=7.9 Hz, $^4J$=1.7 Hz, 1H, Methoxy-Ar), 8.75 (d, $^5J$=1.2 Hz, 1H, Pyrimidin-Ar), 9.10 (d, $^5J$=1.2 Hz, 1H, Pyrimidin-Ar); MS (m/z): 299 (M+H); HPLC (λ=214 nm, [A]): rt 8.1 min (96%).

Example 24

N-(6-(2-ethoxy-4-fluorophenyl)pyrimidin-4-yl)-6-oxopiperidine-3-carboxamide

Example 24 was synthesized according to Method 2 in a yield of 1.5%, purified by flash column chromatography over silica gel (200-400 mesh) using methanol (0-10%) in chloroform, followed by preparative HPLC using LUNA C18(2) 100A column (250×21.2 mm; 10µ), Mobile phase: 0.1% TFA (aq): gradient AcN-water (40/60) at t=0 min to AcN-water (95/5) within 45 min, flow rate: 6 ml/min.

MS (m/z): 359 (M+H); HPLC (λ=214 nm, [A]): rt 10.9 min (100%); mp: 222° C.

Example 25

N-(6-(4-fluoro-2-isopropoxyphenyl)pyrimidin-4-yl)-6-oxopiperidine-3-carboxamide

Example 25 was synthesized according to Method 2 in a yield of 2.1%, purified by preparative HPLC using LUNA C18(2) 100A column (250×21.2 mm; 10µ, Mobile phase: 0.1% TFA (aq): gradient AcN-water (40/60) at t=0 min to AcN-water (95/5) within 45 min, flow rate: 6 ml/min.

MS (m/z): 373 (M+H); HPLC (λ=214 nm, [B]): rt 11.8 min (100%); mp: 105° C.

Example 26

N-(6-(5-fluoro-2-isopropoxyphenyl)pyrimidin-4-yl)-6-oxopiperidine-3-carboxamide

Example 26 was synthesized according to Method 2 in a yield of 18.7%, purified by preparative HPLC using LUNA C18(2) 100A column (250×21.2 mm; 10µ), Mobile phase: 0.1% TFA (aq): gradient AcN-water (40/60) at t=0 min to AcN-water (95/5) within 45 min, flow rate: 6 ml/min.

MS (m/z): 373 (M+H); HPLC (λ=214 nm, [B]): rt 12.2 min (96.4%); mp: 236° C.

Example 27

N-(6-(2-methoxyphenyl)pyrimidin-4-yl)cyclopentanecarboxamide

Example 27 was synthesized according to Method 2 in a yield of 11.2%, purified by preparative HPLC using LUNA C18(2) 100A column (250×21.2 mm; 10µ), Mobile phase: 0.1% TFA (aq): gradient AcN-water (40/60) at t=0 min to AcN-water (95/5) within 45 min, flow rate: 6 ml/min.

MS (m/z): 298 (M+H); HPLC (λ=214 nm, [B]): it 17.1 min (98.1%).

Example 28 tert-butyl 2-(6-(2-methoxyphenyl)pyrimidin-4-ylcarbamoyl)-4,4-difluoropyrrolidine-1-carboxylate Example 28 was synthesized according to Method 4 in a yield of 70.2%, purified by flash column chromatography over silica gel (200-400 mesh) using methanol (0-10%) in chloroform.

$^1$H NMR (400 MHz, CD$_3$OD, Rotameres): δ=1.36, 1.47 (s, 9H, tert.-Bu), 2.49-2.62 (m, 1H, CH$_2$), 2.80-2.90 (m, 1H, CH$_2$), 3.80-3.88 (m, 2H, CH$_2$), 3.91 (s, 3H, CH$_3$), 4.59-4.64, 4.65-4.71 (m, 1H, CH—CH$_2$), 7.08 (t, $^3J$=7.5 Hz, 1H, Methoxy-Ar), 7.17 (d, $^3J$=8.3 Hz, 1H, Methoxy-Ar), 7.47-7.53 (m, 1H, Methoxy-Ar), 7.75-7.81 (m, 1H, Methoxy-Ar), 8.68-8.74 (m, 1H, Pyrimidin-Ar), 8.89 (s, br., 1H, Pyrimidin-Ar); MS (m/z): 435 (M+H); HPLC (λ=214 nm, [C]): rt 16.1 min (100%).

Example 29

4,4-difluoro-N-(6-(2-methoxyphenyl)pyrimidin-4-yl) pyrrolidine-2-carboxamide*HCl Example 29 was synthesized according to Method 7 in a yield of 93%, purified by washing with ethyl ether.

$^1$H NMR (400 MHz, CD$_3$OD): δ=2.80-2.94 (m, 1H, CH$_2$), 3.09-3.21 (m, 1H, CH$_2$), 3.88-3.97 (m, 2H, CH$_2$), 3.96 (s, 3H, CH$_3$), 4.98 (t, $^3J$=8.7 Hz, 1H, CH—CH$_2$), 7.17-7.22 (m, 1H, Methoxy-Ar), 7.28 (d, $^3J$=7.9 Hz, 1H, Methoxy-Ar), 7.63-7.68 (m, 1H, Methoxy-Ar), 7.76 (dd, $^3J$=7.9 Hz, $^4J$=1.7 Hz, 1H, Methoxy-Ar), 8.74 (s, br., 1H, Pyrimidin-Ar), 8.89 (d, $^5J$=0.8 Hz, 1H, Pyrimidin-Ar); MS (m/z): 335 (M+H); HPLC (λ=214 nm, [A]): rt 9.3 min (96.3%).

Example 30

2-amino-N-(6-(2-methoxyphenyl)pyrimidin-4-yl) cyclohexanecarboxamide*HCl

Example 30 was synthesized according to Method 2 in a yield of 23.1%, followed Method 7, purified by preparative HPLC using LUNA C18(2) 100A column (250×21.2 mm; 10µ), Mobile phase: 0.1% TFA (aq): gradient AcN-water (40/60) at t=0 min to AcN-water (95/5) within 45 min, flow rate: 6 ml/min.

MS (m/z): 327 (M+H); HPLC (λ=214 nm, [A]): rt 10.1 min (94.1%).

Example 31

3-amino-N-(6-(2-methoxyphenyl)pyrimidin-4-yl) cyclohexanecarboxamide*HCl

Example 31 was synthesized according to Method 7 in a yield of 81% starting from Example 32, purified by washing with ethyl ether.

MS (m/z): 327 (M+H); HPLC (λ=214 nm, [A]): it 9.9 min (100%).

Example 32 tert-butyl 3-(6-(2-methoxyphenyl)pyrimidin-4-ylcarbamoyl)cyclohexylcarbamate

Example 32 was synthesized according to Method 2 in a yield of 23.1%, purified by preparative HPLC using LUNA C18(2) 100A column (250×21.2 mm; 10µ), Mobile phase: 0.1% TFA (aq): gradient AcN-water (40/60) at t=0 min to AcN-water (95/5) within 45 min, flow rate: 6 ml/min.

MS (m/z): 427 (M+H); HPLC (λ=214 nm, [A]): rt 19.0 min (95.3%).

Example 33 tert-butyl 4-(6-(2-methoxyphenyl)pyrimidin-4-ylcarbamoyl)cyclohexylcarbamate

Example 33 was synthesized according to Method 2 in a yield of 22%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.
MS (m/z): 427 (M+H); HPLC (λ=214 nm, [A]): rt 18.6 min (95.3%).

Example 34

4-amino-N-(6-(2-methoxyphenyl)pyrimidin-4-yl)cyclohexanecarboxamide*HCl

Example 34 was synthesized according to Method 7 in a yield of 76.7% starting from Example 33, purified by washing with ethyl ether.
MS (m/z): 327 (M+H); HPLC (λ=214 nm, [A]): rt 9.7 min (98.1%).

Example 35 tert-butyl 2-(6-(2-methoxyphenyl)pyrimidin-4-ylcarbamoyl)-4-fluoropyrrolidine-1-carboxylate Example 35 was synthesized according to Method 4 in a yield of 57.7%, purified by flash column chromatography over silica gel (200-400 mesh) using methanol (0-10%) in chloroform.
$^1$H NMR (400 MHz, CD$_3$OD, Rotameres): δ=1.39, 1.49 (s, br., 9H, tert.-Bu), 2.36-2.68 (m, 2H, CH$_2$), 3.60-3.86 (m, 2H, CH$_2$), 3.88 (s, 3H, CH$_3$), 4.50-4.62 (m, 1H, CH—CH$_2$), 5.18 (m, 0.5H, CH—CH$_2$), 5.31 (m, 0.5H, CH—CH$_2$), 7.06 (t, $^3$J=7.5 Hz, 1H, Methoxy-Ar), 7.13 (d, $^3$J=8.3 Hz, 1H, Methoxy-Ar), 7.43-7.48 (m, 1H, Methoxy-Ar), 7.75-7.81 (m, 1H, Methoxy-Ar), 8.67 (s, br., 1H, Pyrimidin-Ar), 8.83 (s, 1H, Pyrimidin-Ar); MS (m/z): 417 (M+H); HPLC (λ=214 nm, [A]): rt 16.5 min (95%).

Example 36

4-fluoro-N-(6-(2-methoxyphenyl)pyrimidin-4-yl)pyrrolidine-2-carboxamide*HCl

Example 36 was synthesized according to Method 7 in a yield of 100% starting from Example 35, purified by washing with ethyl ether.
$^1$H NMR (400 MHz, CD$_3$OD): δ=2.62-2.74 (m, 1H, CH$_2$), 2.80-2.99 (m, 1H, CH$_2$), 3.57-3.72 (m, 1H, CH$_2$), 3.78-3.88 (m, 1H, CH$_2$), 3.98 (s, 3H, CH$_3$), 4.88 (dd, $^3$J=3.3 Hz, $^3$J=10.8 Hz, 1H, CH—CH$_2$), 5.41 (t, $^3$J=3.8 Hz, 0.5H, CH—CH$_2$), 5.54 (t, $^3$J=3.8 Hz, 0.5H, CH—CH$_2$), 7.19-7.25 (m, 1H, Methoxy-Ar), 7.31 (d, $^3$J=8.3 Hz, 1H, Methoxy-Ar), 7.67-7.72 (m, 1H, Methoxy-Ar), 7.74 (m, $^3$J=7.9 Hz, $^4$J=1.7 Hz, 1H, Methoxy-Ar), 8.76 (d, $^5$J=7.9 Hz, 1H, Pyrimidin-Ar), 9.18 (d, $^5$J=7.9 Hz, 1H, Pyrimidin-Ar); MS (m/z): 317 (M+H); HPLC (λ=214 nm, [A]): rt 8.6 min (100%).

Example 37

N-(6-(5-fluoro-2-methoxyphenyl)pyrimidin-4-yl)piperidine-2-carboxamide*TFA

The Boc-protected precursor of Example 37 was synthesized according to Method 2, after isolation and purification Example 37 was prepared by Method 9 in a yield of 28.7%.
MS (m/z): 331 (M+H); HPLC (λ=214 nm, [A]): rt 9.0 min (100%); mp: 122° C.

Example 38

4-amino-N-(6-(5-fluoro-2-methoxyphenyl)pyrimidin-4-yl)cyclohexanecarboxamide*TFA The Boc-protected precursor of Example 38 was synthesized according to Method 2, after isolation and purification (yield: 60.5%) Example 38 was prepared by Method 9 in a yield of 39.2%, purified by preparative TLC using silica gel (GF254) and eluting with 3% MeOH in chloroform.
MS (m/z): 345 (M+H); HPLC (λ=214 nm, [A]): rt 9.3 min (98.4%); mp: 162° C.

Example 39

N-(6-(5-fluoro-2-methoxyphenyl)pyrimidin-4-yl)-tetrahydro-2H-pyran-4-carboxamide Example 39 was synthesized according to Method 2 in a yield of 39.2%, purified by flash column chromatography over silica gel (200-400 mesh) using methanol (0-10%) in chloroform.
MS (m/z): 332 (M+H); HPLC (λ=214 nm, [A]): rt 13.9 min (100%); mp: 155° C.

Example 40

N-(6-(5-fluoro-2-methoxyphenyl)pyrimidin-4-yl)-2-oxopiperidine-4-carboxamide

Example 40 was synthesized according to Method 2 in a yield of 12.3%, purified by preparative TLC using silica gel (GF254) and eluting with 3% MeOH in chloroform.
MS (m/z): 345 (M+H); HPLC (λ=214 nm, [A]): rt 11.9 min (100%); mp: 225° C.

Example 41

N-(6-(5-fluoro-2-methoxyphenyl)pyrimidin-4-yl)-2-oxopiperidine-3-carboxamide

Example 41 was synthesized according to Method 2 in a yield of 6.7%.
MS (m/z): 345 (M+H); HPLC (λ=214 nm, [A]): rt 13.6 min (99.3%); mp: 180° C.

Example 42 tetrahydro-N-(6-(2-methoxyphenyl)pyrimidin-4-yl)-2H-pyran-4-carboxamide

Example 42 was synthesized according to Method 2 in a yield of 21.9%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

MS (m/z): 314 (M+H); HPLC (λ=214 nm, [B]): rt 11.9 min (100%).

Example 43 tetrahydro-N-(6-(2-methoxyphenyl)pyrimidin-4-yl)-2H-thiopyran-4-carboxamide

Example 43 was synthesized according to Method 2 in a yield of 8.4%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

MS (m/z): 330 (M+H); HPLC (λ=214 nm, [B]): rt 14.8 min (85.7%).

Example 44

4-acetamido-N-(6-(5-fluoro-2-methoxyphenyl)pyrimidin-4-yl)cyclohexanecarboxamide Example 44 was synthesized according to Method 2 in a yield of 19.2%, purified by flash column chromatography over silica gel (200-400 mesh) using methanol (0-10%) in chloroform.

$^1$H NMR (400 MHz, CDCl$_3$): δ=1.66-1.75 (m, 2H), 1.76-1.88 (m, 6H), 1.99 (s, 3H), 2.51-2.57 (m, 1H), 3.94 (s, 3H), 4.11-4.13 (m, 1H), 5.81 (s, br., 1H), 6.97 (dd, 1H), 7.14-7.19 (m, 1H), 7.78 (dd, 1H), 8.88 (s, 1H), 9.02 (s, 1H), 9.56 (s, br., 1H); MS (m/z): 387 (M+H); HPLC (λ=214 nm, [A]): rt 14.2 min (99.1%).

Example 45

3-amino-N-(6-(5-fluoro-2-methoxyphenyl)pyrimidin-4-yl)cyclohexanecarboxamide*HCl The Boc-protected precursor of Example 45 was synthesized according to Method 2, after isolation and purification (yield: 42.2%) Example 45 was prepared by Method 7 in a yield of 69.2%.

MS (m/z): 345 (M+H); HPLC (λ=214 nm, [A]): rt 10.1 min (100%).

Example 46

(1S,2R)-2-amino-N-(6-(5-fluoro-2-methoxyphenyl)pyrimidin-4-yl)cyclohexanecarboxamide*HCl The Boc-protected precursor of Example 46 was synthesized according to Method 2, after isolation and purification (yield: 16.4%) Example 46 was prepared by Method 7 in a yield of 45.3%.

MS (m/z): 345 (M+H); HPLC (λ=214 nm, [A]): rt 10.2 min (100%); mp: 272° C.

Example 47 tetrahydro-N-(6-(2-methoxyphenyl)pyrimidin-4-yl)-2H-pyran-2-carboxamide

Example 47 was synthesized according to Method 2 in a yield of 28.4%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

MS (m/z): 314 (M+H); HPLC (λ=214 nm, [B]): rt 15.2 min (97.2%).

Example 48

N-(6-(2-methoxyphenyl)pyrimidin-4-yl)cyclobutanecarboxamide

Example 48 was synthesized according to Method 2 in a yield of 29.4%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

MS (m/z): 284 (M+H); HPLC (λ=214 nm, [B]): rt min (92.1%).

Example 49

N-(6-(2-methoxyphenyl)pyrimidin-4-yl)cyclohexanecarboxamide

Example 49 was synthesized according to Method 2 in a yield of 17.8%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

MS (m/z): 312 (M+H); HPLC (λ=214 nm, [B]): rt t 16.7 min (98%).

Example 50

3-acetamido-N-(6-(2-methoxyphenyl)pyrimidin-4-yl)cyclohexanecarboxamide

Example 50 was synthesized according to Method 2 in a yield of 13.5%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

$^1$H NMR (400 MHz, CDCl$_3$): δ=1.10-1.20 (m, 2H), 1.36-1.54 (m, 4H), 1.88-1.94 (m, 2H), 1.98 (s, 3H), 2.22-2.28 (m, 1H), 2.58-2.66 (m, 1H), 3.92 (s, 3H), 5.52 (d, 1H), 7.01-7.13 (m, 2H), 7.46-7.50 (m, 1H), 7.85-7.88 (m, 1H), 8.87 (s, 1H), 9.06 (s, 1H), 9.78 (s, br., 1H); MS (m/z): 369 (M+H); HPLC (λ=214 nm, [A]): rt 11.6 min (99.8%).

Example 51

4-methylsulfon-amino-N-(6-(2-methoxyphenyl)pyrimidin-4-yl)benzamide

Example 51 was synthesized according to Method 11.

Example 52

3-methylsulfon-amino-N-(6-(2-methoxyphenyl)pyrimidin-4-yl)-4-methylbenzamide

Example 52 was synthesized according to Method 11.

Example 53

3-methylsulfon-amino-N-(6-(2-methoxyphenyl)pyrimidin-4-yl)benzamide

Example 53 was synthesized according to Method 11.

Example 54

N-(6-(2-methoxyphenyl)pyrimidin-4-yl)picolinamide

Example 54 was synthesized according to Method 4 in a yield of 25.8%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.
$^1$H NMR (400 MHz, DMSO-$d_6$): δ=4.01 (s, 3H), 7.13-7.17 (m, 1H), 7.27-7.47 (m, 1H), 7.53-7.57 (m, 1H), 7.78-7.82 (m, 1H), 8.07-8.09 (m, 1H), 8.17-8.21 (m, 1H), 8.21-8.31 (m, 1H), 8.81-8.83 (m, 1H), 9.03 (s, 1H), 9.05 (s, 1H), 10.6 (s, 1H); MS (m/z): 307.6 (M+H); HPLC (λ=214 nm, [A]): rt 18.5 min (97.4%).

Example 55

N-(6-(5-fluoro-2-methoxyphenyl)pyrimidin-4-yl)-5-methylisoxazole-3-carboxamide

Example 55 was synthesized according to Method 2 in a yield of 38.7%, purified by preparative HPLC using Zodiacsil 120-5-C18 column (250×32 mm; 10μ), Mobile phase: 0.01 M NH$_4$OAc (aq): AcN (35:65) and flow rate: 40 ml/min.
$^1$H NMR (400 MHz, CDCl$_3$): δ=8.93 (s, 2H), 8.88 (s, 1H), 8.41 (s, br., 1H), 7.77-7.74 (dd, 1H), 7.17-7.12 (m, 1H), 6.99-6.95 (m, 1H), 3.94 (s, 3H), 2.60 (s, 3H); MS (m/z): 329 (M+H); HPLC (λ=214 nm, [A]): rt 16.9 min (92%); mp: 170° C.

Example 56

5-ethyl-N-(6-(5-fluoro-2-methoxyphenyl)pyrimidin-4-yl)pyridine-2-carboxamide

Example 56 was synthesized according to Method 2 in a yield of 13.8%, purified by preparative TLC using silica gel (GF254) and eluting with 10% ethyl acetate in chloroform.
$^1$H NMR (400 MHz, CDCl$_3$): δ=10.63 (s, 1H), 9.02 (s, 1H), 8.99 (s, 1H), 8.50 (s, 1H), 8.20 (d, 1H), 7.77-7.73 (m, 2H), 7.13-7.10 (m, 1H), 6.99-6.95 (m, 1H), 3.95 (s, 3H), 2.77 (q, 2H), 1.32 (t, 3H); MS (m/z): 353 (M+H); HPLC (λ=214 nm, [A]): rt 21.1 min (100%); mp: 176° C.

Example 57

N-(6-(5-fluoro-2-methoxyphenyl)pyrimidin-4-yl)-7-methylH-imidazo[1,2-a]pyridine-2-carboxamide Example 57 was synthesized according to Method 2 in a yield of 5.7%, purified by stirring the crude compound in methanol and un-dissolved solid filtered. The process was repeated once more, drying in vacuo gave pure product.
$^1$H NMR (400 MHz, DMSO-$d_6$): δ=9.19 (s, 1H), 9.12 (s, 1H), 9.0 (s, 1H), 8.97 (s, 1H), 7.84-7.81 (dd, 1H), 7.71 (s, 1H), 7.45-7.41 (m, 2H), 7.31-7.29 (m, 1H), 3.94 (s, 3H), 2.58 (s, 3H); MS (m/z): 378 (M+H); HPLC (λ=214 nm, [A]): rt 14.8 min (100%).

Example 58

5-ethyl-N-(6-(5-fluoro-2-methoxyphenyl)pyrimidin-4-yl)isoxazole-3-carboxamide

Example 58 was synthesized according to Method 4 in a yield of 14.5%, purified by preparative HPLC using Zodiacsil 120-5-C18 column (250×32 mm; 10μ), Mobile phase: 0.01M NH$_4$OAc (aq): AcN (30:70) and flow rate: 48 ml/min.
$^1$H NMR (400 MHz, CDCl$_3$): δ=9.22 (s, 1H), 8.98 (d, 1H), 8.92 (s, 1H), 7.80-7.77 (dd, 1H), 7.16-7.11 (m, 1H), 6.99-6.96 (m, 1H), 6.55 (s, 1H), 3.94 (s, 3H), 2.87 (q, 2H), 1.36 (t, 3H); MS (m/z): 343 (M+H); HPLC (λ=214 nm, [A]): rt 19.9 min (100%); mp: 175° C.

Example 59

N-(6-(5-fluoro-2-methoxyphenyl)pyrimidin-4-yl)-6-methylpyrazolo[1,5-a]pyrimidine-3-carboxamide Example 59 was synthesized according to Method 4 in a yield of 20.4%, purified by preparative HPLC using Zodiacsil 120-5-C18 column (250×32 mm; 10μ), Mobile phase: 0.01 M NH$_4$OAc (aq): AcN (35:65) and flow rate: 48 ml/min.
$^1$H NMR (400 MHz, DMSO-$d_6$): δ=10.65 (s, 1H), 9.31 (s, 1H), 8.98 (s, 1H), 8.92 (s, 1H), 8.75 (s, 1H), 7.79-7.76 (dd, 2H), 7.38 (m, 1H), 7.28 (m, 1H), 3.93 (s, 3H), 2.44 (s, 3H); MS (m/z): 379 (M+H); HPLC (λ=214 nm, [A]): rt 18.1 min (98%); mp: 265° C.

Example 60

N-(6-(5-fluoro-2-methoxyphenyl)pyrimidin-4-yl)-1,2-dihydro-2-oxoquinoline-4-carboxamide Example 60 was synthesized according to Method 4 in a yield of 5.7% purified by preparative TLC using silica gel (GF254) and eluting with 3% MeOH in chloroform.
MS (m/z): 391 (M+H); HPLC (λ=214 nm, [B]): rt 14.6 min (100%); mp: 276° C.

Example 61

N-(6-(5-fluoro-2-methoxyphenyl)pyrimidin-4-yl)-2-oxo-2-phenylacetamide

Example 61 was synthesized according to Method 1 in a yield of 2.5%, purified by preparative HPLC using Zodiacsil 120-5-C18 column (250×32 mm; 10μ), Mobile phase: 0.1% formic acid (aq): AcN (25:75) and flow rate: 4 ml/min.
$^1$H NMR (400 MHz, CDCl$_3$): δ=9.53 (s, br., 1H), 9.01 (s, 1H), 8.95 (s, 1H), 8.40 (d, 2H), 7.81-7.78 (dd, 1H), 7.69 (t, 1H), 7.54 (t, 1H), 7.15 (m, 1H), 7.00-6.97 (m, 1H), 3.95 (s, 3H); MS (m/z): 352 (M+H); HPLC (λ=214 nm, [B]): it 19.4 min (92.7%); mp: 146° C.

Example 62

N-(6-(5-fluoro-2-methoxyphenyl)pyrimidin-4-yl)-2-(2,4,5-trifluorophenyl)acetamide Example 62 was synthesized according to Method 2 in a yield of 34%, purified by column chromatography over silica gel (100-200 mesh) using 0-5% MeOH in chloroform as eluent.
$^1$H NMR (400 MHz, DMSO-$d_6$): δ=11.20 (s, 1H), 8.94 (s, 1H), 8.68 (s, 1H), 7.70-7.67 (m, 1H), 7.55-7.50 (m, 2H), 7.32-7.29 (m, 1H), 7.21-7.17 (m, 1H), 3.87 (s, 3H), 3.81 (s, 2H); MS (m/z): 392 (M+H); HPLC (λ=214 nm, [B]): rt 18.7 min (100%); mp: 208° C.

Example 63

N-(6-(2-methoxyphenyl)pyrimidin-4-yl)-2-(pyridin-2-yl)acetamide

Example 63 was synthesized according to Method 4 in a yield of 85%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

$^1$H NMR (400 MHz, DMSO-d$_6$): δ=3.79 (s, 2H), 4.11 (s, 3H), 7.03-7.06 (m, 1H), 7.13-7.15 (m, 1H), 7.42-7.59 (m, 2H), 7.59-7.61 (m, 1H), 7.83-7.86 (m, 1H), 8.00-8.04 (m, 1H), 8.60 (s, 1H), 8.91 (s, 1H), 11.19 (s, 1H); MS (m/z): 321.1 (M+H); HPLC (λ=214 nm, [A]): rt 9.77 min (98%).

Example 64

(2R)—N-(6-(2-methoxyphenyl)pyrimidin-4-yl)-2-phenylpropanamide

Example 64 was synthesized according to Method 2 in a yield of 3.1%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

MS (m/z): 334 (M+H); HPLC (λ=214 nm, [A]): rt min (100%).

Example 65

(2S)—N-(6-(2-methoxyphenyl)pyrimidin-4-yl)-2-phenylpropanamide

Example 65 was synthesized according to Method 2 in a yield of 7.9%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

$^1$H NMR (400 MHz, CDCl$_3$): δ=1.58 (d, $^3$J=7.0 Hz, 3H, CH$_3$), 3.94-3.99 (m, 4H, OCH$_3$, CH—CH$_3$), 7.04 (d, $^3$J=8.3 Hz, 1H, Methoxy-Ar), 7.09 (td, $^3$J=7.5 Hz, $^4$J=0.8 Hz, 1H, Methoxy-Ar), 7.25-7.31 (m, 1H, Phenyl-Ar), 7.32-7.40 (m, 4H, Phenyl-Ar), 7.48-7.53 (m, 1H, Methoxy-Ar), 7.86 (dd, $^3$J=7.5 Hz, $^4$J=1.7 Hz, 1H, Methoxy-Ar), 8.99 (s, 1H, Pyrimidin-Ar), 9.03 (s, 1H, Pyrimidin-Ar), 10.30 (s, br., 1H, NH); MS (m/z): 334 (M+H); HPLC (λ=214 nm, [A]): rt 19.1 min (98.8%).

Example 66

N-(6-(2-methoxyphenyl)pyrimidin-4-yl)-2-(2-nitrophenyl)acetamide

Example 66 was synthesized according to Method 2 in a yield of 5.1%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

$^1$H NMR (400 MHz, CDCl$_3$): δ=3.90 (s, 3H, CH$_3$), 4.36 (s, 2H, CH$_2$), 7.02 (d, $^3$J=8.3 Hz, 1H, Methoxy-Ar), 7.08 (td, $^3$J=7.5 Hz, $^4$J=0.8 Hz, 1H, Methoxy-Ar), 7.42 (dd, $^3$J=7.9 Hz, $^4$J=1.2 Hz, 1H, Nitro-Ar), 7.52 (tdd, $^3$J=7.5 Hz, $^4$J=1.7 Hz, $^4$J=0.8 Hz, 2H, Nitro-Ar), 7.63 (td, $^3$J=7.5 Hz, $^4$J=1.2 Hz, 1H, Methoxy-Ar), 7.82 (dd, $^3$J=7.9 Hz, $^4$J=1.7 Hz, 1H, Methoxy-Ar), 8.16 (dd, $^3$J=8.3 Hz, $^4$J=1.2 Hz, 1H, Ar), 8.93 (s, 1H, Pyrimidin-Ar), 9.45 (s, 1H, Pyrimidin-Ar), 11.44 (s, br., 1H, NH); MS (m/z): 365 (M+H); HPLC (λ=214 nm, [C]): rt 12.9 min (99%).

Example 67

2-(3,4,5-trifluorophenyl)-N-(6-(2-methoxyphenyl)pyrimidin-4-yl)acetamide

Example 67 was synthesized according to Method 2 in a yield of 4.3%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

$^1$H NMR (400 MHz, CDCl$_3$): δ=3.79 (s, 2H, CH$_2$), 3.93 (s, 3H, CH$_3$), 6.96-7.05 (m, 3H, 1× Methoxy-Ar, 2× Flour-Ar), 7.09 (td, $^3$J=7.5 Hz, $^4$J=0.8 Hz, 1H, Methoxy-Ar), 7.46-7.52 (m, 1H, Methoxy-Ar), 7.92 (dd, $^3$J=7.9 Hz, $^4$J=1.7 Hz, 1H, Methoxy-Ar), 8.92 (s, 1H, Pyrimidin-Ar), 9.15 (s, 1H, Pyrimidin-Ar), 11.44 (s, br., 1H, NH); MS (m/z): 374 (M+H); HPLC (λ=214 nm, [A]): rt 19.2 min (99.6%).

Example 68

N-(6-(2-methoxyphenyl)pyrimidin-4-yl)-2-(naphthalen-1-yl)acetamide

Example 68 was synthesized according to Method 2 in a yield of 4.1%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

$^1$H NMR (400 MHz, CDCl$_3$): δ=3.92 (s, 3H, CH$_3$), 4.00 (s, 2H, CH$_2$), 7.01 (d, $^3$J=8.3 Hz, 1H, Methoxy-Ar), 7.07 (td, $^3$J=7.5 Hz, $^4$J=0.8 Hz, 1H, Methoxy-Ar), 7.43-7.51 (m, 4H, Naphthyl-Ar), 7.80-7.86 (m, 4H, 3× Naphthyl-Ar, 1× Methoxy-Ar), 7.89 (dd, $^3$J=7.9 Hz, $^4$J=1.7 Hz, 1H, Methoxy-Ar), 8.16 (dd, $^3$J=8.3 Hz, $^4$J=1.2 Hz, 1H, Ar), 8.94 (d, $^5$J=0.8 Hz, 1H, Pyrimidin-Ar), 8.97 (d, $^5$J=0.8 Hz, 1H, Pyrimidin-Ar), 9.78 (s, br., 1H, NH); MS (m/z): 370 (M+H); HPLC (λ=214 nm, [C]): rt 17.7 min (99.7%).

Example 69

2-(3-methoxyphenyl)-N-(6-(2-methoxyphenyl)pyrimidin-4-yl)acetamide

Example 69 was synthesized according to Method 2 in a yield of 8.2%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

$^1$H NMR (400 MHz, CDCl$_3$): δ=3.80 (s, 5H, CH$_2$+CH$_3$), 3.92 (s, 3H, CH$_3$), 6.86 (dd, $^3$J=7.9 Hz, $^4$J=2.5 Hz, 1H, Methylen-Ar), 6.88-6.90 (m, 1H, Methylen-Ar), 6.92 (d, $^3$J=7.5 Hz, 1H, Methylen-Ar), 7.01 (d, $^3$J=8.7 Hz, 1H, Methoxy-Ar), 7.07 (td, $^3$J=7.5 Hz, $^4$J=0.8 Hz, 1H, Methoxy-Ar), 7.29 (t, $^3$J=7.9 Hz, 1H, Methylen-Ar), 7.44-7.48 (m, 1H, Methoxy-Ar), 7.88 (dd, $^3$J=7.9 Hz, $^4$J=1.7 Hz, 1H, Methoxy-Ar), 8.90 (s, 1H, Pyrimidin-Ar), 8.99 (s, 1H, Pyrimidin-Ar), 9.49 (s, br., 1H, NH); MS (m/z): 350 (M+H); HPLC (λ=214 nm, [C]): rt 13.8 min (97.7%).

Example 70

1-(4-chlorophenyl)-N-(6-(2-methoxyphenyl)pyrimidin-4-yl)cyclobutanecarboxamide

Example 70 was synthesized according to Method 2 in a yield of 7.2%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

$^1$H NMR (400 MHz, CDCl$_3$): δ=1.89-2.00 (m, 2H, CH$_2$), 2.02-2.11 (m, 2H, CH$_2$), 2.53-2.61 (m, 2H, CH$_2$), 2.87-2.95 (m, 2H, CH$_2$), 3.93 (s, 3H, CH$_3$), 7.03 (d, $^3$J=7.9 Hz, 1H, Methoxy-Ar), 7.07 (td, $^3$J=7.5 Hz, $^4$J=0.8 Hz, 1H, Methoxy-Ar), 7.33-7.39 (m, 4H, Chloro-Ar), 7.48-7.53 (m, 1H, Methoxy-Ar), 7.82 (dd, $^3$J=7.9 Hz, $^4$J=1.7 Hz, 1H, Methoxy-Ar), 8.91 (s, 1H, Pyrimidin-Ar), 8.92 (s, 1H, Pyrimidin-Ar), 9.01 (s, br., 1H, NH); MS (m/z): 394 (M+H); HPLC (λ=214 nm, [C]): rt 15.8 min (99.3%).

Example 71

2-(2-methoxyphenyl)-N-(6-(2-methoxyphenyl)pyrimidin-4-yl)acetamide

Example 71 was synthesized according to Method 3 in a yield of 3.5%, purified by flash column chromatography over silica gel (40 micron) using methanol (0-10%) in chloroform.

MS (m/z): 350 (M+H); HPLC (λ=214 nm, [A]): rt 16.1 min (95.9%).

Example 72

N-(6-(2-methoxyphenyl)pyrimidin-4-yl)-2-(1H-pyrazol-1-yl)acetamide

Example 72 was synthesized according to Method 2 in a yield of 3.5%, purified by flash column chromatography over silica gel (40 micron) using methanol (0-10%) in chloroform.

MS (m/z): 310 (M+H); HPLC (λ=214 nm, [A]): rt 11.8 min (97%); mp: 138° C.

Example 73

N-(6-(5-fluoro-2-methoxyphenyl)pyrimidin-4-yl)-1-(4-methoxyphenyl)cyclopropanecarboxamide Example 73 was synthesized according to Method 1 in a yield of 17.1%, purified by preparative HPLC using Zodiacsil 120-5-C18 column (250×32 mm; 10μ), Mobile phase: 0.1% formic acid (aq): AcN (25:75) and flow rate: 4 ml/min.

$^1$H NMR (400 MHz, CDCl$_3$): δ=8.80 (s, 2H), 7.89 (s, 1H), 7.67 (d, 1H), 7.40 (d, 2H), 7.12-7.08 (m, 1H), 6.97-6.92 (m, 3H), 3.91 (s, 3H), 3.85 (s, 3H), 1.72 (s, 2H), 1.21 (s, 2H); MS (m/z): 394 (M+H); HPLC (λ=214 nm, [B]): rt 21.1 min (96.6%); mp: 145° C.

Example 74

N-(6-(5-fluoro-2-methoxyphenyl)pyrimidin-4-yl)-2-(2-methoxyphenyl)acetamide

Example 74 was synthesized according to Method 1 in a yield of 11.3%, purified by preparative TLC using silica gel (GF254) and eluting with 3% MeOH in chloroform.

$^1$H NMR (400 MHz, CDCl$_3$): δ=8.86 (s, 1H), 8.80 (s, 1H), 8.51 (s, br., 1H), 7.71-7.70 (dd, 1H), 7.33-7.29 (m, 2H), 7.14-7.06 (m, 1H), 7.01-6.94 (m, 3H), 3.97 (s, 3H), 3.90 (s, 3H), 3.77 (s, 2H); MS (m/z): 368 (M+H); HPLC (λ=214 nm, [A]): 18.1 rt min (96.3%); mp: 170° C.

Example 75

2-(3,4-dimethoxyphenyl)-N-(6-(2-methoxyphenyl)pyrimidin-4-yl)acetamide

Example 75 was synthesized according to Method 2 in a yield of 2.8%, purified by flash column chromatography over silica gel (40 micron) using methanol (0-10%) in chloroform.

MS (m/z): 380 (M+H); HPLC (λ=214 nm, [B]): rt 13:6 min (100%); mp: 194° C.

Example 76

1-(4-methoxyphenyl)-N-(6-(2-methoxyphenyl)pyrimidin-4-yl)cyclopropanecarboxamide Example 76 was synthesized according to Method 2 in a yield of 2.7%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

MS (m/z): 376 (M+H); HPLC (λ=214 nm, [19,1]): rt 19.1 min (100%); mp: 123° C.

Example 77

N-(6-(2-methoxyphenyl)pyrimidin-4-yl)-2-oxo-2-phenylacetamide

Example 77 was synthesized according to Method 2 in a yield of 10.3%, purified by flash column chromatography over silica gel (40 micron) using methanol (0-10%) in chloroform.

MS (m/z): 334 (M+H); HPLC (λ=214 nm, [B]): rt 18.1 min (100%); mp: 109° C.

Example 78

N-(6-(2-methoxyphenyl)pyrimidin-4-yl)-2-(pyridin-4-yl)acetamide

Example 78 was synthesized according to Method 4 in a yield of 25.5%, purified by flash column chromatography over silica gel (40 micron) using methanol (0-10%) in chloroform.

MS (m/z): 321 (M+H); HPLC (λ=214 nm, [B]): rt 7.2 min (98.6%); mp: 128° C.

Example 79

N-(6-(2-methoxyphenyl)pyrimidin-4-yl)-2-(thiophen-2-yl)acetamide

Example 79 was synthesized according to Method 4 in a yield of 55%, purified by flash column chromatography over silica gel (40 micron) using methanol (0-10%) in chloroform.

MS (m/z): 326 (M+H); HPLC (λ=214 nm, [B]): rt 13.2 min (96.2%); mp: 135° C.; HRMS: cal.: 348.0777600, found:

348.0777185 NaC$_{17}$H$_{15}$N$_3$O$_2$S), cal.: 326.0958800, found: 326.0957739 (C$_{17}$H$_{16}$N$_3$O$_2$S).

Example 80

N-(6-(2-methoxyphenyl)pyrimidin-4-yl)-2-(pyridin-3-yl)acetamide

Example 80 was synthesized according to Method 8 in a yield of 37.3%, purified by flash column chromatography over silica gel (40 micron) using methanol (0-10%) in chloroform.

$^1$H NMR (400 MHz, DMSO-d$_6$): δ=3.79 (s, 3H, OCH$_3$), 4.12 (s, 2H, CH$_2$), 7.05 (t, $^3$J=7.5 Hz, 1H, Ar), 7.14 (d, $^3$J=8.3 Hz, 1H, Ar), 7.42-7.46 (m, 1H, Ar), 7.84-7.87 (m, 3H, Pyr., Ar), 8.60 (s, 1H, Pyrimidin), 8.77 (d, $^3$J=6.0 Hz, 2H, Pyr.), 8.92 (s, 1H, Pyrimidin), 11.26 (s, 1H, NH); MS (m/z): 321 (M+H); HPLC (λ=214 nm, [B]): rt 8.4 min (92%); mp: 87° C.

Example 81

N-(6-(5-fluoro-2-methoxyphenyl)pyrimidin-4-yl)-2-(pyridin-2-yl)acetamide

Example 81 was synthesized according to Method 2 in a yield of 23.8%, purified by flash column chromatography over silica gel (200-400 mesh) using 0-3% MeOH in chloroform as eluent.

$^1$H NMR (400 MHz, DMSO-d$_6$): δ=11.17 (s, 1H), 8.95 (s, 1H), 8.75 (s, 1H), 8.51 (d, 1H), 7.77-7.69 (m, 2H), 7.41-7.20 (m, 4H), 4.01 (s, 2H), 3.83 (s, 3H); MS (m/z): 339 (M+H); HPLC (λ=214 nm, [A]): rt 9.8 min (100%); mp: 176° C.

Example 82

N-(6-(5-fluoro-2-methoxyphenyl)pyrimidin-4-yl)-2-(pyridin-3-yl)acetamide

Example 82 was synthesized according to Method 4 in a yield of 12.1%, purified by flash column chromatography over silica gel (200-400 mesh) using 0-3% MeOH in chloroform as eluent.

$^1$H NMR (400 MHz, DMSO-d$_6$): δ=11.22 (s, 1H), 8.95 (s, 1H), 8.73 (s, 1H), 8.53 (s, 1H), 8.47 (d, 1H), 7.76-7.69 (m, 2H), 7.38-7.31 (m, 2H), 7.22-7.19 (m, 1H), 3.87 (s, 2H), 3.83 (s, 3H); MS (m/z): 339 (M+H); HPLC (λ=214 nm, [A]): rt 9.2 min (100%); mp: 197° C.

Example 83

N-(6-(5-fluoro-2-methoxyphenyl)pyrimidin-4-yl)-2-(pyridin-4-yl)acetamide

Example 83 was synthesized according to Method 2 in a yield of 16.1%, purified by running preparative TLC over silica gel (GF254) using 40% ethyl acetate in chloroform twice.

$^1$H NMR (400 MHz, DMSO-d$_6$): δ=11.24 (s, 1H), 8.95 (s, 1H), 8.73 (s, 1H), 8.52 (d, 2H), 7.70 (d, 1H), 7.36-7.34 (m, 3H), 7.23-7.20 (m, 1H), 3.87 (s, 2H), 3.83 (s, 3H); MS (m/z): 339 (M+H); HPLC (λ=214 nm, [A]): rt 9.3 min (98.9%); mp: 197° C.

Example 84

N-(6-(5-fluoro-2-methoxyphenyl)pyrimidin-4-yl)-2-(1H-pyrazol-1-yl)acetamide

Example 84 was synthesized according to Method 2 in a yield of 4.8%, purified by running preparative TLC over silica gel (GF254) using 5% MeOH in chloroform.

$^1$H NMR (400 MHz, CD$_3$OD): δ=8.87 (s, 1H), 8.74 (s, 1H), 7.74 (s, 1H), 7.65 (d, 1H), 7.57 (s, 1H), 7.20-7.13 (m, 2H), 6.37 (s, 1H), 5.17 (s, 2H), 3.87 (s, 3H); MS (m/z): 328 (M+H); HPLC (λ=214 nm, [A]): rt 13.9 min (100%); mp: 190° C.

Example 85

N-(6-(5-fluoro-2-methoxyphenyl)pyrimidin-4-yl)-2-(1H-imidazol-1-yl)acetamide Example 85 was synthesized according to Method 2 in a yield of 23.6%, purified by column chromatography over silica gel (60-120 mesh) using 0-10% MeOH in chloroform.

$^1$H NMR (400 MHz, DMSO-d$_6$): δ=11.28 (s, 1H), 8.97 (s, 1H), 8.71 (s, 1H), 7.74-7.68 (m, 2H), 7.35-7.32 (m, 1H), 7.24-7.20 (m, 2H), 6.93 (s, 1H), 5.05 (s, 2H), 3.84 (s, 3H); MS (m/z): 328 (M+H); HPLC (λ=214 nm, [A]): rt 8.9 min (96.6%); mp: 243° C.

Example 86

N-(6-(5-fluoro-2-methoxyphenyl)pyrimidin-4-yl)-2-(thiophen-2-yl)acetamide

Example 86 was synthesized according to Method 2 in a yield of 20.7%, purified by flash column chromatography over silica gel (100-200 mesh) using methanol (0-10%) in chloroform.

$^1$H NMR (400 MHz, DMSO-d$_6$): δ=11.17 (s, 1H), 8.95 (s, 1H), 8.74 (s, 1H), 7.72-7.69 (dd, 1H), 7.41 (d, 1H), 7.35-7.32 (m, 1H), 7.24-7.20 (m, 1H), 7.00-6.97 (m, 2H), 4.03 (s, 2H), 3.85 (s, 3H); MS (m/z): 344 (M+H); HPLC (λ=214 nm, [A]): rt 18.2 min (98.3%); mp: 160° C.

Example 87

N-(6-(5-fluoro-2-methoxyphenyl)pyrimidin-4-yl)-1-(4-methoxyphenyl)cyclohexanecarboxamide Example 87 was synthesized according to Method 1 in a yield of 18.2%, purified by preparative HPLC using Zodiacsil 120-5-C18 column (250×32 mm; 10μ), Mobile phase: 0.1% formic acid (aq): AcN (25:75) and flow rate: 4 ml/min.

$^1$H NMR (400 MHz, CD$_3$OD): δ=8.76 (s, 2H), 7.62-7.59 (dd, 1H), 7.40 (d, 2H), 7.22-7.14 (m, 2H), 6.94 (d, 2H), 3.93 (s, 3H), 3.78 (s, 3H), 2.47-2.43 (m, 2H), 1.99-1.95 (m, 2H), 1.65-1.63 (m, 2H), 1.43-1.42 (m, 2H), 0.91-0.85 (m, 2H); MS (m/z): 436 (M+H); HPLC (λ=214 nm, [A]): rt 21.7 min (100%); mp: 129° C.

Example 88

N-(6-(5-fluoro-2-methoxyphenyl)pyrimidin-4-yl)-2-(3,4-dimethoxyphenyl)acetamide Example 88 was synthesized according to Method 2 in a yield of 29.4%, purified by preparative TLC using silica gel (GF254) and eluting with 3% MeOH in chloroform.

$^1$H NMR (400 MHz, DMSO-d$_6$): δ=11.07 (s, 1H), 8.93 (s, 1H), 8.73 (s, 1H), 7.71-7.68 (dd, 1H), 7.36-7.31 (m, 1H), 7.23-7.19 (m, 1H), 6.96 (s, 1H), 6.91-6.85 (m, 2H), 3.84 (s, 3H), 3.74 (s, 3H), 3.72 (s, 3H), 3.70 (s, 2H); MS (m/z): 398 (M+H); HPLC (λ=214 nm, [A]): rt 16.9 min (100%); mp: 168° C.

Example 89

2-(5-chloropyridin-2-yloxy)-N-(6-(5-fluoro-2-methoxyphenyl)pyrimidin-4-yl)acetamide Example 89 was synthesized according to Method 2 in a yield of 5.7%, purified by preparative TLC over silica gel (GF254) using 10% ethyl acetate in chloroform as eluent.

$^1$H NMR (400 MHz, CDCl$_3$): δ=8.92 (s, 1H), 8.91 (s, 1H), 8.72 (s, 1H), 8.12 (d, 1H), 7.78-7.74 (dd, 1H), 7.66-7.63 (dd, 1H), 7.15-7.10 (m, 1H), 6.98-6.91 (m, 2H), 4.97 (s, 2H), 3.93 (s, 3H); MS (m/z): 389 (M+H); HPLC (λ=214 nm, [C]): rt 18.8 min (98.7%); mp: 185° C.

Example 90

N-(6-(5-fluoro-2-methoxyphenyl)pyrimidin-4-yl)-2-(1H-pyrrol-3-yl)acetamide

Example 90 was synthesized according to Method 2 in a yield of 4.6%, purified by preparative TLC over silica gel (GF254) using 10% ethyl acetate in chloroform as eluent.

$^1$H NMR (400 MHz, CDCl$_3$): δ=8.8 (s, 1H), 8.84 (s, 1H), 8.34 (s, br., 1H), 8.18 (s, 1H), 7.73-7.70 (dd, 1H), 7.13-7.09 (m, 1H), 6.97-6.93 (m, 1H), 6.86 (s, 1H), 6.81 (s, 1H), 6.22 (s, 1H), 3.92 (s, 3H), 3.69 (s, 2H); MS (m/z): 327 (M+H); HPLC (λ=214 nm, [A]): it 15.4 min (100%); mp: 150° C.

Example 91

N-(6-(5-fluoro-2-methoxyphenyl)pyrimidin-4-yl)-2-(thiophen-3-yl)acetamide

Example 91 was synthesized according to Method 2 in a yield of 19.9%, purified by preparative HPLC using Zodiacsil 120-5-C18 column (250×32 mm; 10μ), Mobile phase: 0.1% formic acid (aq): AcN (25:75) and flow rate: 48 ml/min, λ=235 nm.

$^1$H NMR (400 MHz, CDCl$_3$): δ=8.86 (s, 1H), 8.84 (s, 1H), 7.90 (s, 1H), 7.74-7.71 (dd, 1H), 7.43-7.41 (m, 1H), 7.14-7.07 (m, 3H), 6.99-6.93 (m, 1H), 3.92 (s, 3H), 3.83 (s, 2H); MS (m/z): 344 (M+H); HPLC (λ=214 nm, [A]): rt 18.2 min (94.4%); mp: 172° C.

Example 92

(2R)—N-(6-(5-fluoro-2-methoxyphenyl)pyrimidin-4-yl)-2-phenylpropanamide

Example 92 was synthesized according to Method 1 in a yield of 8.5%, purified by preparative TLC using silica gel (GF254) using 50% ethyl acetate in petroleum ether.

$^1$H NMR (400 MHz, CDCl$_3$): δ=8.83 (s, 1H), 8.81 (s, 1H), 7.91 (s, br., 1H), 7.71-7.68 (dd, 1H), 7.40-7.30 (m, 5H), 7.13-7.09 (m, 1H), 6.96-6.93 (m, 1H), 3.90 (s, 3H), 3.76 (q, 1H), 1.60 (d, 3H); MS (m/z): 352 (M+H); HPLC (λ=214 nm, [A]): rt 19.4 min (91.5%); light brown semi solid.

Example 93

(2S)—N-(6-(5-fluoro-2-methoxyphenyl)pyrimidin-4-yl)-2-phenylpropanamide

Example 93 was synthesized according to Method 1 in a yield of 8.7%, purified by preparative HPLC using Zodiacsil 120-5-C18 column (250×46 mm; 5μ), Mobile phase: 0.01 M NH$_4$OAc (aq): AcN (55:45) and flow rate: 48 ml/min, λ=235 nm.

$^1$H NMR (400 MHz, DMSO-d$_6$): δ=11.07 (s, 1H), 8.91 (s, 1H), 8.75 (s, 1H), 7.70-7.66 (dd, 1H), 7.40 (d, 2H), 7.36-7.26 (m, 3H), 7.24-7.20 (m, 2H), 4.08 (q, 1H), 3.86 (s, 3H), 1.42 (d, 3H); MS (m/z): 352 (M+H); HPLC (λ=214 nm, [C]): rt 17.7 min (100%); mp: 110° C.

Example 94

N-(6-(5-fluoro-2-methoxyphenyl)pyrimidin-4-yl)-2-(2-nitrophenyl)acetamide

Example 94 was synthesized according to Method 2 in a yield of 6.6%, purified by preparative HPLC using Gemini C18 column (50×30 mm; 5μ) and mobile phase: 0.01M NH$_4$OAc (aq): AcN (60:40), flow rate: 1 ml/min.

$^1$H NMR (400 MHz, DMSO-d$_6$): δ=8.96 (s, 1H), 8.63 (s, 1H), 8.09 (d, 1H), 7.76-768 (m, 2H), 7.61-7.57 (m, 2H), 7.35-7.30 (m, 1H), 7.21-7.17 (m, 1H), 4.27 (s, br., 2H), 3.80 (s, 3H); MS (m/z): 383 (M+H); HPLC (λ=214 nm, [C]): rt 14.9 min (90.7%); mp: 177° C.

Example 95

N-(6-(5-fluoro-2-methoxyphenyl)pyrimidin-4-yl)-2-(5-(phenoxymethyl)-2H-tetrazol-2-yl)acetamide Example 95 was synthesized according to Method 3 in a yield of 10.8%, purified by preparative HPLC using Zodiacsil 120-5-C18 column (250×32 mm; 10μ), Mobile phase: 0.01M NH$_4$OAc (aq): AcN (40:60) and flow rate: 4 ml/min.

$^1$H NMR (400 MHz, DMSO-d$_6$): δ=11.57 (s, 1H), 9.01 (s, 1H), 8.65 (s, 1H), 7.75-7.71 (dd, 1H), 7.37-7.30 (m, 3H), 7.23-7.20 (m, 1H), 7.07 (d, 2H), 6.98 (t, 1H), 5.90 (s, 2H), 5.41 (s, 2H), 3.82 (s, 3H); MS (m/z): 436 (M+H); HPLC (λ=214 nm, [C]): rt 17.1 min (100%); mp: 155° C.

Example 96

N-(6-(5-fluoro-2-methoxyphenyl)pyrimidin-4-yl)-2-(5-(phenoxymethyl)-1H-tetrazol-1-yl)acetamide Example 96 was synthesized according to Method 3 as side product of Example 95 in a yield of 13.6%, purified by preparative HPLC using Zodiacsil 120-5-C18 column (250×32 mm; 10μ), Mobile phase: 0.01M NH$_4$OAc (aq): AcN (40:60) and flow rate: 4 ml/min.

$^1$H NMR (400 MHz, DMSO-d$_6$): δ=11.52 (s, 1H), 8.99 (s, 1H), 8.62 (s, 1H), 7.74-7.70 (dd, 1H), 7.37-7.32 (m, 1H), 7.29-7.19 (m, 3H), 6.99-6.93 (m, 3H), 5.68 (s, 2H), 5.52 (s,

2H), 3.80 (s, 3H); MS (m/z): 436 (M+H); HPLC (λ=214 nm, [C]): rt 15.1 min (83.5%); mp: 190° C.

Example 97

2-(3-(1H-tetrazol-1-yl)phenoxy)-N-(6-(5-fluoro-2-methoxyphenyl)pyrimidin-4-yl)acetamide Example 97 was synthesized according to Method 2 in a yield of 52.3%, purified by preparative HPLC using Zodiacsil 120-5-C18 column (250×32 mm; 10μ), Mobile phase: 0.1% formic acid (aq): AcN (40:60) and flow rate: 48 ml/min.

$^1$H NMR (400 MHz, DMSO-d$_6$): δ=11.12 (s, 1H), 10.09 (s, 1H), 8.98 (s, 1H), 8.73 (s, 1H), 7.74-7.71 (dd, 1H), 7.60-7.51 (m, 3H), 7.37-7.32 (m, 1H), 7.24-7.16 (m, 2H), 5.01 (s, 2H), 3.84 (s, 3H); MS (m/z): 422 (M+H); HPLC (λ=214 nm, [C]): rt 14.1 min (97.8%); mp: 213° C.

Example 98

N-(6-(5-fluoro-2-methoxyphenyl)pyrimidin-4-yl)-2-(furan-2-yl)acetamide

Example 98 was synthesized according to Method 2 in a yield of 5.1%, initial purification was done by preparative HPLC using Zodiacsil 120-5-C18 column (250×32 mm; 10μ), Mobile phase: 0.01M NH$_4$OAc (aq): AcN (40:60) and flow rate: 48 ml/min. Further purification, by preparative TLC using 10% ethyl acetate in petroleum ether and washings with ether, gave pure product.

$^1$H NMR (400 MHz, CDCl$_3$): δ=8.88 (s, 1H), 8.83 (s, 1H), 8.09 (s, br., 1H), 7.75-7.72 (dd, 1H), 7.46 (s, 1H), 7.26 (merged with solvent, ~1H), 7.12-7.09 (m, 1H), 6.96-6.93 (m, 1H), 6.42 (m, 1H), 6.35 (d, 1H), 3.91 (s, 2H), 3.84 (s, 1H); MS (m/z): 328 (M+H); HPLC (λ=214 nm, [A]): rt 17.2 min (100%); mp: 141° C.

Example 99

N-(6-(5-fluoro-2-methoxyphenyl)pyrimidin-4-yl)-2-(furan-3-yl)acetamide

Example 99 was synthesized according to Method 2 in a yield of 11.5%, purified by column chromatography over neutral alumina using 0-45% ethyl acetate in petroleum ether.

$^1$H NMR (400 MHz, CDCl$_3$): δ=8.86 (s, 1H), 8.84 (s, 1H), 8.00 (s, 1H), 7.75-7.71 (dd, 1H), 7.50 (s, 2H), 7.14-7.10 (m, 1H), 6.97-6.93 (m, 1H), 6.43 (s, 1H), 3.92 (s, 3H), 3.64 (s, 2H); MS (m/z): 328 (M+H); HPLC (λ=214 nm, [A]): rt 16.9 min (100%); mp: 168° C.

Example 100

2-(5-chloropyridin-2-yloxy)-N-(6-(5-fluoro-2-methoxyphenyl)pyrimidin-4-yl)acetamide Example 100 was synthesized according to Method 2 in a yield of 5.7%, purified by preparative TLC over silica gel (GF254) using 10% ethyl acetate in chloroform as eluent.

$^1$H NMR (400 MHz, CDCl$_3$): δ=8.92 (s, 1H), 8.91 (s, 1H), 8.72 (s, 1H), 8.12 (d, 1H), 7.78-7.74 (dd, 1H), 7.66-7.63 (dd, 1H), 7.15-7.10 (m, 1H), 6.98-6.91 (m, 2H), 4.97 (s, 2H), 3.93 (s, 3H); MS (m/z): 389 (M+H); HPLC (λ=214 nm, [C]): rt 18.8 min (98.7%); mp: 185° C.

Example 101

2-(4-aminobenzyloxy)-N-(6-(5-fluoro-2-methoxyphenyl)pyrimidin-4-yl)acetamide

The precursor of Example 101 was synthesized according to Method 1, after isolation and purification (yield: 25.6%) Example 101 was prepared by Method 10 in a yield of 54.5%, purified by column chromatography over silica gel (100-200 mesh) using 20-25% ethyl acetate in petroleum ether as eluent.

$^1$H NMR (400 MHz, CDCl$_3$): δ=9.01 (s, br., 1H), 8.93 (s, 1H), 8.84 (s, 1H), 7.76-7.72 (dd, 1H), 7.17-7.10 (m, 3H), 6.96-6.93 (m, 1H), 6.68 (d, 2H), 4.54 (s, 2H), 4.07 (s, 2H), 3.90 (s, 3H), 3.73 (s, br., 2H); MS (m/z): 383 (M+H); HPLC (λ=214 nm, [A]): rt 11.4 min (89.6%); mp: 153° C.

Example 102

N-(6-(5-fluoro-2-methoxyphenyl)pyrimidin-4-yl)-2-(1H-pyrrol-2-yl)acetamide

Example 102 was synthesized according to Method 4 in a yield of 8.4%, purified by preparative TLC using silica gel (GF254) and eluting with 10% ethyl acetate in chloroform.

$^1$H NMR (400 MHz, DMSO-d$_6$): δ=10.92 (s, 1H), 10.64 (s, 1H), 8.93 (d, 1H), 8.76 (s, 1H), 7.73-7.70 (dd, 1H), 7.37-7.31 (m, 1H), 7.24-7.20 (m, 1H), 6.65 (s, 1H), 5.94-5.90 (m, 2H), 3.85 (s, 3H), 3.73 (s, 2H); MS (m/z): 327 (M+H); HPLC (λ=214 nm, [A]): rt 16.4 min (93.2%); mp: 186° C.

Example 103

N-(6-(5-fluoro-2-methoxyphenyl)pyrimidin-4-yl)-2-(5-(pyridin-3-yl)-2H-tetrazol-2-yl)acetamide Example 103 was synthesized according to Method 3 in a yield of 25.5%, the product precipitated from reaction mixture and was filtered, washed with water and dried in vacuo to afford pure product.

$^1$H NMR (400 MHz, DMSO-d$_6$): δ=11.61 (s, 1H), 9.26 (s, 1H), 9.02 (s, 1H), 8.76 (d, 1H), 8.67 (s, 1H), 8.45 (d, 1H), 7.75-7.74 (dd, 1H), 7.63 (m, 1H), 7.34 (m, 1H), 7.21 (m, 1H), 5.98 (s, 2H), 3.82 (s, 3H); MS (m/z): 407 (M+H); HPLC (λ=214 nm, [A]): 13.2 rt min (95%); mp: 277° C.

Example 104

1-(4-methoxyphenyl)-N-(6-(2-methoxyphenyl)pyrimidin-4-yl)cyclohexanecarboxamide

Example 104 was synthesized according to Method 2 in a yield of 4.7%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.

MS (m/z): 418 (M+H); HPLC (λ=214 nm, [B]): rt 20.2 min (100%).

Example 105

2-(4-methoxyphenyl)-N-(6-(2-methoxyphenyl)pyrimidin-4-yl)acetamide

Example 105 was synthesized according to Method 2 in a yield of 1.5%, purified by flash column chromatography over silica gel (40 micron) using methanol (0-10%) in chloroform.

MS (m/z): 350 (M+H); HPLC (λ=214 nm, [B]): it 14.3 min (95.9%).

Example 106

2-(2,3,5-trifluorophenyl)-N-(6-(2-methoxyphenyl)pyrimidin-4-yl)acetamide

Example 106 was synthesized according to Method 2 in a yield of 32.2%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.
MS (m/z): 374 (M+H); HPLC (λ=214 nm, [C]): it 16.5 min (97.8%).

Example 107

N-(6-(2-methoxyphenyl)pyrimidin-4-yl)-2-(4-((4-methylpiperazin-1-yl)methyl)phenyl)acetamide Example 107 was synthesized according to Method in a yield of 2%, purified by flash column chromatography over silica gel (40 micron) using methanol (0-10%) in chloroform.
$^1$H NMR (400 MHz, CD$_3$OD): δ=2.84 (s, 3H, N—CH$_3$), 2.90-2.96 (m, 4H, 2×CH$_2$), 3.83 (d, $^3$J=5.0 Hz, 4H, 2×CH$_2$), 3.88 (s, 3H, O—CH$_3$), 7.08 (td, $^3$J=7.5 Hz, $^4$J=0.8 Hz, 1H, Methoxy-Ar), 7.16 (d, $^3$J=8.3 Hz, 1H, Methoxy-Ar), 7.48-7.53 (m, 1H, Methoxy-Ar), 7.72 (dd, $^3$J=7.5 Hz, $^4$J=1.7 Hz, 1H, Methoxy-Ar), 8.65 (d, $^5$J=0.8 Hz, 1H, Pyrimidin-Ar), 8.89 (d, $^5$J=1.2 Hz, 1H, Pyrimidin-Ar); MS (m/z): 432 (M+H); HPLC (λ=214 nm, [A]): rt 8.2 min (92.1%).

Example 108

2-(2,5-dimethoxyphenyl)-N-(6-(2-methoxyphenyl)pyrimidin-4-yl)acetamide

Example 108 was synthesized according to Method 2 in a yield of 63.2%, purified by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min.
MS (m/z): 380 (M+H); HPLC (λ=214 nm, [A]): rt 17.4 min (91%).

Example 109

N-(6-(2-ethoxy-5-fluorophenyl)pyrimidin-4-yl)-2-(pyridin-3-yl)acetamide

Example 109 was synthesized according to Method 2 in a yield of 17.7%, purified by preparative HPLC using Zodiacsil 120-5-C18 column (250×32 mm; 10μ), Mobile phase: 0.1% formic acid (aq): AcN (25:75) and flow rate: 4 ml/min.
MS (m/z): 353 (M+H); HPLC (λ=214 nm, [A]): rt 10.5 min (100%); mp: 175° C.

Example 110

N-(6-(5-fluoro-2-isopropoxyphenyl)pyrimidin-4-yl)-2-(pyridin-3-yl)acetamide

Example 110 was synthesized according to Method 2 in a yield of 25.7%, purified by preparative HPLC using Zodiacsil 120-5-C18 column (250×32 mm; 10μ), Mobile phase: 0.1% formic acid (aq): AcN (25:75) and flow rate: 4 ml/min.
MS (m/z): 367 (M+H); HPLC (λ=214 nm, [A]): rt 11.4 min (100%); mp: 175° C.

Example 111

N-(6-(2-ethoxy-5-fluorophenyl)pyrimidin-4-yl)-2-(pyridin-4-yl)acetamide

Example 111 was synthesized according to Method 2 in a yield of 18.6%, purified by preparative HPLC using Zodiacsil 120-5-C18 column (250×32 mm; 10μ), Mobile phase: 0.1% formic acid (aq): AcN (25:75) and flow rate: 4 ml/min.
MS (m/z): 353 (M+H); HPLC (λ=214 nm, [A]): rt 16.6 min (100%); mp: 221° C.

Example 112

N-(6-(5-fluoro-2-isopropoxyphenyl)pyrimidin-4-yl)-2-(pyridin-4-yl)acetamide

Example 112 was synthesized according to Method 2 in a yield of 27%. purified by preparative HPLC using Zodiacsil 120-5-C18 column (250×32 mm; 10μ), Mobile phase: 0.1% formic acid (aq): AcN (25:75) and flow rate: 4 ml/min.
MS (m/z): 367.2 (M+H); HPLC (λ=214 nm, [A]): rt 11.44 min (97.4%).

Example 113

N-(6-(2-ethoxy-4-fluorophenyl)pyrimidin-4-yl)-2-(pyridin-4-yl)acetamide

Example 113 was synthesized according to Method 2 in a yield of 19% and purified by preparative HPLC using Zodiacsil 120-5-C18 column (250×32 mm; 10μ), Mobile phase: 0.1% formic acid (aq): AcN (25:75) and flow rate: 4 ml/min.
MS (m/z): 353.4 (M+H); HPLC (λ=214 nm, [A]): rt 10.32 min (100%).

Example 114

N-(6-(2-ethoxy-4-fluorophenyl)pyrimidin-4-yl)-2-(pyridin-3-yl)acetamide*HCl

Example 114 was synthesized according to Method 2 in a yield of 17%, followed by conversation to the HCl-salt by dissolving in DCM and addition of 1.2 eq. of ethereal HCl.
MS (m/z): 353.5 (M+H); HPLC (λ=214 nm, [A]): rt 10.38 min (98.6%).

Example 115

N-(6-(5-fluoro-2-methoxyphenyl)pyrimidin-4-yl)-2-methyl-2-(pyridin-4-yl)propanamide Example 115 was synthesized according to Method 2 in a yield of 25%.
MS (m/z): 367.3 (M+H); HPLC (λ=214 nm, [A]): rt 11.03 min (99.6%).

Example 116

N-(6-(2-ethoxy-4-fluorophenyl)pyrimidin-4-yl)-2-(pyridin-4-yl)acetamide*HCl

Example 116 was synthesized according to Method 2 in a yield of 20%, followed by conversation to the HCl-salt by dissolving in DCM and addition of 1.2 eq. of ethereal HCl.

MS (m/z): 339.3 (M+H); HPLC (λ=214 nm, [A]): rt 9.31 min (96.0%).

Example 117

N-(6-(5-fluoro-2-methoxyphenyl)pyrimidin-4-yl)-2-(pyridin-4-ylthio)acetamide

Example 117 was synthesized according to Method 3 in a yield of 8.6%.
MS (m/z): 371.3 (M+H); HPLC (λ=214 nm, [A]): it 10.35 min (96.0%).

Example 118

N-(6-(2-methoxyphenyl)pyrimidin-4-yl)-2-(pyridin-3-yloxy)propanamide

Example 118 was synthesized according to Method 2 in a yield of 38.6%, purified by flash column chromatography over silica gel (100-200 mesh) using methanol (0-10%) in chloroform.
$^1$H NMR (400 MHz, CDCl$_3$): δ=1.68 (d, 3H, CH$_3$), 3.93 (s, 3H, CH$_3$), 4.83 (q, $^3$J=6.6 Hz, 1H, CH), 7.01 (d, $^3$J=8.3 Hz, 1H, Methoxy-Ar), 7.07 (t, $^3$J=7.5 Hz, 1H, Methoxy-Ar), 7.25-7.29 (m, 1H, Methoxy-Ar), 7.40-7.45 (m, 1H, Methoxy-Ar), 7.94 (dd, $^3$J=6.1 Hz, $^4$J=1.6 Hz, 1H, Pyridin-Ar), 8.32 (s, br., 1H, Pyridin-Ar), 8.42 (s, br., 1H, Pyridin-Ar), 8.81-8.83 (m, 2H, Pyrimidin-Ar, Pyridin-Ar), 8.90 (d, $^5$J=1.3 Hz, 1H, Pyrimidin-Ar); MS (m/z): 351 (M+H); HPLC (λ=214 nm, [A]): it 10.1 min (96.9%).

Example 119

N-(6-(5-fluoro-2-isopropoxyphenyl)pyrimidin-4-yl)-2-(pyridin-3-yl)acetamide*HCl

Example 119 was synthesized according to Method 2 in a yield of 24%, followed by conversation to the HCl-salt by dissolving in DCM and addition of 1.2 eq. of ethereal HCl.
MS (m/z): 367.1 (M+H); HPLC (λ=214 nm, [A]): rt 11.1 min (94%).

Example 120

N-(6-(5-fluoro-2-isopropoxyphenyl)pyrimidin-4-yl)-2-(pyridin-4-yl)acetamide*HCl

Example 120 was synthesized according to Method 2 in a yield of 23%, followed by conversation to the HCl-salt by dissolving in DCM and addition of 1.2 eq. of ethereal HCl.
MS (m/z): 367.2 (M+H); HPLC (λ=214 nm, [A]): rt 11.2 min (83%).

Example 121

N-(6-(5-fluoro-2-methoxyphenyl)pyrimidin-4-yl)-4-methoxy-2-(pyridin-3-yl)butanamide Example 121 was synthesized according to Method 2 in a yield of 80%, purified by preparative TLC using silica gel (GF254) and eluting with 3% MeOH in chloroform.

MS (m/z): 397 (M+H); HPLC (λ=214 nm, [A]): rt 10.7 min (100%).

Example 122

N-(6-(5-fluoro-2-methoxyphenyl)pyrimidin-4-yl)-3-(pyridin-4-yl)propanamide*HCl

Example 122 was synthesized according to Method 2 in a yield of 32%, followed by conversation to the HCl-salt by dissolving in DCM and addition of 1.2 eq. of ethereal HCl
MS (m/z): 353 (M+H); HPLC (λ=214 nm, [A]): rt 9.7 min (100%).

Example 123

N-(6-(5-fluoro-2-methoxyphenyl)pyrimidin-4-yl)-2-(pyridin-3-yloxy)acetamide

Example 123 was synthesized according to Method 3 in a yield of 21%, purified by preparative HPLC using Zodiacsil 120-5-C18 column (250×32 mm; 10μ), Mobile phase: 0.01 M NH$_4$OAc (aq): AcN (35:65) and flow rate: 48 ml/min.
MS (m/z): 355 (M+H); HPLC (λ=214 nm, [A]): rt 10 min (100%).

Example 124

N-(6-(2-ethoxy-4-fluorophenyl)pyrimidin-4-yl)-2-(pyridin-3-yl)acetamide

Example 124 was synthesized according to Method 2 in a yield of 14.7%, purified by preparative TLC using silica gel (GF254) and eluting with 60% ethyl acetate in petroleum ether.
MS (m/z): 339 (M+H); HPLC (λ=214 nm, [A]): rt 8.9 min (98.5%).

Example 125

N-(6-(2-methoxyphenyl)pyrimidin-4-yl)-2-(pyridin-4-yl)propanamide

Example 125 was synthesized according to Method 2 in a yield of 35.9%, purified by preparative HPLC using Zodiacsil 120-5-C18 column (250×32 mm; 10μ), Mobile phase: 0.01M NH$_4$OAc (aq): AcN (35:65) and flow rate: 48 ml/min.
MS (m/z): 335 (M+H); HPLC (λ=214 nm, [A]): rt 10.1 min (96.2%).

Example 126

N-(6-(2-methoxyphenyl)pyrimidin-4-yl)-2-(pyridin-3-yl)propanamide

Example 126 was synthesized according to Method 2 in a yield of 53.7%, purified by preparative HPLC using Zodiacsil 120-5-C18 column (250×32 mm; 10μ), Mobile phase: 0.01 M NH$_4$OAc (aq): AcN (35:65) and flow rate: 40 ml/min.
MS (m/z): 335 (M+H); HPLC (λ=214 nm, [A]): it 10 min (98.4%).

Example 127

N-(6-(5-fluoro-2-methoxyphenyl)pyrimidin-4-yl)-1-(pyridin-4-yl)cyclopropanecarboxamide*HCl Example 127 was synthesized according to Method 4 in a yield of 45.2%, purified by preparative TLC using silica gel (GF254), followed by conversation to the HCl-salt by dissolving in DCM and addition of 1.2 eq. of ethereal HCl.

MS (m/z): 365 (M+H); HPLC (λ=214 nm, [A]): rt 10.6 min (100%); mp: 142° C.

Example 128

N-(6-(5-fluoro-2-methoxyphenyl)pyrimidin-4-yl)-2-(4-methylpyridin-3-yl)acetamide Example 128 was synthesized according to Method 4 in a yield of 71%, purified by preparative TLC using silica gel (GF254).

MS (m/z): 353 (M+H); HPLC (λ=214 nm, [A]): rt 9.8 min (92.7%); mp: 260° C.

Example 129

3-amino-N-(6-(5-fluoro-2-methoxyphenyl)pyrimidin-4-yl)-2-(pyridin-3-yl)propanamide*HCl Example 129 was synthesized according to Method 2 in a yield of 13%, purified by preparative HPLC using Zodiacsil 120-5-C18 column (250×32 mm; 10μ), Mobile phase: 0.01 M NH$_4$OAc (aq): AcN (35:65) and flow rate: 40 ml/min, followed by Method 7 (yield: 100%).

MS (m/z): 368 (M+H); HPLC (λ=214 nm, [A]): rt 8.0 min (100%).

Example 130

N-(6-(5-fluoro-2-methoxyphenyl)pyrimidin-4-yl)-2-(3-methylpyridin-4-yl)acetamide*HCl Example 130 was synthesized according to Method 2 in a yield of 16.4%, purified by column chromatography over silica gel (100-200 mesh) using 30% ethyl acetate in petroleum ether as eluent, followed by conversation to the HCl-salt by dissolving in DCM and addition of 1.2 eq. of ethereal HCl.

MS (m/z): 353 (M+H); HPLC (λ=214 nm, [A]): rt 9.8 min (100%).

Example 131

N-(6-(2-methoxyphenyl)pyrimidin-4-yl)-2-(pyrimidin-2-yloxy)acetamide

Example 131 was synthesized according to Method 2 in a yield of 25.1%, purified by flash column chromatography over silica gel (100-200 mesh) using methanol (0-10%) in chloroform.

$^1$H NMR (400 MHz, CDCl$_3$): δ=3.92 (s, 3H, CH$_3$), 5.04 (s, 2H, CH$_2$), 7.01 (d, 1H, Methoxy-Ar), 7.04-7.08 (m, 1H, Methoxy-Ar), 7.38-7.45 (m, 1H, Methoxy-Ar), 7.92 (dd, 1H, Methoxy-Ar), 8.57 (d, 2H, Pyrimidin-Ar), 8.81 (s, br., 1H, Pyrimidin-Ar), 8.91 (s, br., 2H, Pyrimidin-Ar); MS (m/z): 338 (M+H); HPLC (λ=214 nm, [A]): rt 11.7 min (97%).

Example 132

2-(2-bromopyridin-3-yloxy)-N-(6-(2-methoxyphenyl)pyrimidin-4-yl)acetamide*TFA

Example 132 was synthesized according to Method 2 in a yield of 14%, first step for purification was done by flash column chromatography over silica gel (100-200 mesh) using methanol (0-10%) in chloroform, final purification was done by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min as TFA salt.

$^1$H NMR (400 MHz, CDCl$_3$): δ=3.92 (s, 3H, CH$_3$), 4.72 (s, 2H, CH$_2$), 7.02 (d, 1H, Methoxy-Ar), 7.08 (td, 1H, Methoxy-Ar), 7.20 (dd, 1H, Methoxy-Ar), 7.27-7.30 (m, 1H, Methoxy-Ar), 7.90 (dd, 1H, Pyridin-Ar), 8.13 (dd, 1H, Pyridin-Ar), 8.82 (d, 1H, Pyrimidin-Ar), 9.03 (d, 1H, Pyrimidin-Ar), 8.91 (s, br., 1H, Pyridin-Ar); MS (m/z): 415 (M+H); HPLC (λ=214 nm, [A]): rt 16.5 min (100%).

Example 133

N-(6-(5-fluoro-2-methoxyphenyl)pyrimidin-4-yl)-3-(4-methylpyridin-3-yl)propanamide*HCl Example 133 was synthesized according to Method 2 in a yield of 45%, followed by conversation to the HCl-salt by dissolving in DCM and addition of 1.2 eq. of ethereal HCl.

MS (m/z): 367 (M+H); HPLC (λ=214 nm, [A]): rt 11.7 min (98.1%); mp: decomp.: 110° C.

Example 134

N-(6-(5-fluoro-2-methoxyphenyl)pyrimidin-4-yl)-6,7-dihydro-5H-cyclopenta[b]pyridine-7-carboxamide*HCl Example 134 was synthesized according to Method 4 in a yield of 10%, purified by preparative HPLC using Zodiacsil 120-5-C18 column (250×32 mm; 10μ), Mobile phase: 0.01M NH$_4$OAc (aq): AcN (35:65) and flow rate: 40 ml/min, followed by conversation to the HCl-salt by dissolving in DCM and addition of 1.2 eq. of ethereal HCl.

MS (m/z): 365 (M+H); HPLC (λ=214 nm, [A]): rt 13.7 min (83.2%); mp: decomp.: 200° C.

Example 135

N-(6-(5-fluoro-2-methoxyphenyl)pyrimidin-4-yl)-6,7-dihydro-5H-cyclopenta[b]pyridine-7-carboxamide Example 135 was synthesized according to Method 2 in a yield of 3%, first step for purification was done by flash column chromatography over silica gel (100-200 mesh) using methanol (0-10%) in chloroform, final purification was done by preparative HPLC using LUNA C18(2) 100A column (250×21.2 mm; 10μ), Mobile phase: 0.1% TFA (aq): gradient AcN-water (40/60) at t=0 min to AcN-water (95/5) within 45 min, flow rate: 6 ml/min; mp: 220° C.

$^1$H NMR (400 MHz, CDCl$_3$): δ=5.08 (s, 2H, CH$_2$), 7.34 (d, 1H), 7.54-7.59 (m, 1H), 7.64-7.68 (m, 2H), 7.74 (d, 1H), 7.79-7.84 (m, 1H), 7.90-7.95 (m, 1H), 7.97 (d, 1H), 8.24-8.33 (m, 3H), 8.72 (d, 1H); MS (m/z): 403 (M+H); HPLC (λ=214 nm, [A]): rt 18.1 min (92.1%).

Example 136

2-amino-N-(6-(5-fluoro-2-methoxyphenyl)pyrimidin-4-yl)-2-(pyridin-3-yl)acetamide*HCl Example 136 was synthesized according to Method 2 in a yield of 24%, purified by preparative HPLC using Zodiacsil 120-5-C18 column (250×32 mm; 10μ), Mobile phase: 0.01M NH$_4$OAc (aq): AcN (35:65) and flow rate: 40 ml/min, followed by Method 7 (yield: 100%).

MS (m/z): 354 (M+H); HPLC (λ=214 nm, [A]): rt 9.8 min (78.7%).

Example 137

N-(6-(5-fluoro-2-methoxyphenyl)pyrimidin-4-yl)-2-(piperazin-1-yl)-2-(pyridin-3-yl)acetamide*TFA Example 137 was synthesized according to Method 2 and 9 in a yield of 15% for Method 2 and 95% for Method 9.
MS (m/z): 423 (M+H); HPLC (λ=214 nm, [A]): rt 9.4 min (98.1%).

Example 138

N-(6-(2-methoxyphenyl)pyrimidin-4-yl)piperidine-1-carboxamide

Example 138 was synthesized according to Method 4 in a yield of 35%.
MS (m/z): 313 (M+H); HPLC (λ=214 nm, [A]): rt 12.2 min (100%).

Example 139

N-(6-(2-methoxyphenyl)pyrimidin-4-yl)piperidine-1-carboxamide*TFA

Example 139 was synthesized according to Method 4, followed by Method 9 in a yield of 5%.
MS (m/z): 314 (M+H); HPLC (λ=214 nm, [A]): rt rotameres: 7.1+7.4 min (94.4%).

Example 140

4-ethyl-N-(6-(5-fluoro-2-methoxyphenyl)pyrimidin-4-yl)piperazine-1-carboxamide*HCl Example 140 was synthesized according to Method 4 in a yield of 25.3%, purified by preparative HPLC using Zodiacsil 120-5-C18 column (250×32 mm; 10µ), Mobile phase: 0.1% formic acid (aq): AcN (25:75) and flow rate: 4 ml/min, followed by washing with 5% acetone in petroleum ether and conversation to the HCl-salt by dissolving in DCM and addition of 1.2 eq. of ethereal HCl in a yield of 100%.
MS (m/z): 360 (M+H); HPLC (λ=214 nm, [A]): rt 9.1 min (99%); mp: 219° C.

Example 141

1-(6-(5-fluoro-2-methoxyphenyl)pyrimidin-4-yl)-3-(pyridin-3-yl)urea*HCl

Example 141 was synthesized according to Method 12 in a yield of 21.2%, purified by diluting with 5% methanol in DCM to precipitate a solid, followed by conversation to the HCl-salt by dissolving in DCM and addition of 1.2 eq. of ethereal HCl in a yield of 100%.
MS (m/z): 340 (M+H); HPLC (λ=214 nm, [B]): rt 10.2 min (99.8%); mp: 224° C.

Example 142

1-(6-(5-fluoro-2-methoxyphenyl)pyrimidin-4-yl)urea

Example 142 was synthesized according to Method 4 in a yield of 11.8%, purified by preparative HPLC using Zodiacsil 120-5-C18 column (250×32 mm; 10µ), Mobile phase: 0.1% formic acid (aq): AcN (25:75) and flow rate: 4 ml/min.
MS (m/z): 262 (M); HPLC (λ=214 nm, [A]): rt 12.3 min (98%); mp: 170° C.

Example 143

N-(6-(5-fluoro-2-methoxyphenyl)pyrimidin-4-yl)-2-(pyrrolidin-1-yl)acetamide

Example 143 was synthesized according to Method 3 in a yield of 11.2%, purified by preparative TLC (silica gel GF254) using 1% methanol in chloroform as eluent.
$^1$H NMR (400 MHz, CDCl$_3$): δ=9.76 (s, 1H), 8.93 (s, 1H), 8.89 (s, 1H), 7.77-7.74 (dd, 1H), 7.14-7.12 (m, 1H), 6.97-6.94 (m, 1H), 3.92 (s, 3H), 3.34 (s, 2H), 2.72 (m, 4H), 1.88 (m, 4H); MS (m/z): 331 (M+H); HPLC (λ=214 nm, [B]): rt 9.1 min (98.3%); mp: 115° C.

Example 144

N-(6-(5-fluoro-2-methoxyphenyl)pyrimidin-4-yl)-2-(2-oxopiperidin-1-yl)acetamide

Example 144 was synthesized according to Method 2 in a yield of 8.8%, purified by 2 runs of preparative TLC using 7% MeOH in chloroform as eluent.
$^1$H NMR (400 MHz, DMSO-d$_6$): δ=8.94 (s, 1H), 8.66 (s, 1H), 7.69-7.66 (dd, 1H), 7.37-7.32 (m, 1H), 7.24-7.20 (m, 1H), 4.20 (s, 2H), 3.86 (s, 3H), 3.34 (m, 2H), 2.26 (m, 2H), 1.75 (s, br., 4H); MS (m/z): 359 (M+H); HPLC (λ=214 nm, [A]): rt 12.9 min (100%); mp: 220° C.

Example 145

N-(6-(5-fluoro-2-methoxyphenyl)pyrimidin-4-yl)-3-(2-oxopiperidin-1-yl)propanamide Example 145 was synthesized according to Method 2 in a yield of 13.9%, purified by preparative TLC over silica gel (GF254) using 5% MeOH in chloroform as eluent.
$^1$H NMR (400 MHz, DMSO-d$_6$): δ=8.92 (s, 1H), 8.72 (s, 1H), 7.71-7.68 (dd, 1H), 7.37-7.32 (m, 1H), 7.24-7.21 (m, 1H), 3.87 (s, 3H), 3.59-3.56 (merged with solvent, ~1H), 3.55 (t, 2H), 3.30 (t, 2H), 2.69 (t, 2H), 2.20 (t, 2H), 1.70-1.67 (m, 4H); MS (m/z): 373 (M+H); HPLC (λ=214 nm, [A]): rt 13.3 min (%); mp: 208° C.

Example 146

2-(4-benzylpiperazin-1-yl)-N-(6-(5-fluoro-2-methoxyphenyl)pyrimidin-4-yl)acetamide Example 146 was synthesized according to Method 3 in a yield of 29.2%, purified by preparative TLC (silica gel GF254) using 1% methanol in chloroform as eluent.
$^1$H NMR (400 MHz, CD$_3$OD): δ=8.86 (s, 1H), 8.83 (s, 1H), 7.67-7.64 (dd, 1H), 7.33-7.31 (m, ~4H), 7.25-7.15 (m, 3H), 3.90 (s, 3H), 3.57 (s, 2H), 3.26 (s, 2H), 2.67 (s, br., 4H), 2.60 (s, br., 4H); MS (m/z): 436 (M+H); HPLC (λ=214 nm, [A]): rt 11.9 min (93.8%); mp: 136° C.

Example 147

N-(6-(5-fluoro-2-methoxyphenyl)pyrimidin-4-yl)-2-(4,4-dimethyl-2,5-dioxoimidazolidin-1-yl)acetamide Example 147 was synthesized according to Method 3 in a yield of 25.4%, purified by preparative HPLC using Zodiacsil 120-5-C18 column (250×32 mm; 10µ), Mobile phase: 0.1% formic acid (aq): AcN (25:75) and flow rate: 4 ml/min.

$^1$H NMR (400 MHz, CD$_3$OD): δ=8.87 (s, 1H), 8.67 (s, 1H), 7.64-7.61 (dd, 1H), 7.23-7.12 (m, 3H), 4.39 (s, 2H), 3.88 (s, 3H), 1.45 (s, 6H); MS (m/z): 388 (M+H); HPLC (λ=214 nm, [A]): rt 13.0 min (97.7%); mp: 260° C.

Example 148

N-(6-(5-fluoro-2-methoxyphenyl)pyrimidin-4-yl)-2-oxo-2-(piperidin-1-yl)acetamide Example 148 was synthesized according to Method 2 in a yield of 26.3%, purified by preparative HPLC using Zodiacsil 120-5-C18 column (250×32 mm; 10µ), Mobile phase: 0.1% formic acid (aq): AcN (25:75) and flow rate: 4 ml/min.

$^1$H NMR (400 MHz, CDCl$_3$): δ=9.60 (s, 1H), 8.97 (s, 1H), 8.78 (s, 1H), 7.76-7.73 (dd, 1H), 7.15-7.10 (m, 1H), 6.98-6.94 (m, 1H), 4.03-4.01 (m, 2H), 3.92 (s, 3H), 3.66 (t, 2H), 1.70 (s, br., 6H); MS (m/z): 359 (M+H); HPLC (λ=214 nm, [A]): rt 17.1 min (100%); mp: 165° C.

Example 149

N-(6-(5-fluoro-2-methoxyphenyl)pyrimidin-4-yl)-2-(2-oxopyrrolidin-1-yl)acetamide Example 149 was synthesized according to Method 2 in a yield of 14.5%, purified by flash column chromatography over neutral alumina using ethyl acetat as eluent.

$^1$H NMR (400 MHz, CDCl$_3$): δ=8.92 (s, 1H), 8.76 (s, 1H), 8.68 (s, br., 1H), 7.75-7.72 (dd, 1H), 7.14-7.09 (m, 1H), 6.99-6.93 (m, 1H), 4.13 (s, 2H), 3.91 (s, 3H), 3.56 (t, 2H), 2.51 (t, 2H), 2.17-2.14 (m, 2H); MS (m/z): 345 (M+H); HPLC (λ=214 nm, [A]): rt 12.1 min (97.6%); mp: 219° C.

Example 150

N-(6-(2-methoxyphenyl)pyrimidin-4-yl)-2-(2-oxopyrrolidin-1-yl)acetamide

Example 150 was synthesized according to Method 4 in a yield of 88.2%, purified by flash column chromatography over silica gel (100-200 mesh) using methanol (0-10%) in chloroform.

$^1$H NMR (400 MHz, CD$_3$OD): δ=2.07-2.15 (m, 2H, CH$_2$—CH$_2$—CH$_2$), 2.44 (t, $^3$J=7.5 Hz, 2H, CH$_2$—CH$_2$—CH$_2$—C(O)), 3.56 (t, $^3$J=7.5 Hz, 2H, CH$_2$—CH$_2$—CH$_2$—N), 3.88 (s, 3H, CH$_3$), 4.22 (s, 2H, N—CH$_2$—C(O)), 7.06 (t, $^3$J=7.5 Hz, 1H, Methoxy-Ar), 7.14 (d, $^3$J=8.3 Hz, 1H, Methoxy-Ar), 7.43-7.48 (m, 1H, Methoxy-Ar), 7.76 (dd, $^3$J=7.5 Hz, $^4$J=1.7 Hz, 1H, Methoxy-Ar), 8.61 (s, 1H, Pyrimidin-Ar), 8.82 (s, 1H, Pyrimidin-Ar); MS (m/z): 327 (M+H); HPLC (λ=214 nm, [A]): rt 10.9 min (100%).

Example 151

2-(2,5-dihydro-1-isobutyl-5-oxo-1H-pyrazol-3-yl)-N-(6-(2-methoxyphenyl)pyrimidin-4-yl)acetamide Example 151152 was synthesized according to Method 2 in a yield of 3.4%, purified by preparative HPLC using LUNA C18(2) 100A column (250×21.2 mm; 10µ), Mobile phase: 0.1% TFA (aq): gradient AcN-water (40/60) at t=0 min to AcN-water (95/5) within 45 min, flow rate: 6 ml/min.

$^1$H NMR (400 MHz, CD$_3$OD): δ=0.91 (d, $^3$J=6.6 Hz, 6H, 2×CH$_3$), 2.09-2.20 (m, 1H, CH—CH$_3$), 3.80 (d, $^3$J=7.5 Hz, 2H, CH—CH$_2$), 3.89 (s, 3H, CH$_3$), 3.90-3.92 (m, 2H, CH$_2$), 7.11 (td, $^3$J=7.5 Hz, $^4$J=0.8 Hz, 1H, Methoxy-Ar), 7.18 (d, $^3$J=7.9 Hz, 1H, Methoxy-Ar), 7.51-7.56 (m, 1H, Methoxy-Ar), 7.73 (dd, $^3$J=7.5 Hz, $^4$J=1.7 Hz, 1H, Methoxy-Ar), 8.68 (d, $^5$J=0.8 Hz, 1H, Pyrimidin-Ar), 8.92 (d, $^5$J=0.8 Hz, 1H, Pyrimidin-Ar); MS (m/z): 382 (M+H); HPLC (λ=214 nm, [A]): rt 13.4 min (86.7%).

Example 152

N-(6-(5-fluoro-2-methoxyphenyl)pyrimidin-4-yl)-2-(2,5-dihydro-1-isobutyl-5-oxo-1H-pyrazol-3-yl)acetate Example 152 was synthesized according to Method 4 in a yield of 9.9%, purified by preparative HPLC using Gemini C18 (50×30 mm; 5µ) column.

$^1$H NMR (400 MHz, CDCl$_3$): δ=9.22 (s, 1H), 8.93 (s, 1H), 8.78 (s, 1H), 8.55 (s, 1H), 7.75 (dd, 2H), 7.20-7.15 (m, 2H), 6.95 (m, 2H), 6.12 (s, 1H), 4.30 (s, 2H), 4.03 (d, 2H), 3.91 (d, 6H), 2.15 (m, 1H), 1.04 (d, 6H); MS (m/z): 400 (M+H); HPLC (λ=214 nm, [A]): rt 22.2 min (86.2%).

Example 153

N-(6-(5-fluoro-2-methoxyphenyl)pyrimidin-4-yl)-2-(piperidin-4-yl)acetamide*HCl

Example 153 was synthesized according to Method 2 in a yield of 27.4%, followed by deprotection according to Method 9, conversation to the free base by dissolving in an aqueous solution of NaHCO$_3$ and conversation to the HCl-salt by dissolving in DCM and addition of 1.2 eq. of ethereal HCl in a yield of 23.3% for the last steps.

MS (m/z): 345 (M+H); HPLC (λ=214 nm, [A]): rt 9.4 min (95.8%).

Example 154

N-(6-(2-methoxyphenyl)pyrimidin-4-yl)-2-(2,6-dioxopiperidin-4-yl)acetamide

Example 154 was synthesized according to Method 2 in a yield of 4.0%, purified by preparative HPLC using Zodiacsil 120-5-C18 column (250×32 mm; 10µ), Mobile phase: 0.1% formic acid (aq):AcN (25:75) and flow rate: 4 ml/min and washing with ether.

MS (m/z): 355 (M+H); HPLC (λ=214 nm, [A]): rt 10.6 min (92.5%).

Example 155

N-(6-(5-fluoro-2-methoxyphenyl)pyrimidin-4-yl)-2-(2-oxopiperidin-4-yl)acetamide

Example 155 was synthesized according to Method 2 in a yield of 4.4%, purified by flash column chromatography over silica gel (40 micron) using methanol (0-10%) in chloroform followed by preparative TLC using silica gel (GF254) and eluting with 3% MeOH in chloroform.

MS (m/z): 359 (M+H); HPLC (λ=214 nm, [A]): rt 12.6 min (99.5%); mp: 217° C.

Example 156

N-(6-(2-methoxyphenyl)pyrimidin-4-yl)-2-(5-oxopyrrolidin-3-yl)acetamide

Example 156 was synthesized according to Method 2 in a yield of 3.8%, purified by preparative HPLC using Zodiacsil® 120-5-C18 column (250×32 mm; 10μ), Mobile phase: 0.1% formic acid (aq): AcN (25:75) and flow rate: 4 ml/min.

MS (m/z): 327 (M+H); HPLC (λ=214 nm, [A]): rt 10.4 min (100%); mp: 220° C.

Example from Table 2

Methods

Preparation of Common Intermediate (VIII):

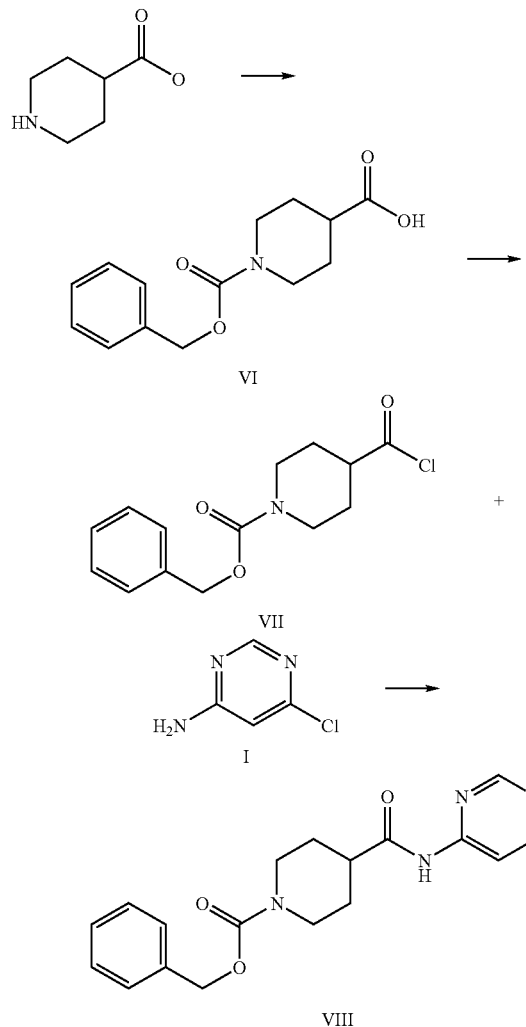

Preparation of Cbz-piperidine-4-carboxylic acid (VI)

To a stirred solution of piperidine-4-carboxylic acid (5.0 g, 38.7 mmol) and NaOH (1.86 g, 46.5 mmol) in H₂O (15 ml) was added dropwise a 50% solution of benzyl chloroformate in toluene (13.6 mL, 40.6 mmol) over a period of half an hour at 0° C. The reaction mixture was stirred at room temperature for 6 hours. The progress of the reaction was monitored by TLC. After completion, the reaction mixture was acidified with dil. HCl (pH 3) and extracted with ethyl acetate (3×100 ml). The combined organic phases were dried over sodium sulfate and concentrated. The crude product was purified by flash column chromatography (silica gel, elution with 30% ethyl acetate/n-hexanes) to afford piperidine-1,4-dicarboxylic acid monobenzyl ester (VI) (6.5 g, 64%) as a pale yellow oil.

HPLC purity λ=220 nm: 95%.

ESMS: m/z=264 (M+1).

Preparation of Compound (VII):

Piperidine-1,4-dicarboxylic acid monobenzyl ester (VI) (5.0 g, 19 mmol) was suspended in thionyl chloride (10 ml) and stirred at room temperature for one hour. Excess thionyl chloride was distilled out and the obtained crude 4-chlorocarbonyl-piperidine-1-carboxylic acid benzyl ester (VII) was used for the next reaction immediately.

Preparation of Compound (VIII):

A mixture of 4-chlorocarbonyl-piperidine-1-carboxylic acid benzyl ester (VII) (5.70 g, 20.2 mmol), 4-amino-6-chloropyrimidine (I) (2.10 g, 16.2 mmol) and 4-(N,N-dimethylamino)-pyridine (2.90 g, 23.7 mmol) in dichloromethane (50 ml) was heated to reflux temperature for 18 hours. The progress of the reaction was monitored by TLC, then dichloromethane was completely distilled off. Aqueous sodium bicarbonate solution was added to the residue and the mixture was extracted with ethyl acetate (3×100 ml). The organic layers were separated, dried over sodium sulfate and concentrated to obtain 4-(6-chloro-pyrimidin-4-ylcarbamoyl)-piperidine-1-carboxylic acid benzyl ester (VIII) (5.9 g, 79%) as a yellow solid.

HPLC purity λ=220 nm: 82%.

ESMS: m/z=375 (M+1).

Synthesis of Examples

Example 1A

Synthesis of Piperidine-4-carboxylic acid [6-(2-ethoxy-phenyl)-pyrimidin-4-yl]-amide (Compound #1A)

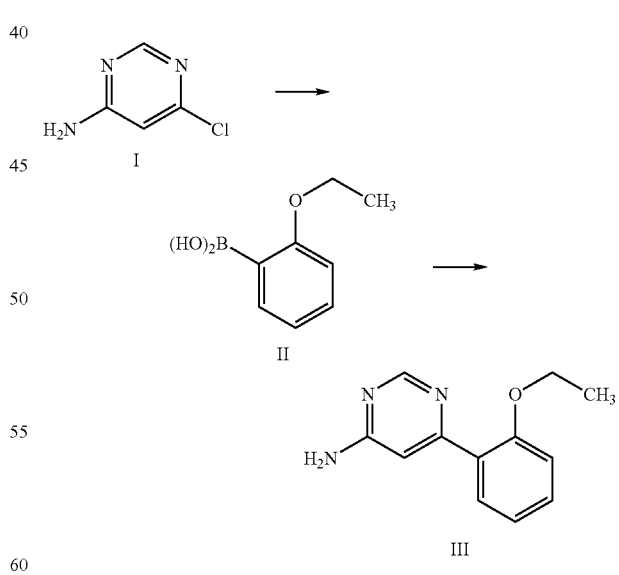

To a solution of 2-ethoxyphenylboronic acid (II) (1.73 g, 10.4 mmol) in 30 ml of 1,4-dioxane 10 ml of saturated aqueous sodium carbonate solution were added. Argon gas was purged for 10 min at room temperature. 6-Chloro-pyrimidin-4-ylamine (I) (1.50 g, 11.5 mmol) and tetrakis(triphenylphosphine)palladium(0) (0.66 g, 0.57 mmol) were added to the reaction mixture simultaneously and argon gas was bubbled in for another 5 min. The reaction mixture was heated to reflux for 12 hours. After completion of the reaction as indicated by TLC the mixture was concentrated under reduced pressure. The residue was partitioned between dichloromethane and water. The organic layer was separated, washed with water and brine, dried over sodium sulfate and concentrated. The obtained crude residue was purified by column chromatography eluting with 15% ethyl acetate in dichloromethane to provide 6-(2-ethoxy-phenyl)-pyrimidin-4-ylamine (III) (2.17 g, 87.3%).

$^1$H NMR (CDCl$_3$) δ=8.64 (1H, s), 7.90-7.86 (1H, m), 7.41-6.88 (4H, m), 4.85 (2H, bs), 4.15 (2H, q), 1.40 (3H, t).

MS: m/z=216 (M+1).

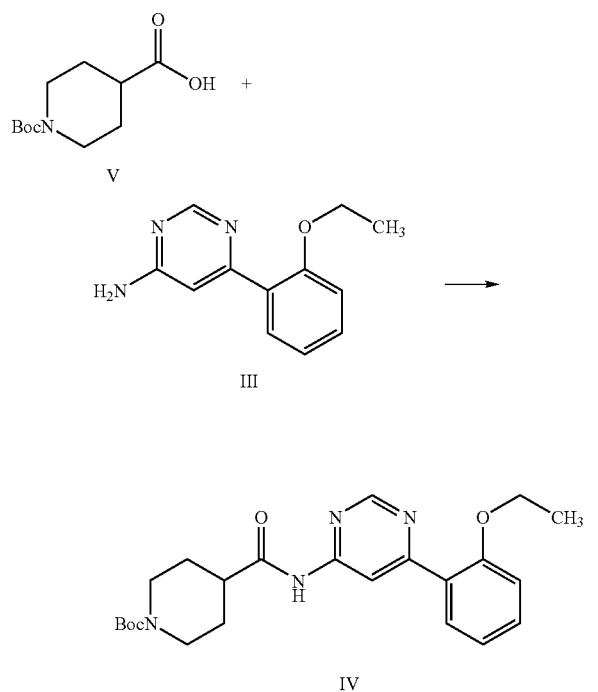

To a stirred solution of piperidine-1,4-dicarboxylic acid mono-tert-butyl ester (V), (1.27 g, 5.54 mmol) in dry dichloromethane, HOBt (1.27 g, 9.30 mmol) and EDCI (1.78 g, 9.30 mmol) were added at 0° C. and the reaction mixture was stirred for 5-10 minutes. Then 6-(2-ethoxy-phenyl)-pyrimidin-4-ylamine (III) (1.00 g, 4.65 mmol) was added and the reaction mixture was heated to reflux under an atmosphere of nitrogen for 48 hours. The reaction mixture was diluted with dichloromethane and washed with 1N HCl, aqueous sodium bicarbonate, water and brine and dried over anhydrous sodium sulfate. The solvent was removed under reduced pressure and the crude product was purified by column chromatography to obtain 4-[6-(2-ethoxy-phenyl)-pyrimidin-4-ylcarbamoyl]-piperidine-1-carboxylic acid tert-butyl ester (IV) (0.79 g, 40%).

$^1$H NMR (CDCl$_3$) δ=8.86-8.83 (2H, m), 8.17 (1H, bs), 8.05-7.88 (1H, m), 7.42-7.28 (1H, m), 7.16-6.87 (2H, m), 4.25-4.08 (4H, m), 2.86-2.68 (2H, m), 2.48-2.28 (1H, m), 2.00-1.62 (4H, m), 1.59-1.41 (12H, m).

MS: m/z=427 (M+1).

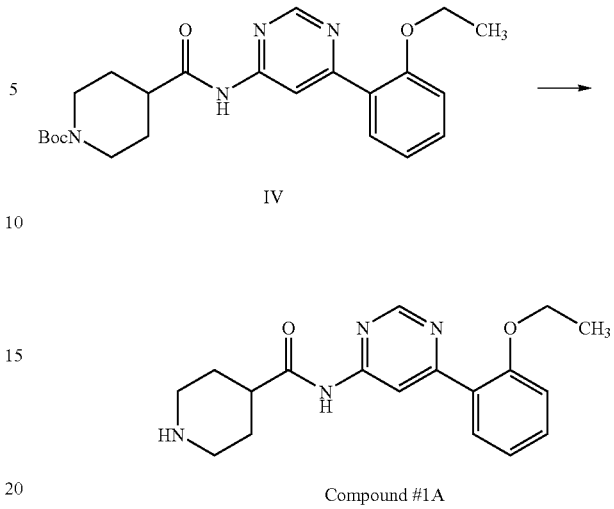

To a stirred solution of 4-[6-(2-ethoxy-phenyl)-pyrimidin-4-ylcarbamoyl]-piperidine-1-carboxylic acid tert-butyl ester (IV), (0.500 g, 1.17 mmol) in dry dichloromethane (1.5 ml), TFA (1.5 ml) was added at 0° C. and the reaction mixture was stirred for 2-3 hours. After completion of the reaction (monitored by TLC) the solvent mixture was removed under reduced pressure and dichloromethane was added to the residue. Solid sodium carbonate was added and the mixture was stirred for 3-4 hours. Then it was filtered and washed with dichloromethane. The combined filtrate was concentrated under reduced pressure to obtain a solid which was washed with 10% ethyl acetate/hexane to remove nonpolar impurities, giving piperidine-4-carboxylic acid [6-(2-ethoxy-phenyl)-pyrimidin-4-yl]-amide (compound #1A) as pure white solid (0.19 g, 50%).

$^1$H NMR (CDCl$_3$) δ=8.87-8.84 (2H, m), 8.01-7.84 (2H, m), 7.42-7.27 (1H, m), 7.15-6.89 (2H, m), 4.18 (2H, q), 3.24-3.16 (2H, m), 2.80-2.60 (2H, m), 2.47-2.38 (1H, m), 2.01-1.63 (4H, m), 1.45 (3H, t).

MS: m/z=327 (M+1).

Alternative Synthesis of Example 1A

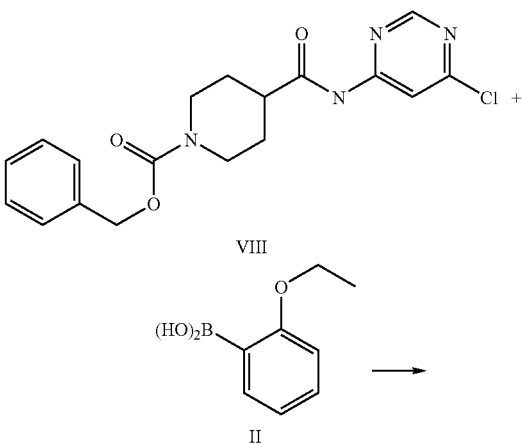

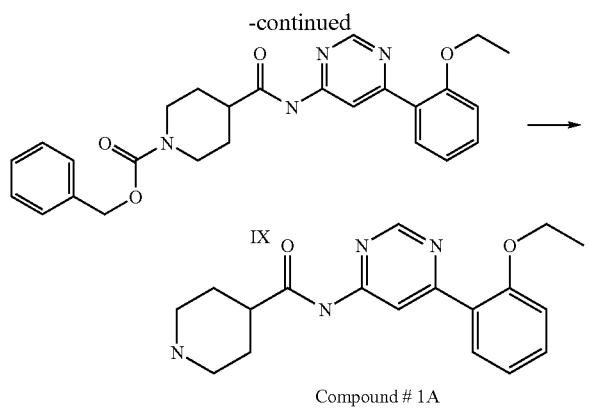

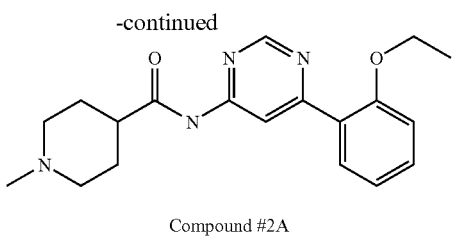

Compound #1A

Step I:

To a stirred mixture of 4-(6-chloro-pyrimidin-4-ylcarbamoyl)-piperidine-1-carboxylic acid benzyl ester (VIII) (6.15 g, 16.4 mmol), 2-ethoxyphenylboronic acid (II) (3.00 g, 18.1 mmol) in saturated sodium carbonate solution (10 ml) and 1,4-dioxane (10 ml) was added palladium(II) acetate (0.81 g, 3.6 mmol) followed by triphenylphosphine (0.94 g, 3.6 mmol) at room temperature under an atmosphere of nitrogen. The resulting reaction mixture was heated to reflux at 110° C. for one hour and monitored by TLC. The reaction mixture was filtered through a celite bed and the filtrate was extracted with ethyl acetate (3×100 ml). The organic layers were separated, combined, dried over sodium sulfate, filtered and concentrated under reduced pressure. The crude product was purified by flash column chromatography (silica gel, elution with 50% ethyl acetate/n-hexanes) to afford 4-[6-(2-ethoxy-phenyl)-pyrimidin-4-ylcarbamoyl]-piperidine-1-carboxylic acid benzyl ester (IX) (3.8 g, 50%) as a pale yellow oil.

HPLC purity λ=220 nm: 94%.
ESMS: m/z=461 (M+1).

Step II:

4-[6-(2-Ethoxy-phenyl)-pyrimidin-4-ylcarbamoyl]-piperidine-1-carboxylic acid benzyl ester (IX) (1.47 g, 3.19 mmol) was dissolved in methanol (20 ml) and 10% Pd/C (0.81 g) was added under an atmosphere of nitrogen. The reaction was stirred at room temperature under hydrogen balloon pressure for 18 hours. The catalyst was filtered from the reaction mixture through a celite bed and the filtrate was evaporated to dryness to obtain piperidine-4-carboxylic acid [6-(2-ethoxy-phenyl)-pyrimidin-4-yl]-amide (compound #1A) (0.61 g, 58%).

HPLC purity λ=220 nm: 87%.
ESMS: m/z=327 (M+1).

Example 2A

Synthesis of 1-Methyl-piperidine-4-carboxylic acid [6-(2-ethoxy-phenyl)-pyrimidin-4-yl]-amide (Compound #2A)

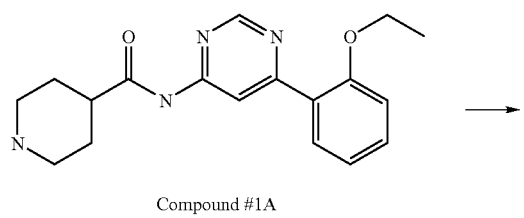

Compound #1A

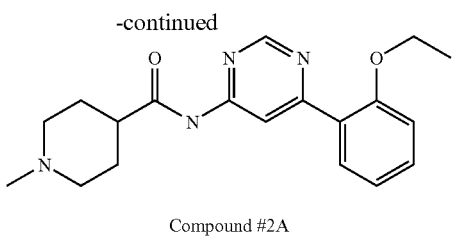

Compound #2A

To a stirred mixture of piperidine-4-carboxylic acid [6-(2-ethoxy-phenyl)-pyrimidin-4-yl]-amide (compound #1A) (0.28 g, 0.86 mmol) and 33% formalin solution (0.045 ml) in 10 ml of AcN:MeOH:H₂O (2:1:1) at 0° C. was added NaCNBH₃ (0.13 g, 2.1 mmol). The reaction mixture was stirred at room temperature for 30 min and extracted with ethyl acetate (3×20 ml). The organic layers were separated, combined, dried over sodium sulfate, filtered and concentrated under reduced pressure. The crude product was purified by preparative HPLC (C-18, AcN:H₂O with 0.05% TFA) to afford 1-ethyl-piperidine-4-carboxylic acid [6-(2-ethoxy-phenyl)-pyrimidin-4-yl]-amide (compound #2A) (0.195 g, 66%) as a white solid.

HPLC purity λ=220 nm: 99%.
ESMS: m/z=341(M+1).
¹H NMR (500 MHz, DMSO-d₆) δ=11.0 (s, —NH, 1H); 9.20 (br, —NH, 1H); 8.95 (s, Ar—H, 1H); 8.85 (s, Ar—H, 1H); 8.0 (m, Ar—H, 1H); 7.45 (m, Ar—H, 1H); 7.2 (m, Ar—H, 1H); 7.05 (m, Ar—H, 1H); 4.2 (q, J=7.4 Hz, —OCH₂CH₃, 2H); 3.41 (m, 2H); 2.95 (m, 2H); 3.0 (m, 2H); 2.80 (s, —NCH₃, 3H); 2.5 (br, overlapped with DMSO, 1H); 2.1 (m, 2H); 1.8 (m, 2H); 1.4 (t, J=7.4 Hz, —OCH₂CH₃, 2H).

Melting point: 65-67° C.

Example 3A

Synthesis of 1-ethyl-piperidine-4-carboxylic acid [6-(2-ethoxy-phenyl)-pyrimidin-4-yl]-amide (Compound #3A)

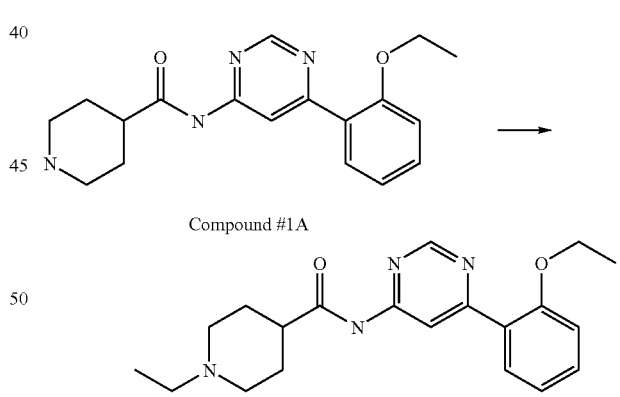

To the stirred solution of piperidine-4-carboxylic acid [6-(2-ethoxy-phenyl)-pyrimidin-4-yl]-amide (compound #1A) (0.20 g, 0.61 mmol) and potassium carbonate (0.10 g, 0.72 mmol) in DMF (3 ml) was added ethyl bromide (0.07 g, 0.05 ml, 0.61 mmol) at room temperature. The reaction mixture was heated at 60° C. for one hour. The progress of the reaction was monitored by TLC. The reaction mixture was poured onto ice water and extracted with ethyl acetate (3×100 mL). The organic layers were separated, combined, dried over sodium sulfate, filtered and concentrated under reduced pressure. The crude product was purified by trituration with diethyl ether (3 ml), filtered and dried under high vacuum to afford 1-ethyl-piperidine-4-carboxylic acid [6-(2-ethoxy-phenyl)-pyrimidin-4-yl]-amide (compound #3A) (0.093 g, 43%) as a white solid.

HPLC purity λ=220 nm: 96%.

ESMS: m/z=355 (M+1).

$^1$H NMR (500 MHz, CDCl$_3$) δ=8.95 (s, Ar—H, 1H); 8.90 (s, Ar—H, 1H); 8.0 (s, Ar—H and —NH, 2H); 7.4 (s, Ar—H, 1H); 7.05-7.0 (m, Ar—H, 2H); 4.2 (q, J=7.4 Hz, —OCH$_2$CH$_3$, 2H); 3.05 (m, 2H); 2.4 (q, J=7.3 Hz, —NCHCH$_3$, 2H); 2.35 (s, 1H); 2.1-1.8 (m, 6H); 1.5 (t, J=7.4 Hz, —OCH$_2$CH$_3$, 3H); 0.5 (t, J=7.3 Hz —NCH$_2$CH$_3$, 3H).

Melting point: 137-139° C.

Example 4A

Synthesis of 1-isopropyl-piperidine-4-carboxylic acid [6-(2-ethoxy-phenyl)-pyrimidin-4-yl]-amide (Compound #4A)

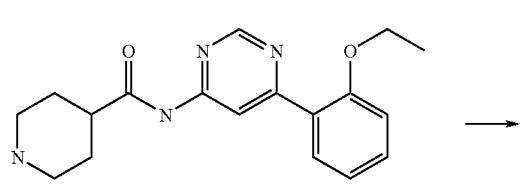

Compound #1A

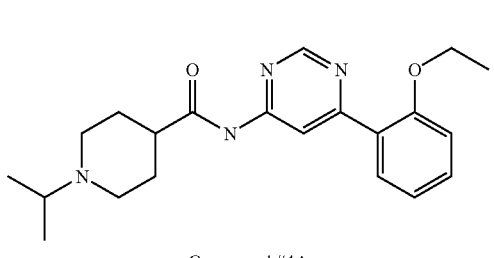

Compound #4A

To a stirred solution of piperidine-4-carboxylic acid [6-(2-ethoxy-phenyl)-pyrimidin-4-yl]-amide (compound #1A) (0.35 g, 1.0 mmol) and potassium carbonate (0.17 g, 1.2 mmol) in DMF (4 ml) was added 2-bromopropane (0.10 ml, 1.07 mmol) at room temperature. The reaction mixture was heated at 60° C. for one hour. The progress of the reaction was monitored by TLC. The reaction mixture was poured onto ice water and extracted with ethyl acetate (3×100 ml). The organic layers were separated, combined, dried over sodium sulfate, filtered and concentrated under reduced pressure. The crude product was purified by preparative HPLC (C-18, AcN:H$_2$O with 0.05% TFA) and lyophilized to afford 1-isopropyl-piperidine-4-carboxylic acid [6-(2-ethoxy-phenyl)-pyrimidin-4-yl]-amide (compound #4A) (0.2 g, 51%) as a white solid.

HPLC purity λ=220 nm: 99%.

ESMS: m/z=369 (M+1).

$^1$H NMR (500 MHz, CDCl$_3$) δ: 8.95 (s, Ar—H, 2H); 8.4 (br, —NH 1H); 8.05 (m, Ar—H, 1H); 7.42 (m, Ar—H, 1H); 7.1-7.0 (m, Ar—H, 2H); 4.2 (q, J=7.4 Hz, —OCH$_2$CH$_3$, 2H); 4.0 (m, 1H); 3.6 (m, 2H); 3.3 (m, 2H); 2.8-2.5 (m, 3H); 2.2 (m, 2H); 1.3 (t, J=7.4 Hz, —OCH$_2$CH$_3$, 3H); 1.10 (d, 6H).

Melting point: 173-175° C.

Example 5A

Synthesis of 1-benzyl-piperidine-4-carboxylic acid [6-(2-ethoxy-phenyl)-pyrimidin-4-yl]-amide (Compound #5A)

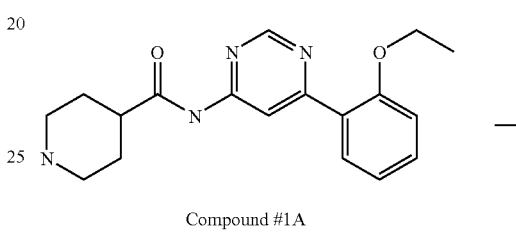

Compound #1A

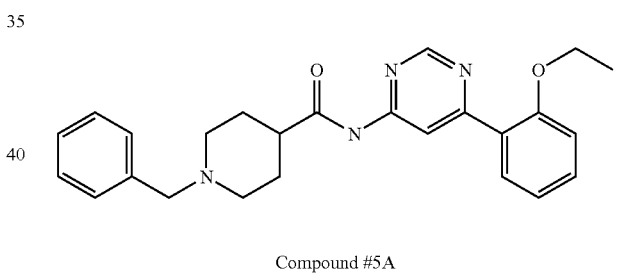

Compound #5A

To a stirred solution of piperidine-4-carboxylic acid [6-(2-ethoxy-phenyl)-pyrimidin-4-yl]-amide (compound #1A) (0.60 g, 1.84 mmol) and potassium carbonate (0.25 g, 1.8 mmol) in DMF (40 mL) was added benzyl bromide (0.31 g, 0.22 ml, 1.84 mmol) at room temperature. The reaction mixture was heated at 60° C. for one hour and the progress of the reaction was monitored by TLC. The mixture was poured onto ice water and extracted with ethyl acetate (3×100 ml). The organic layers were separated, combined, dried over sodium sulfate, filtered and concentrated under reduced pressure. The crude product was triturated with dry diethyl ether and the solid was filtered to obtain 1-benzyl-piperidine-4-carboxylic acid [6-(2-ethoxy-phenyl)-pyrimidin-4-yl]-amide (compound #5A) (0.165 g. 21%) as a yellow solid.

HPLC purity λ=220 nm: 96%.

ESMS: m/z=417 (M+1).

$^1$H NMR (500 MHz, DMSO-d$_6$) δ=10.8 (s, —NH, 1H); 8.90 (s, Ar—H, 1H); 8.89 (s, Ar—H, 1H); 7.42 (m, Ar—H, 1H); 7.30 (m, Ar—H, 5H); 7.2 (m, Ar—H, 1H); 7.05 (m, Ar—H, 1H); 4.2 (q, OCH$_2$CH$_3$, 2H); 3.42 (s, 2H); 2.9 (br,

2H); 2.5 (br, overlapped with DMSO protons, 1H); 2.0 (m, 2H); 1.8 (m, 2H); 1.6 (m, 2H); 1.4 (t, J=7.3 Hz, OCH$_2$CH$_3$, 3H).

Example 6A

Synthesis of piperidine-4-carboxylic acid [6-(2-methoxy-phenyl)-pyrimidin-4-yl]-amide (Compound #6A)

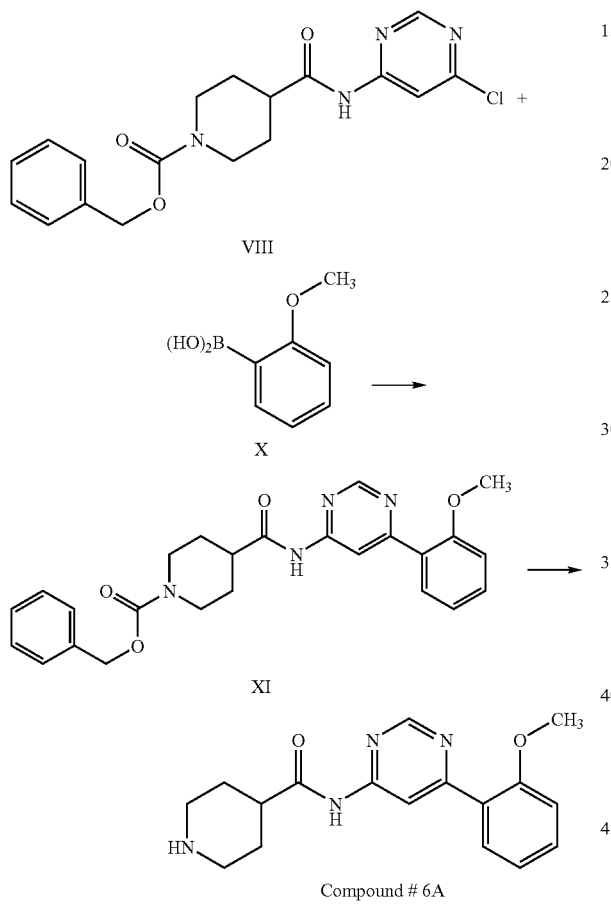

Step I:

To a stirred mixture of 4-(6-chloro-pyrimidin-4-ylcarbamoyl)-piperidine-1-carboxylic acid benzyl ester (VIII) (0.730 g, 1.95 mmol), 2-methoxyphenylboronic acid (0.300 g, 1.97 mmol) in saturated sodium carbonate solution (10 ml) and 1,4-dioxane (10 ml) was added palladium(II) acetate (0.088 g, 0.39 mmol) followed by triphenylphosphine (0.103 g, 0.39 mmol) at room temperature under an atmosphere of nitrogen. The resulting mixture was heated to reflux at 110° C. for one hour and monitored by TLC. The reaction mixture was filtered through a celite bed and the filtrate was extracted with ethyl acetate (3×100 ml). The organic layers were separated, combined, dried over sodium sulfate and concentrated under reduced pressure. The crude product was purified by flash column chromatography (silica gel, elution with 50% ethyl acetate/n-hexanes) to afford 4-[6-(2-methoxy-phenyl)-pyrimidin-4-ylcarbamoyl]-piperidine-1-carboxylic acid benzyl ester (XI) (0.47 g, 53%) as a white solid.

HPLC purity λ=220 nm: 89%.

ESMS: m/z=447 (M+1).

Step II:

4-[6-(2-Methoxy-phenyl)-pyrimidin-4-ylcarbamoyl]-piperidine-1-carboxylic acid benzyl ester (XI) (0.45 g, 1.00 mmol) was dissolved in methanol:dichloromethane (4:1) (24 ml) and 10% Pd/C (0.2 g) was added under an atmosphere of nitrogen. The reaction was stirred at room temperature under hydrogen balloon pressure for 18 hours. The catalyst was removed from the reaction mixture by filtration through a celite bed and the filtrate was evaporated to dryness. Then the crude product was treated with dry diethyl ether (10 ml) and the solid was filtered to obtain piperidine-4-carboxylic acid [6-(2-methoxy-phenyl)-pyrimidin-4-yl]-amide (compound #6A) (0.19 g, 42%) as a white solid.

HPLC purity λ=220 nm: 97%.

ESMS: m/z=313 (M+1).

$^1$H NMR (500 MHz, DMSO-d$_6$) δ=11.2 (s, —NH, 1H); 9.05 (s, br., NH, 1H); 8.95 (s, Ar—H, 1H); 8.70 (s, Ar—H, 1H); 7.95 (m, Ar—H, 1H); 7.5 (m, Ar—H, 1H); 7.2 (m, Ar—H, 1H), 7.1 (m, Ar—H, 1H); 3.95 (s, 3H); 3.3 (m, 2H); 2.95 (m, 3H); 2.05 (m, 2H); 1.85 (m, 2H).

Melting point: 279-280° C.

Example 7A

Synthesis of piperidine-4-carboxylic acid [6-(2-isopropoxy-phenyl)-pyrimidin-4-yl]-amide (Compound #7A)

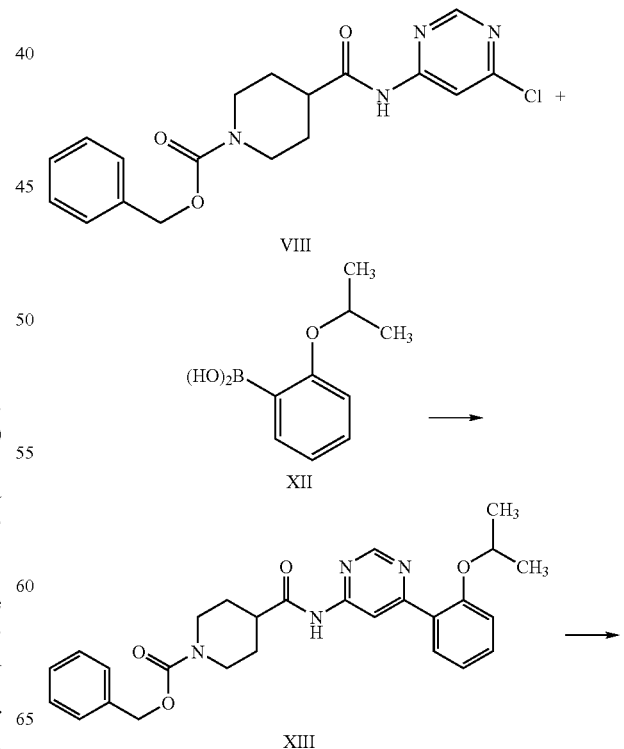

145

-continued

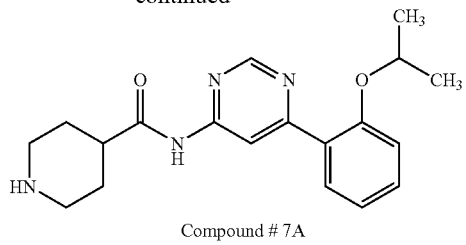

Compound # 7A

Step I:

To a stirred mixture of 4-(6-chloro-pyrimidin-4-ylcarbamoyl)-piperidine-1-carboxylic acid benzyl ester (VIII) (0.830 g, 2.22 mmol), 2-isopropyloxyphenylboronic acid (0.400 g, 2.22 mmol) in saturated sodium carbonate solution (10 ml) and 1,4-dioxane (10 ml) was added palladium(II) acetate (0.1 g, 0.44 mmol) followed by triphenylphosphine (0.11 g, 0.42 mmol) at room temperature under an atmosphere of nitrogen. The resulting mixture was heated to reflux at 110° C. for one hour and monitored by TLC. The reaction mixture was filtered through a celite bed and the filtrate was extracted with ethyl acetate (3×100 ml). The organic layers were separated, combined, dried over sodium sulfate and concentrated under reduced pressure. The crude product was purified by flash column chromatography (silica gel, elution with 50% ethyl acetate/n-hexanes) to afford 4-[6-(2-isopropoxy-phenyl)-pyrimidin-4-ylcarbamoyl]-piperidine-1-carboxylic acid benzyl ester (XIII) (0.36 g, 37%) as a white solid.

HPLC purity λ=220 nm: 98%.

ESMS: m/z=448 (M+1).

Step II:

4-[6-(2-Isopropoxy-phenyl)-pyrimidin-4-ylcarbamoyl]-piperidine-1-carboxylic acid benzyl ester (XIII) (0.32 g, 0.67 mmol) was dissolved in methanol (20 ml) and 10% Pd/C (0.17 g) was added under an atmosphere of nitrogen. The reaction was stirred at room temperature under hydrogen balloon pressure for 18 hours. The catalyst was removed from reaction mixture by filtration through a celite bed and the filtrate was evaporated to dryness. Then the crude product was triturated with dry diethyl ether (10 mL) and the resulting solid was filtered to obtain piperidine-4-carboxylic acid [6-(2-isopropoxy-phenyl)-pyrimidin-4-yl]-amide (compound #7A) (0.12 g, 52%) as a white solid.

HPLC purity λ=220 nm: 99%.

ESMS: m/z=341 (M+1).

$^1$H NMR (500 MHz, CDCl$_3$) δ=8.95 (s, Ar—H, 1H); 8.92 (s, Ar—H, 1H); 8.05 (m, —NH and Ar—H, 2H); 7.4 (m, Ar—H, 1H); 7.05 (m, Ar—H, 2H); 4.7 (m, OCH, 1H); 3.20 (m, 2H); 2.7 (m, 2H); 2.41 (m, 1H); 1.95-1.75 (m, 5H); 1.40 (d, 6H).

146

Example 8A

Synthesis of piperidine-4-carboxylic acid [6-(2-cyclopropylmethoxy-phenyl)-pyrimidin-4-yl]-amide (Compound #8A)

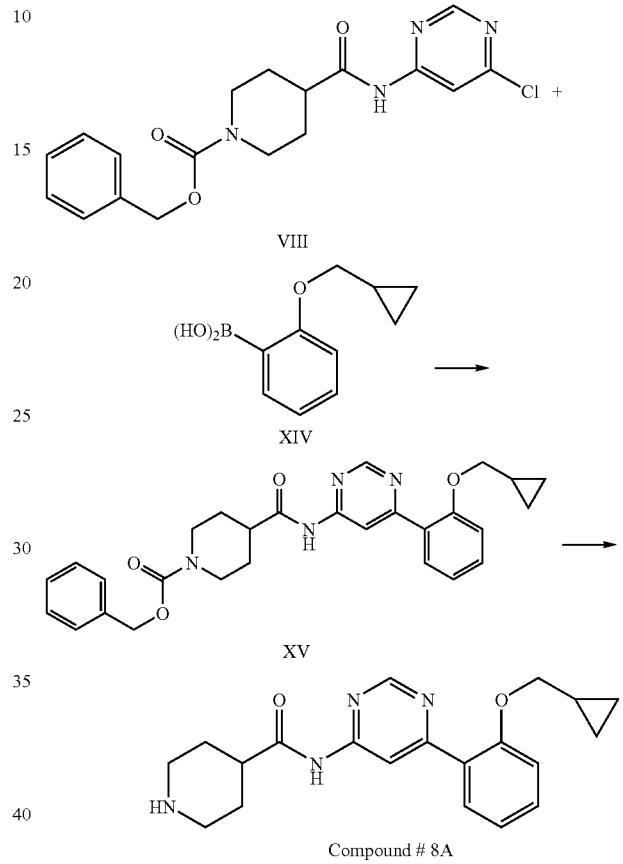

Compound # 8A

Step I:

To the stirred mixture of 4-(6-chloro-pyrimidin-4-ylcarbamoyl)-piperidine-1-carboxylic acid benzyl ester (VIII) (0.59 g, 1.6 mmol) and 2-(cyclopropylmethoxy)phenyl boronic acid (0.34 g, 1.9 mmol) in saturated sodium carbonate solution (5 ml) and 1,4-dioxane (5 ml) was added palladium(II) acetate (0.071 g, 0.32 mmol) followed by triphenylphosphine (0.083 g, 0.32 mmol) at room temperature under an atmosphere of nitrogen. The resulting mixture was heated to reflux at 110° C. for one hour and monitored by TLC. The reaction mixture was filtered through a celite bed and the filtrate was extracted with ethyl acetate (3×100 mL). The organic layers were separated, combined, dried over sodium sulfate and concentrated under reduced pressure. The crude product was purified by flash column chromatography (silica gel, elution with 50% ethyl acetate/n-hexanes) to afford 4-[6-(2-cyclopropylmethoxy-phenyl)-pyrimidin-4-ylcarbamoyl]-piperidine-1-carboxylic acid benzyl ester (XV) (0.4 g, 35%) as a white solid.

HPLC purity λ=220 nm: 98%.

ESMS: m/z=487 (M+1).

Step II:

4-[6-(2-Cyclopropylmethoxy-phenyl)-pyrimidin-4-ylcarbamoyl]-piperidine-1-carboxylic acid benzyl ester (XV) (0.41 g, 0.84 mmol) was dissolved in methanol (20 ml) and 10% Pd/C (0.2 g) was added under an atmosphere of nitrogen. The reaction was stirred at room temperature under hydrogen balloon pressure for 18 hours. The catalyst was removed from the reaction mixture by filtration through a celite bed and the filtrate was evaporated to dryness. Then the crude product was triturated with dry diethyl ether (10 ml) and the solid was filtered off to obtain piperidine-4-carboxylic acid [6-(2-cyclopropylmethoxy-phenyl)-pyrimidin-4-yl]-amide (compound #8A) (0.11 g, 37%) as a white solid.

HPLC purity λ=220 nm: 97%.

ESMS: m/z=353 (M+1).

$^1$H NMR (500 MHz, CDCl$_3$) δ 8.90 (s, Ar—H, 1H); 8.95 (s, Ar—H, 1H); 8.05 (m, —NH, 1H); 8.0 (m, Ar—H, 1H); 7.4 (m, Ar—H, 1H); 7.05 (m, Ar—H, 1H); 6.95 (m, Ar—H, 1H); 3.95 (d, OCH$_2$, 2H); 3.0 (m, 2H); 2.40 (br, 3H); 2.1-1.9 (br, 4H); 1.2. (m, 1H); 0.6 (m, 2H); 0.45 (m, 2H).

Example 9A

Synthesis of piperidine-4-carboxylic acid [6-(2-benzyloxy-phenyl)-pyrimidin-4-yl]-(Compound #9A)

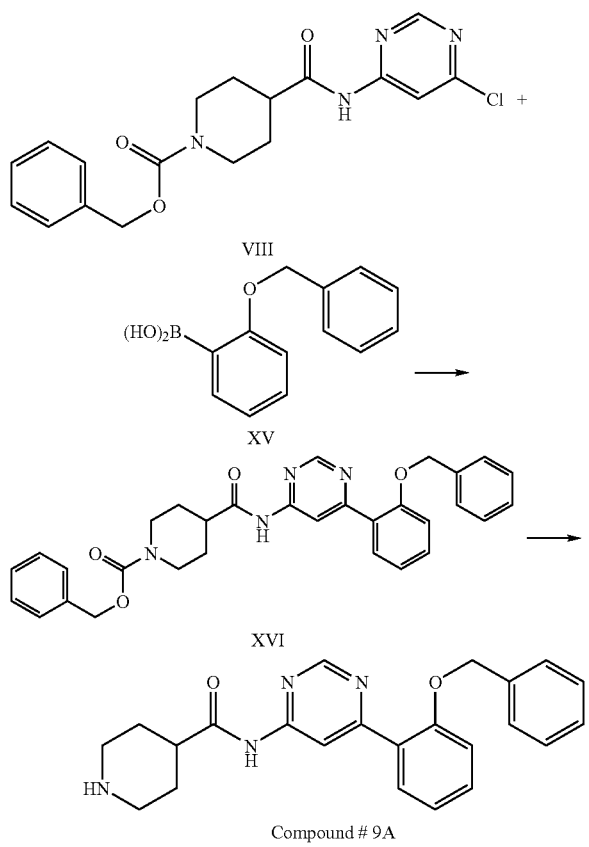

Step I:

To a stirred mixture of 4-(6-chloro-pyrimidin-4-ylcarbamoyl)-piperidine-1-carboxylic acid benzyl ester (VIII) (0.74 g, 2.0 mmol) and 2-benzyloxyphenylboronic acid (0.50 g, 2.2 mmol) in saturated sodium carbonate solution (4 ml) and 1,4-dioxane (4 ml) was added palladium(II) acetate (0.09 g, 0.40 mmol) followed by triphenylphosphine (0.105 g, 0.400 mmol) at room temperature under an atmosphere of nitrogen. The resulting mixture was heated to reflux at 110° C. for one hour and monitored by TLC. The reaction mixture was filtered through a celite bed and the filtrate was extracted with ethyl acetate (3×100 ml). The organic layers were separated, combined, dried over sodium sulfate and concentrated under reduced pressure. The crude product was purified by preparative HPLC to afford 4-[6-(2-benzyloxy-phenyl)-pyrimidin-4-ylcarbamoyl]-piperidine-1-carboxylic acid benzyl ester (XVI) (0.65 g, 62%).

HPLC purity λ=220 nm: 95%.

ESMS: m/z=523 (M+1).

Step II:

4-[6-(2-Benzyloxy-phenyl)-pyrimidin-4-ylcarbamoyl]-piperidine-1-carboxylic acid benzyl ester (XVI) (0.5 g, 1 mmol) was dissolved in 33% HBr in acetic acid (3 ml) and stirred at room temperature for 45 minutes. A yellow solid precipitated out; the reaction mixture was quenched at 0° C. with aqueous sodium hydroxide solution and extracted with ethyl acetate (3×10 ml). The organic phases were separated, combined, dried over sodium sulfate and concentrated under reduced pressure. The crude product was purified by preparative HPLC (C-18, AcN:H$_2$O with 0.05% TFA) and lyophilized to afford piperidine-4-carboxylic acid [6-(2-benzyloxy-phenyl)-pyrimidin-4-yl]-amide (compound #9A) (0.028 g, 7%) as a white solid.

HPLC purity λ=220 nm: 98%.

ESMS: m/z=389 (M+1).

$^1$H NMR (500 MHz, DMSO-d$_6$) δ 11.2 (s, —NH, 1H); 9.40 (s, br., —NH, 1H); 8.95 (s, Ar—H, 1H); 8.70 (s, Ar—H, 1H); 7.8 (m, Ar—H, 1H); 7.5 (br, Ar—H, 5H); 7.35 (m, Ar—H, 1H); 7.0 (m, Ar—H, 1H); 4.3 (s, 2H); 3.3 (m, overlapped with DMSO, 2H); 2.95 (m, 2H); 2.8 (m, 1H); 2.1 (m, 2H); 1.8 (m, 2H).

Melting point: 224-227° C.

Example 10A

Synthesis of piperidine-4-carboxylic acid [6-(4-fluoro-2-methoxy-phenyl)-pyrimidin-4-yl]-amide (Compound #10A)

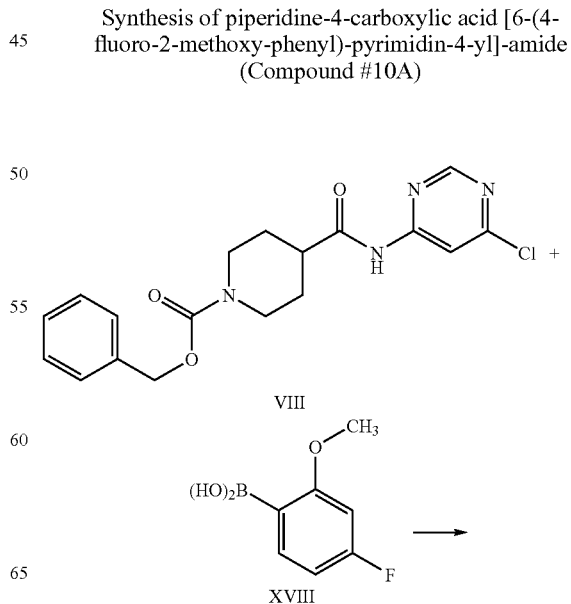

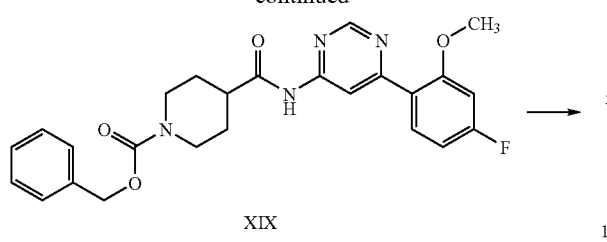

Ar—H, 1H), 3.95 (s, 3H); 3.25 (br, 2H, overlapped with DMSO signal); 2.95 (m, 2H); 2.0 (m, 2H); 1.8 (m, 2H).

Example 11A

Synthesis of piperidine-4-carboxylic acid [6-(5-fluoro-2-methoxy-phenyl)-pyrimidin-4-yl]-amide (Compound #11A)

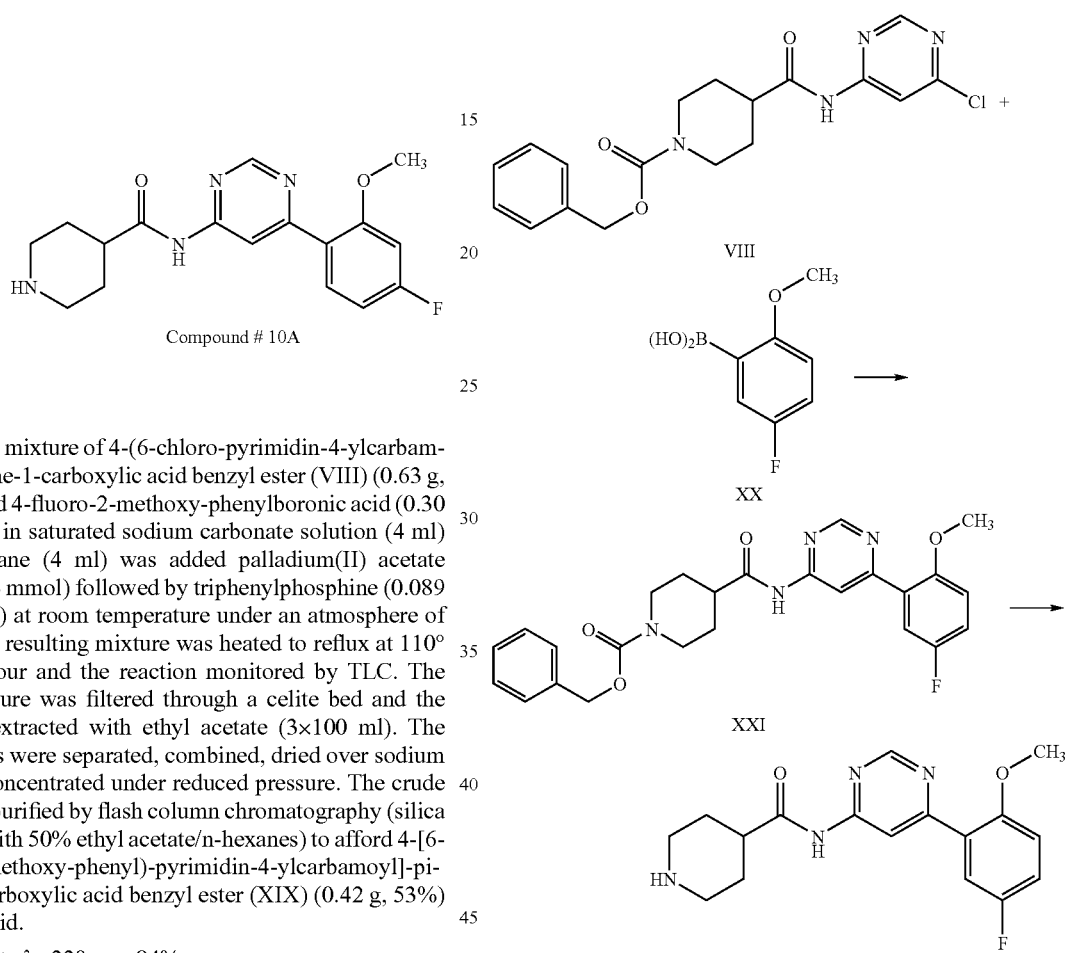

Step I:

To a stirred mixture of 4-(6-chloro-pyrimidin-4-ylcarbamoyl)-piperidine-1-carboxylic acid benzyl ester (VIII) (0.63 g, 1.7 mmol) and 4-fluoro-2-methoxy-phenylboronic acid (0.30 g, 1.8 mmol) in saturated sodium carbonate solution (4 ml) and 1,4-dioxane (4 ml) was added palladium(II) acetate (0.076 g, 0.34 mmol) followed by triphenylphosphine (0.089 g, 0.34 mmol) at room temperature under an atmosphere of nitrogen. The resulting mixture was heated to reflux at 110° C. for one hour and the reaction monitored by TLC. The reaction mixture was filtered through a celite bed and the filtrate was extracted with ethyl acetate (3×100 ml). The organic layers were separated, combined, dried over sodium sulfate and concentrated under reduced pressure. The crude product was purified by flash column chromatography (silica gel, elution with 50% ethyl acetate/n-hexanes) to afford 4-[6-(4-fluoro-2-methoxy-phenyl)-pyrimidin-4-ylcarbamoyl]-piperidine-1-carboxylic acid benzyl ester (XIX) (0.42 g, 53%) as a white solid.

HPLC purity λ=220 nm: 84%.

Step II:

4-[6-(4-Fluoro-2-methoxy-phenyl)-pyrimidin-4-ylcarbamoyl]-piperidine-1-carboxylic acid benzyl ester (XIX) (0.42 g, 0.9 mmol) was dissolved in methanol (20 ml) and 10% Pd/C (0.2 g) was added under an atmosphere of nitrogen. The reaction was stirred at room temperature under hydrogen balloon pressure for 18 hours. The catalyst was removed from the reaction mixture by filtration through a celite bed and the filtrate was evaporated to dryness. Then the crude product was triturated with dry diethyl ether (5 ml) and the solid was filtered off to obtain piperidine-4-carboxylic acid [6-(4-fluoro-2-methoxy-phenyl)-pyrimidin-4-yl]-amide (compound #10A,) (0.22 g, 76%) as a white solid.

HPLC purity=220 nm: 99%.

ESMS: m/z=331 (M+1).

$^1$H NMR (500 MHz, DMSO-$d_6$) δ=11.0 (s, —NH, 1H); 8.95 (s, Ar—H, 1H); 8.70 (s, br., —NH, 1H); 8.6 (s, Ar—H, 1H); 8.0 (m, Ar—H, 1H); 7.2 (m, Ar—H, 1H); 6.95 (m,

Step I:

To a stirred mixture of 4-(6-chloro-pyrimidin-4-ylcarbamoyl)-piperidine-1-carboxylic acid benzyl ester (VIII) (0.60 g, 1.6 mmol) and 5-fluoro-2-methoxy-phenylboronic acid (0.300 g, 1.76 mmol) in saturated sodium carbonate solution (5 ml) and 1,4-dioxane (5 ml) was added palladium(II) acetate (0.072 g, 0.32 mmol) followed by triphenylphosphine (0.084 g, 0.32 mmol) at room temperature under an atmosphere of nitrogen. The resulting mixture was heated to reflux at 110° C. for one hour and the reaction monitored by TLC. The reaction mixture was filtered through a celite bed and the filtrate was extracted with ethyl acetate (3×100 ml). The organic layers were separated, combined, dried over sodium sulfate and concentrated under reduced pressure. The crude product was purified by flash column chromatography (silica gel, elution with 50% ethyl acetate/n-hexanes) to afford 4-[6-(5-fluoro-2-methoxy-phenyl)-pyrimidin-4-ylcarbamoyl]-piperidine-1-carboxylic acid benzyl ester (XXI) (0.39 g, 52%) as a pale yellow oil.

HPLC purity=220 nm: 80%).

ESMS: m/z=465 (M+1).

Step II:

4-[6-(5-Fluoro-2-methoxy-phenyl)-pyrimidin-4-ylcarbamoyl]-piperidine-1-carboxylic acid benzyl ester (XXI) (0.39 g, 0.84 mmol) was dissolved in methanol (15 ml) and 10% Pd/C (0.2 g) was added under an atmosphere of nitrogen. The mixture was stirred at room temperature under hydrogen balloon pressure for 18 hours. The catalyst was removed from the reaction mixture by filtration through a celite bed and the filtrate was evaporated to dryness. The resulting crude product was triturated with dry diethyl ether (5 ml) and the solid was filtered off to obtain piperidine-4-carboxylic acid [6-(5-fluoro-2-methoxy-phenyl)-pyrimidin-4-yl]-amide (compound #11A) (0.076 g, 27%) as a white solid.

HPLC purity λ=220 nm: 98%.

ESMS: m/z=331 (M+1).

$^1$H NMR (500 MHz, DMSO-$d_6$) δ=11 (s, —NH, 1H); 8.99 (s, Ar—H, 1H); 8.89 (s, Ar—H, 1H); 7.70 (m, Ar—H, 1H); 7.20 (m, Ar—H, 1H); 3.95 (s, OCH$_3$, 3H); 2.90 (m, 2H); 2.55 (br, 3H, overlapped with DMSO protons); 2.00 (m, 2H); 1.80 (br, 2H).

Example 12A

Synthesis of piperidine-4-carboxylic acid [6-(2-fluoro-6-methoxy-phenyl)-pyrimidin-4-yl]-amide (Compound #12A)

Step I:

To the stirred mixture of 4-(6-chloro-pyrimidin-4-ylcarbamoyl)-piperidine-1-carboxylic acid benzyl ester (VIII) (0.75 g, 2 mmol) and 6-fluoro-2-methoxy-phenyl boronic acid (0.37 g, 2.2 mmol) in saturated sodium carbonate solution (4 ml) and 1,4-dioxane (4 ml) was added palladium(II) acetate (0.09 g, 0.4 mmol) followed by triphenylphosphine (0.105 g, 0.00 mmol) at room temperature under an atmosphere of nitrogen. The resulting mixture was heated to reflux at 110° C. for one hour and the reaction monitored by TLC. The reaction mixture was filtered through a celite bed and the filtrate was extracted with ethyl acetate (3×100 ml). The organic layers were separated, combined, dried over sodium sulfate and concentrated under reduced pressure. The resulting crude product was purified by preparative HPLC (C-18, AcN:H$_2$O with 0.05% TFA) to afford 4-[6-(2-fluoro-6-methoxy-phenyl)-pyrimidin-4-ylcarbamoyl]-piperidine-1-carboxylic acid benzyl ester (XXIII) (0.05 g, 4%).

HPLC purity λ=220 nm: 98%.

ESMS: m/z=465 (M+1).

Step II:

4-[6-(2-Fluoro-6-methoxy-phenyl)-pyrimidin-4-ylcarbamoyl]-piperidine-1-carboxylic acid benzyl ester (XXIII) (0.05 g, 0.1 mmol) was dissolved in methanol (5 ml) and 10% Pd/C (0.03 g) was added under an atmosphere of nitrogen. The mixture was stirred at room temperature under hydrogen balloon pressure for 18 hours. The catalyst was removed from the reaction mixture by filtration through a celite bed and the filtrate was evaporated to dryness. The resulting crude product was triturated with dry diethyl ether (2 ml) and concentrated to yield piperidine-4-carboxylic acid [6-(2-fluoro-6-methoxy-phenyl)-pyrimidin-4-yl]-amide (compound #12A) (0.029 g, 81%) as a white solid.

HPLC purity λ=220 nm: 96%.

ESMS: m/z=331 (M+1).

$^1$H NMR (500 MHz, DMSO-$d_6$) δ 11.2 (s, —NH, 1H); 9.0 (s, Ar—H, 1H); 8.60 (br, —NH, 1H); 8.10 (s, Ar—H, 1H); 7.50 (m, Ar—H, 1H); 7.05 (m, Ar—H, 1H); 6.95 (m, Ar—H, 1H); 3.85 (s, 3H); 3.3 (m, 2H, overlapped with DMSO protons); 3.0-2.8 (m, 2H); 2.5 (br, 1H, overlapped with DMSO protons); 2.0 (m, 2H); 1.75 (m, 2H).

Melting point: 140-143° C.

Example 13A

Synthesis of 1-acetyl-piperidine-4-carboxylic acid [6-(2-ethoxy-phenyl)-pyrimidin-4-yl]-amide ((Compound #13A)

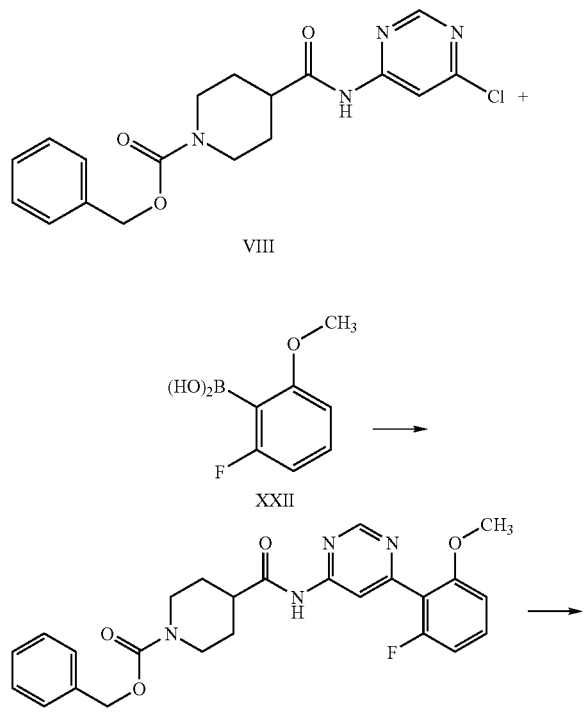

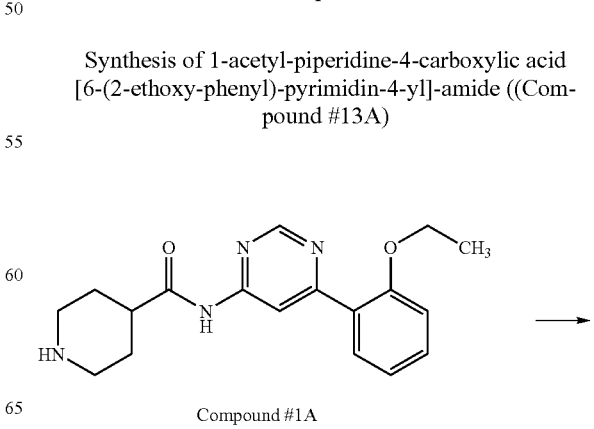

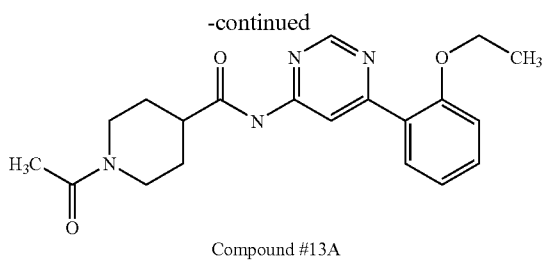

Compound #13A

To a stirred mixture of piperidine-4-carboxylic acid [6-(2-ethoxy-phenyl)-pyrimidin-4-yl]-amide (compound #1A) (0.25 g, 0.76 mmol) and NEt₃ (0.01 mL, 0.76 mmol) in THF (10 ml) was added acetyl chloride (0.053 ml, 0.76 mmol) at 0° C. The mixture was stirred at room temperature for 20 min, then the solvent was distilled off; the residue was dissolved in water and extracted with ethyl acetate (3×10 ml). The organic layers were separated, combined, dried over sodium sulfate, filtered and concentrated under reduced pressure. The resulting crude product was triturated with dry diethyl ether and the solid was filtered off to obtain 1-acetyl-piperidine-4-carboxylic acid [6-(2-ethoxy-phenyl)-pyrimidin-4-yl]-amide (compound #13A) (0.208 g, 73%) as a white solid.

HPLC purity λ=220 nm: 98%.

ESMS: m/z=369 (M+1).

¹H NMR (500 MHz, CDCl₃) δ=8.90 (s, Ar—H, 1H); 8.95 (s, Ar—H, 1H); 8.05 (m, —NH, 1H); 8.0 (m, Ar—H, 1H); 7.4 (m, Ar—H, 1H); 7.1 (m, Ar—H, 1H); 7.0 (m, Ar—H, 1H), 4.62 (d, 1H); 4.2 (q, J=7.3 Hz, OCH₂CH₃, 2H); 3.95 (d, 1H); 3.1 (m, 1H); 2.75 (m, 1H); 2.55 (m, 1H); 2.05 (s, 3H); 2.0 (m, 2H); 1.8 (m, 2H); 1.45 (t, J=7.3 Hz, OCH₂CH₃, 3H).

Melting point: 171-173° C.

Example 14A

Synthesis of piperidine-4-carboxylic acid [6-(2-methoxy-phenyl)-pyrimidin-4-yl]-amide hydrochloride (Compound #14A) (HCl salt)

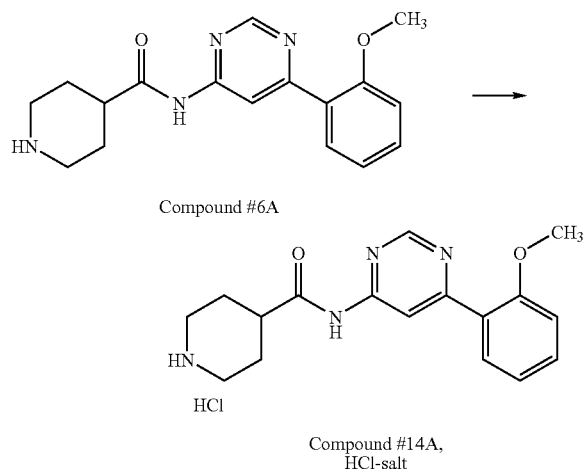

Piperidine-4-carboxylic acid [6-(2-methoxy-phenyl)-pyrimidin-4-yl]amide (compound #6A) (2.0 g, 6.4 mmol) was dissolved in a saturated solution of HCl in 1,4-dioxane (50 ml) and the clear solution was stirred at room temperature for half an hour. A pale yellow solid precipitated out. Diethyl ether (50 ml) was added to precipitate more of the solid. After filtration, the solid was washed with diethyl ether (50 ml) and dried under high vacuum to obtain piperidine-4-carboxylic acid [6-(2-methoxy-phenyl)-pyrimidin-4-yl]-amide hydrochloride (compound #14A, HCl salt of compound #6A), 2.2 g, 98%) as a white solid.

HPLC purity λ=220 nm: 98%.

ESMS: m/z=313 (M+1).

¹H NMR (500 MHz, DMSO-d₆) δ=11.2 (s, —NH, 1H); 9.05 (br, NH, 1H); 8.95 (s, Ar—H, 1H); 8.70 (s, Ar—H, 1H); 7.95 (m, Ar—H, 1H); 7.5 (m, Ar—H, 1H); 7.2 (m, Ar—H, 1H); 7.1 (m, Ar—H, 1H); 3.95 (s, —OCH₃, 3H); 3.3 (m, 2H); 2.95 (m, 3H); 2.05 (m, 2H); 1.85 (m, 2H).

Melting point: 214-217° C.

Example 15A

Synthesis of piperidine-4-carboxylic acid [6-(2-methoxy-phenyl)-pyrimidin-4-yl]-amide mesylate (Compound #15A) (methane sulfonic acid salt)

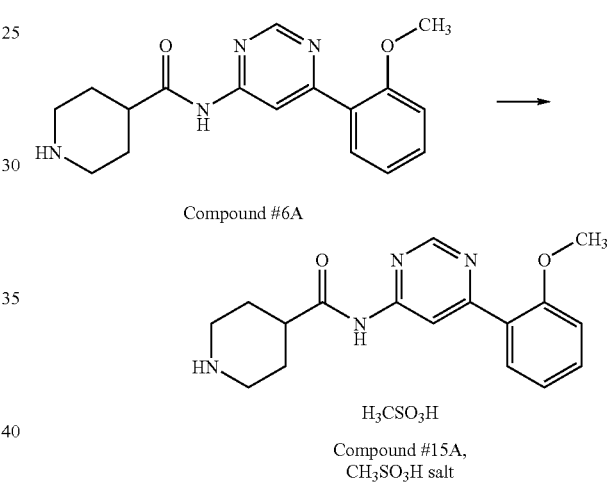

To a clear solution of piperidine-4-carboxylic acid [6-(2-methoxy-phenyl)-pyrimidin-4-yl]-amide (compound #6A) (2.5 g, 8 mmol) in methanol:chloroform (1:1, 75 ml) was added methane sulfonic acid (5 ml, 80 mmol) dropwise at 0° C. and the formed clear solution was stirred at room temperature for half an hour. A white solid precipitated out and diethyl ether (150 ml) was added to precipitate more of the solid which was then filtered off and washed with diethyl ether (50 ml). This crude solid was dissolved in 90 ml of chloroform:methanol (2:1) and the mixture heated at 60° C. to become a clear solution. Then diethyl ether (90 ml) was added and the turbid solution was kept at room temperature for one hour. The formed crystalline solid was filtered off, washed with diethyl ether (50 ml) and dried under high vacuum to give piperidine-4-carboxylic acid [6-(2-methoxy-phenyl)-pyrimidin-4-yl]amide methane sulfonate (compound #15A, methane sulfonic acid salt of compound #6A) (2.9 g, 89%) as a white solid.

HPLC purity λ=220 nm: 99%.

ESMS: m/z=313 (M+1).

¹H NMR (500 MHz, DMSO-d₆) δ=11.2 (s, —NH, 1H); 9.0 (s, Ar—H, 1H); 8.7 (s, Ar—H, 1H); 8.6 (br, NH, 1H); 8.4 (br, 1H); 7.92 (m, Ar—H, 1H); 7.55 (m, Ar—H, 1H); 7.25 (m,

Ar—H, 1H), 7.1 (m, Ar—H, 1H); 3.95 (s, —OCH$_3$, 3H); 3.35 (m, 2H); 2.9 (m, 3H); 2.35 (s, CH$_3$SO$_3$H, 3H); 2.05 (m, 2H); 1.80 (m, 2H).

Melting point: 268-270° C.

Example 16A

Synthesis of piperidine-3-carboxylic acid [6-(2-methoxy-phenyl)-pyrimidin-4-yl]-(Compound #16A)

Step I:

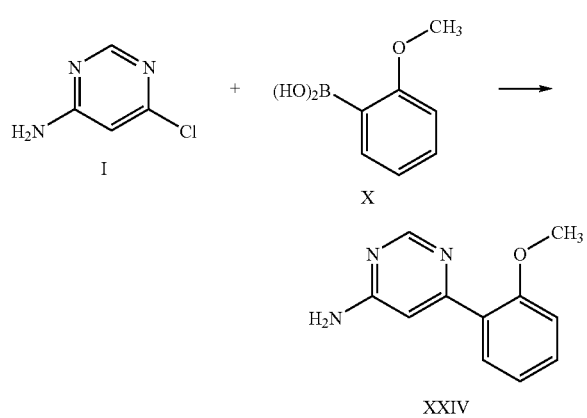

To a solution of 2-methoxyphenyl boronic acid (X) (10.3 g, 68.2 mmol) in 300 ml of 1,4-dioxane was added 100 ml of saturated aqueous sodium carbonate solution. Argon gas was purged for 30 min at room temperature. Then 4-amino-6-chloropyrimidine (I) (8.8 g, 68.2 mmol) and tetrakis(triphenylphosphine)palladium(0) (3.9 g, 3.4 mmol) were added simultaneously and argon gas was bubbled through the mixture for another 20 min. The reaction mixture was heated to reflux for 12 hours (TLC confirmed completion of the reaction) and was then concentrated under reduced pressure. The residue was partitioned between dichloromethane and water. The organic layer was separated, washed with water and brine, dried over sodium sulfate and concentrated. The obtained crude residue was purified by silica gel column chromatography eluting with 15% ethyl acetate in dichloromethane to provide 6-(2-methoxy-phenyl)-pyrimidin-4-ylamine (XXIV) (8.0 g).

$^1$H NMR (DMSO-d$_6$) δ=8.17 (1H, s), 7.71 (1H, d), 7.41 (1H, t), 6.96-7.06 (2H, m), 6.95 (1H, s), 3.98 (3H, s).

MS: m/z=202.1 (M+1).

Step II:

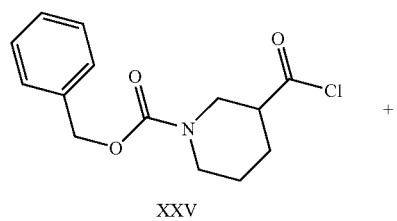

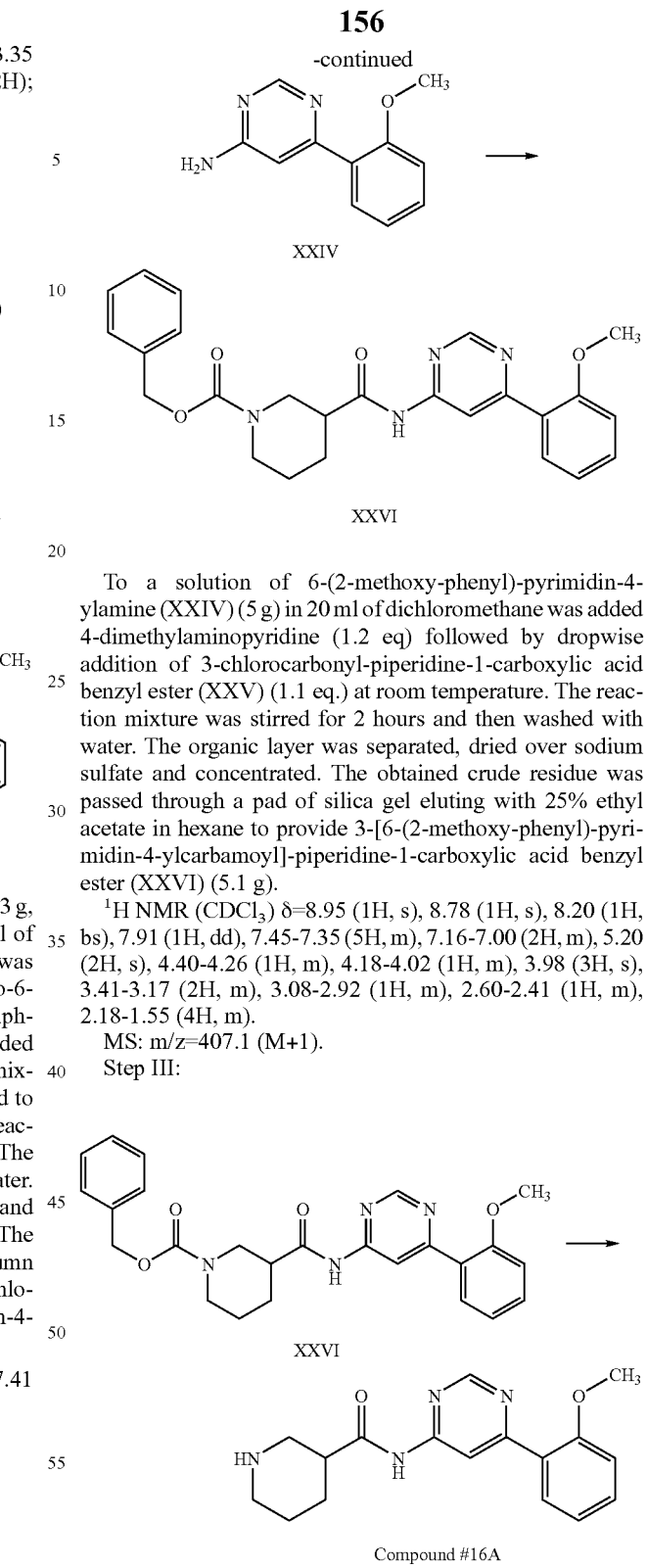

To a solution of 6-(2-methoxy-phenyl)-pyrimidin-4-ylamine (XXIV) (5 g) in 20 ml of dichloromethane was added 4-dimethylaminopyridine (1.2 eq) followed by dropwise addition of 3-chlorocarbonyl-piperidine-1-carboxylic acid benzyl ester (XXV) (1.1 eq.) at room temperature. The reaction mixture was stirred for 2 hours and then washed with water. The organic layer was separated, dried over sodium sulfate and concentrated. The obtained crude residue was passed through a pad of silica gel eluting with 25% ethyl acetate in hexane to provide 3-[6-(2-methoxy-phenyl)-pyrimidin-4-ylcarbamoyl]-piperidine-1-carboxylic acid benzyl ester (XXVI) (5.1 g).

$^1$H NMR (CDCl$_3$) δ=8.95 (1H, s), 8.78 (1H, s), 8.20 (1H, bs), 7.91 (1H, dd), 7.45-7.35 (5H, m), 7.16-7.00 (2H, m), 5.20 (2H, s), 4.40-4.26 (1H, m), 4.18-4.02 (1H, m), 3.98 (3H, s), 3.41-3.17 (2H, m), 3.08-2.92 (1H, m), 2.60-2.41 (1H, m), 2.18-1.55 (4H, m).

MS: m/z=407.1 (M+1).

Step III:

To a solution of compound 3-[6-(2-methoxy-phenyl)-pyrimidin-4-ylcarbamoyl]-piperidine-1-carboxylic acid benzyl ester (3 g) in 20 mL of methanol was added 10% palladium hydroxide (300 mg) under an atmosphere of nitrogen and the mixture was stirred at room temperature under an atmosphere of hydrogen for 4 hours. The reaction mixture was filtered through celite and the solvent was evaporated. Diethyl ether was added to the product, the mixture was stirred, filtered and the obtained solid was rewashed with diethyl ether and dried under vacuum to yield piperidine-3-carboxylic acid [6-(2-methoxy-phenyl)-pyrimidin-4-yl]-amide (compound #16A) as a white solid (1.8 g).

MS: m/z=312.9 (M+1).

¹HNMR (DMSO-d₆) δ=11.10 (1H, s), 8.95 (1H, s), 8.67 (1H, s), 7.84 (1H, d, J=10 Hz), 7.48 (1H, dd), 7.20-7.04 (2H, m), 3.98 (3H, s), 3.06-2.56 (5H, m), 1.96-1.32 (4H, m).

Example 17A

Synthesis of (S)-piperidine-3-carboxylic acid [6-(2-methoxy-phenyl)-pyrimidin-4-yl]-amide (Compound #17A)

Step I

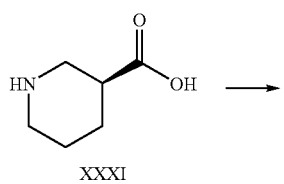

XXXI

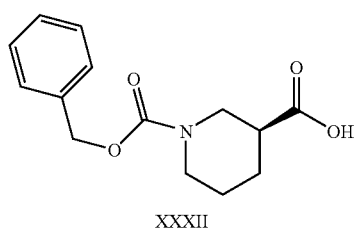

XXXII

A solution of (S)-piperidine-3-carboxylic acid (XXXI) (10.0 g, 77.4 mmol) in a mixture of 80 ml of THF and 50 ml of water was cooled to 0° C. and sodium bicarbonate (13.0 g, 15.5 mmol) and benzyl chloroformate (15.8 g, 92.9 mmol) were added simultaneously. The reaction mixture was stirred at 0° C. for 6 hours and concentrated under reduced pressure. The aqueous layer was extracted with ethyl ether to remove excess of benzyl chloroformate, then it was acidified with 1 M HCl solution to pH 6 followed by extraction with ethyl acetate. The organic layer was separated, dried over sodium sulfate and concentrated to provide (S)-piperidine-1,3-dicarboxylic acid 1-benzyl ester (XXXII) (10.0 g, 49%).

¹H-NMR (DMSO-d₆) δ=7.38 (5H, m), 5.12 (2H, s), 4.19-3.90 (2H, m), 3.02 (1H, m), 2.44 (1H, m), 2.05 (1H, m), 1.80-1.40 (3H, m).

MS: m/z=263.9 (M+1).

Step II

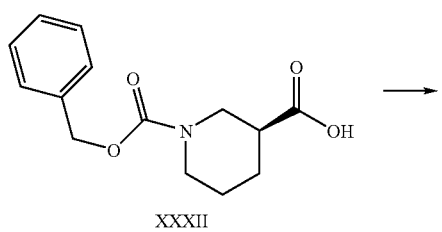

XXXII

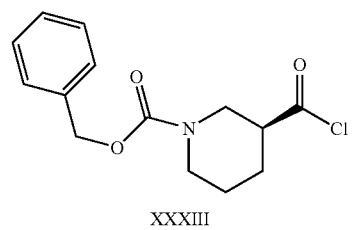

XXXIII (S)-Piperidine-1,3-dicarboxylic acid 1-benzyl ester (XXXII) (12.0 g, 45.6 mmol) was taken in neat oxalyl chloride (30 ml), 0.2 mL of DMF was added and the mixture was stirred at room temperature for 1 hour. Completion of the reaction was monitored by TLC which showed the formation of a non-polar spot after treatment of a small amount with methanol. Then the reaction mixture was concentrated under reduced pressure to provide (S)-3-chlorocarbonyl-piperidine-1-carboxylic acid benzyl ester (XXXIII) (12.66 g) which was directly used in the next reaction.

Step III

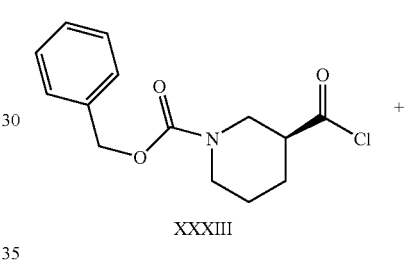

XXXIII

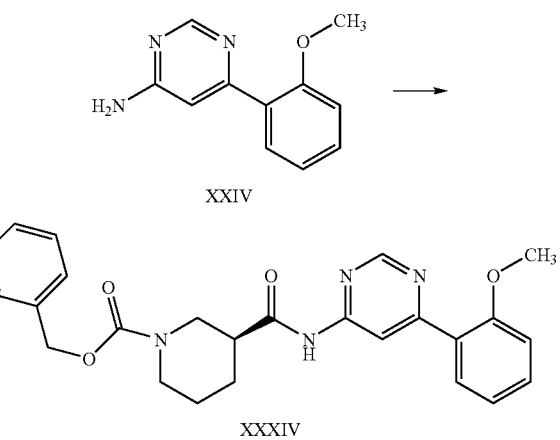

XXIV

XXXIV

To a solution of 6-(2-methoxy-phenyl)-pyrimidin-4-ylamine (XXIV) (7.80 g, 39.1 mmol) in 90 ml of dichloromethane was added 4-dimethylaminopyridine (5.70 g, 47.0 mmol) followed by dropwise addition of N—(S)-3-chlorocarbonyl-piperidine-1-carboxylic acid benzyl ester (XXXIII) (11.0 g, 39.1 mmol) at room temperature. The reaction mixture was stirred for 2 hours and washed with water. The organic layer was separated, dried over sodium sulfate and concentrated. The obtained crude residue was passed through a pad of silica gel eluting with 25% ethyl acetate in hexane to provide (S)-3-[6-(2-methoxy-phenyl)-pyrimidin-4-ylcarbamoyl]-piperidine-1-carboxylic acid benzyl ester (XXXIV) (9.4 g, 54%).

MS: m/z=407.1 (M+1).

$^1$H NMR (CDCl$_3$) δ=8.95 (1H, s), 8.78 (1H, s), 8.20 (1H, bs), 7.91 (1H, dd), 7.45-7.35 (5H, m), 7.16-7.00 (2H, m), 5.20 (2H, s), 4.40-4.26 (1H, m), 4.18-4.02 (1H, m), 3.98 (3H, s), 3.41-3.17 (2H, m), 3.08-2.92 (1H, m), 2.60-2.41 (1H, m), 2.18-1.55 (4H, m).

Step IV

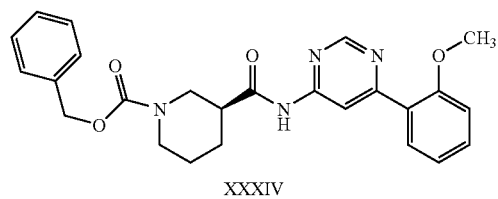

XXXIV

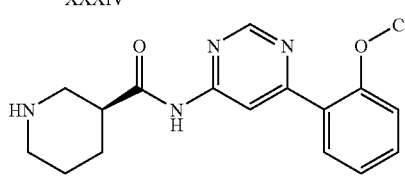

Compound # 17A

To a solution of (S)-3-[6-(2-methoxy-phenyl)-pyrimidin-4-ylcarbamoyl]-piperidine-1-carboxylic acid benzyl ester (XXXIV) (7.0 g) in 50 ml of methanol was added 10% palladium hydroxide (1.5 g) under an atmosphere of nitrogen and the mixture was stirred at room temperature under an atmosphere of hydrogen for 8 hours. The reaction mixture was filtered through celite and the solvent was evaporated. The obtained product was taken in diethyl ether, stirred, filtered, washed with diethyl ether and dried under vacuum to obtain (S)-piperidine-3-carboxylic acid [6-(2-methoxy-phenyl)-pyrimidin-4-yl]-amide (compound #17A) as a white solid (3.0 g, 62%), melting point 163-165° C.

MS: m/z=312.9 (M+1).

$^1$H NMR (DMSO-d$_6$) δ=11.10 (1H, bs), 8.95 (1H, s), 8.67 (1H, s), 7.84 (1H, d, J=10 Hz), 7.48 (1H, dd), 7.20-7.04 (2H, m), 3.98 (3H, s), 3.06-2.56 (5H, m), 1.99-1.32 (4H, m).

Analytical purity: 98.2%; Chiral purity: (R)-enantiomer: 8.82%, (S)-enantiomer: 91.17%.

Melting point: 163-165° C.

Example 18A

Synthesis of (R)-piperidine-3-carboxylic acid [6-(2-methoxy-phenyl)-pyrimidin-4-yl]-amide (R) (Compound #18A)

Step II

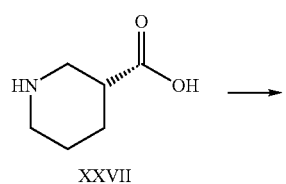

XXVII

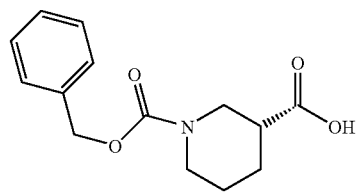

XXVIII

A solution of (R)-piperidine-3-carboxylic acid (XXVII) (5.0 g, 39 mmol) in a mixture of 50 ml of THF and 20 ml of water was cooled to 0° C. and sodium bicarbonate (6.5 g, 77.4 mmol) and benzyl chloroformate (8.0 g, 46.4 mmol) were added simultaneously. The reaction mixture was stirred at 0° C. for 30 min and at room temperature for 3 hours and concentrated under reduced pressure. The remaining aqueous phase was extracted with ethyl ether to remove excess of benzyl chloroformate, then it was acidified with 1 M HCl solution to pH 6 followed by extraction with ethyl acetate. The organic layer was separated, dried over sodium sulfate and evaporated to provide (R)-piperidine-1,3-dicarboxylic acid 1-benzyl ester (XXVIII) (3.7 g, 36%).

MS: m/z=263.9 (M+1).

$^1$H NMR (DMSO-d$_6$) δ=7.38 (5H, m), 5.12 (2H, s), 4.19-3.90 (2H, m), 3.02 (1H, m), 2.44 (1H, m), 2.05 (1H, m), 1.80-1.40 (3H, m).

Step III

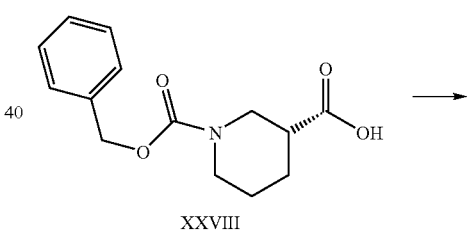

XXVIII

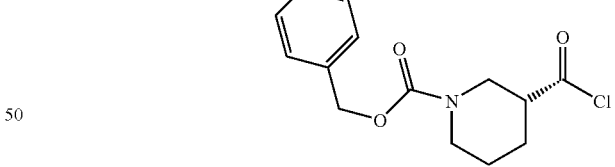

XXIX (R)-Piperidine-1,3-dicarboxylic acid 1-benzyl ester (XXVIII) (8.00 g, 30.4 mmol) was taken in neat oxalyl chloride (20 ml), 0.2 ml of DMF were added and the mixture was stirred at room temperature for 1 hour. The completion of reaction was monitored by TLC which showed the formation of a non-polar spot after treatment of a small amount with methanol. The reaction mixture was concentrated under reduced pressure to provide (R)-3-chlorocarbonyl-piperidine-1-carboxylic acid benzyl ester (XXIX) (8.33 g) which was directly used in the next reaction.

Step IV

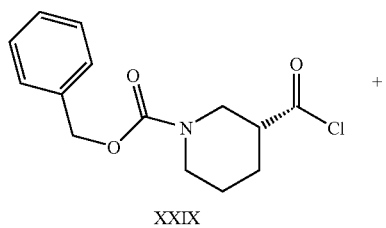

XXIX

+

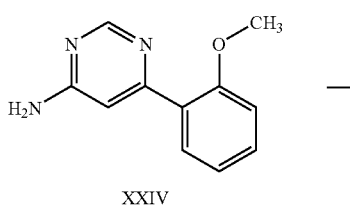

XXIV

→

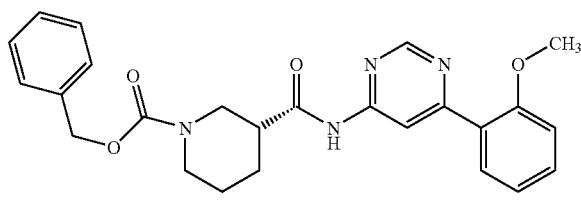

XXX

To a solution of 6-(2-methoxy-phenyl)-pyrimidin-4-ylamine (XXIV) (5.80 g, 28.5 mmol) in 60 ml of dichloromethane was added 4-dimethylaminopyridine (4.16 g, 34.2 mmol) followed by dropwise addition of (R)-3-chlorocarbonyl-piperidine-1-carboxylic acid benzyl ester (XXIX) (8.00 g, 28.5 mmol) at room temperature. The reaction mixture was stirred for 2 hours and washed with water. The organic layer was separated, dried over sodium sulfate and concentrated. The obtained crude residue was passed through a pad of silica gel eluting with 25% ethyl acetate in hexane to provide (R)-3-[6-(2-methoxy-phenyl)-pyrimidin-4-ylcarbamoyl]-piperidine-1-carboxylic acid benzyl ester (XXX) (8.5 g, 67%).

MS: m/z=407.1 (M+1).

$^1$H NMR (CDCl$_3$) δ=8.95 (1H, s), 8.78 (1H, s), 8.20 (1H, bs), 7.91 (1H, dd), 7.45-7.35 (5H, m), 7.16-7.00 (2H, m), 5.20 (2H, s), 4.40-4.26 (1H, m), 4.18-4.02 (1H, m), 3.98 (3H, s), 3.41-3.17 (2H, m), 3.08-2.92 (1H, m), 2.60-2.41 (1H, m), 2.18-1.55 (4H, m).

Step V

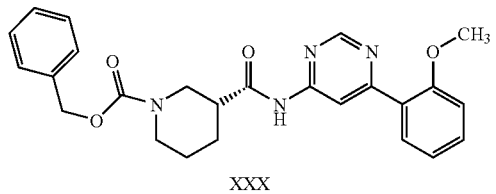

XXX

→

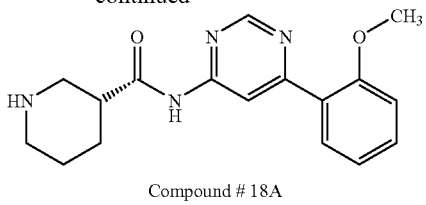

Compound # 18A

To a solution of (R)-3-[6-(2-methoxy-phenyl)-pyrimidin-4-ylcarbamoyl]-piperidine-1-carboxylic acid benzyl ester (XXX) (7.0 g) in 50 mL of methanol was added 10% palladium hydroxide (1.5 g) under an atmosphere of nitrogen and the mixture was stirred at room temperature under an atmosphere of hydrogen for 8 hours. The reaction mixture was filtered through celite and the solvent was evaporated. The obtained product was taken in diethyl ether, stirred, filtered, the residue was washed with diethyl ether and dried under vacuum to yield (R)-piperidine-3-carboxylic acid [6-(2-methoxy-phenyl)-pyrimidin-4-yl]-amide (compound #18A) as a white solid (3.5 g, 72%), melting point 210-213° C.

Analytical purity: 95.49%. Chiral purity: (R)-enantiomer 91.62%, (S)-enantiomer 8.37%.

MS: m/z=312.9 (M+1).

$^1$H NMR (DMSO-d$_6$) δ=11.10 (1H, s), 8.95 (1H, s), 8.67 (1H, s), 7.84 (1H, d, J=10 Hz), 7.48 (1H, dd), 7.20-7.04 (2H, m), 3.98 (3H, s), 3.06-2.56 (5H, m), 1.96-1.32 (4H, m).

Example 19A

Synthesis of 1-[6-(2-methoxy-phenyl)-pyrimidin-4-ylcarbamoyl]-pyrrolidine-2-carboxylic acid (Compound 19A)

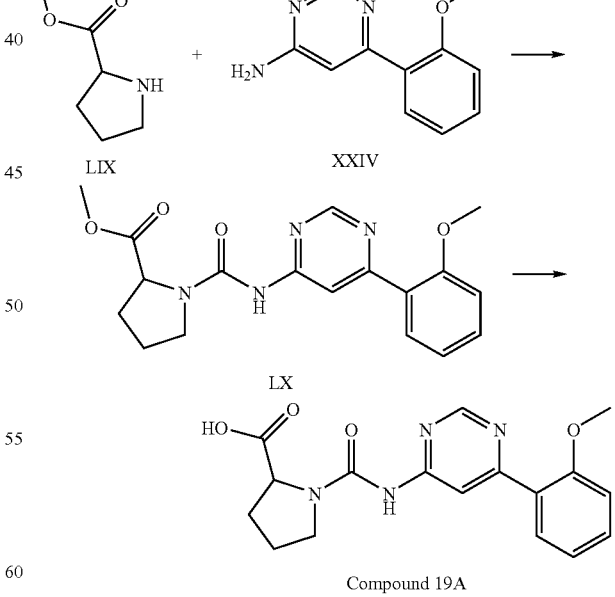

Compound 19A

Step 1:

Phenyl chloroformate (0.20 g, 1.3 mmol) was added dropwise to a solution of 6-(2-methoxy-phenyl)-pyrimidin-4-ylamine (0.26 g, 1.3 mmol) and DIPEA (0.33 g, 2.6 mmol) in dry dichloromethane (10 ml) at −78° C. and the mixture was allowed to stir overnight at room temperature. Then dichloromethane was evaporated, dry 1,4-dioxane and proline methyl ester hydrochloride (0.26 g, 1.3 mmol) and DIPEA (0.33 g, 2.6 mmol) were added and the mixture was heated overnight at 70° C. The solvent was evaporated and the crude product was extracted with ethyl acetate (2×100 ml). The combined organic phases were washed with water (2×50 ml) and brine, dried over anhydrous sodium sulfate and concentrated in a vacuum rotavapour. The residue was purified by silicagel column chromatography (eluent: 70% ethyl acetate/hexane) leading to 1-[6-(2-methoxy-phenyl)-pyrimidin-4-yl-carbamoyl]-pyrrolidine-2-carboxylic acid methyl ester.

Yield: 500 mg, ~quantitative.

Step 2:

To a solution of 1-[6-(2-methoxy-phenyl)-pyrimidin-4-yl-carbamoyl]-pyrrolidine-2-carboxylic acid methyl ester (LX) (500 mg, 1.40 mmol) in a mixture of THF and water (1:1) was added a solution of LiOH (0.118 g, 2.80 mmol) in water at ice bath temperature over 10 min and then allowed to stir for two hours at room temperature. THF was evaporated and the aqueous solution was acidified with 2N HCl. This aqueous phase was then extracted with ethyl acetate (2×100 ml), the combined organic phases were washed with water and brine, dried over anhydrous sodium sulfate and concentrated in a vacuum rotavapor to afford 1-[6-(2-methoxy-phenyl)-pyrimidin-4-ylcarbamoyl]-pyrrolidine-2-carboxylic acid as a white solid. Yield: 210 mg, 43.8%.

MS: m/z=343 (M+1).

1H NMR (500 MHz, DMSO-$d_6$) δ=1.91-1.99 (3H, m), 2.19 (1H, m), 365-3.56 (2H, m), 3.84 (3H, s), 4.04-4.03 (1H, m), 7.10-7.07 (1H, m), 7.18 (1H, d, J=8.35 Hz), 7.49-7.46 (1H, m), 7.81 (1H, d, J=7.5 Hz), 8.41 (1H, s), 8.82 (1H, s), 9.43 (1H, br. s), 12.25 (1H, br. s).

Example 20A

Synthesis of 1-acetyl-piperidine-3-carboxylic acid [6-(2-methoxy-phenyl)-pyrimidin-4-yl]-amide (Compound #20A)

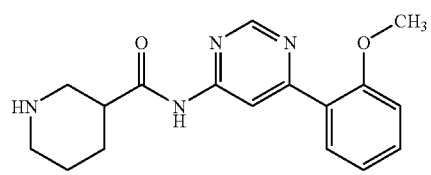

Compound # 16A

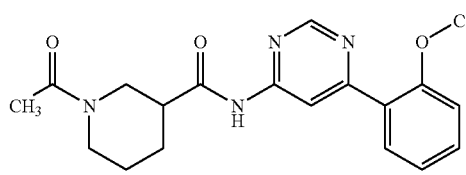

Compound # 20A

Piperidine-3-carboxylic acid [6-(2-methoxy-phenyl)-pyrimidin-4-yl]amide (compound #16A) (110 mg, 0.352 mmol) was dissolved in 5 ml of anhydrous dichloromethane, cooled to 0° C. and 4-N,N-dimethylaminopyridine (90 mg, 0.70 mmol) and acetic anhydride (54 mg, 0.53 mmol) were added simultaneously. The reaction mixture was stirred for 3 hours at room temperature, treated with crushed ice and partitioned between water and dichloromethane. The organic layer was separated, dried over sodium sulfate and concentrated to provide 1-acetyl-piperidine-3-carboxylic acid [6-(2-methoxy-phenyl)-pyrimidin-4-yl]-amide (compound #20A) (105 mg, 84.13%).

MS: m/z=356.1 (M+1).

$^1$H NMR (DMSO-$d_6$) δ=11.0 (1H, s), 8.95 (1H, s), 8.69 (1H, 2s), 7.88 (1H, d, J=10 Hz), 7.48 (1H, t), 7.20 (1H d, J=10 Hz), 7.09 (1H, t), 4.36 (1H, m), 3.92 (3H, s), 3.06-2.56 (5H, m), 2.08-1.32 (7H, m).

Example 21A

Synthesis of 1-methanesulfonyl-piperidine-3-carboxylic acid [6-(2-methoxy-phenyl)-pyrimidin-4-yl]-amide (Compound #21A)

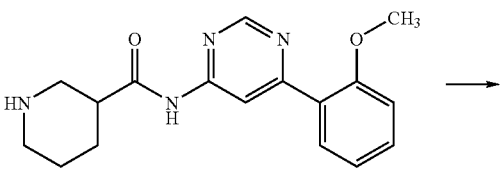

Compound # 16A

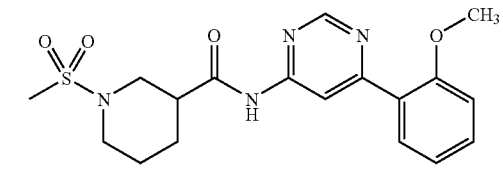

Compound # 21A

Piperidine-3-carboxylic acid [6-(2-methoxy-phenyl)-pyrimidin-4-yl]-amide (compound #16A) (110 mg, 0.352 mmol) was dissolved in 5 mL of anhydrous dichloromethane, cooled to 0° C. and triethyl amine (13.0 g, 15.5 mmol) and methane sulfonyl chloride (60 mg, 0.53 mmol) were added simultaneously. The mixture was stirred for two hours at room temperature, treated with crushed ice and partitioned with between water and dichloromethane. The organic layer was separated, dried over sodium sulfate and concentrated to provide 1-methanesulfonyl-piperidine-3-carboxylic acid [6-(2-methoxy-phenyl)-pyrimidin-4-yl]-amide (compound #21A) (90 mg, 80.3%).

MS: m/z=391.46 (M+1).

$^1$H NMR: (DMSO-$d_6$) δ=11.2 (1H, s), 8.94 (1H, s), 8.67 (1H, 1), 7.88 (1H, d, J=10 Hz), 7.48 (1H, t), 7.20 (1H, d, J=10 Hz), 7.07 (1H, t), 3.88 (3H, s), 3.72 (1H, m), 3.60-3.02 (2H, m), 2.98 (3H, s), 2.96-2.60 (2H, m), 2.02-1.43 (4H, m).

Example 22A

Synthesis of piperidine-3-carboxylic acid [6-(2-methoxy-phenyl)-2-methyl-pyrimidin-4-yl]-amide (Compound #22A)

Step I

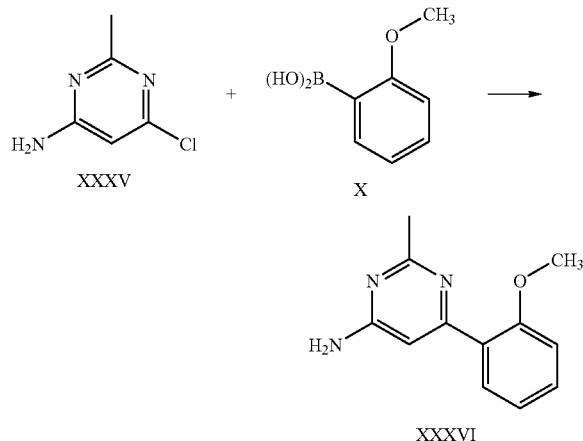

To a solution of 2-methoxyphenyl boronic acid (X) (1 g, 6.6 mmol) in THF (10 ml) and water (4 ml) 6-chloro-2-methyl-pyrimidin-4-ylamine (XXXV) (0.947 g, 6.6 mmol) was added. Palladium diacetate (0.074 g, 0.3 mmol), triphenylphosphine (0.175 g, 6.6 mmol) and sodium carbonate (2.06 g, 19.8 mmol) were added to the mixture at 0° C. The reaction mixture was stirred overnight at room temperature and the reaction monitored by TLC. After completion of the reaction, the reaction mixture was concentrated under reduced pressure and the residue was extracted with ethyl acetate and water. The organic layer was separated, washed with brine, dried over sodium sulfate and concentrated. The obtained crude residue was purified by silica gel column chromatography eluting with 25% to 30% ethyl acetate in hexane to provide 0.450 g of 6-(2-methoxy-phenyl)-2-methyl-pyrimidin-4-ylamine (XXXVI).

Step II

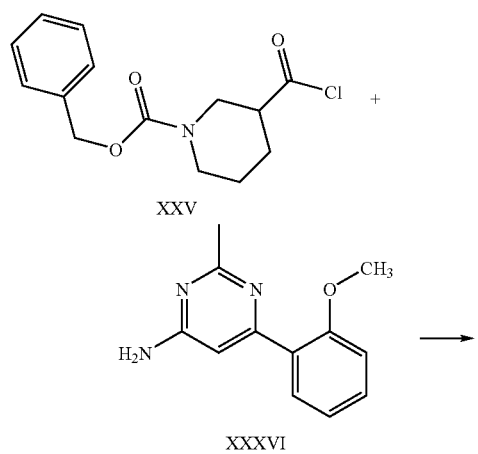

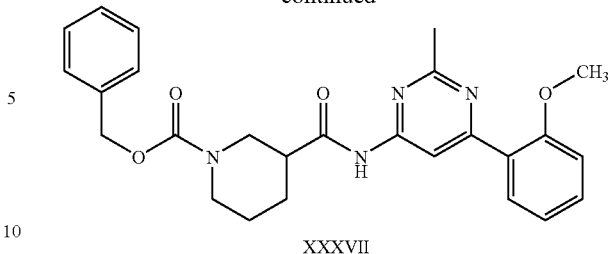

6-(2-Methoxy-phenyl)-2-methyl-pyrimidin-4-ylamine (XXXVI) (0.111 g, 0.512 mmol) was taken in 3 ml of dry dichloromethane, DMAP (0.075 g, 0.614 mmol) and a solution of 3-chlorocarbonyl-piperidine-1-carboxylic acid benzyl ester (XXV) (0.155 g, 0.563 mmol) in dichloromethane (1 ml) were added dropwise at room temperature and the reaction mixture was stirred for 3 hours. Then water was added to the reaction mixture followed by extraction with dichloromethane. The organic layer was separated, dried over anhydrous sodium sulfate and concentrated to provide 0.270 g of 3-[6-(2-methoxy-phenyl)-2-methyl-pyrimidin-4-ylcarbamoyl]-piperidine-1-carboxylic acid benzyl ester (XXXVII).

Step V

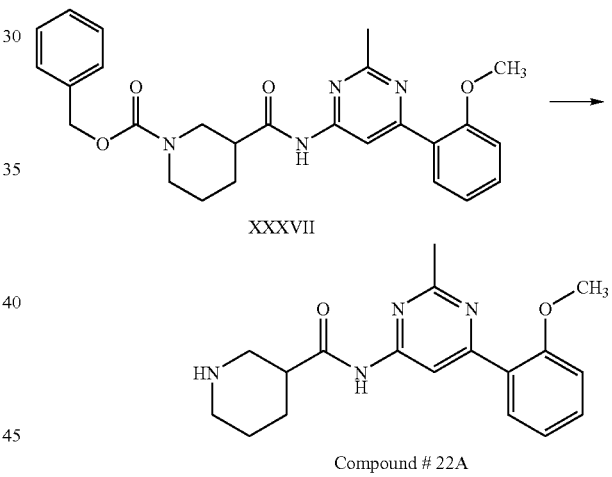

3-[6-(2-Methoxy-phenyl)-2-methyl-pyrimidin-4-ylcarbamoyl]-piperidine-1-carboxylic acid benzyl ester (XXXVII) (0.270 g, 0.586 mmol) was taken in methanol (5 ml) to which 10% Pd(OH)$_2$ (0.125 g) was added and the mixture was stirred overnight under an atmosphere of hydrogen. The reaction was monitored by TLC. After completion, the reaction mixture was filtered through a celite bed and concentrated to get a viscous oil which was stirred in ether to precipitate a white solid. Filtration provided 0.160 g of piperidine-3-carboxylic acid [6-(2-methoxy-phenyl)-2-methyl-pyrimidin-4-yl]-amide (compound #22A).

MS: m/z=327 (M+1).

$^1$H NMR (400 MHz, DMSO-d$_6$) δ=1.5-1.6 (m, 2H); 1.7-1.9 (m, 2H); 2.0-2.1 (m, 2H); 2.5 (s, 3H);2.8-3.0 (t, 1H); 3.0-3.1 (m, 2H); 3.1-3.2 (d, 2H); 3.1-3.2 (d, 2H); 3.8 (s, 3H); 7.0-7.1 (m, 1H); 7.1-7.2 (m, 1H); 7.4-7.5 (m, 1H); 7.8-7.9 (m, 1H); 8.5 (s, 1H); 8.8 (bs, 2H); 11.0 (s, 1H).

Melting point: 229-230° C.

Example 23A

Synthesis of 1-[6-(2-methoxy-phenyl)-pyrimidin-4-yl]-3-piperidin-3-yl-urea hydrochloride (Compound #23A)

Step I

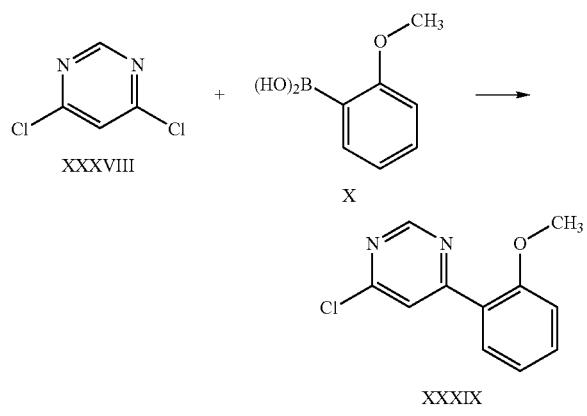

To a 250 ml round bottomed flask was added 4,6-dichloropyrimidine (2.67 g, 17.95 mmol), 2-methoxyphenyl boronic acid (3.00 g, 19.7 mmol), acetonitrile (50 ml) and sodium carbonate (2.95 g, 26.9 mmol). The mixture was sparged with nitrogen for 15 minutes, Pd(PPh$_3$)$_4$ (0.48 g, 0.41 mmol) was then added, and the resulting yellow mixture was heated under an atmosphere of nitrogen at 80° C. for 48 hours. After cooling, the solution was diluted with aqueous NaHCO$_3$ and extracted with dichloromethane. The combined organic extracts were dried over sodium sulfate, filtered and concentrated in vacuum. Purification of the residue by silica gel chromatography (2 to 5% ethyl acetate/hexane) afforded 4-chloro-6-(2-methoxy-phenyl)-pyrimidine as a white solid. Yield: 2.5 g MS: m/z=221 (M+1).

$^1$H NMR (500 MHz, DMSO-d$_6$) δ=3.95 (3H, s), 7.03 (1H, d, J=8.5 Hz), 7.12-7.09 (1H, m), 7.49-7.46 (2H, m), 8.09-8.06 (1H, m), 9.02 (1H, s).

Step II

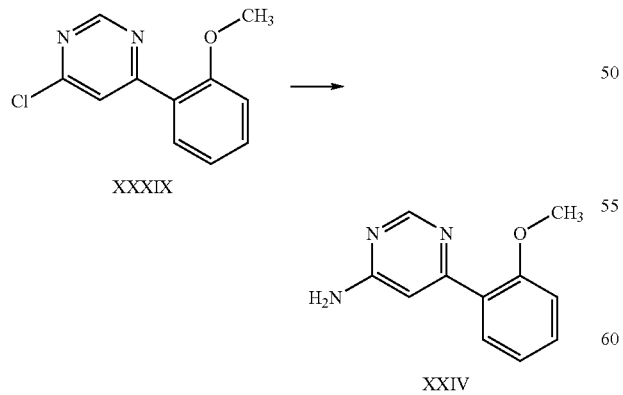

25% ammonia solution (10 ml) was added to a solution of 4-chloro-6-(2-methoxy-phenyl)-pyrimidine (2 g, 9.06 mmol) in 1,4-dioxane (10 ml) and the mixture was heated in a sealed tube at 110° C. for 8 hours with continuous stirring. The reaction mixture was allowed to cool to room temperature, concentrated under reduced pressure and extracted with ethyl acetate. The combined organic extracts were dried over sodium sulfate, filtered and concentrated under vacuum to give 6-(2-methoxy-phenyl)-pyrimidin-4-ylamine as a white solid. Yield: 1.6 g, 87.9%.

MS: m/z=202 (M+1).

$^1$H NMR (500 MHz, DMSO-d$_6$) δ=3.85 (3H, s), 6.81 (2H, br. s), 7.06-7.01 (2H, m), 7.14 (1H, d, J=8.2 Hz), 7.43-7.40 (1H, m), 7.85 (1H, d, J=7.4 Hz), 8.41 (1H, s).

Step III

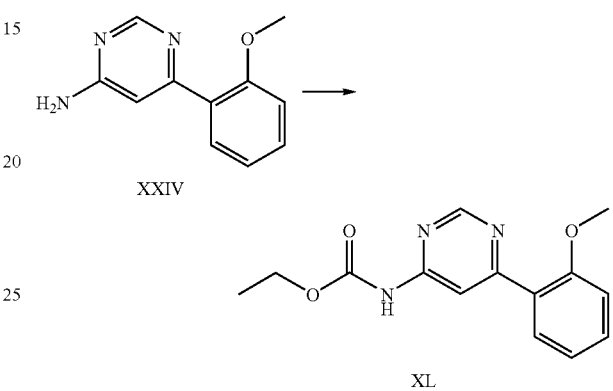

To a mixture of 6-(2-methoxy-phenyl)-pyrimidin-4-ylamine (XXIV) (1.0 g, 4.9 mmol) and potassium carbonate (4.0 g, 29 mmol) in 2-butanone (10 ml), chloroethylformate (0.50 ml, 4.9 mmol) was added and the mixture was refluxed for 3 hours at 80° C. The reaction was monitored by TLC. After completion of the reaction, water was added and the mixture was extracted with ethyl acetate. The organic layer was separated, dried over anhydrous sodium sulfate and concentrated to provide 0.60 g of [6-(2-methoxy-phenyl)-pyrimidin-4-yl]-carbamic acid ethyl ester (XL).

Step IV

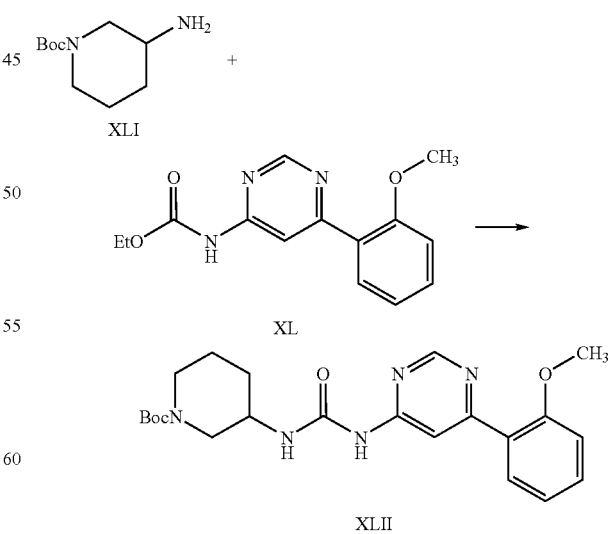

A mixture of [6-(2-methoxy-phenyl)-pyrimidin-4-yl]-carbamic acid ethyl ester (XL) (0.32 g, 1.1 mmol), 3-amino-piperidine-1-carboxylic acid tert-butyl ester (XLI) (0.23 g, 1.1 mmol) and toluene (4 ml) was subjected to microwave conditions at 120° C. and 100 psi pressure for 10 min. The reaction was monitored by TLC. After completion of the reaction, water was added and the mixture was extracted with ethyl acetate. The organic layer was separated, dried over anhydrous sodium sulfate and concentrated to provide 0.40 g of 3-{3-[6-(2-methoxy-phenyl)-pyrimidin-4-yl]-ureido}-piperidine-1-carboxylic acid tert-butyl ester (XLII).

Step V

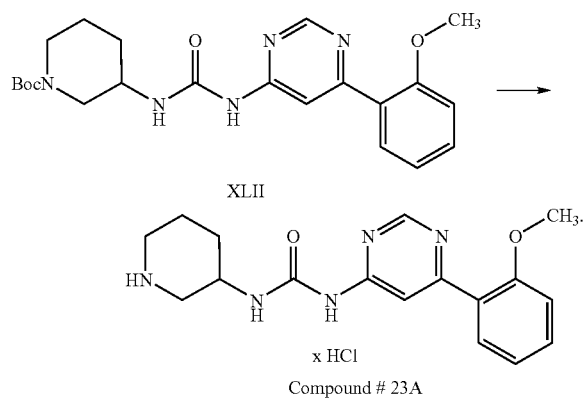

Ethereal HCl (2 ml) was added to a solution of 3-{3-[6-(2-methoxy-phenyl)-pyrimidin-4-yl]-ureido}-piperidine-1-carboxylic acid tert-butyl ester (XLII) (0.20 g, 0.47 mmol) in dry dichloromethane (2 ml) and the mixture was stirred for 2 hours at room temperature. The reaction was monitored by TLC. After completion, the solvent was removed from the reaction mixture to provide 0.20 g of 1-[6-(2-methoxy-phenyl)-pyrimidin-4-yl]-3-piperidin-3-yl-urea hydrochloride (compound #23A).

MS: m/z=328 (M+1).

$^1$H NMR (400 MHz, DMSO-$d_6$) δ=1.1-1.2 (m, 1H); 1.6-1.7 (m, 2H); 1.9-2.1 (m, 2H); 2.9-3.1 (m, 2H); 3.2-3.3 (m, 2H); 4.0 (s, 3H); 7.0-7.1 (m, 1H); 7.1-7.2 (m, 1H); 7.4-7.5 (m, 1H); 7.8-7.9 (m, 1H); 8.19 (d, 1H); 8.2 (s, 1H); 8.8 (s, br., 1H); 8.9 (s, 1H); 10.0 (s, 1H).

Example 24A

Synthesis of 1-[6-(2-methoxy-phenyl)-pyrimidin-4-yl]-3-piperidin-4-yl-urea hydrochloride (Compound #24A)

Step I:

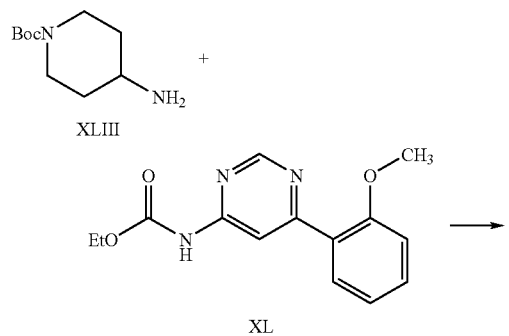

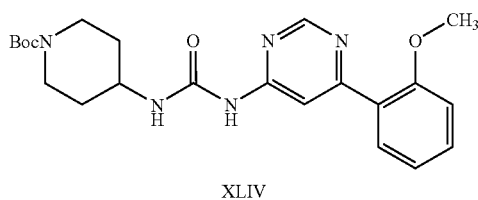

A mixture of [6-(2-methoxy-phenyl)-pyrimidin-4-yl]-carbamic acid ethyl ester (XL) (0.30 g, 1.1 mmol), 4-amino-piperidine-1-carboxylic acid tert-butyl ester (0.23 g, 1.1 mmol) and toluene (4 ml) was subjected to microwave conditions at 120° C. and 100 psi pressure for 10 minutes. The reaction was monitored by TLC. After completion of the reaction, water was added and the mixture was extracted with ethyl acetate. The organic layer was separated, dried over anhydrous sodium sulfate and concentrated to provide 0.250 g of 4-{3-[6-(2-methoxy-phenyl)-pyrimidin-4-yl]-ureido}-piperidine-1-carboxylic acid tert-butyl ester (XLIV).

Step II:

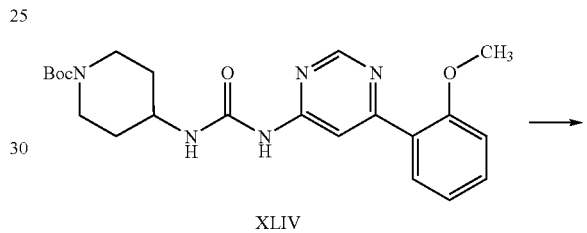

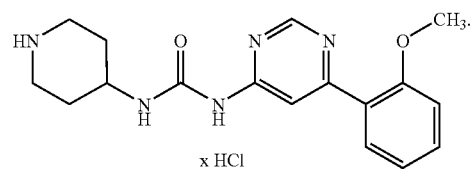

To a solution of 4-{3-[6-(2-methoxy-phenyl)-pyrimidin-4-yl]-ureido}-piperidine-1-carboxylic acid tert-butyl ester (XLIV) (0.250 g, 0.585 mmol) in dry dichloromethane (2 ml) ethereal HCl (2 ml) was added and the mixture was stirred for 2 hours at room temperature. The reaction was monitored by TLC. After completion, the solvent was removed from the reaction mixture to provide 0.20 g of 1-[6-(2-methoxy-phenyl)-pyrimidin-4-yl]-3-piperidin-4-yl-urea hydrochloride (Compound #24A).

MS: m/z=328 (M+1).

$^1$H NMR (400 MHz, DMSO-$d_6$) δ=1.1-1.2 (m, 1H); 1.5-1.7 (m, 2H); 1.9-2.0 (m, 2H); 2.9-3.1 (m, 2H); 3.2-3.3 (m, 2H); 3.9 (s, 3H); 7.0-7.1 (m, 1H); 7.1-7.2 (m, 1H); 7.4-7.5 (m,

1H); 7.8-7.9 (m, 2H); 8.0-8.1 (m, 1H); 8.2 (s, 1H); 8.5 (bs, 1H); 8.7 (bs, 1H); 8.8 (s, 1H); 9.6 (s, 1H).

Example 25A

Synthesis of N-[6-(2-methoxy-phenyl)-pyrimidin-4-yl]-2,2-dimethyl-propionamide (Compound #25A)

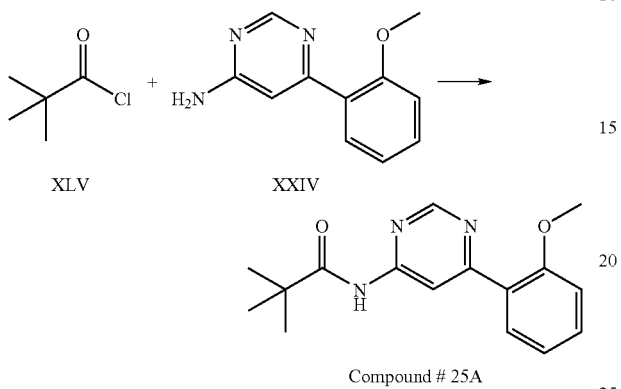

Compound # 25A

To a solution of 6-(2-methoxy-phenyl)-pyrimidin-4-ylamine (XXIV) (0.15 g, 0.74 mmol) in THF (10 ml) was added NEt$_3$ (0.210 ml, 1.49 mmol) under an atmosphere of nitrogen at ice bath temperature, followed by trimethyl acetyl chloride (XLV) (0.819 mmol) at the same temperature. The reaction mixture was stirred for 1 hour at 0° C., then it was brought to room temperature and stirred for another hour. After completion of the reaction, the solvent was removed under reduced pressure. The crude reaction product was taken in ethyl acetate (50 ml) and washed with water (2×20 ml). The organic layer was separated, washed with brine, dried over anhydrous sodium sulfate and concentrated to dryness at reduced pressure to give crude product which was further purified by column chromatography over silica gel (20% ethylacetate/hexane) to yield N-[6-(2-methoxy-phenyl)-pyrimidin-4-yl]-2,2-dimethyl-propionamide. Yield: 106 mg, 50%.

Example 26A

Synthesis of N-[6-(2-methoxy-phenyl)-pyrimidin-4-yl]-2-phenyl-acetamide (compound #26A)

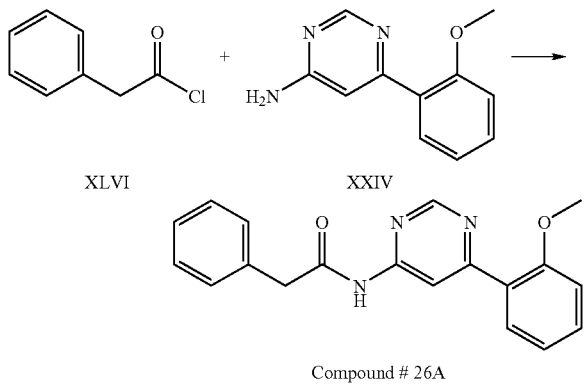

Compound # 26A

To a solution of 6-(2-methoxy-phenyl)-pyrimidin-4-ylamine (XXIV) (0.15 g, 0.74 mmol) in THF (10 ml) was added NEt$_3$ (0.210 ml, 1.49 mmol) under an atmosphere of nitrogen at ice bath temperature, followed by phenyl acetyl chloride (XLVI) (0.819 mmol) at the same temperature. The reaction mixture was stirred for 1 hour at 0° C. and then brought to room temperature and stirred for another hour. Usual work up as described above followed by column chromatographic purification over silica gel (30% ethyl acetate/hexane) yielded N-[6-(2-methoxy-phenyl)-pyrimidin-4-yl]-2-phenyl-acetamide.
Yield: 75 mg, 30%.

Example 27A

Synthesis of N-[6-(2-methoxy-phenyl)-pyrimidin-4-yl]-benzamide compound #27A)

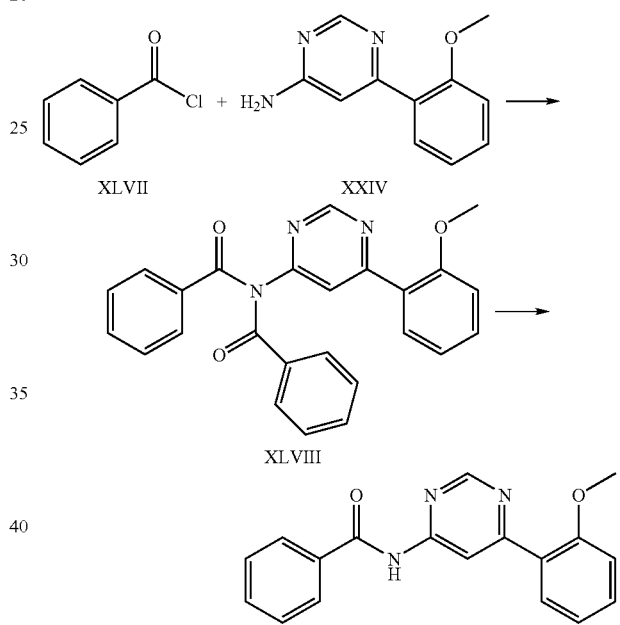

Compound # 27A

To a solution of 6-(2-methoxy-phenyl)-pyrimidin-4-ylamine (XXIV) (0.15 g, 0.74 mmol) in THF (10 ml) was added NEt$_3$ (0.210 ml, 1.49 mmol) under an atmosphere of nitrogen at ice bath temperature, followed by benzoyl chloride (XLVII) (0.819 mmol) at the same temperature. The reaction mixture was stirred for 1 hour at 0° C. and then brought to room temperature and stirred for another hour. Usual work up as described above followed by column chromatographic purification over silica gel (20% ethylacetate/hexane) yielded N-benzoyl-N-[6-(2-methoxy-phenyl)-pyrimidin-4-yl]-benzamide (XLVIII). Yield: 122 mg, 40%.

1 N aqueous NaOH (2 equiv.) was added slowly to a mixture of the obtained N-benzoyl-N-[6-(2-methoxy-phenyl)-pyrimidin-4-yl]-benzamide and 2 ml of water-methanol at ice bath temperature.

The reaction was completed within 10 minutes, as monitored by TLC. The solvent was removed and the residue was taken in dichloromethane (50 ml) and washed with water (2×20 ml), and then with brine. The combined organic layers were dried over anhydrous sodium sulfate, then concentrated to dryness to give crude product, which was further purified by column chromatography over silica gel using 20 ethyl acetate/hexane providing N-[6-(2-methoxy-phenyl)-pyrimidin-4-yl]-benzamide. Yield: 45.5 mg, 50%.

Example 28A

Synthesis of 6-oxo-piperidine-3-carboxylic acid [6-(2-methoxy-phenyl)-pyrimidin-4-yl]-amide (compound #28A)

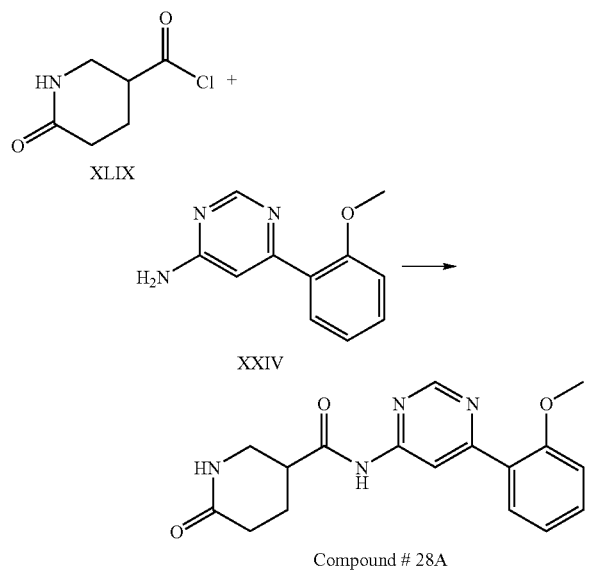

Compound # 28A

To a solution of 6-oxo-piperidine-3-carboxylic acid (XLIX) (0.22 g, 1.5 mmol) in dry DMF (10 ml) was added HBTU (1.13 g, 2.98 mmol) and DIPEA (0.40 ml, 2.3 mmol) under ice cooled condition, and then it was allowed to stir at room temperature for 45 minutes. To this reaction mixture was added 6-(2-methoxy-phenyl)-pyrimidin-4-ylamine (XXIV) (0.30 g, 1.5 mmol) in dry DMF dropwise at ice bath temperature. The reaction mixture was then heated for 4 hours at 120° C. After completion of the reaction, it was cooled and DMF was evaporated completely. The residue was dissolved in ethyl acetate (30 ml), washed with water (2×15 ml) and brine, dried over anhydrous sodium sulfate and evaporated under reduced pressure. Final purification was achieved by flash column chromatography using silica gel (10% methanol/dichloromethane) to give 6-oxo-piperidine-3-carboxylic acid [6-(2-methoxy-phenyl)-pyrimidin-4-yl] amide. Yield: 78.2 mg, 17%.

Example 29A

Synthesis of 1-(2-dimethylamino-ethyl)-3-[6-(2-methoxy-phenyl)-pyrimidin-4-yl]-urea (compound #29A)

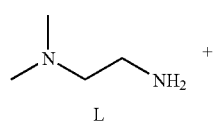

L

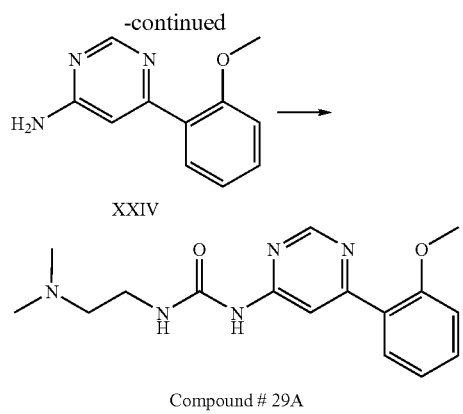

Compound # 29A

To a solution of 6-(2-methoxy-phenyl)-pyrimidin-4-ylamine (XXIV) (0.400 g, 1.98 mmol) and DIPEA (0.300 g, 2.38 mmol) in dry dichloromethane (10 ml) was added phenyl chloroformate (0.370 g, 1.98 mmol) dropwise at −78° C. The reaction mixture was then allowed to stir for 16 hours at room temperature. Dichloromethane was evaporated and the residue was dissolved in 1,4-dioxane (15 ml). N,N-dimethylethylenediamine (L) (0.160 g, 1.98 mmol) was added and the mixture was refluxed for 14 hours. The solvent was evaporated and the crude product was re-dissolved in ethyl acetate, washed with water (2×50 ml) and brine, dried over anhydrous sodium sulfate and concentrated under reduced pressure. The obtained crude solid product was further purified by silica gel column chromatography (15% methanol/dichloromethane) yielding 1-(2-dimethylamino-ethyl)-3-[6-(2-methoxy-phenyl)-pyrimidin-4-yl]-urea. Yield: 293 mg, 47%.

Example 30A

Synthesis of (3-{3-[6-(2-methoxy-phenyl)-pyrimidin-4-yl]-ureido}-phenyl)-acetic acid (Compound 30A)

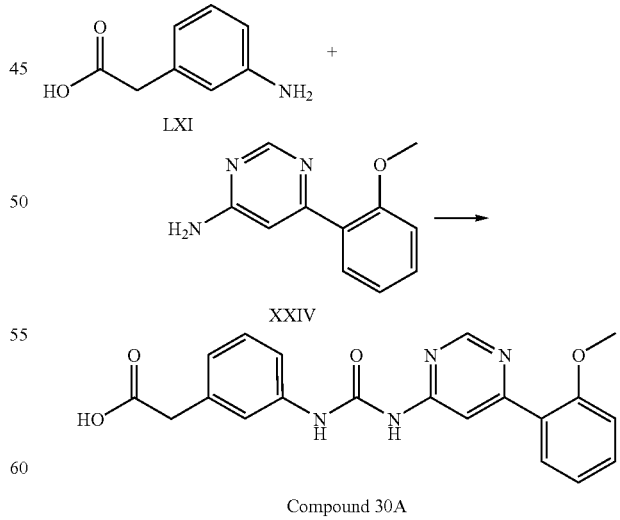

Compound 30A

Phenyl chloroformate (0.15 g, 99 mmol) was added dropwise to a solution of 6-(2-methoxy-phenyl)-pyrimidin-4-ylamine (XXIV) (0.20 g, 0.99 mmol) and DIPEA (0.250 g, 1.98 mmol) in dry dichloromethane (10 ml) at −78° C. and the mixture was allowed to stir overnight at room temperature. Then dichloromethane was evaporated, dry 1,4-dioxane and (3-amino-phenyl)-acetic acid (0.15 g, 0.99 mmol) were added and the mixture was heated overnight at 70° C. The solvent was evaporated and the crude product was extracted with ethyl acetate (2×100 ml). The combined organic phases were washed with water (2×50 ml) and by brine, dried over anhydrous sodium sulfate and concentrated in a vacuum rotavapor. The residue was washed with ether to give (3-{3-[6-(2-methoxy-phenyl)-pyrimidin-4-yl]-ureido}-phenyl)-acetic acid as a coloured solid.

MS: m/z=379 (M+1).

1H NMR (500 MHz, DMSO-$d_6$) δ 3.57 (2H, s), 3.90 (3H, s), 6.96 (1H, d, J=7.5 Hz), 7.11 (1H, d, J=7.5 Hz), 7.21 (1H, d, J=8 Hz), 7.20 (1H, d, J=8 Hz), 7.45-7.43 (1H, s), 7.50 (1H, d, J=6.5 Hz), 7.94 (1H, d, J=3 Hz), 8.23 (1H, s), 8.88 (1H, s), 9.82 (1H, br. s), 10.21 (1H, br. s), 12.34 (1H, br. s).

Example 31A

Synthesis of {3-[6-(2-methoxy-phenyl)-pyrimidin-4-yl]-ureido}-acetic acid (Compound 31A)

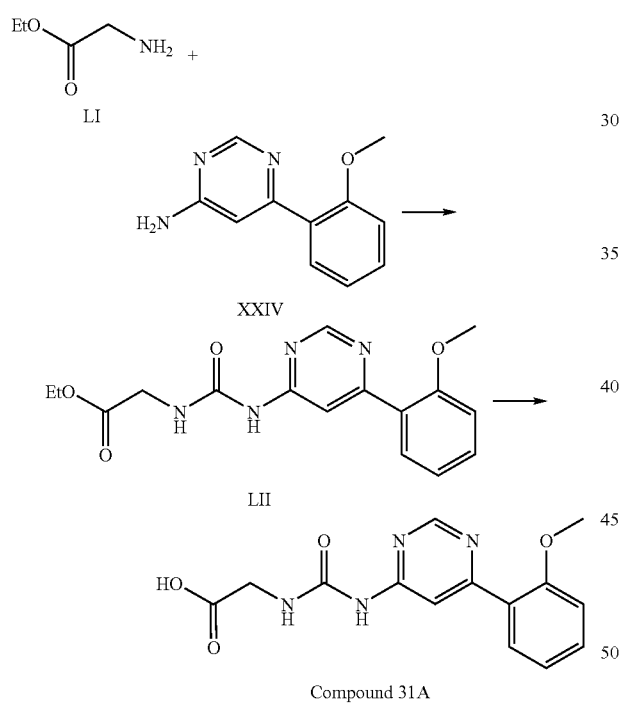

Compound 31A

Step 1:

Phenyl chloroformate (0.370 g, 1.98 mmol) was added dropwise to a solution of 6-(2-methoxy-phenyl)-pyrimidin-4-ylamine (XXIV) (0.25 g, 1.2 mmol) and DIPEA (0.31 g, 2.4 mmol) in dichloromethane (10 ml) at −78° C. and the mixture was allowed to stir overnight at room temperature. Then dichloromethane was evaporated, dry 1,4-dioxane and glycine ethyl ester hydrochloride (0.17 g, 1.2 mmol) and DIPEA (0.31 g, 2.4 mmol) were added and the mixture was heated overnight at 70° C. The solvent was evaporated and the crude product was extracted with ethyl acetate (2×100 ml). The ethyl acetate phase was washed with water (2×50 ml) and brine, dried over anhydrous sodium sulfate and concentrated in a vacuum rotavapor. The residue was purified by silica gel column chromatography (eluent: 70% ethyl acetate/hexane) giving {3-[6-(2-methoxy-phenyl)-pyrimidin-4-yl]-ureido}-acetic acid ethyl ester. Yield: 190 mg, 47.8%.

Step 2:

To a solution of {3-[6-(2-methoxy-phenyl)-pyrimidin-4-yl]-ureido}-acetic acid ethyl ester (LII) (190 mg, 0.57 mmol) in a mixture of THF and water (1:1) was added LiOH (50.0 mg, 1.12 mmol) solution in water at ice bath temperature over 10 min and the mixture was then allowed to stir for 2 hours. THF was evaporated and the aqueous solution was acidified with 2N HCl. This aqueous phase was then extracted with ethyl acetate (2×100 ml). The organic phases were separated, combined, washed with water and brine, dried over anhydrous sodium sulfate and concentrated in a vacuum rotavapor to afford {3-[6-(2-methoxy-phenyl)-pyrimidin-4-yl]-ureido}-acetic acid as a white solid. Yield: 184 mg, ~quantitative.

MS: m/z=303 (M+1).

1H NMR (500 MHz, DMSO-$d_6$) δ=3.73 (3H, s), 3.91 (2H, s), 7.12-7.10 (1H, m), 7.21 (1H, d, J=8 Hz), 7.54-7.51 (1H, m), 7.86 (1H, d, J=7.5 Hz), 8.18 (2H, m), 8.21 (1H, br. s), 8.87 (1H, br. s), 10.28 (1H, br. s).

Example 32A

Synthesis of 2-{3-[6-(2-methoxy-phenyl)-pyrimidin-4-yl]-ureido}-propionic acid (Compound 32A)

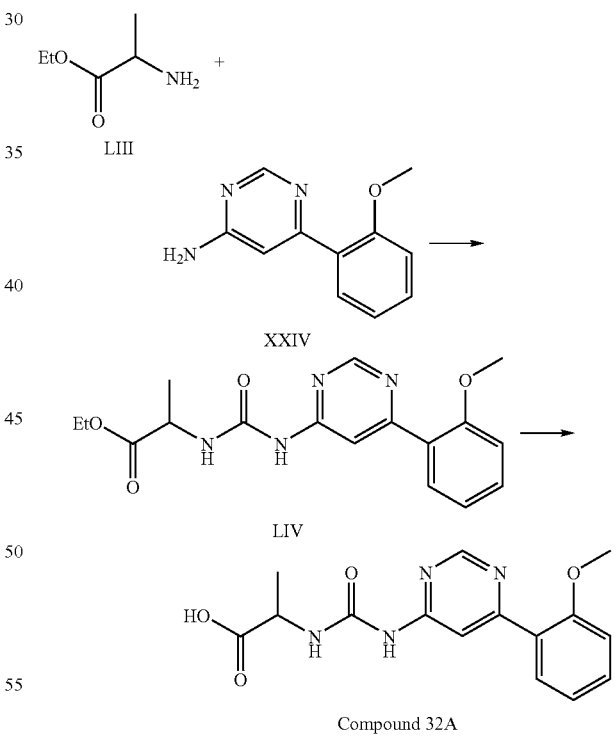

Compound 32A

Step 1:

Phenyl chloroformate (0.21 g, 1.4 mmol) was added dropwise to a solution of 6-(2-methoxy-phenyl)-pyrimidin-4-ylamine (XXIV) (0.28 g, 1.4 mmol) and DIPEA (0.35 g, 2.8 mmol) in dry dichloromethane (10 ml) at −78° C. and the mixture was allowed to stir overnight at room temperature. Then dichloromethane was evaporated, dry 1,4-dioxane and alanine ethyl ester hydrochloride (0.21 g, 1.4 mmol) and DIPEA (0.35 g, 2.8 mmol) were added and the mixture was heated at 70° C. for overnight. The solvent was evaporated and the crude product was extracted with ethyl acetate (2×100 ml). The combined organic phases were washed with water (2×50 ml) and brine, dried over anhydrous sodium sulfate and concentrated in a vacuum rotavapor. The residue was purified by silica gel column chromatography (eluent: 45% ethyl acetate/hexane) leading to 2-{3-[6-(2-methoxy-phenyl)-pyrimidin-4-yl]-ureido}-propionic acid ethyl ester. Yield: 470 mg, 97.2%.

Step 2:
To a solution of 2-{3-[6-(2-methoxy-phenyl)-pyrimidin-4-yl]-ureido}-propionic acid ethyl ester (LIV) (470 mg, 1.4 mmol) in a mixture of THF and water (1:1) was added a solution of LiOH (0.11 g, 2.7 mmol) in water at ice bath temperature over 30 min and then allowed to stir for 2 hours. THF was evaporated and the aq. solution was acidified with 2N HCl. This aq. phase was then extracted with ethyl acetate (2×100 ml), the separated and combined organic phases were washed with water and brine, dried over anhydrous sodium sulfate and concentrated in a vacuum rotavapor to afford 2-{3-[6-(2-methoxy-phenyl)-pyrimidin-4-yl]-ureido}-propionic acid (compound #32A) as a white solid. Yield: 223 mg, 50.4%.

MS: m/z=317 (M+1).

1H NMR (500 MHz, DMSO-$d_6$) δ=1.38-1.37 (3H, d, J=6.5 Hz), 3.87 (3H, s), 4.29-4.26 (1H, m), 7.10 (1H, d, J=7.5 Hz), 7.19 (1H, d, J=7.5 Hz), 7.48 (1H, s), 7.92 (1H, m), 8.11 (1H, s), 8.27 (1H, br. s), 8.80 (1H, s), 9.74 (1H, s), 12.80 (1H, br. s).

Example 33A

Synthesis of 2-{3-[6-(2-methoxy-phenyl)-pyrimidin-4-yl]-ureido}-2-methyl-propionic acid (Compound 33A)

Step 1:
Phenyl chloroformate (0.21 g, 1.4 mmol) was added dropwise to a solution of 6-(2-methoxy-phenyl)-pyrimidin-4-ylamine (XXIV) (0.28 g, 1.4 mmol) and DIPEA (0.36 g, 2.8 mmol) in dry dichloromethane (10 ml) at −78° C. and the mixture was allowed to stir overnight at room temperature. Then dichloromethane was evaporated, dry 1,4-dioxane and 2-amino-2-methyl-propionic acid ethyl ester (0.17 g, 1.2 mmol) and DIPEA (0.36 g, 2.8 mmol) were added and the mixture was heated overnight at 70° C. The solvent was evaporated and the crude product was extracted with ethyl acetate (2×100 ml). The combined organic phases were washed with water (2×50 ml) and brine, dried over anhydrous sodium sulfate and concentrated in a vacuum rotavapor. The residue was purified by silica gel column chromatography (eluent: 30% ethyl acetate/hexane) leading to 2-{3-[6-(2-methoxy-phenyl)-pyrimidin-4-yl]-ureido}-2-methyl-propionic acid ethyl ester.

Yield: 370 mg, 73.5%.

Step 2:
To a solution of 2-{3-[6-(2-methoxy-phenyl)-pyrimidin-4-yl]-ureido}-2-methyl-propionic acid ethyl ester (LVI) (370 mg, 1.03 mmol) in a mixture of THF and water (1:1) was added a solution of LiOH (87.0 mg, 2.06 mmol) in water at ice bath temperature over 10 min and then allowed to stir for two hours at room temperature. THF was evaporated and the aqueous solution was acidified with 2N HCl. This aqueous phase was then extracted with ethyl acetate (2×100 ml), the combined organic phases were washed with water and brine, dried over anhydrous sodium sulfate and concentrated in a vacuum rotavapor to afford 2-{3-[6-(2-methoxy-phenyl)-pyrimidin-4-yl]-ureido}-2-methyl-propionic acid as a white solid. Yield: 235 mg, 69.1%.

MS: m/z=331 (M+1).

1H NMR (500 MHz, DMSO-$d_6$) δ 1.48 (6H, s), 3.87 (3H, s), 7.10-7.04 (1H, m), 7.18 (1H, d, J=8 Hz), 7.5-7.46 (1H, m), 7.90 (1H, d, 7.5 Hz), 8.04 (1H, s), 8.37 (1H, br. s), 8.78 (1H, s), 9.62 (1H, br. s), 12.50 (1H, br. s).

Example 34A

Synthesis of {3-[6-(2-methoxy-phenyl)-pyrimidin-4-yl]-1-methyl-ureido}-acetic acid (Compound 34A)

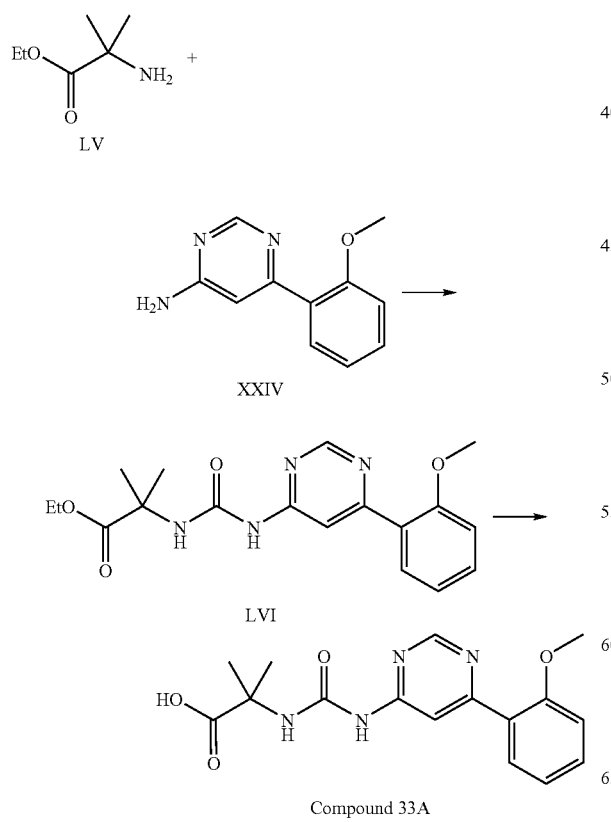

Compound 33A

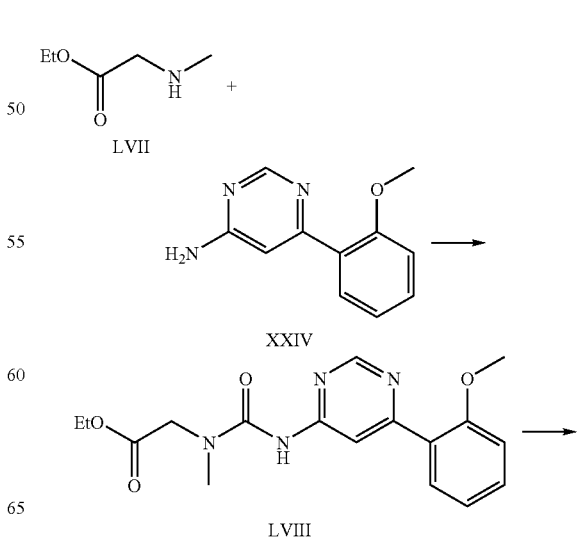

LVIII

-continued

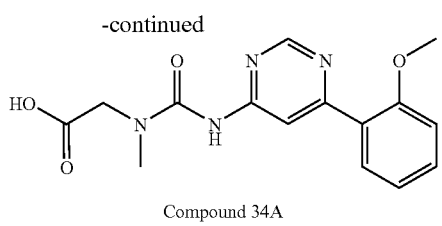

Compound 34A

Step 1:

Phenyl chloroformate (0.21 g, 1.4 mmol) was added dropwise to a solution of 6-(2-methoxy-phenyl)-pyrimidin-4-ylamine (XXIV) (0.28 g, 1.4 mmol) and DIPEA (0.35 g, 2.8 mmol) in dry dichloromethane (10 ml) at −78° C. and the mixture was allowed to stir overnight at room temperature. Then dichloromethane was evaporated, dry 1,4-dioxane, sarcosine ethyl ester hydrochloride (0.213 g, 1.4 mmol) and DIPEA (0.35 g, 2.8 mmol) were added and the mixture was heated overnight at 70° C. The solvent was evaporated and the crude product was extracted with ethyl acetate (2×100 ml). The combined organic phases were washed with water (2×50 ml) and brine, dried over anhydrous sodium sulfate and concentrated in a vacuum rotavapor. The residue was purified by silica gel column chromatography (eluent: 70% ethyl acetate/hexane) leading to {3-[6-(2-methoxy-phenyl)-pyrimidin-4-yl]-1-methyl-ureido}-acetic acid ethyl ester.

Yield: 217 mg, 44.9%.

Step 2:

To a solution of {3-[6-(2-methoxy-phenyl)-pyrimidin-4-yl]-1-methyl-ureido}-acetic acid ethyl ester (LVIII) (370 mg, 1.03 mmol) in a mixture of THF and water (1:1) was added a solution of LiOH (87.0 mg, 2.06 mmol) in water at ice bath temperature over 10 min and then allowed to stir for two hours at room temperature. THF was evaporated and the aqueous solution was acidified with 2N HCl. This aqueous phase was then extracted with ethyl acetate (2×100 ml), the combined organic phases were washed with water and brine, dried over anhydrous sodium sulfate and concentrated in a vacuum rotavapor to give {3-[6-(2-methoxy-phenyl)-pyrimidin-4-yl]-1-methyl-ureido}-acetic acid as a brown coloured solid.

Yield: 34 mg, 10.4%.

MS: m/z=317 (M+1).

1H NMR (500 MHz, DMSO-$d_6$) δ=3.03 (3H, s), 3.85 (3H, s), 4.11 (2H, s), 7.10-7.07 (1H, s), 7.18 (1H, d, J=8 Hz), 7.49-7.76 (1H, m), 7.82 (1H, d, J=6.5 Hz), 8.36 (1H, s), 8.82 (1H, s), 9.57 (1H, br. s), 12.70 (1H, br. s).

Biological Examples

Biological Example 1

I. Behavioral Animal Models for the Analysis of Inflammatory and Neuropathic Pain Several animal models for the analysis of inflammatory and neuropathic pain are known. Said models share the common feature that after e.g., induction of a nerve lesion (e.g., spared nerve injury, SNI) or after exposing experimental animals to a noxious stimulus (e.g., injection of formalin or carrageenan), the signs of pain as induced by said interventions are measured by quantifiable behavioral components such as, e.g., paw withdrawal threshold to mechanical stimulation with von Frey hairs (or to thermal stimulation using a laser source or licking behaviour). These reactions are interpreted as being equivalent to mechanical and thermal allodynia (hypersensitivity to mechanical stimuli) or hyperalgesia in humans.

The spared nerve injury model (SNI model, as developed by Decosterd and Woolf (2000), see FIG. 1) is characterized by the induction of clinically relevant nerve lesions and after surgical intervention, subsequent behavioral experiments (e.g., von Frey Assay). Said model constitutes a common nerve injury model which consists of ligation and section of two branches of the sciatic nerve (namely tibial and common peroneal nerves) leaving the sural nerve intact. The SNI model results in early (less than 24 hours), prolonged and substantial changes in mechanical and cold sensitivity that closely mimic the features of clinical neuropathic pain. Animals with these types of nerve injury have been shown to develop abnormal pain sensations and hypersensitivity to mechanical stimuli (allodynia) similar to those reported by neuropathic pain patients. Alternatively, the formalin assay in mice is a valid and reliable behavioral model of nociception in inflammatory and neuropathic pain. It is sensitive to various classes of analgesic drugs (Hunskaar S, Hole K, Pain. 1987 July; 30(1):103-14.) The noxious stimulus consists of an injection of 10 µl diluted formalin (2% in saline) under the skin of the dorsal surface of the left hindpaw (subcutaneous or interplantar into the left hindpaw). The response is licking and flinching of the injected paw.

For the carrageenan assay a subcutaneous injection of 25 µl of 1% carrageenan (in saline) into a single hind paw (ipsilateral paw) of mice is applied. Subsequent inflammation results in long lasting swelling and hypersensitivity (against mechanical and thermal stimuli) of the paw. The carrageenan assay is a standard laboratory assay used to predict anti-inflammatory activity of test compounds. Paw edema measurements and Hargreaves Assay (withdrawal of paws due to thermal stimulation via a light source) are used for read out.

Regarding the present invention, the effect of administration of cyclin-dependent kinase (CDK)-inhibiting compounds according to Formula I on the development of inflammatory and neuropathic pain is assayed in a SNI model, in a carrageenan and in a formalin assay. The experimental procedure and results are described in detail below.

Biological Example 2

A. Spared Nerve Injury (SNI)—Model of Chronic Neuropathic Pain

As outlined above, the spared nerve injury (SNI) model (see FIG. 1) involves a lesion of two of the three terminal branches of the sciatic nerve (tibial and common peroneal nerves) of experimental animals, leaving the sural nerve intact. SNI results in mechanical and thermal allodynia in the non-injured sural nerve skin territory (Decosterd and Woolf, Pain 2000; 87:149-158. (2) Tsujino et al., Mol. Cel. Neurosci. 2000; 15:170-182).

1. Induction of Spared Nerve Injury (Nerve Lesion) in Wildtype Mice

Wildtype mice (strain C3HeB/FeJ) (age, sex and weight matched) were anesthetized with Hypnorm (0.315 mg/ml fentanyl citrate+10 mg/ml fluanisone; Janssen)/Hypnovel (5 mg/ml midazolam; Roche Applied Sciences)/water at a ratio of 1:1:2 at 4 µl/g prior to surgical preparation.

Subsequently, an incision was made under aseptic precautions in the ipsi-lateral right hind leg of all mice just above the level of the knee, exposing the three terminal branches of the sciatic nerve: the common peroneal, tibial, and sural nerves.

The common peroneal and tibial nerves were ligated tightly with 7/0 silk and sectioned distal to the ligation removing ≈2 mm of distal nerve stump. The sural branch remained untouched during the procedure (denoted herein "SNI ipsi"). The overlying muscle and skin was sutured, and the animals were allowed to recover and to permit wound healing. In the same mice the sciatic nerve branches of the contra-lateral left hind leg were exposed but not lesioned (denoted herein "SNI contra-lateral"). Mice that underwent spared nerve injury are hereinafter denoted "SNI mice".

2. Administration of CDK-Inhibiting Compounds to SNI Mice

After recovery from surgery and wound healing, SNI mice received per oral (p.o.) injections of CDK-inhibiting compounds. In this example, compound #16A was administered.

30 mg/kg of a CDK inhibitor, dissolved in 400 µl of 2% Hydroxprolylcellulose; 0.25% Lactic Acid (85% solution) was administered via per oral application 30 min prior to von Frey measurements (mechanical allodynia). As a negative control, the same amount (400 µl) of 2% Hydroxprolylcellulose; 0.25% Lactic Acid (85% solution) vehicle was administered by a single per oral application 30 min prior to von Frey measurements. Injection of inhibitor or vehicle, and subsequent measurements of paw withdrawal threshold to mechanical stimulation in von Frey assays were performed at day 107 post SNI. Reflex nociceptive responses to mechanical stimulation were measured in a von Frey assay 30 min after each injection.

The effect of administration of CDK inhibitors to SNI mice on the development of mechanical allodynia was analyzed in a von Frey assay, as described below.

3. Behavioral Testing of SNI Mice after Administration of CDK-Inhibiting Compounds (von Frey Assay)

Mice that underwent SNI and subsequent administration of the compounds of the present invention were tested for signs of mechanical allodynia post nerve injury and post administration in a von Frey assay (Decosterd and Woolf, Pain 2000; 87:149-158). This assay determines the mechanical threshold upon which a stimulus, which normally is not painful, is recognized by an animal as uncomfortable or painful. SNI ipsi and SNI contra baselines, respectively, were established.

Mechanical thresholds of SNI mice were quantified using the up-down method based on Chaplan et al. (1994) and Malmberg and Basbaum (1998).

Mice were placed in plexiglass cylinders of about 9.5 cm in diameter, 14 cm high with four vent holes toward the top and a plexiglass lid. The cylinders were placed on an elevated mesh surface (7×7 mm squares). Prior to the day of testing, the mice were acclimated to the testing cylinders for 1-2 hours. On the day of testing the mice were acclimated to the cylinders for about an hour, wherein the acclimation time depends on factors such as the strain of the mouse and the number of times they have been tested previously. In general, testing may begin once the mice are calm and stop exploring the new environment.

For testing mice, filaments 2.44, 2.83, 3.22, 3.61, 3.84, 4.08, and 4.31 (force range=0.04 to 2.0 g) were used. The 3.61 mN filament was applied first. Said filament was gently applied to the plantar surface of one paw, allowed to bend, and held in position for 2-4 seconds. Whenever a positive response to the stimulus (flexion reaction) occurred the next weaker von Frey hair was applied; whenever a negative response (no reaction) occurred the next stronger force was applied. The test was continued until the response to 4 more stimuli after the first change in response had been obtained. The highest force tested was 4.31. The cut-off threshold was 2 g.

The series of scores (i.e, "flexion reaction" and "no reaction") and the force of the last filament applied were used to determine the mechanical threshold as described in Chaplan et al., Journal of Neuroscience Methods. 53(1):55-63, 1994 July. The threshold determined is that to which the animal would be expected to respond to 50% of the time. Mice were sacrificed after von Frey measurements were accomplished.

4. Effects of Administration of Compound #16A on the Development of Neuropathic Pain Compound #16A was administered to SNI mice as described above. Von Frey measurements were performed as described above. Compound #16A had a hypoalgesic effect on SNI mice. Von Frey measurements were performed at ipsi-lateral and contra-lateral paws of the animals at day 107 after surgery. Animals treated with compound #16A displayed a significant increase of threshold values indicating reduced sensitivity to mechanical stimuli (reduced allodynia). In comparison, animals treated with vehicle per os alone displayed low thresholds indicating high allodynia.

These findings signify that compound #16A is effective as a hypoalgesic drug in models of chronic neuropathic pain.

Biological Example 3

Formalin Assay—Model of Inflammatory Processes/Inflammatory and Chronic Neuropathic Pain The formalin assay in mice is a valid and reliable behavioral model of nociception and is sensitive to various classes of analgesic drugs (Hunskaar S, Hole K, Pain. 1987 July; 30(1):103-14.) The noxious stimulus is an injection of 10 µl diluted formalin (2% in saline) subcutaneous or intraplantar into the left hind paw. The response is licking and flinching of the injected paw. The response shows two phases, which reflect different parts of the inflammatory process (Abbott et al 1995), an early/acute phase 0-5 min post-injection, and a late/chronic phase 5-30 min post-injection. The following protocol describes one possible way to conduct the experiment:

1. Injection of Formalin and Administration of CDK-Inhibiting Compound

Age, sex and weight matched wildtype mice (C3HeB/FeJ) are used in this assay. Prior to formalin injection the animals are randomly subdivided into experimental groups of 10 animals each. Thirty minutes prior to formalin injection, a suitable dose of a CDK inhibitor dissolved in (400 µl) of 2% Hydroxprolylcellulose; 0.25% Lactic Acid (85% solution)) can be administered by i.p. injection. Similarly, Iκ Kinase (IKK) inhibitor (30 mg/kg) in (400 µl) of 2% Hydroxprolylcellulose; 0.25% Lactic Acid (85% solution) (positive control), or vehicle alone ((400 µl) of 2% Hydroxprolylcellulose; 0.25% Lactic Acid (85% solution)) (negative control) can be administered by i.p. injection 30 min before formalin injection.

For formalin injection the mouse is held with a paper towel, in order to avoid disturbance of the injection by movements. The injected hind paw is held between thumb and forefinger and 10 µl of Formalin (2%) is injected subcutaneously (s.c.) between the two front tori into the plantar hind paw using a Hamilton syringe. The behavior of the formalin- and inhibitor-treated mice is analyzed as described below.

2. Behavioral Analysis of Mice after Injection of Formalin and Administration of CDK-Inhibiting Compound The behaviour of the formalin-treated mice, i.e. licking and flinching, is monitored by an automated tracking system (Ethovision 3.0 Color Pro, Noldus, Wageningen, Netherlands) over a defined period of time: measurement is initiated 5 min after formalin injection and terminated 30 min after formalin injection. This time frame covers phase II of formalin-induced nociception (pain), which is hyperalgesia.

Two different fluorescent dyes are used for topically marking the injected hind paw (yellow dye) (Lumogenyellow; BASF Pigment, Cologne, Germany) and the contralateral paw (blue dye) (Lumogenviolet; Kremer Pigmente, Aichstetten, Germany) respectively. To determine licking behaviour, mice are monitored with a CCD camera. After monitoring and recording, the video is analyzed using the EthoVision software (Ethovision 3.0 Color Pro, Noldus, Wageningen, Netherlands) or by manual analysis. Fluorescent dot sizes and fluorescence intensities were measured and reduction of fluorescent dot size through licking and biting was calculated. The overall licking time intensity was automatically calculated by comparison of dot size reduction of treated versus untreated paws.

As another variant of assay read out, the licking behaviour of the individual animals was tracked manually based on video files. Licking times were recorded over 30 minutes after formalin injection and subdivided for three different licking zones (dorsum, plantar, toes). Overall licking times can be calculated for each animal as well as each experimental group and be used as a parameter for determination of compound efficacy.

As a result it was found that mice receiving vehicle treatment prior to formalin injection (negative control) displayed a prolonged licking time and a significant reduction of fluorescent dot size at the formalin-treated paw.

Figure 2:
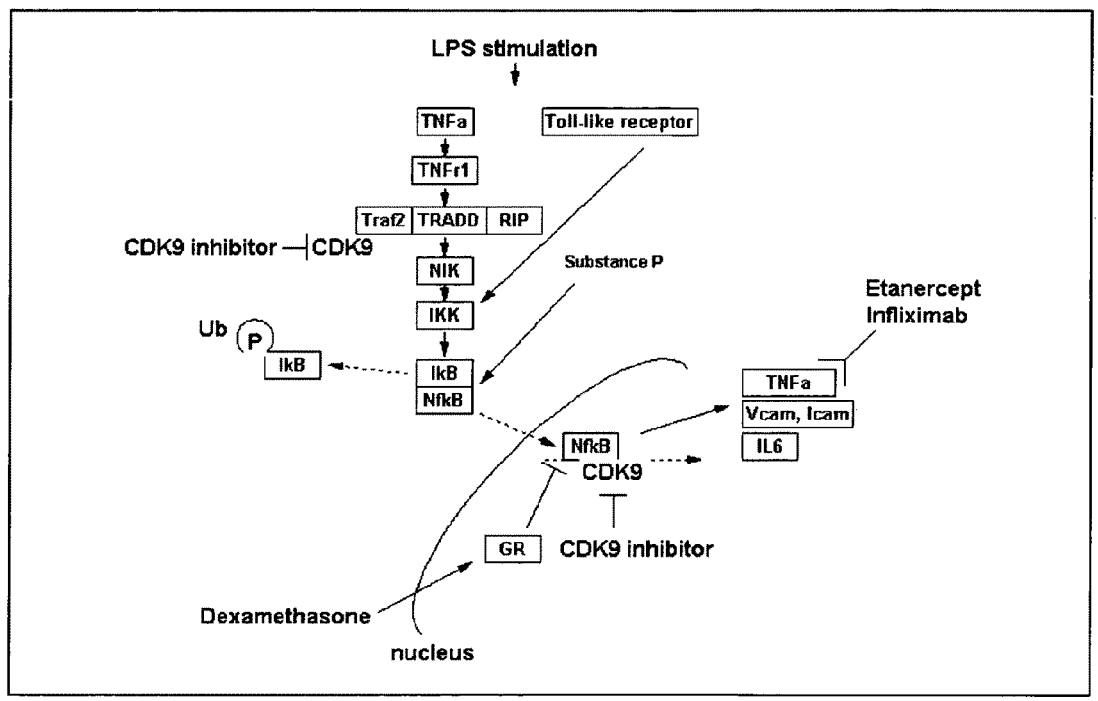

In contrast, a reduction in licking time and in consequence no significant reduction of fluorescent dot size of the formalin-treated paw could be observed in test compound/formalin-treated mice. The same effect, i.e. a reduction in licking time and a minor change in fluorescent dot size, was observed in control mice treated with Ikappa kinase inhibitor (IKK; for function of IKK see FIG. 2, positive control).

This observation is indicative for reduced inflammatory/chronic inflammatory pain perception in CDK9 inhibitor-treated mice and for a hypoalgesic effect of the tested compound.

Biological Example 4

Carrageenan Assay in Mice—Model of Inflammation and Inflammatory Pain

The model of carrageenan induced paw edema is a standard laboratory assay used to predict anti-inflammatory activity and reduction of inflammation-induced pain perception of respective compounds. The following protocol describes one possible way to conduct the experiment.

The basic measurement constitutes in the measurement of edema and mechanical as well as thermal hypersensitivity in response to irritants, such as carrageenan.

Inflammation and resulting inflammatory pain is induced by subcutaneous injection of 25 µl of 1% carrageenan (in saline) into mice hind paw (ipsi-lateral paw). Each group of 10 mice receives administration of a compound according to Formula I, 30 mg/kg body weight, vehicle ((400 µl) of 2% Hydroxprolylcellulose; 0.25% Lactic Acid (85% solution)) and saline (physiol. NaCl) by i.p. injection 30 min prior to carrageenan injection. Contra-lateral paws do not receive carrageenan injection.

1.1 Effects of Administration of a CDK-Inhibiting Compound on Carrageenan-Treated Mice Paw edema induced by carrageenan injection are detected by increased paw size measured from dorsal to plantar at the metatarsus region of the injected (ipsi-lateral) paws. Sizes of ipsi- and contra-lateral paws serve as surrogate markers for inflammation and are measured at several time points after carrageenan injection: before injection (−1), 2 h (2), 3 h (3) 4 h (4), 5 h (5), 6 h (6), 24 h (24) after injection.

The paw size of all mice may increase, e.g., by 2 to 3 mm (+10%) within the first hour after carrageenan injection, independent of the type of treatment substance injected 30 minutes prior to carrageenan. During the time course, mice which received treatment with a CDK-inhibiting compound prior to carrageenan injection may display a reduction of the edema until 24 h after carrageenan injection: the increase in paw size could drop e.g. from 10% down to 8%. In contrast, the paw size of the control mice could increase by 30% in average at this time point. After 24 h post carrageenan injection, the size of all paws treated with carrageenan may increase to reach its maximum at 96 h after injection.

As a read-out of the carrageenan assay, a Hargreaves Assay may be performed, wherein said assay allows the measuring of thermal sensitivity to radiant heat. The Hargreaves assay (Hargreaves et al., 1988) measures nociceptive sensitivity in a freely moving animal by focusing a radiant heat source on the plantar surface of an animal's hindpaw as it stands in a plexiglass chamber. Specifically, the lower side of a paw is exposed to a luminous source, generating a temperature of, e.g. 55° C. Thermal sensitivity is measured as latency between start of exposure and lifting/pulling the exposed paw.

Mice treated with a CDK9 inhibitor as disclosed herein and carrageenan, or with Naproxen and carrageenan, or with solvent and carrageenan, respectively, are subjected to a Hargreaves assay. Mice treated with a CDK inhibitor and carrageenan could display a longer latency, compared to negative control mice. This observation would be indicative for a hypoalgesic effect of the CDK inhibitors as disclosed herein.

Biological Example 5

Carrageenan Assay in Rats—Model of Inflammation and Inflammatory Pain

The following depicts one possible way of performing the carrageenan assay in rats. Said assay detects analgesic/anti-inflammatory activity in rats with inflammatory pain, following the protocol as described by Winter et al (Proc. Soc. Exp. Biol. Med., 111, 544-547, 1962).

Rats (200-250 g) are injected with a suspension of carrageenan into the lower surface of the right hindpaw (0.75 mg per paw in 0.05 ml physiological saline). Two hours later rats are submitted consecutively to tactile and thermal stimulation of both hindpaws. For tactile stimulation, the animal is placed under an inverted acrylic plastic box (18×11.5×13 cm) on a grid floor. The tip of an electronic Von Frey probe (Bioseb, Model 1610) is then applied with increasing force first to the non-inflamed and then the inflamed hindpaw and the force required to induce paw-withdrawal is automatically recorded. This procedure is carried out 3 times and the mean force per paw is calculated.

For thermal stimulation, the apparatus (Ugo Basile, Reference: 7371) consists of individual acrylic plastic boxes (17× 11×13 cm) placed upon an elevated glass floor. A rat is placed in the box and left free to habituate for 10 minutes. A mobile infrared radiant source (96±10 mW/cm$^2$) is then focused first under the non-inflamed and then the inflamed hindpaw and the paw-withdrawal latency is automatically recorded. In order to prevent tissue damage the heat source is automatically turned off after 45 seconds.

After the behavioral measures, the paw edema is evaluated by measuring the volume of each hindpaw using a digital plethysmometer (Letica, Model 7500), which indicates water displacement (in ml) induced by paw immersion.

10 rats are studied per group. The test is performed blind.

The test substance, such as a CDK inhibitor according to Formula I as presented herein, will be evaluated at 2 doses (10 and 30 mg/kg), administered p.o. 60 minutes before the test, and compared with a vehicle control group.

Morphine (128 mg/kg p.o.) and acetylsalicylic acid (512 mg/kg p.o.), administered under the same experimental conditions, will be used as reference substances.

The experiment will therefore include 6 groups. Data will be analyzed by comparing treated groups with vehicle control using unpaired Student's t tests.

Rats treated with a CDK9 inhibitor as disclosed herein and carrageenan, or with Naproxen and carrageenan, or with solvent and carrageenan, respectively, are subjected to a Hargreaves assay. Rats treated with a CDK inhibitor and carrageenan should display a longer latency, compared to negative control rats. This observation would be indicative for a hypoalgesic effect of the CDK inhibitors as disclosed herein.

Biological Example 6

A. LPS In Vivo Assay (LPS)—Model of Cytokine Repression In Vivo

For the LPS induced model of septic shock, mice receive an intraperitoneal (i.p.) injection of 30 µg bacterial Lipopolysaccharide (LPS; L2630 SIGMA) in saline. Said LPS-mediated initiation of the inflammatory signalling cascade results in increasing blood serum concentrations of cytokines such as e.g. TNFα, IL-6 and IL1β. Blood can be taken from these animals at defined time points. Thereafter, serum will be separated and the samples can be stored at −80° C. until cytokine concentrations are measured using commercial ELISA assays. (A L Moreira et al., Braz J Med Biol Res 1997; 30:1199-1207).

It has been recognized that inflammatory mediators such as the cytokines TNFα, IL6 and IL1β can contribute to persistent pain states as well as inflammatory disorders. After being released from immune cells like macrophages in peripheral and microglia in CNS tissues, these mediators seem to play a pivotal role not only in inflammatory and neuropathic pain but also in inflammatory disorders such as rheumatoid arthritis (F Marchand et al., Nat Rev Neurosci 2005; 6 (7); 521-532). Thus, inhibition of tumor necrosis factor α (TNFα) represents a relevant target for the treatment of inflammatory diseases as well [Lavagno et al., Eur J Pharmacol 2004; 501, 199-208].

The LPS in vivo assay can be used as a powerful model to address repression of cytokine expression by pharmacological treatments.

1. Induction of Cytokine Expression in Wildtype Mice

Wildtype mice (strain C3HeB/FeJ) (age, sex and weight matched) were injected with 30 µg LPS (SIGMA) intraperitoneally. 90 minutes after LPS administration these animals were anaesthetized with 0.1 ml/10 g bodyweight Ketamine-Rompun (50/20 mg/ml), and blood for serum preparation was taken via cardiac puncture.

2. Administration of CDK-Inhibiting Compounds to LPS Mice

Pharmacological treatment groups (n=4) of LPS mice received intraperitoneal (i. p.) injections of CDK-inhibiting compounds or the vehicle (negative control), respectively. In particular, compounds #1A and 16A were administered.

10 or 30 mg/kg (compound per bodyweight) of a CDK inhibitor, dissolved in 20% DMSO, 5% Tween 80, 10% Tris 1M pH8, 20% PEG400, 45% PBS was administered as a single dosage 30 min prior to LPS stimulation. Vehicle control was administered in the same manner.

90 minutes (min) after LPS stimulation, blood samples were taken from the mice. Previously, the 90 min time point had been identified as the peak of TNF alpha expression in this animal model by a time course experiment.

The effect of pharmacological treatment with CDK inhibitors on cytokine levels in LPS mice was analyzed in commercial ELISA assays as described below.

3. Determination of Cytokine Blood Serum Concentrations in LPS Mice After Administration of CDK-Inhibiting Compounds Blood samples (~500 µl/animal) from the LPS animals were incubated on wet ice for 30 min after cardiac puncture. Afterwards the samples were centrifuged for 15 min at 13.000 rpm. Serum was separated from the clot and stored frozen at −80° C.

Serum concentrations of TNF alpha and IL6 within the samples were measured by using commercial ELISA Kits (Natutec) according to the manufacturers instructions.

Figure 3:
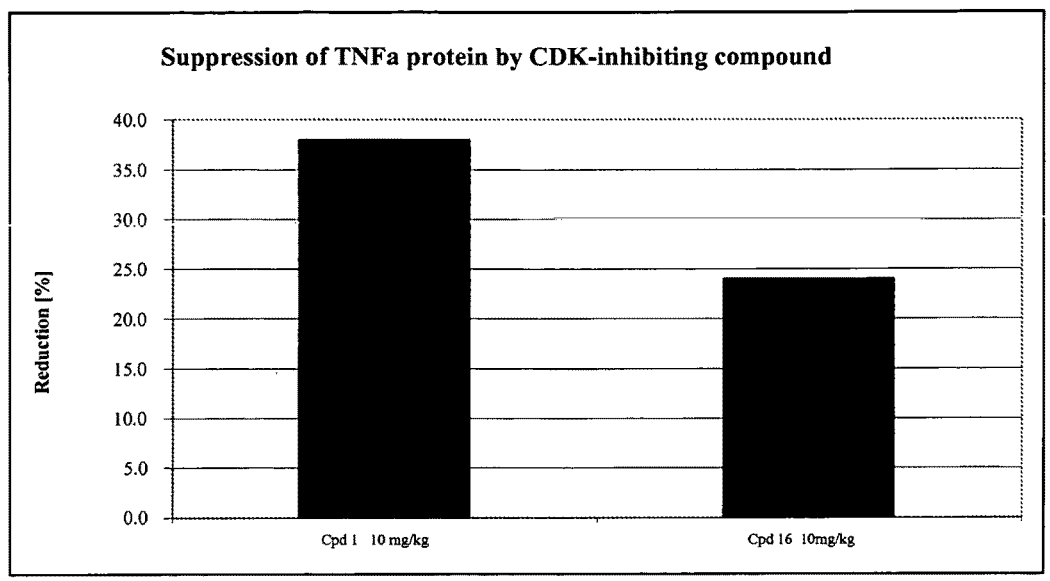
FIG. 3 depicts the results of cytokine measurements (TN-Falpha) performed with LPS induced mice after administration of Compounds 1A and 16A.

4. Effects of Administration of Compounds #1A and 16A on the Protein Expression of Cytokines Compounds #1A and 16A were administered to LPS mice as described above. ELISA based determinations of cytokine serum concentrations were performed as described above. Comparison of compounds #1A and 16A treated versus vehicle treated control animals displayed a significant repressive effect on TNFα and IL6 protein concentration in the blood serum. The results of administration of compounds #1A and 16A on LPS induced mice are shown in FIG. 3, which depicts the results of cytokine measurements (TNFalpha) performed with LPS induced mice.

These findings indicate that compounds #1A and 16A are effective suppressive drugs of cytokines TNF alpha and IL6 in models of cytokine expression.

Biological Example 7

A. In Vitro THP-1 Assay—In Vitro Model of Cytokine Inhibition

The human THP-1 cell line can be utilized as an in vitro model of cytokine expression as mediated by Lipopolysaccharide (LPS) or Tumor Necrosis Factorα [TNFα].

Monocytic THP-1 cells (ATCC; TIB-202) can be differentiated into macrophage-like cells expressing pro-inflammatory cytokines like TNFα, IL6 and IL1β upon induction with LPS or by TNFα (autocrine induction) itself.

It has been recognized that inflammatory mediators such as the cytokines TNFα, IL6 and IL1β can contribute to persistent pain states as well as to inflammatory disorders. After being released from immune cells like macrophages in peripheral and microglia in CNS tissues, these mediators seem to play a pivotal role not only in inflammatory and neuropathic pain but also in inflammatory disorders such as rheumatoid arthritis (F Marchand et al., Nat Rev Neurosci 2005; 6 (7); 521-532). Hence inhibition of tumor necrosis factor α (TNFα) represents a relevant target in the treatment of inflammatory disorders as well [Lavagno et al., Eur J Pharmacol 2004; 501, 199-208].

Therefore, the THP-1 in vitro assay can be used as a powerful screening model to address pharmacological inhibition of cytokine expression (U Singh et al, Clin Chem 2005; 51 (12); 2252-6], K Rutault et al., J Biol Chem 2001; 276 (9); 6666-74].

1. Growth and Differentiation of THP-1 Cells

THP-1 cells are grown in modified RPMI-1640 medium (ATCC, Cat. No. 30-2001) supplemented with 10% FCS and 1% Pen/Strep. For cytokine inhibition assays, cells are seeded at a density of $5 \times 10^5$ cells/ml into 6-well plates in standard growth medium supplemented with 100 ng/ml PMA (Sigma, P1585) to induce differentiation into macrophage-like cells. After 24 hours, the medium is replaced with standard growth medium (without PMA) and the cells are incubated for another 48 hours to complete differentiation.

2. Treatment of Differentiated THP-1 Cells with CDK-Inhibiting Compounds and LPS Stimulation After 72 h of differentiation, the medium is replaced with serum free growth medium, and CDK-inhibiting compounds as well as reference compounds such as positive and negative controls, each dissolved in DMSO are added at concentrations ranging from 0.5 to 5 µM (final concentration of DMSO in the well is 0.1%). Cells are incubated for 60 min with compounds prior to stimulation with 100 ng/ml LPS (Sigma, L2630) for another 4-48 hours. Supernatants are collected and assayed immediately for cytokine expression, e.g. for TNFα, IL-6 and IL-1b using commercially available sandwich ELISA assays (eBioscience, Cat. No 88-7346, 88-7066, 88-7010) or kept frozen at 20° C. until evaluation.

3. Determination of Cytokine Concentrations in THP-1 Supernatant after Administration of CDK-Inhibiting Compounds Concentrations of TNFα, IL6 and IL1β within the cell culture supernatants are measured by using commercial ELISA Kits (eBioscience) according to the manufacturers instructions.

4. Effects of Treatment with CDK-Inhibiting Compounds on the Protein Expression of Cytokines in THP-1 Cell Supernatants CDK-inhibitory compounds #1A, 16A, 20A, and 25A were administered to differentiated THP-1 cells in triplicates as described above (see section 2.). After 60 min of pre-incubation with test or reference compound (SB203580, a p38 inhibitor and BMS345541, an IKK-inhibitor) alone, cells were stimulated with LPS. After incubation for 4-48 h, supernatants were collected and ELISA based determinations of cytokine supernatant concentrations were performed as described in section 3, supra.

Comparison of cells treated with compounds #1A, 16A, 20A, and 25A and reference compounds versus cells treated with vehicle (DMSO) displayed a significant inhibitory effect of compound #1A, 16A, 20A, and 25A on TNFα and IL6 protein concentration in the cell supernatant. Compared to reference compounds SB203580 or BMS345541, these compounds exhibited a similar or better inhibition of TNFα/Il-6 expression.

Figure 4A:
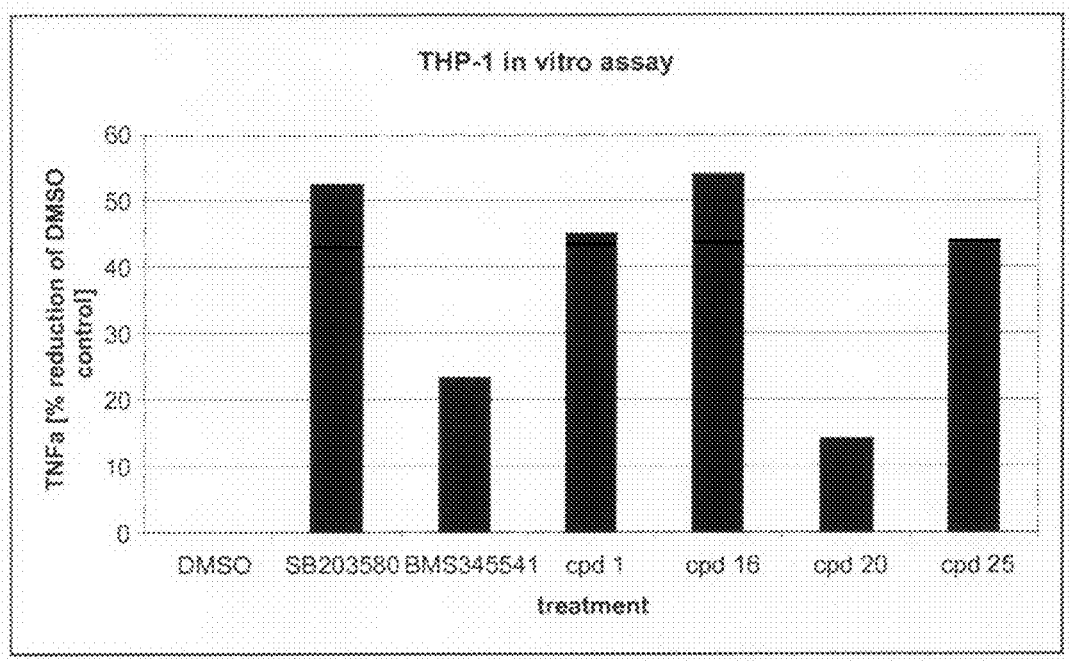
FIGS. 4A and 4B depicts the effects of administration of Compounds 1A, 16A, 20A, and 25A on expression of TNFα and IL-6 in LPS induced THP-1 macrophages.
Figure 4B:
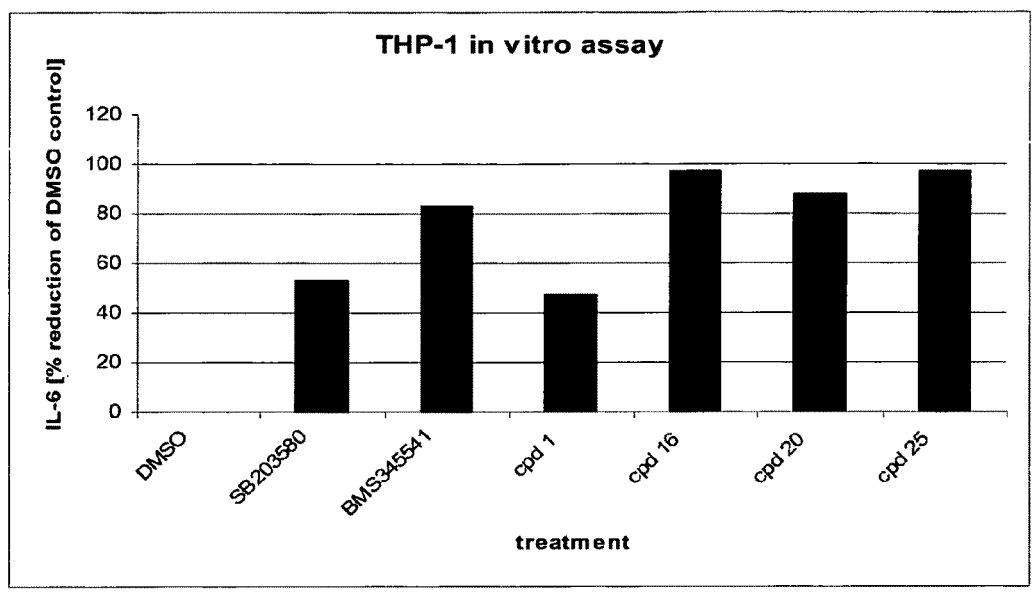

The effects of administration of compounds #1A, 16A, 20A, and 25A on expression of TNFα and IL-6 in LPS induced THP-1 macrophages are shown in FIGS. 4A and 4B. FIG. 4A shows the results of TNFα-measurements in LPS-induced THP-1 macrophages, while FIG. 4B shows the results of IL-6 measurements in LPS-induced THP-1 macrophages.

These findings indicate that CDK-inhibitory compounds #1A, 16A, 20A, and 25A are effective suppressors of expression of cytokines TNFα and IL-6.

Biological Example 8

A. In Vitro Kinase Inhibition Assays

IC50 profiles of compounds 1A-30A were determined for cyclin-dependent kinases CDK2/CycA, CDK4/CycD1, CDK5/p35NCK, CDK6/CycD1 and CDK9/CycT in enzymatic kinase inhibition assays in vitro. IC50 values as obtained in these assays were used for evaluating the specific selectivity and potency of the compounds with respect to CDK9 inhibition.

Results obtained in these assays were used to select compounds displaying specificity for CDK9. Specifically, it was intended to distinguish the CDK9-specific compounds from other compounds having significant inhibitory potency also with regard to other CDKs, i.e. on some or all of CDKs 2, 4, 5, and 6. This separation is essential in order to avoid adverse (cytostatic/cytotoxic) effects, which may occur upon inhibition of cell cycle relevant CDKs 2, 4, 5, and 6.

Furthermore, these data were used to establish structure activity relationships (SAR) supporting the design of new and even improved structures/compounds with respect to potency and selectivity.

1. Test Compounds

Compounds were used as $1 \times 10^{-02}$ M stock solutions in 100% DMSO, 100 µl each in column 2 of three 96-well V-shaped microtiterplates (in the following, said plates are referred to as "master plates").

Subsequently, the $1 \times 10^{-02}$ M stock solutions in column 2 of the master plates were subjected to a serial, semi-logarithmic dilution using 100% DMSO as a solvent, resulting in 10 different concentrations, the dilution endpoint being $3 \times 10^{-07}$ M/100% DMSO in column 12. Column 1 and 7 were filled with 100% DMSO as controls. Subsequently, 2×5 µl of each well of the serial diluted copy plates were aliquoted in 2 identical sets of "compound dilution plates", using a 96-channel pipettor.

On the day of the kinase inhibition assay, 45 µl H₂O were added to each well of a set of compound dilution plates. To minimize precipitation, the H₂O was added to the plates only a few minutes before the transfer of the compound solutions into the assay plates. The plates were shaken thoroughly, resulting in "compound dilution plates/10% DMSO" with a concentration of $1 \times 10^{-03}$ M/10% DMSO to $3 \times 10^{-08}$ M/10% DMSO in semilog steps. These plates were used for the transfer of 5 µl compound solution into the "assay plates". The compound dilution plates were discarded at the end of the working day. For the assays (see below), 5 µl solution from each well of the compound dilution plates were transferred into the assay plates. The final volume of the assay was 50 µl. All compounds were tested at 10 final assay concentrations in the range from $1 \times 10^{-04}$ M to $3 \times 10^{-09}$ M. The final DMSO concentration in the reaction mixtures was 1% in all cases.

2. Recombinant Protein Kinases

For the determination of inhibitory profiles, the following 5 protein kinases were used: CDK2/CycA, CDK4/CycD1, CDK5/p35NCK, CDK6/CycD1 and CDK9/CycT. Said protein kinases were expressed in Sf9 insect cells as human recombinant GST-fusion proteins or His-tagged proteins by means of the baculovirus expression system. Kinases were purified by affinity chromatography using either GSH-agarose (Sigma) or Ni-NTH-agarose (Qiagen). The purity of each kinase was determined by SDS-PAGE/silver staining and the identity of each kinase was verified by western blot analysis with kinase specific antibodies or by mass spectroscopy.

3. Protein Kinase Assay

All kinase assays were performed in 96-well FlashPlates™ from Perkin Elmer/NEN (Boston, Mass., USA) in a 50 µl reaction volume. The reaction mixture was pipetted in four steps in the following order:

20 µl of assay buffer (standard buffer)

5 µl of ATP solution (in $H_2O$)

5 µl of test compound (in 10% DMSO)

10 µl of substrate/10 µl of enzyme solution (premixed)

The assay for all enzymes contained 60 mM HEPES-NaOH, pH 7.5, 3 mM $MgCl_2$, 3 mM $MnCl_2$, 3 µM Na-Orthovanadate, 1.2 mM DTT, 50 µg/ml PEG20000, 1 µM $[-^{33}P]$-ATP (approx. 5×1005 cpm per well).

The following amounts of enzyme and substrate were used per well:

| # | Kinase | Kinase Lot # | Kinase ng/50 µl | Substrate | Substrate ng/50 µl |
|---|--------|--------------|-----------------|-----------|---------------------|
| 1 | CDK2/CycA | SP005 | 100 | Histone H1 | 250 |
| 2 | CDK4/CycD1 | SP005 | 50 | Rb-CTF (Lot 009) | 500 |
| 3. | CDK5/p35NCK | SP001 | 50 | Rb-CTF (Lot 009) | 1000 |
| 3 | CDK6/CycD1 | SP003 | 400 | Rb-CTF (Lot 009) | 500 |
| 4 | CDK9/CycT | 003 | 100 | Rb-CTF (Lot 009) | 1000 |

Reaction mixtures were incubated at 30° C. for 80 minutes. The reaction was stopped with 50 µl of 2% (v/v) $H_3PO_4$, plates were aspirated and washed two times with 200 µl $H_2O$ or 200 µl 0.9% (w/v) NaCl. Incorporation of $^{33}P$ was determined with a microplate scintillation counter (Microbeta, Wallac).

All assays were performed with a BeckmanCoulter/Sagian robotic system.

4. Evaluation of Raw Data

The median value of the counts in column 1 (n=8) of each assay plate was defined as "low control". This value reflects unspecific binding of radioactivity to the plate in the absence of a protein kinase but in the presence of the substrate. The median value of the counts in column 7 of each assay plate (n=8) was taken as the "high control", i.e. full activity in the absence of any inhibitor. The difference between high and low control was referred to as 100% activity. As part of the data evaluation, the low control value from a particular plate was subtracted from the high control value as well as from all 80 "compound values" of the corresponding plate. The residual activity (in %) for each well of a particular plate was calculated by using the following formula:

Res. Activity (%)=100×[(cpm of compound−low control)/(high control−low control)]

The residual activities for each concentration and the compound IC50 values were calculated using Quattro Workflow V2.0.1.3 (Quattro Research GmbH, Munich, Germany; www.quattro-research.com). The model used was "Sigmoidal response (variable slope)" with parameters "top" fixed at 100% and "bottom" at 0%. On testing, the IC50 values of compounds 1A-30A were all between 1 nM and 10 uM.

Results

Table 3 shows the biological data for examples 1 to 157.

TABLE 3

| Compound | Efficacy | CDK9-$IC_{50}$ | CDK9-0.1 M |
|----------|----------|----------------|------------|
| 1 | 0.99 | 10 | |
| 2 | 0.28 | 0.018 | 26 |
| 3 | 0.77 | 0.039 | 45 |
| 4 | 1.39 | | 75 |
| 5 | 0.22 | 0.019 | |
| 6 | 1.02 | 0.173 | |
| 7 | 0.83 | | 59 |
| 8 | 0.64 | | 41 |
| 9 | 0.71 | | 48 |
| 10 | 1.17 | | 96 |
| 11 | 1.17 | | 106 |
| 12 | 1.31 | | 63 |
| 13 | 1.33 | | 48 |
| 14 | 1 | | 58 |
| 15 | 0.43 | | 27 |
| 16 | 0.71 | | 28 |
| 17 | 0.79 | | 84 |
| 18 | 0.25 | | 17 |
| 19 | 0.99 | | 29 |
| 20 | 1.06 | | 108 |
| 21 | 1.3 | | 109 |
| 22 | 1.02 | | 107 |
| 23 | 1.14 | | 61 |
| 24 | 0.23 | | 17 |
| 25 | 0.13 | | 10 |
| 26 | 0.49 | | 21 |
| 27 | 0.21 | | 12 |
| 28 | 0.95 | | 108 |
| 29 | 1.07 | | 84 |
| 30 | 0.52 | | 33 |
| 31 | 0.51 | | 30 |
| 32 | 0.15 | | 10 |
| 33 | 0.4 | | 19 |
| 34 | 0.15 | | 12 |
| 35 | 1.13 | | 106 |
| 36 | 1.1 | | 88 |
| 37 | 1.09 | | 81 |
| 38 | 0.16 | | 9 |
| 39 | 0.87 | | 42 |
| 40 | 1.17 | | 56 |
| 41 | 0.98 | | 45 |
| 42 | | | |
| 43 | | | |
| 44 | | | |
| 45 | 0.97 | | 38 |
| 46 | 0.87 | | 34 |
| 47 | | | |
| 48 | | | |
| 49 | | | |
| 50 | | | |
| 51 | 1.08 | 1.25 | |
| 52 | 1.06 | 0.116 | |
| 53 | 1.01 | 1.08 | |
| 54 | 1.08 | | 111 |
| 55 | 1.01 | | 56 |
| 56 | 1.12 | | 83 |
| 57 | 1.06 | | 100 |
| 58 | 0.98 | | 102 |
| 59 | 1 | | 112 |
| 60 | 1.1 | | 116 |
| 61 | 0.95 | | 86 |
| 62 | 0.92 | | 27 |
| 63 | 1.21 | | 70 |
| 64 | 0.94 | | 21 |
| 65 | 0.4 | | 17 |
| 66 | 1.09 | | 26 |
| 67 | 0.96 | | 23 |
| 68 | 1.02 | | 23 |
| 69 | 0.55 | | 17 |
| 70 | 1.08 | | 104 |
| 71 | 1 | | 74 |
| 72 | 1.12 | | 58 |
| 73 | 1.19 | | 92 |
| 74 | 0.97 | | 61 |

TABLE 3-continued

| Compound | Efficacy | CDK9-IC$_{50}$ | CDK9-0.1 M |
|---|---|---|---|
| 75 | 0.44 | | 48 |
| 76 | 0.95 | | 88 |
| 77 | 1.17 | | 92 |
| 78 | 0.52 | | 36 |
| 79 | 0.25 | | 23 |
| 80 | 0.39 | | 28 |
| 81 | 0.86 | | 55 |
| 82 | 0.07 | 0.015 | 26 |
| 83 | 0.19 | 0.029 | 21 |
| 84 | 0.99 | | 46 |
| 85 | 0.97 | | 37 |
| 86 | 0.21 | | 10 |
| 87 | 0.98 | | 83 |
| 88 | 0.3 | | 14 |
| 89 | 0.11 | 0.005 | 3 |
| 90 | 0.72 | | 31 |
| 91 | 0.85 | | 22 |
| 92 | 0.92 | | 44 |
| 93 | 0.04 | | 12 |
| 94 | 0.99 | | 28 |
| 95 | 1.25 | | 15 |
| 96 | 1.18 | | 12 |
| 97 | 1.11 | | 18 |
| 98 | 0.22 | | 24 |
| 99 | 0.37 | | 23 |
| 100 | 1.4 | | 55 |
| 101 | 1.22 | | 60 |
| 102 | 0.44 | | 20 |
| 103 | 1.05 | | 52 |
| 104 | 0.74 | | 107 |
| 105 | 1.19 | | 92 |
| 106 | 0.95 | | 38 |
| 107 | 0.79 | | 33 |
| 108 | 0.91 | | 79 |
| 109 | 0.64 | | 32 |
| 110 | 0.37 | | 22 |
| 111 | 0.9 | | 49 |
| 112 | 0.48 | | 26 |
| 113 | 0.12 | | 15 |
| 114 | 0.07 | | 15 |
| 115 | 1.01 | | 95 |
| 116 | 0.07 | | 20 |
| 117 | 0.25 | | 22 |
| 118 | | | |
| 119 | 0.14 | | 6 |
| 120 | 0.14 | | 11 |
| 121 | 0.82 | | 92 |
| 122 | 0.28 | | 13 |
| 123 | 0.89 | | 71 |
| 124 | 0.13 | | 10 |
| 125 | | | |
| 126 | | | |
| 127 | | | |
| 128 | | | |
| 129 | | | |
| 130 | | | |
| 131 | | | |
| 132 | | | |
| 133 | | | |
| 134 | | | |
| 135 | | | |
| 136 | | | |
| 137 | | | |
| 138 | 1.2 | | 82 |
| 139 | 0.96 | | 80 |
| 140 | 1.24 | | 93 |
| 141 | 1.09 | | 57 |
| 142 | | | |
| 143 | | | |
| 144 | 1.17 | | 52 |
| 145 | 0.73 | | 66 |
| 146 | 0.96 | | 84 |
| 147 | 0.9 | | 58 |
| 148 | 0.93 | | 59 |
| 149 | 1.01 | | 127 |
| 150 | 0.91 | | 32 |
| 151 | 1.06 | | 31 |
| 152 | 1.01 | | 83 |
| 153 | | | |
| 154 | 0.84 | | 18 |
| 155 | 0.49 | | 25 |
| 156 | | | |
| 157 | | | |

GENERAL ABBREVIATIONS

Ac Acetate
AcN Acetonitrile
Boc tert.-Butyloxycarbonyl
CAIBE Isobutyl chloroformate
Cbz Benzyloxycarbonyl
DCM Dichloromethane
DIPEA Diisopropylethylamine
DMF Dimethylformamide
ESMS electron spray mass spectrum
HATU 2-(1H-7-Azabenzotriazol-1-yl)-1,1,3,3-tetramethyl-uronium-hexafluoro-phosphate
HBTU O-Benzotriazole-N,N,N',N'-tetramethyl-uronium-hexafluoro-phosphate
HOBt 1-hydroxybenzotriazole
HPLC High performance liquid chromatography
NEt$_3$ Triethylamine
NMM N-Methylmorpholine
rt Retention time
Ph Phenyl
PPh$_3$ Triphenylphosphine
THF Tetrahydrofuran
TFA Trifluoroacetic acid
TLC Thin Layer Chromatography

The invention claimed is:
1. A compound of general Formula I:

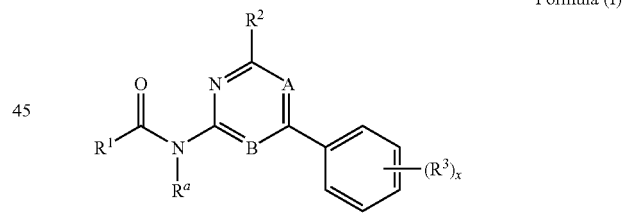

or a pharmaceutically acceptable salt or polymorph thereof, including all tautomers and stereoisomers thereof wherein:
A is N and B is CH, C(C$_{1-4}$alkyl) or C(NH$_2$),
R$^a$ is H or methyl;
R$^1$ is selected from the group consisting of:
C$_{1-8}$ alkyl; —NR$^6$R$^7$, C$_{1-6}$ alkyl-NR$^6$R$^7$, R$^{20}$, —C$_{1-6}$ alkyl-R$^{20}$, —C$_{1-6}$alkyl-C(O)OR$^4$, C$_{1-6}$alkyl-C(O)R$^4$, —NR$^{10}$—(C$_{1-6}$ alkyl)-NR$^6$R$^7$, —NR$^{10}$—(C$_{1-6}$ alkyl)-R$^{20}$, —NR$^{10}$—(C$_{1-6}$ alkyl)-C(O)OR$^4$, —NR$^{10}$R$^{20}$, O—(C$_{1-6}$ alkyl)-NR$^6$R$^7$, —O—(C$_{1-6}$ alkyl)-R$^{20}$, —O—(C$_{1-6}$alkyl)-C(O)OR$^4$, —OR$^{20}$, C$_{1-6}$ alkyl-OR$^{20}$, C$_{1-6}$ alkyl-SR$^{20}$, C$_1$-C$_6$ alkyl-NR$^{10}$R$^{20}$, (C$_{1-6}$ alkyl)-O—(C$_{1-6}$ alkyl)-R$^{20}$, (C$_{1-6}$ alkyl)-S—(C$_{1-6}$ alkyl)-R$^{20}$, C(O)R$^{20}$;
where alkyl moieties may be straight or branched and may be substituted by one or more substituents chosen from halo, methoxy, ethoxy NR$^6$R$^7$ or a nitrogen-containing heterocyclic ring;

$R^4$ represents H or $C_{1-4}$-alkyl;
$R^6$ and $R^7$ are each independently selected from the group consisting of H, $C_{1-6}$alkyl, hydroxy-$C_{2-6}$alkyl-;
$R^{10}$ represents H or $C_{1-4}$alkyl;
$R^{20}$ is selected from aryl, heteroaryl, carbocyclyl and heterocyclyl and may be substituted by one or more substituents selected from:
$C_{1-6}$alkyl, $C_{2-6}$alkenyl, $C_{2-6}$alkynyl any of which may be substituted by one or more halo or OH substituents;
$R^{21}$, —$C_{1-4}$ alkyl-$R^{21}$; $OR^{21}$, $O(C_{1-4}$alkyl$)R^{12}$, $SR^{21}$, $SOR^{21}$, $SO_2R^{21}$, $C(O)R^{21}$, $C_{1-4}$ alkyl-$OR^{21}$,
—$O(C_{2-6}$alkenyl), —$O(C_{2-6}$alkynyl), any of which may be substituted by one or more halo or OH substituents;
$OR^{22}$, $SR^{22}$—$SR^{22}$, —$SO_2R^2$, —$C(O)R^{22}$, —$C(O)OR^{22}$, —$C_{1-4}$alkyl-O—$R^{22}$, —$C_{1-4}$alkyl-O—$C_{1-4}$alkyl-O—$R^2$, $C_{1-4}$alkyl-$C(O)R^{22}$, —$C_{1-4}$alkyl-$C(O)R^2$, $NR^{11}C(O)OR^{22}$, $NR^{11}C(O)R^{22}$, —$SO_2$—$NR^{11}R^{12}$, —$C(O)$—$NR^{11}R^{12}$, —$C_{1-4}$alkyl-$C(O)$—$NR^{11}R^{12}$, —NH—$SO_2R^{15}$, —$N(C_{1-4}$alkyl)-$SO_2R^{15}$, —$(C_{1-4}$alkyl)$NR^{11}R^{12}$, $NR^{11}R^{12}$, —$(C_{1-6}$alkyl)$NR^{11}R^{12}$, nitro, halogen, cyano and hydroxyl; and when $R^{20}$ is carbocyclyl or heterocyclyl or an aromatic group in which an aromatic ring is fused to a non-aromatic ring, $R^{20}$ may additionally be substituted by oxo;
$R^{21}$ is selected from aryl, heteroaryl, carbocyclyl and heterocyclyl and may be substituted by one or more substituents as defined below;
when $R^{21}$ is an aryl or heteroaryl group, it may be substituted by one or more substituents selected from: wherein phenyl is optionally substituted by methyl, methoxy, halogen, halomethyl fluoromethoxy or trifluoromethoxy;
when $R^{21}$ is a carbocyclic or heterocyclic group it may be substituted by one or more substituents selected from methyl, oxo or halogen;
$R^{22}$ is hydrogen or $C_{1-6}$alkyl optionally substituted by halo or hydroxyl;
$R^{11}$ and $R^{12}$ each independently represent a substituent selected from H or $C_{1-4}$alkyl or $R^{11}$ and $R^{12}$ are joined such that together they form a 3-8 membered non-aromatic ring;
$R^{15}$ represents H or $C_{1-4}$alkyl;
$R^2$ represents H or $NH_2$;
each $R^3$ independently represents a substituent selected from the group consisting of $C_{1-6}$alkyl, $C_{2-6}$alkenyl, $C_{2-6}$alkynyl, $C_{1-6}$haloalkyl, $C_{3-8}$cycloalkyl (optionally substituted by methyl, oxo or halogen), phenyl (optionally substituted by methyl, methoxy, halogen, halomethyl fluoromethoxy or trifluoromethoxy), —$C_{1-6}$alkyl-OH, —$C_{1-4}$alkylphenyl (optionally substituted by methyl, methoxy, halogen, halomethyl fluoromethoxy or trifluoromethoxy), $C_{1-6}$alkoxy-, $C_{1-6}$alkenyloxy, $C_{3-4}$alkynyloxy-, $C_{1-6}$haloalkoxy-, —O—$C_{3-8}$cycloalkyl, —O—$C_{1-4}$alkyl-$C_{3-8}$cycloalkyl, —O-phenyl (optionally substituted by methyl, methoxy, halogen, halomethyl fluoromethoxy or trifluoromethoxy), —O—$C_{1-4}$alkylphenyl (optionally substituted by methyl, methoxy, halogen, halomethyl fluoromethoxy or trifluoromethoxy), —$S(C_{1-6}$alkyl), —$SO(C_{1-6}$alkyl), —$SO_2C_{1-6}$alkyl, —$SO_2C_{3-8}$cycloalkyl, —$SO_2$—$NR^{31}R^{32}$, —$C(O)C_{1-6}$alkyl, —$C(O)C_{3-8}$cycloalkyl, —$C(O)OH$, —$C(O)OC_{1-6}$alkyl, —$C(O)$—$NR^{31}R^{32}$, —$C_{1-4}$alkyl-O—$C_{1-4}$alkyl, —$C_{1-4}$alkyl-O—$C_{1-4}$alkyl-OH, —$C_{1-4}$alkyl-O—$C_{1-4}$alkyl-O—$C_{1-4}$alkyl, —$C_{1-4}$alkyl-O—$C_{3-7}$cycloalkyl, —$C_{1-4}$alkyl-$C(O)C_{1-6}$alkyl, —$C_{1-4}$alkyl-$C(O)OH$, —$C_{1-4}$alkyl-$C(O)OC_{1-4}$alkyl, —$C_{1-4}$alkyl-$C(O)$—$NR^{31}R^{32}$, —NH—$SO_2R^{33}$, —$N(C_{1-4}$alkyl)-$SO_2R^3$, —$(C_{1-4}$alkyl)$NR^{31}R^{32}$, —$NR^{31}R^{32}$, —$(C_{1-6}$alkyl)$NR^{31}R^{32}$, nitro, halogen, cyano, hydroxyl;
$R^{31}$ and $R^{32}$ each independently represent a substituent selected from H, $C_{1-4}$alkyl or $C_{1-4}$haloalkyl or $R^{31}$ and $R^{32}$ are joined such that together they form a 3-8 membered non-aromatic ring;
$R^{33}$ represents H or $C_{1-4}$alkyl;
x represents the number of independently selected $R^3$ substituents on the phenyl ring, in the range 1-2.

2. The compound of claim 1 wherein:
A is N and B is CH, $C(C_{1-4}$alkyl) or $C(NH_2)$,
$R^1$ is selected from the group consisting of:
$C_{1-8}$alkyl;
$C_{1-8}$haloalkyl;

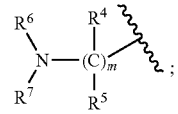

aryl;
heteroaryl;
$C_{3-12}$ carbocyclyl;
heterocyclyl;
—$C_{1-6}$alkyl-aryl;
—$C_{1-6}$alkyl-heteroaryl;
—$C_{1-6}$alkyl-carbocyclyl;
—$C_{1-6}$alkyl-heterocyclyl;
—$C_{1-6}$alkyl-$C(O)OH$;
—$C_{1-6}$alkyl-$C(O)OC_{1-4}$alkyl;

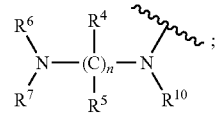

—$NR^{10}C_{1-6}$alkyl-aryl;
—$NR^{10}C_{1-6}$alkyl-heteroaryl;
—$NR^{10}C_{1-6}$alkyl-carbocyclyl;
—$NR^{10}C_{1-6}$alkyl-heterocyclyl;
—$NR^{10}C_{1-6}$alkyl-$C(O)OH$;
—$NR^{10}C_{1-6}$alkyl-$C(O)OC_{1-4}$alkyl;
—$NR^{10}$aryl;
—$NR^{10}$heteroaryl;
—$NR^{10}$carbocyclyl;
—$NR^{10}$heterocyclyl;

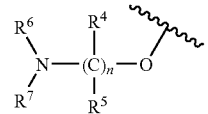

—$OC_{1-6}$alkyl-aryl;
—$OC_{1-6}$alkyl-heteroaryl;
—$OC_{1-6}$alkyl-carbocyclyl;
—$OC_{1-6}$alkyl-heterocyclyl;
—$OC_{1-6}$alkyl-$C(O)OH$;
—$OC_{1-6}$alkyl-$C(O)OC_{1-4}$alkyl;
—Oaryl;
—Oheteroaryl;

—Ocarbocyclyl; and
—Oheterocyclyl;
wherein any of the aforesaid aryl and heteroaryl may optionally be substituted by one or more groups independently selected from the group consisting of $C_{1-6}$alkyl, $C_{2-6}$alkenyl, $C_{2-6}$alkynyl, $C_{4-6}$haloalkyl, $C_{3-8}$cycloalkyl (optionally substituted by methyl, oxo or halogen), phenyl (optionally substituted by methyl, methoxy, halogen, halomethyl fluoromethoxy or trifluoromethoxy)-$C_{1-6}$alkyl-OH, —$C_{1-4}$alkylphenyl (wherein phenyl is optionally substituted by methyl, methoxy, halogen, halomethyl fluoromethoxy or trifluoromethoxy), $C_{1-6}$alkoxy-, $C_{1-6}$alkenyloxy, $C_{3-6}$alkynyloxy-, $C_{1-6}$haloalkoxy-, —O—$C_{3-8}$cycloalkyl, —O—$C_{1-4}$alkyl-$C_{3-8}$cycloalkyl, —O-phenyl (optionally substituted by methyl, methoxy, halogen, halomethyl fluoromethoxy or trifluoromethoxy), —O—$C_{1-4}$alkylphenyl (optionally substituted by methyl, methoxy, halogen, halomethyl fluoromethoxy or trifluoromethoxy), —S($C_{1-6}$alkyl), —SO($C_{1-6}$alkyl), —SO$_2$$C_{1-6}$alkyl, —SO$_2$$C_{3-8}$cycloalkyl, —SO$_2$—NR$^{11}$R$^{12}$, —C(O)$C_{1-6}$alkyl, —C(O)$C_{3-8}$cycloalkyl, —C(O)OH, —C(O)OC$_{11}$ alkyl, —C(O)—NR$^{11}$R$^{12}$, —$C_{1-4}$alkyl-O—$C_{1-4}$alkyl, —$C_{1-4}$alkyl-O—$C_{1-4}$alkyl-OH, —$C_{1-4}$alkyl-O—$C_{1-4}$alkyl-O—$C_{1-4}$alkyl, —$C_{1-4}$alkyl-O—$C_{3-7}$cycloalkyl, —$C_{1-4}$alkyl-C(O)$C_{1-6}$alkyl, —$C_{1-4}$alkyl-C(O)OH, —$C_{1-4}$alkyl-C(O)OC$_{1-4}$alkyl, —$C_{1-4}$alkyl-C(O)—NR$^{11}$R$^{12}$, —NH—SO$_2$R$^{15}$, —N($C_{1-4}$alkyl)-SO$_2$R$^{15}$, —($C_{1-4}$alkyl)NR$^{11}$R$^{12}$, NR$^{11}$R$^{12}$, —($C_{1-6}$alkyl)NR$^{11}$R$^{12}$, nitro, halogen, cyano and hydroxyl; and
wherein any of the aforesaid carbocyclyl and heterocyclyl may optionally be substituted by one or more groups independently selected from the group consisting of $C_{1-6}$alkyl, $C_{2-6}$alkenyl, $C_{2-6}$alkynyl, $C_{1-6}$haloalkyl, $C_{3-8}$cycloalkyl (optionally substituted by methyl, oxo or halogen), phenyl (optionally substituted by methyl, methoxy, halogen, halomethyl fluoromethoxy or trifluoromethoxy), —$C_{1-6}$alkyl-OH, —$C_{1-4}$alkylphenyl (wherein phenyl is optionally substituted by methyl, methoxy, halogen, halomethyl fluoromethoxy or trifluoromethoxy), $C_{1-6}$alkoxy-, $C_{1-6}$alkenyloxy, $C_{3-6}$alkynyloxy-, $C_{1-6}$haloalkoxy-, —O—$C_{3-8}$cycloalkyl, —O—$C_{1-4}$alkyl-$C_{3-8}$cycloalkyl, —O-phenyl (optionally substituted by methyl, methoxy, halogen, halomethyl fluoromethoxy or trifluoromethoxy), —O—$C_{1-4}$alkylphenyl (optionally substituted by methyl, methoxy, halogen, halomethyl fluoromethoxy or trifluoromethoxy), —S($C_{1-6}$alkyl), —SO($C_{1-6}$alkyl), —SO$_2$$C_{1-6}$alkyl, —SO$_2$$C_{3-8}$cycloalkyl, —SO$_2$—NR$^{11}$R$^{12}$, —C(O)$C_{1-6}$alkyl, —C(O)$C_{3-8}$cycloalkyl, —C(O)OH, —C(O)OC$_{1-6}$alkyl, —C(O)—NR$^{11}$R$^{12}$, —$C_{1-4}$alkyl-O—$C_{1-4}$alkyl, —$C_{1-4}$alkyl-O—$C_{1-4}$alkyl-OH, —$C_{1-4}$alkyl-O—$C_{1-4}$alkyl-O—$C_{1-4}$ally-O—$C_{1-4}$alkyl, —$C_{1-4}$alkyl-O—$C_{3-7}$cycloalkyl, —$C_{1-4}$alkyl-C(O)$C_{1-6}$alkyl, —$C_{1-4}$alkyl-C(O)OH, —$C_{1-4}$alkyl-C(O)OC$_{1-4}$alkyl, —$C_{1-4}$alkyl-C(O)—NR$^{11}$R$^{12}$, —NH—SO$_2$R$^{15}$, —N($C_{1-4}$alkyl)-SO$_2$R$^{15}$, —($C_{1-4}$alkyl)NR$^{11}$R$^{12}$, —NR$^{11}$R$^{12}$, —($C_{1-6}$alkyl)NR$^{11}$R$^{12}$, nitro, halogen, cyano, hydroxyl and oxo;
R$^2$ represents H or NH$_2$;
R$^3$ represents a substituent, selected from the group consisting of $C_{1-6}$alkyl, $C_{2-6}$alkenyl, $C_{2-6}$alkynyl, $C_{1-6}$haloalkyl, $C_{3-8}$cycloalkyl (optionally substituted by methyl, oxo or halogen), phenyl (optionally substituted by methyl, methoxy, halogen, halomethyl fluoromethoxy or trifluoromethoxy), —$C_{1-6}$alkyl-OH, —$C_{1-4}$alkylphenyl (optionally substituted by methyl, methoxy, halogen, halomethyl fluoromethoxy or trifluoromethoxy), $C_{1-6}$alkoxy-, $C_{1-16}$alkenyloxy, $C_{1-6}$alkynyloxy-, $C_{1-6}$haloalkoxy-, —O—$C_{3-8}$cycloalkyl, —O—$C_{1-4}$alkyl-$C_{3-8}$cycloalkyl, —O-phenyl (optionally substituted by methyl, methoxy, halogen, halomethyl fluoromethoxy or trifluoromethoxy), —O—$C_{1-4}$alkylphenyl (optionally substituted by methyl, methoxy, halogen, halomethyl fluoromethoxy or trifluoromethoxy), —S($C_{1-6}$alkyl), —SO($C_{1-6}$alkyl), —SO$_2$$C_{1-6}$alkyl, —SO$_2$$C_{3-8}$cycloalkyl, —SO$_2$—NR$^{31}$R$^{32}$, —C(O)$C_{1-6}$alkyl, —C(O)$C_{3-8}$cycloalkyl, —C(O)OH, —C(O)OC$_{1-6}$alkyl, —C(O)—NR$^{31}$R$^{32}$, —$C_{1-4}$alkyl-O—$C_{1-4}$alkyl, —$C_{1-4}$alkyl-O—$C_{1-6}$alkyl-OH, —$C_{1-4}$alkyl-O—$C_{1-4}$alkyl-O—$C_{1-4}$alkyl, —$C_{1-4}$alkyl-O—$C_{3-7}$cycloalkyl, —$C_{1-4}$alkyl-C(O)$C_{1-6}$alkyl, —$C_{1-4}$alkyl-C(O)OH, —$C_{1-4}$alkyl-C(O)OC$_{1-4}$alkyl, —$C_{1-4}$alkyl-C(O)—NR$^{31}$R$^{32}$, —NH—SO$_2$R$^{33}$, —N($C_{1-4}$alkyl)-SO$_2$R$^{33}$, —($C_{1-4}$alkyl)NR$^{31}$R$^{32}$, —NR$^{31}$R$^{32}$, —($C_{1-6}$alkyl)NR$^{31}$R$^{32}$, nitro, halogen, cyano, hydroxyl;

R$^4$ and R$^5$ independently represent H or $C_{1-4}$-alkyl;

R$^6$ and R$^7$ are each independently selected from the group consisting of H, $C_{1-6}$alkyl, hydroxy-$C_{2-6}$alkyl-;

R$^{10}$ represents H or $C_{1-4}$alkyl;

R$^{11}$ and R$^{12}$ each independently represent a substituent selected from H or $C_{1-4}$alkyl or R$^{11}$ and R$^{12}$ are joined such that together they form a 3-8 membered non-aromatic ring;

R$^{15}$ represents H or $C_{1-4}$alkyl;

R$^{31}$ and R$^{32}$ each independently represent a substituent selected from H, $C_{1-4}$alkyl or $C_{1-4}$haloalkyl or R$^{31}$ and R$^{32}$ are joined such that together they form a 3-8 membered non-aromatic ring;

R$^{33}$ represents H or $C_{1-14}$alkyl;

x represents the number of independently selected R$^3$ substituents on the phenyl ring, in the range 1-2;

m represents an integer 1-4; and n represents an integer 2-4.

3. The compound of claim 1 wherein, independently or in any combination:

R$^a$ is hydrogen;

B is CH or $C_{1-4}$ alkyl;

R$^2$ is hydrogen,

R$^3$ is halogen, $C_{1-6}$alkoxy, —O—$C_{1-4}$alkylphenyl (e.g. —O-benzyl) or —O—$C_{1-4}$alkyl-$C_{3-8}$cycloalkyl;

and x is 1 or 2.

4. The compound of claim 3 wherein, independently or in any combination:

B is CH;

R$^2$ is hydrogen; and

R$^3$ is halogen, methoxy, ethoxy, isopropyloxy, benzyloxy or —OCH$_2$cyclopropyl.

5. The compound of claim 3 wherein x is 1 and R$^3$ represents $C_{1-6}$ alkoxy, —O—$C_{1-4}$alkylphenyl or —O—$C_{1-4}$alkyl-$C_{3-8}$cycloalkyl.

6. A compound of general Formula I:

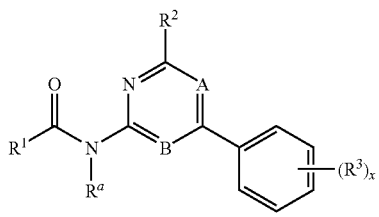

Formula (I)

or a pharmaceutically acceptable salt or polymorph thereof, including all tautomers and stereoisomers thereof wherein:

A is N and B is CH or $C_{1-4}$alkyl, $R^a$ is H;

$R^1$ is selected from the group consisting of:

$C_{1-8}$ alkyl; —$NR^6R^7$, $C_{1-6}$ alkyl-$NR^6R^7$, $R^{20}$, —$C_{1-6}$alkyl-$R^{20}$, —$C_{1-6}$alkyl-C(O)$OR^4$, $C_{1-6}$alkyl-C(O)$R^4$, —$NR^{10}$—($C_{1-6}$ alkyl)-$NR^6R^7$, —$NR^{10}$—($C_{1-6}$alkyl)-$R^{20}$, —$NR^{10}$—($C_{1-6}$alkyl)-C(O)$OR^4$, —$NR^{10}R^{20}$, O—($C_{1-6}$ alkyl)-$NR^6R^7$, —O—($C_{1-6}$alkyl)-$R^{20}$, —O—($C_{1-6}$alkyl)-C(O)$OR^4$, —$OR^{20}$, $C_{1-6}$ alkyl-$OR^{20}$, $C_{1-6}$alkyl-$SR^{20}$, $C_{1-6}$ alkyl-$NR^{10}R^{20}$, ($C_{1-6}$ alkyl)-O—($C_{1-6}$ alkyl)-$R^{20}$, $C_{1-6}$ alkyl)-S—($C_{1-6}$ alkyl)-$R^{20}$, C(O)$R^{20}$;

where alkyl moieties may be straight or branched and may be substituted by one or more substituents chosen from halo, methoxy, ethoxy $NR^6R^7$ or a nitrogen-containing heterocyclic ring;

$R^4$ represents H or $C_{1-4}$-alkyl;

$R^6$ and $R^7$ are each independently selected from the group consisting of H, $C_{1-6}$alkyl, hydroxy-$C_{2-6}$alkyl-;

$R^{10}$ represents H or C-alkyl;

$R^{20}$ is selected from aryl, heteroaryl, carbocyclyl and heterocyclyl and may be substituted by one or more substituents selected from:

$C_{1-6}$alkyl, $C_{2-6}$alkenyl, $C_{2-6}$alkynyl any of which may be substituted by one or more halo or OH substituents;

$R^{21}$, —$C_{1-4}$ alkyl-$R^{21}$; $OR^{21}$, O($C_{1-4}$ alkyl)$R^{21}$, $SR^{21}$, $SOR^{21}$, $SO_2R^{21}$, C(O)$R^{21}$, $C_{1-4}$ alkyl-$OR^{21}$, —O($C_{2-6}$alkenyl), —O($C_{2-6}$alkynyl), any of which may be substituted by one or more halo or OH substituents;

$OR^{22}$—$SR^{22}$—$SOR^{22}$—$SO_2R^{22}$, —C(O)$R^2$, —C(O)$OR^{22}$, —$C_{1-4}$ alkyl-O—$R^2$, —$C_{1-4}$alkyl-O—$C_{1-4}$ alkyl-O—$R^{22}$, $C_{1-4}$alkyl-C(O)$R^{22}$, —$C_{1-4}$alkyl-C(O)$R^{22}$, $NR^{11}$C(O)$OR^{22}$, $NR^{11}$C(O)$R^{22}$, —$SO_2$—$NR^{11}R^{12}$—C(O)—$NR^{11}R^{12}$, —$C_{1-4}$alkyl-C(O)—$NR^{11}R^{12}$—NH—$SO_2R^{15}$, —N($C_{1-4}$alkyl)-$SO_2R^{15}$, —($C_{1-4}$alkyl)$NR^{11}R^{12}$, $NR^{11}NR^{12}$, —($C_{1-6}$alkyl)$NR^{11}R^{12}$, nitro, halogen, cyano and hydroxyl; and when $R^{20}$ is carbocyclyl or heterocyclyl or an aromatic group in which an aromatic ring is fused to a non-aromatic ring, $R^{20}$ may additionally be substituted by oxo;

$R^{21}$ is selected from aryl, heteroaryl, carbocyclyl and heterocyclyl and may be substituted by one or more substituents as defined below;

when $R^{21}$ is an aryl or heteroaryl group, it may be substituted by one or more substituents selected from: wherein phenyl is optionally substituted by methyl, methoxy, halogen, halomethyl fluoromethoxy or trifluoromethoxy;

when $R^{21}$ is a carbocyclic or heterocyclic group it may be substituted by one or more substituents selected from methyl, oxo or halogen;

$R^{22}$ is hydrogen or $C_{1-6}$ alkyl optionally substituted by halo or hydroxyl;

$R^{11}$ and $R^{12}$ each independently represent a substituent selected from H or $C_{1-4}$alkyl or $R^{11}$ and $R^{12}$ are joined such that together they form a 3-8 membered non-aromatic ring;

$R^{15}$ represents H or C-alkyl:

$R^2$ represents H or $C_{1-4}$ alkyl;

x is 2 and one of the $R^3$ groups is methoxy, ethoxy, -isopropyloxy, benzyloxy or (1-cyclopropyl)methoxy, and the other $R^3$ group is halo.

7. The compound of claim 6 wherein $R^1$ is:

—$C_1$-$C_6$ alkyl;

—$R^{20}$;

—C(O)$R^{20}$;

—$C_1$-$C_6$ alkyl-$R^{20}$, wherein the alkyl group is optionally substituted with halo, methoxy, ethoxy, —$NR^6R^7$ or a nitrogen-containing heterocyclyl ring;

—$C_1$-$C_6$ alkyl-$OR^{20}$;

—($C_1$-$C_6$ alkyl)-O—($C_1$-$C_6$ alkyl)-$R^{20}$;

—$C_1$-$C_6$ alkyl-$NR^{10}R^{20}$;

—$C_1$-$C_6$ alkyl-$SR^{20}$;

—$NR^{10}R^{20}$;

—$NR^6R^7$;

—$NR^{10}$—($C_1$-$C_6$ alkyl)-$NR^6R^7$ or

—$NR^{10}$—($C_{1-6}$ alkyl)-C(O)OH.

8. The compound of claim 7, wherein $R^1$ represents $R^{20}$ or $NR^{10}R^{20}$ and $R^{20}$ is a substituted or unsubstituted carbocyclyl, heterocyclyl, aryl or heteroaryl group.

9. The compound of claim 7, wherein $R^1$ is a substituted carbocyclyl group wherein the substitutent is on the same atom which links the carbocyclyl group to the remainder of the molecule.

10. The compound of claim 7 wherein $R^1$ represents C(O)$R^{20}$ and $R^{20}$ is an aryl or heteroaryl group, which may be unsubstituted or substituted, or a heterocyclyl group.

11. The compound of claim 10, wherein $R^{20}$ is phenyl or a 6-membered heterocyclyl group.

12. The compound of claim 7, wherein $R^1$ represents $C_1$-$C_6$ alkyl-$R^{20}$ and $R^{20}$ is an aryl, heteroaryl or heterocyclyl group, any of which may optionally be substituted.

13. The compound of claim 7 wherein $R^1$ represents $C_1$-$C_6$ alkyl-$OR^{20}$, —($C_1$-$C_6$ alkyl)-O—($C_1$-$C_6$ alkyl)-$R^{20}$, $C_1$-$C_6$ alkyl-$NR^{10}R^{20}$ or $C_1$-$C_6$ alkyl-$SR^{20}$ and $R^{20}$ is an aryl or heteroaryl group optionally substituted.

14. The compound of claim 1 wherein $R^{20}$ is a 5- or 6-membered heterocyclyl ring containing one or two heteroatoms independently selected from oxygen, sulfur or nitrogen.

15. The compound of claim 14, wherein $R^{20}$ is a piperidinyl, pyrrolidinyl, tetrahydropyranyl or tetrahydrothiopyranyl ring.

16. The compound of claim wherein the heterocyclyl ring $R^{20}$ is unsubstituted or substituted by one or more substituents independently selected from oxo, —$C_{1-4}$alkyl, —$C_{1-4}$alkyl-O—$C_{1-4}$alkyl, —C(O)$C_{1-4}$alkyl, —C(O)O$C_{1-4}$alkyl, halogen and —$C_{1-4}$alkyl$R^{21}$.

17. The compound of claim 1 wherein $R^{20}$ represents a cycloalkyl group which is unsubstituted or substituted by one or more —$C_{1-8}$alkyl, oxo, —$NH_2$, —NHC(O)$C_{1-4}$alkyl, —NHC(O)O$C_{1-4}$alkyl, —C(O)$NH_2$, optionally substituted aryl or heteroaryl groups.

18. The compound of claim 1 wherein $R^{20}$ represents naphthyl or phenyl, optionally substituted with one or more substituents selected from —NH—SO$_2$C$_{1-4}$alkyl, C$_{1-4}$ alkyl, —O(C$_{1-4}$ alkyl), —NHR$^{12}$, where R$^{12}$ is as defined above, aryl, heteroaryl, nitro and halo.

19. The compound of claim 1 wherein R$^{20}$ represents a monocyclic 5- or 6-membered heteroaryl ring system.

20. The compound of claim 1 wherein R$^{20}$ represents a bicyclic heteroaryl group comprising phenyl fused to unsaturated heterocyclyl ring or a heteroaryl moiety fused to an unsaturated ring optionally containing one or more further heteroatoms.

21. The compound of claim 19 wherein R$^{20}$ is unsubstituted or substituted with one or more substituents selected from C$_{1-4}$alkyl, halo, —(C$_1$-C$_4$ alkyl)-O—R$^{21}$ or R$^{21}$, where R$^{21}$ is unsubstituted phenyl or heteroaryl.

22. The compound of claim 1 wherein R$^1$ is —NR$^6$R$^7$; or —NR$^{10}$—(C$_1$-C$_6$ alkyl)-NR$^6$R$^7$ and R$^6$ and R$^7$ are each independently hydrogen or C$_1$-C$_4$ alkyl.

23. The compound of claim 1 wherein R$^1$ is —C$_1$-C$_6$ alkyl-NR$^{10}$R$^{20}$; —NR$^{10}$R$^{20}$; —NR$^{10}$—(C$_1$-C$_6$ alkyl)-NR$^6$R$^7$ or —NR$^{10}$—(C$_{1-6}$alkyl)-C(O)OH; and R$^{10}$ is hydrogen or methyl.

24. A pharmaceutical composition comprising the compound of claim 1 as active ingredient together with a pharmaceutically acceptable excipient or diluent.

25. A process for the preparation of the compound of formula (I) of claim 1, or a protected derivative thereof, the process comprising (a) converting one compound of formula (I) to another compound of formula (I); or (b) reacting a compound of formula A

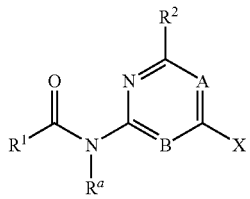

Formula A wherein A, B, R$^1$, R$^a$ and R$^2$ are as defined in general formula (I) and X is a suitable substituent for a cross coupling reaction, or a protected derivative thereof with a compound of formula B

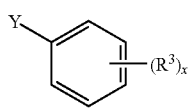

Formula B wherein R$^3$ and x are as defined in general formula (I) and Y is a suitable substituent for a cross coupling reaction, or a protected derivative thereof;

wherein X and Y represent suitable substituents for a cross-coupling reaction and are chosen to react with one another; or (c) reacting a compound of formula E

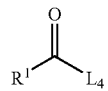

Formula E or a protected derivative thereof wherein R$^1$ is as defined for general formula (I) and L$_4$ represents a suitable leaving group;

with a compound of formula F

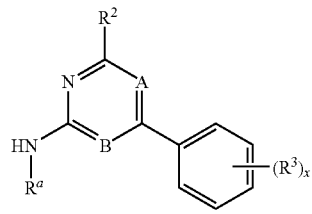

Formula F wherein R$^a$, R$^2$, R$^3$, x, A and B are as defined in general formula (I), or a protected derivative thereof; or (d) preparing a compound of formula (I), in which R$^1$ is a moiety which connects to the main carbonyl of formula (I) via a nitrogen atom by a process comprising reaction of the corresponding amine or a protected derivative thereof with a compound of formula G

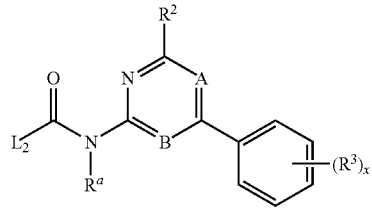

Formula G wherein R$^a$, R$^2$, R$^3$, x, A and B are as defined for general formula (I) and L$_2$ represents a suitable leaving group;

or a protected derivative thereof;

(e) reacting a compound of formula F as defined above or a protected derivative thereof with a compound of formula J

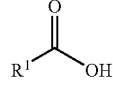

Formula J wherein R$^1$ is as defined for general formula (I);

in the presence of a suitable coupling agent; or (f) reacting a compound of formula K

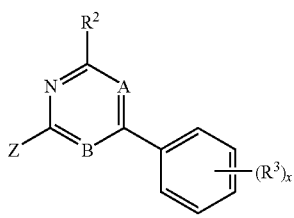

Formula K wherein $R^2$, $R^3$, x, A and B are as defined for general formula (I) and Z represents a suitable substituent for a cross-coupling reaction
with a compound of formula L

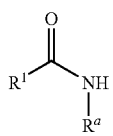

Formula L wherein $R^1$ and $R^a$ are as defined for general formula (I); under suitable conditions for coupling reaction; or (g) preparing a compound of formula (I), in which $R^1$ is —$NHR^{20}$ or —NH—($C_{1-6}$ alkyl)-$R^{20}$ by reacting a compound of formula F as defined above with a compound of formula:

$R^{20}$N=C=O or $R^{20}$—($C_{1-6}$ alkyl)-N=C=O wherein $R^2$ is as defined for general formula (I), for example $R^{20}$ represents a heteroaryl group such as pyridine.

26. The compound of claim 1 which is piperidine-4-carboxylic acid [6-(2-methoxy-phenyl)-pyrimidin-4-yl]-amide.

27. The composition of claim 24 wherein the active ingredient is piperidine-4-carboxylic acid [6-(2-methoxy-phenyl)-pyrimidin-4-yl]-amide.

28. The compound as defined in claim 1 and selected from the group consisting of Example compounds 1 to 156:

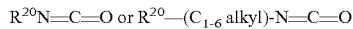

1

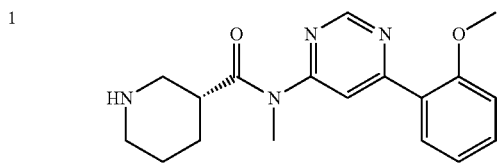

2  TFA

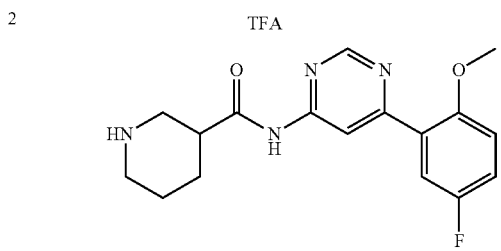

3  TFA

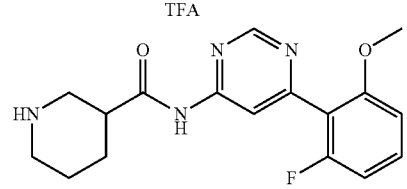 [SMILES: COc1cccc(F)c1-c1cc(NC(=O)C2CCCNC2)ncn1]

4  TFA

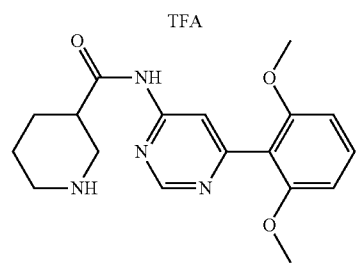 [SMILES: COc1cccc(OC)c1-c1cc(NC(=O)C2CCCNC2)ncn1]

5  enantiomeric pure

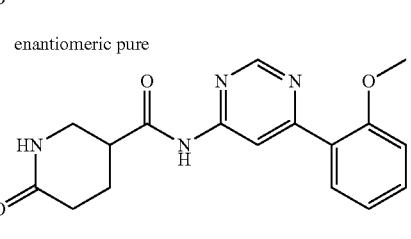

6  enantiomeric pure

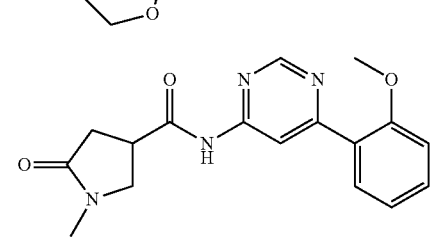

7

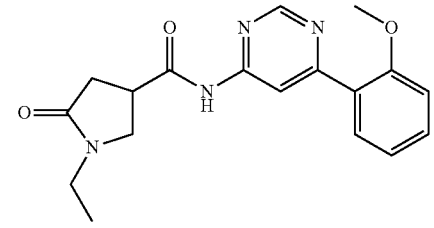 [SMILES: CCN1CC(C(=O)Nc2cc(-c3ccccc3OC)ncn2)CC1=O]

8

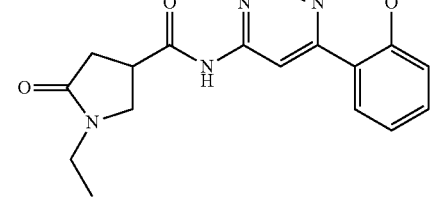

9

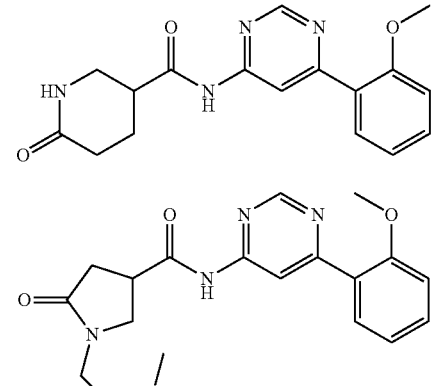

| 203 -continued | 204 -continued |
|---|---|
| 10 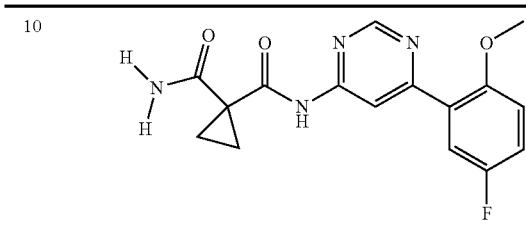 | 17 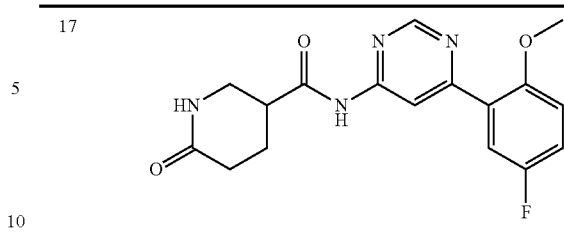 |
| 11 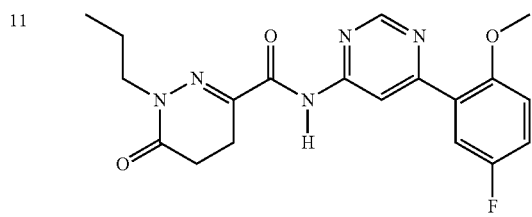 | 18 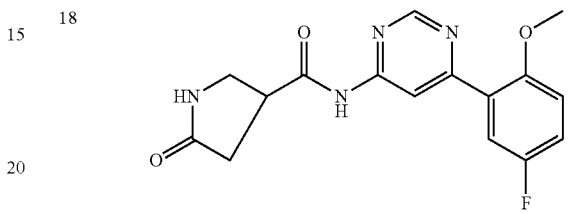 |
| 12 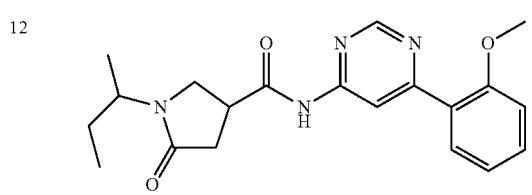 | 19 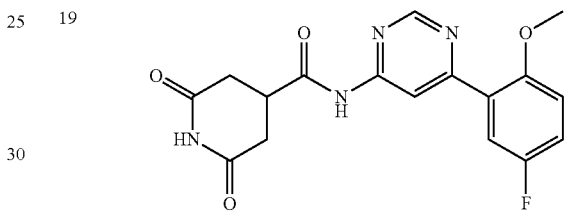 |
| 13 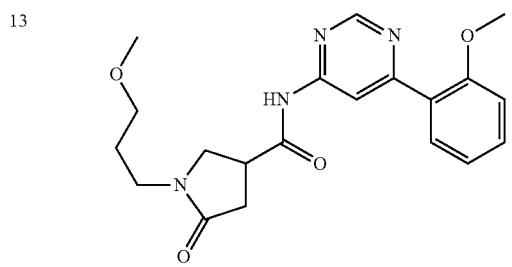 | 20 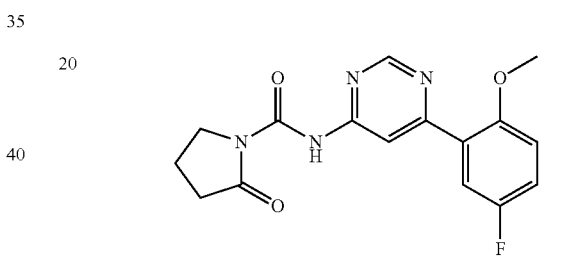 |
| 14 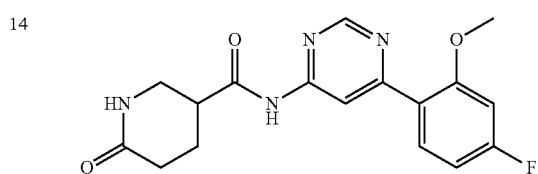 | 21 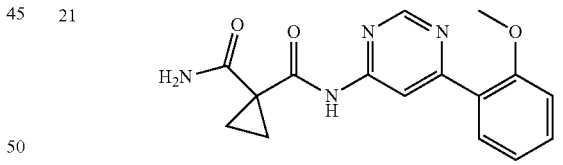 |
| 15 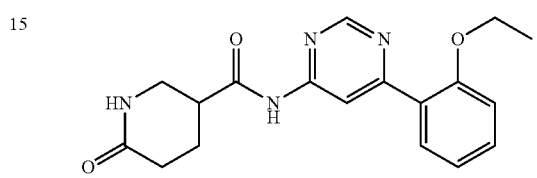 | 22 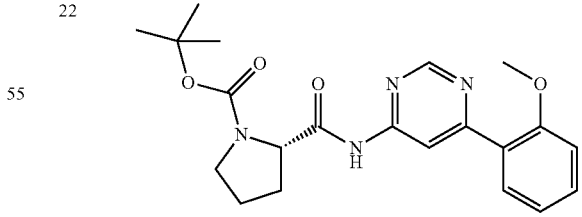 |
| 16 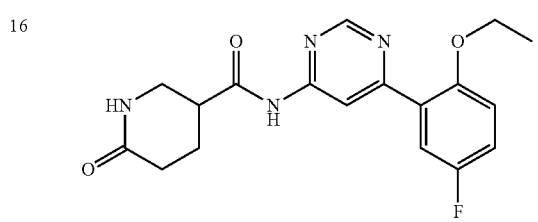 | 23 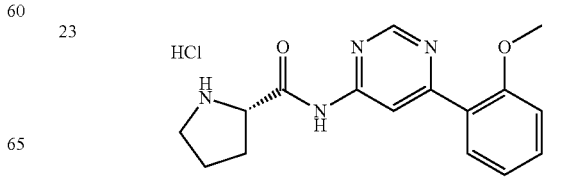 |

| 24 | 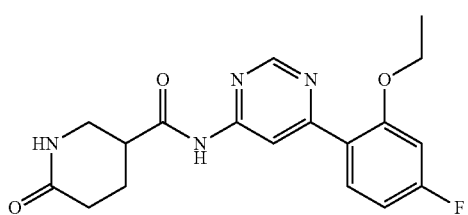 | 31 | 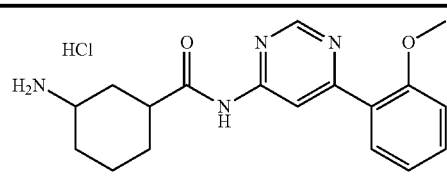 |
| 25 | 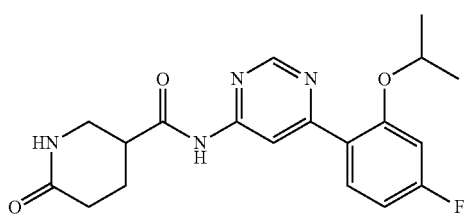 [SMILES: CC(C)Oc1cc(F)ccc1-c1cc(NC(=O)C2CCC(=O)NC2)ncn1] | 32 | 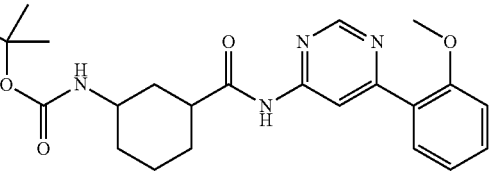 |
| 26 | 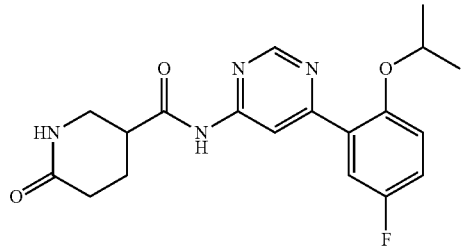 [SMILES: CC(C)Oc1ccc(F)cc1-c1cc(NC(=O)C2CCC(=O)NC2)ncn1] | 33 | 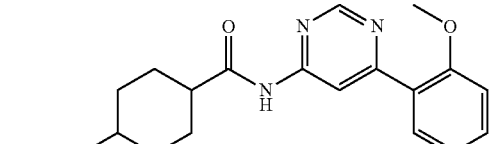 |
| 27 | 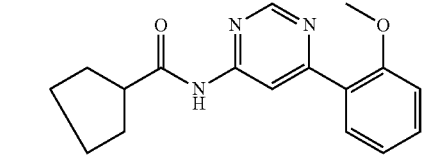 [SMILES: COc1ccccc1-c1cc(NC(=O)C2CCCC2)ncn1] | 34 | 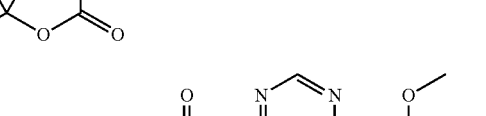 |
| 28 | 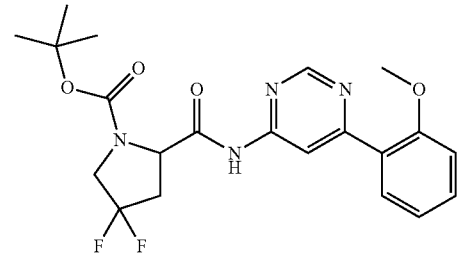 [SMILES: COc1ccccc1-c1cc(NC(=O)C2CC(F)(F)CN2C(=O)OC(C)(C)C)ncn1] | 35 | 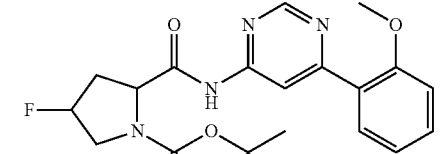 |
| 29 | 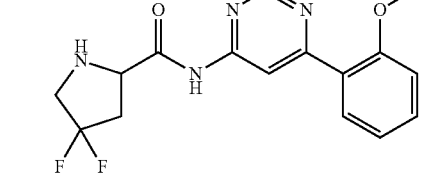 | 36 | 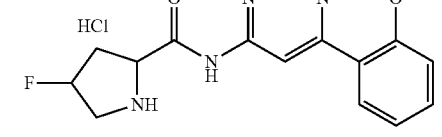 |
| 30 | 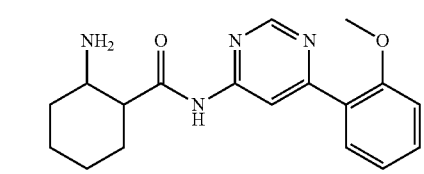 | 37 | 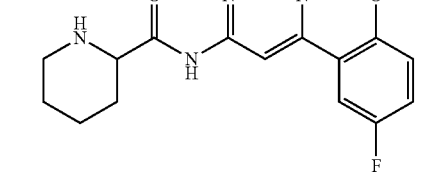 |
|    |                      | 38 | 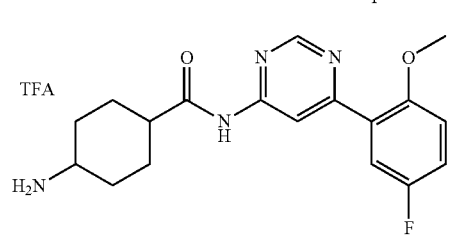 |

| # | | # | |
|---|---|---|---|
| 39 | 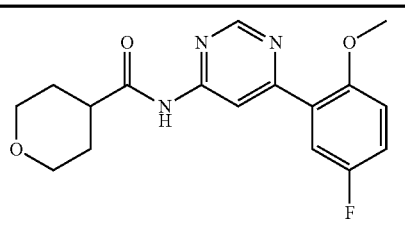 | 47 | 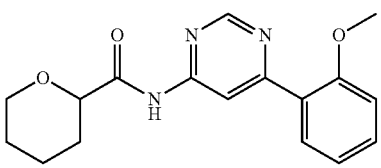 |
| 40 | 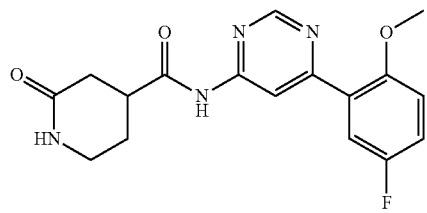 [SMILES: COc1ccc(F)cc1-c1cc(NC(=O)C2CCNC(=O)C2)ncn1] | 48 | 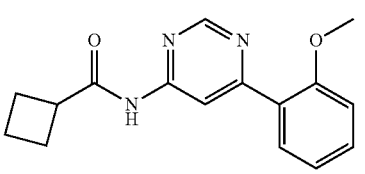 |
| 41 | 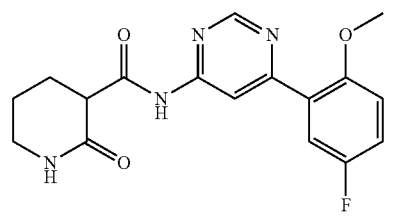 [SMILES: COc1ccc(F)cc1-c1cc(NC(=O)C2CCCNC2=O)ncn1] | 49 | 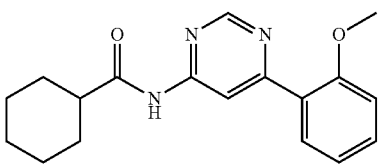 |
| 42 | 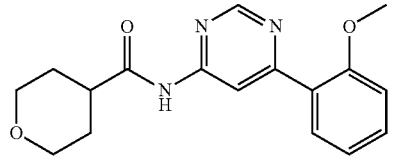 [SMILES: COc1ccccc1-c1cc(NC(=O)C2CCOCC2)ncn1] | 50 | 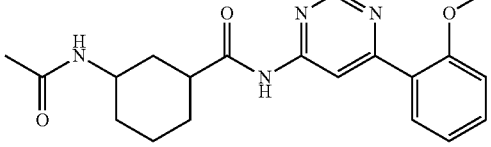 |
| 43 | 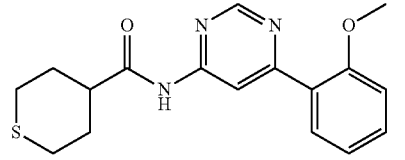 [SMILES: COc1ccccc1-c1cc(NC(=O)C2CCSCC2)ncn1] | 51 | 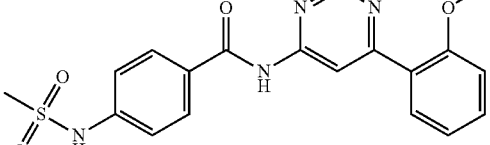 |
| 44 | 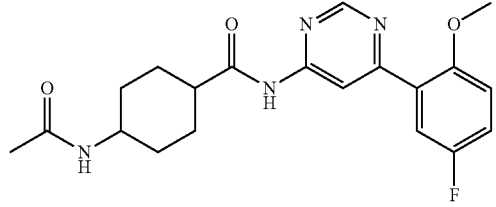 [SMILES: COc1ccc(F)cc1-c1cc(NC(=O)C2CCC(NC(C)=O)CC2)ncn1] | 52 | 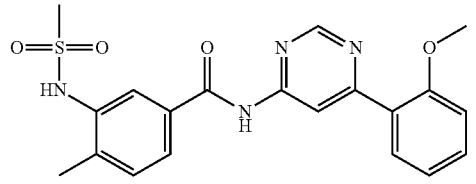 |
| 45 | 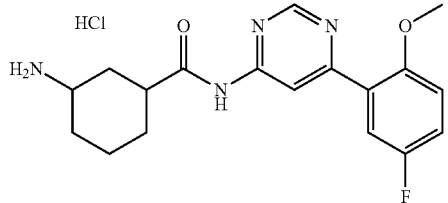 [SMILES: COc1ccc(F)cc1-c1cc(NC(=O)C2CCCC(N)C2)ncn1 ; Cl] | 53 | 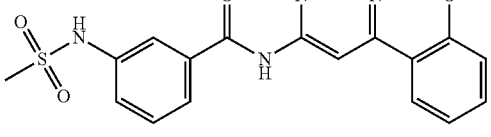 |
|  |  | 54 | 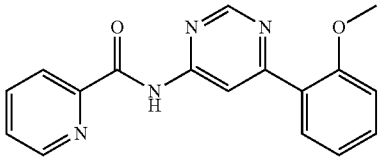 |
| 46 | 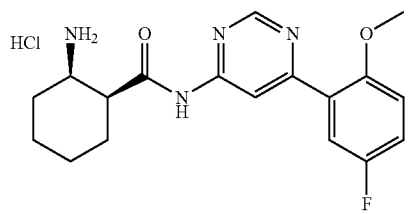 [SMILES: Cl ; COc1ccc(F)cc1-c1cc(NC(=O)[C@H]2CCCC[C@H]2N)ncn1] | 55 | 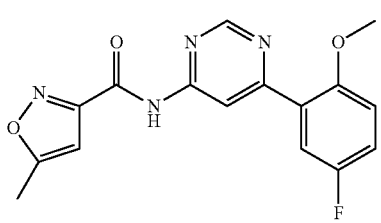 [SMILES: COc1ccc(F)cc1-c1cc(NC(=O)c2cc(C)on2)ncn1] |

| | | | |
|---|---|---|---|
| 56 | 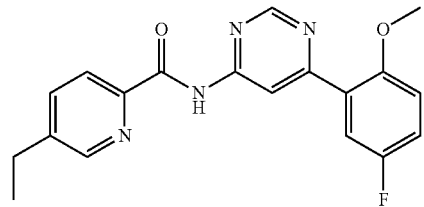 [SMILES: CCc1ccc(C(=O)Nc2cc(-c3cc(F)ccc3OC)ncn2)nc1] | 63 | 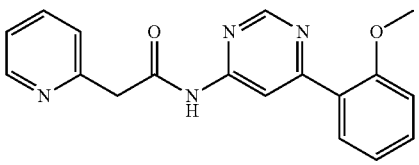 |
| 57 | 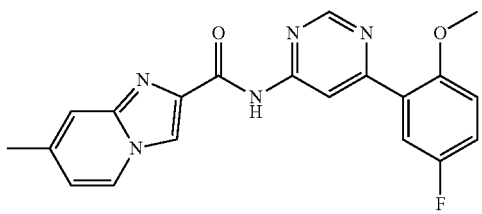 | 64 | 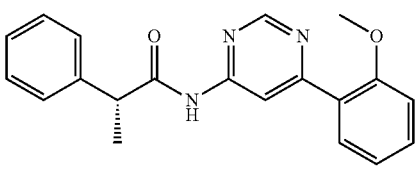 |
| 58 | 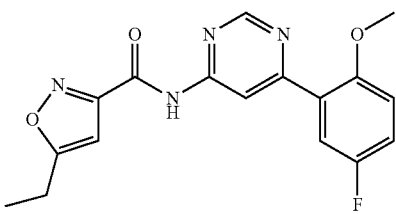 [SMILES: CCc1cc(C(=O)Nc2cc(-c3cc(F)ccc3OC)ncn2)no1] | 65 | 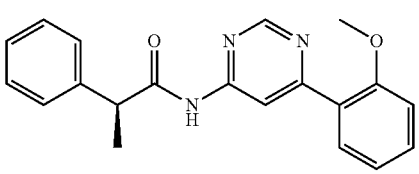 |
| 59 | 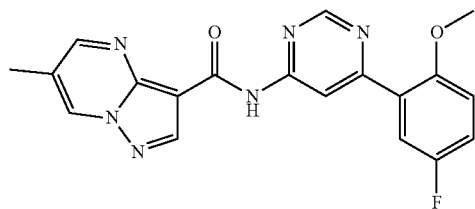 | 66 | 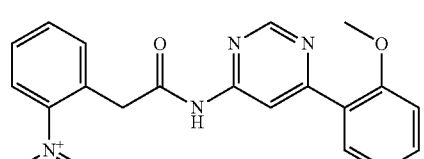 |
| 60 | 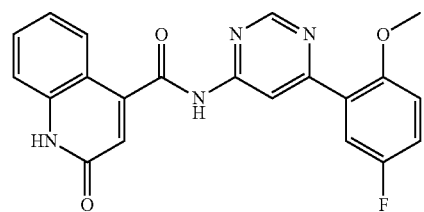 [SMILES: COc1ccc(F)cc1-c1cc(NC(=O)c2cc(=O)[nH]c3ccccc23)ncn1] | 67 | 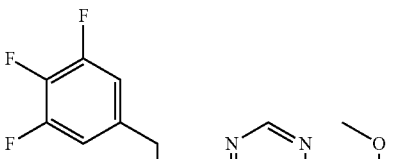 |
| 61 | 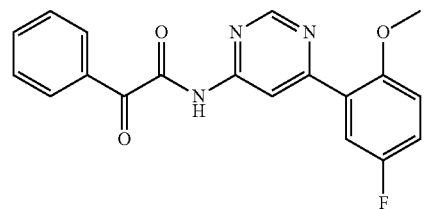 [SMILES: COc1ccc(F)cc1-c1cc(NC(=O)C(=O)c2ccccc2)ncn1] | 68 | 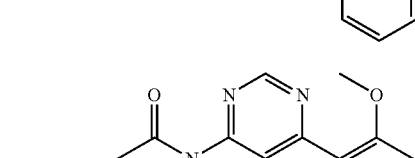 |
| 62 | 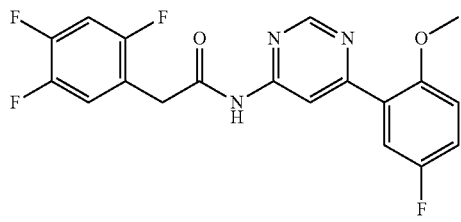 [SMILES: COc1ccc(F)cc1-c1cc(NC(=O)Cc2cc(F)c(F)cc2F)ncn1] | 69 | 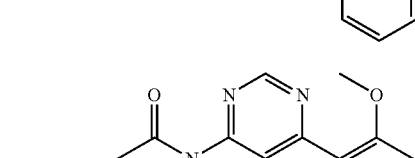 |

| 211 -continued | 212 -continued |
|---|---|
| 70 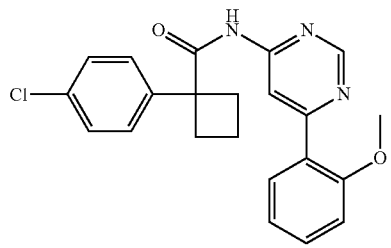 [SMILES: COc1ccccc1-c1cc(NC(=O)C2(c3ccc(Cl)cc3)CCC2)ncn1] | 77 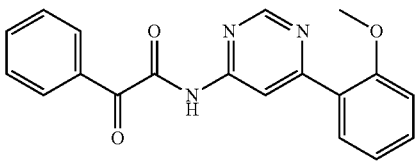 |
| 71 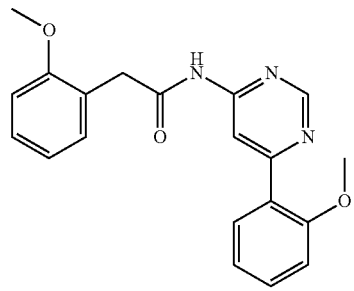 [SMILES: COc1ccccc1CC(=O)Nc1cc(-c2ccccc2OC)ncn1] | 78 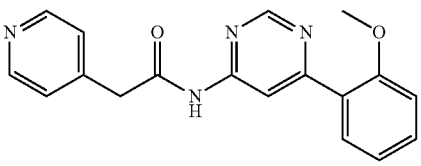 |
| | 79 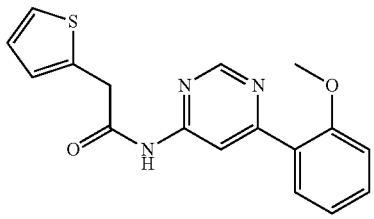 |
| 72  | 80 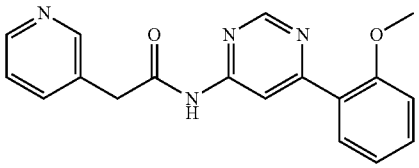 |
| 73 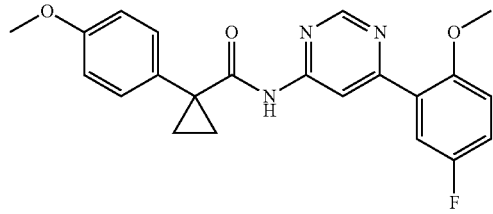 | 81 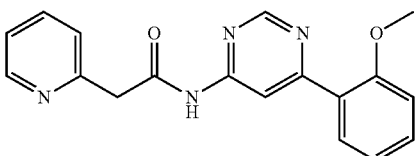 |
| 74 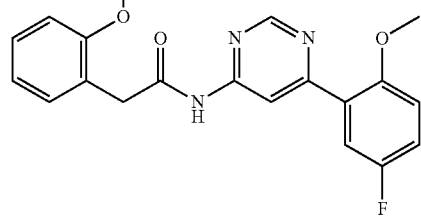 | 82 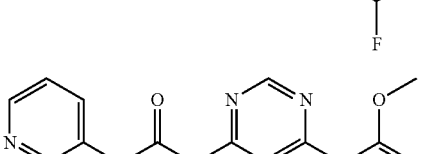 |
| | 83 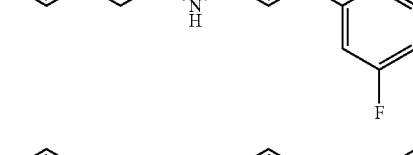 |
| 75 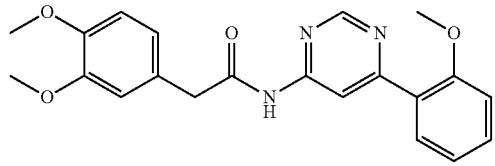 [SMILES: COc1ccc(CC(=O)Nc2cc(-c3ccccc3OC)ncn2)cc1OC] | |
| 76 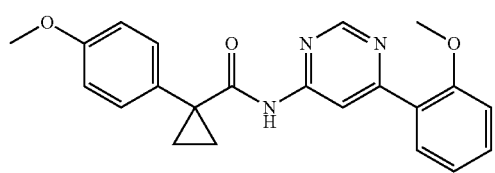 [SMILES: COc1ccc(C2(C(=O)Nc3cc(-c4ccccc4OC)ncn3)CC2)cc1] | 84 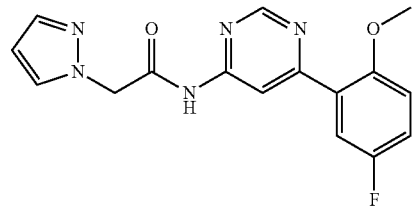 [SMILES: COc1ccc(F)cc1-c1cc(NC(=O)Cn2cccn2)ncn1] |

| 213 -continued | 214 -continued |
|---|---|
| 85 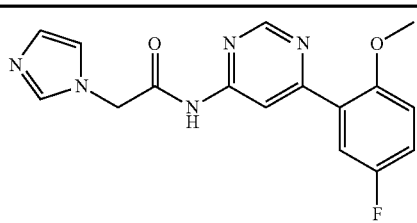 | 92 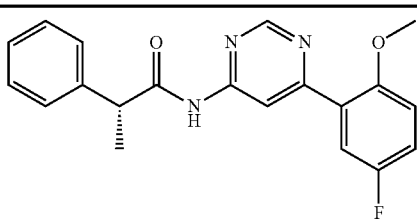 |
| 86 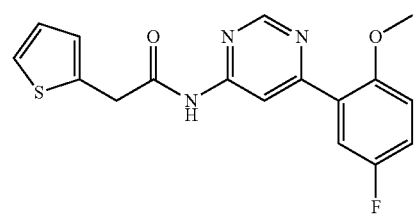 [SMILES: COc1ccc(F)cc1-c1cc(NC(=O)Cc2cccs2)ncn1] | 93 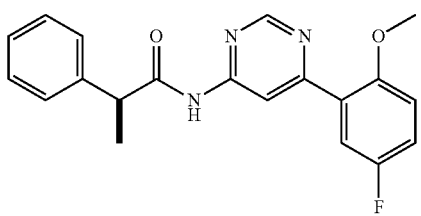 |
| 87 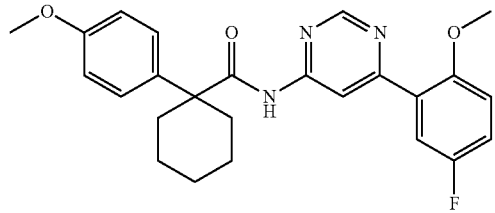 | 94 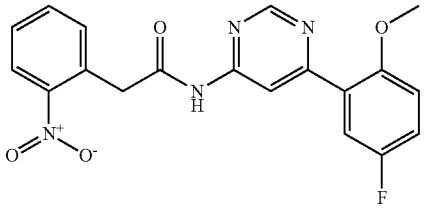 |
| 88 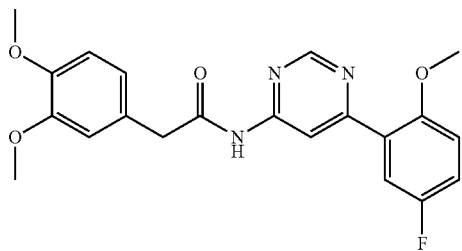 [SMILES: COc1ccc(CC(=O)Nc2cc(-c3cc(F)ccc3OC)ncn2)cc1OC] | 95 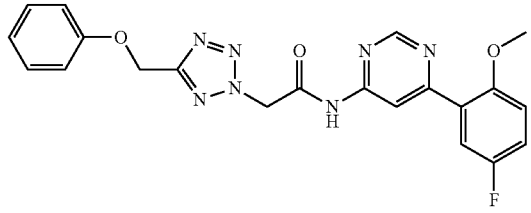 |
| 89 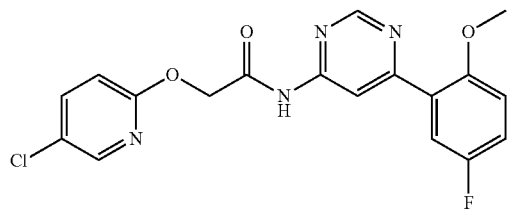 [SMILES: COc1ccc(F)cc1-c1cc(NC(=O)COc2ccc(Cl)cn2)ncn1] | 96 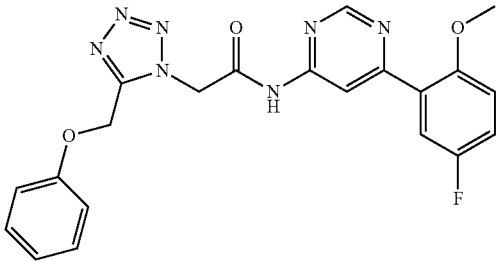 |
| 90 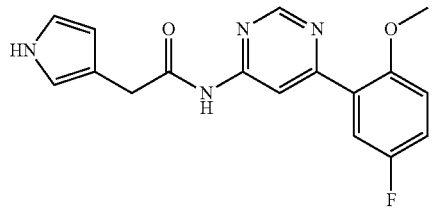 | 97 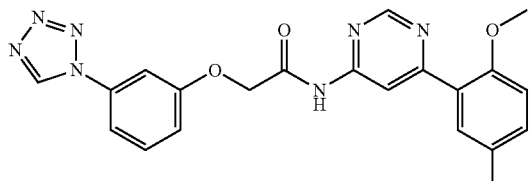 |
| 91 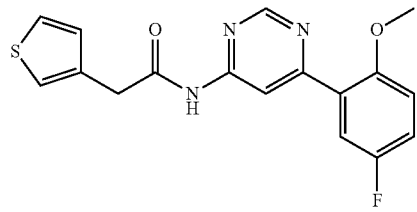 [SMILES: COc1ccc(F)cc1-c1cc(NC(=O)Cc2ccsc2)ncn1] | 98 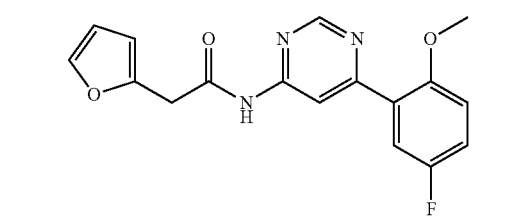 |

215
-continued
| | |
|---|---|
| 99 | 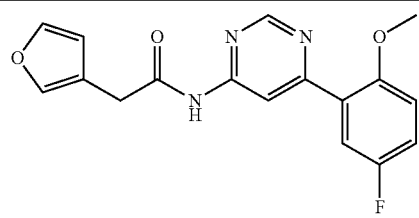 |
| 100 | 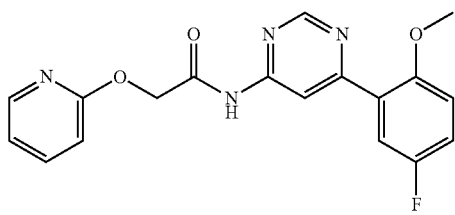 [SMILES: COc1ccc(F)cc1-c1cc(NC(=O)COc2ccccn2)ncn1] |
| 101 | 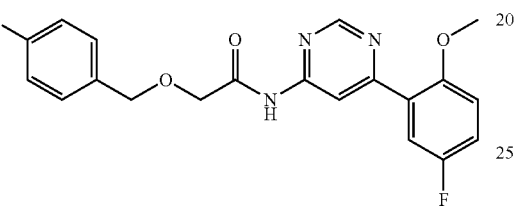 |
| 102 | 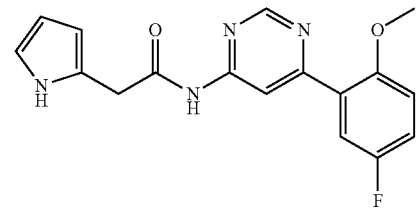 |
| 103 | 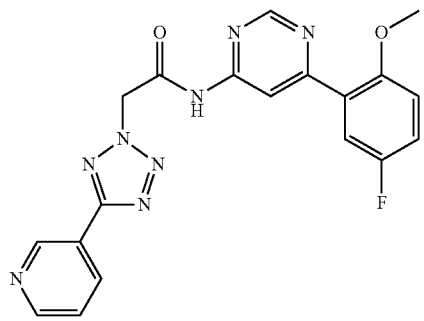 [SMILES: COc1ccc(F)cc1-c1cc(NC(=O)Cn2nnc(-c3cccnc3)n2)ncn1] |
| 104 | 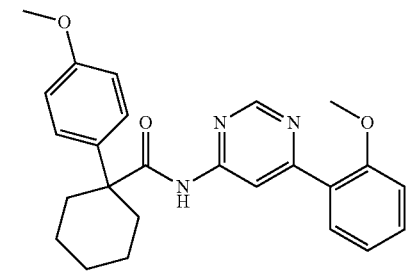 [SMILES: COc1ccc(C2(C(=O)Nc3cc(-c4ccccc4OC)ncn3)CCCCC2)cc1] |
| 105 | 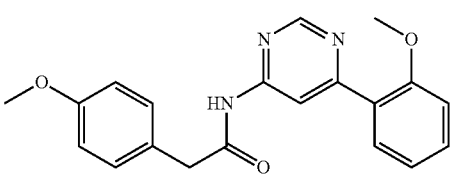 [SMILES: COc1ccc(CC(=O)Nc2cc(-c3ccccc3OC)ncn2)cc1] |
216
-continued
| | |
|---|---|
| 106 | 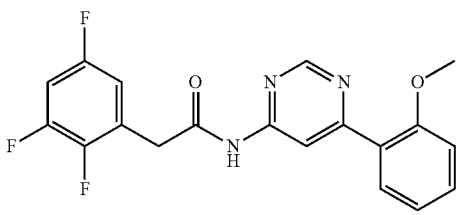 [SMILES: COc1ccccc1-c1cc(NC(=O)Cc2cc(F)cc(F)c2F)ncn1] |
| 107 | 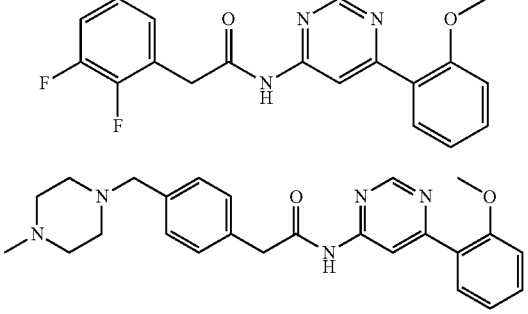 |
| 108 | 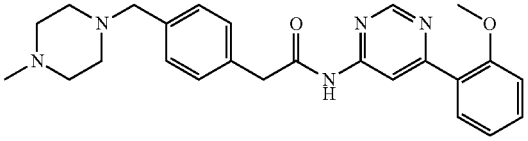 [SMILES: COc1ccccc1-c1cc(NC(=O)Cc2ccc(CN3CCN(C)CC3)cc2)ncn1] |
| 109 | 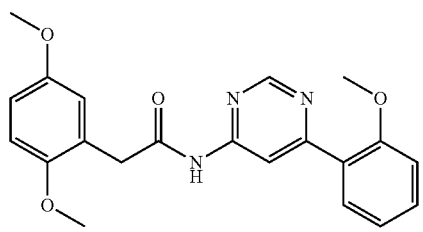 [SMILES: COc1ccc(OC)c(CC(=O)Nc2cc(-c3ccccc3OC)ncn2)c1] |
| 110 | 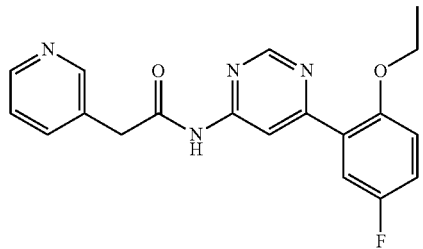 [SMILES: CCOc1ccc(F)cc1-c1cc(NC(=O)Cc2cccnc2)ncn1] |
| 111 | 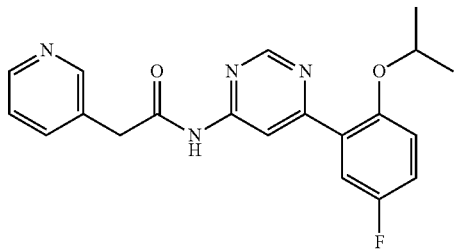 [SMILES: CC(C)Oc1ccc(F)cc1-c1cc(NC(=O)Cc2cccnc2)ncn1] |
| 112 | 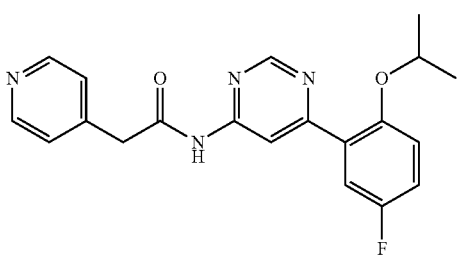 [SMILES: CC(C)Oc1ccc(F)cc1-c1cc(NC(=O)Cc2ccncc2)ncn1] |

| | |
|---|---|
| 113 | 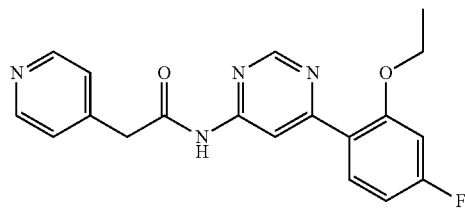 [SMILES: CCOc1cc(F)ccc1-c1cc(NC(=O)Cc2ccncc2)ncn1] |
| 114 | 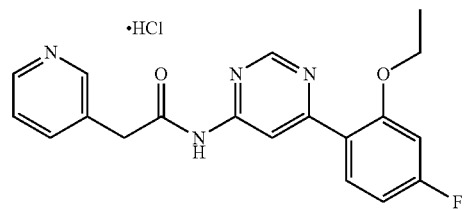 [SMILES: CCOc1cc(F)ccc1-c1cc(NC(=O)Cc2cccnc2)ncn1 ; Cl] ·HCl |
| 115 | 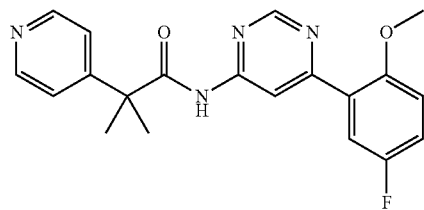 [SMILES: COc1ccc(F)cc1-c1cc(NC(=O)C(C)(C)c2ccncc2)ncn1] |
| 116 | 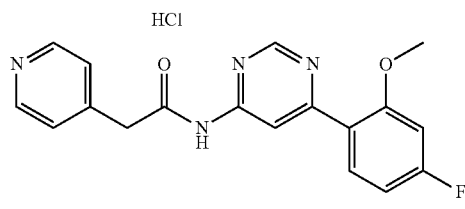 [SMILES: Cl ; COc1cc(F)ccc1-c1cc(NC(=O)Cc2ccncc2)ncn1] HCl |
| 117 | 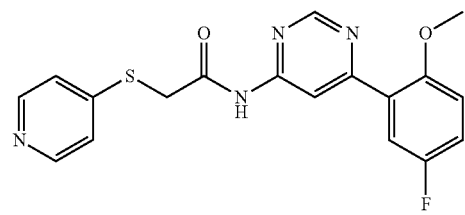 [SMILES: COc1ccc(F)cc1-c1cc(NC(=O)CSc2ccncc2)ncn1] |
| 118 | 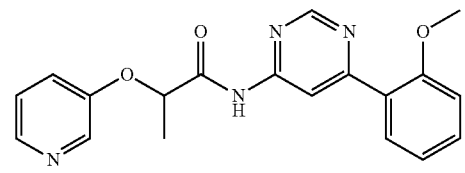 [SMILES: COc1ccccc1-c1cc(NC(=O)C(C)Oc2cccnc2)ncn1] |
| 119 | 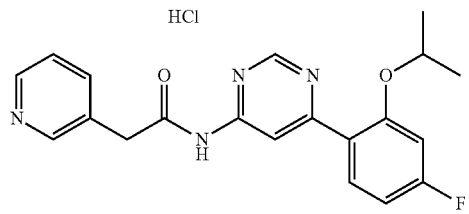 [SMILES: CC(C)Oc1cc(F)ccc1-c1cc(NC(=O)Cc2cccnc2)ncn1 ; Cl] HCl |
| 120 | 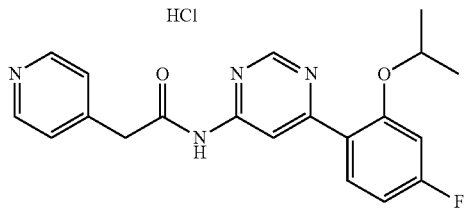 [SMILES: CC(C)Oc1cc(F)ccc1-c1cc(NC(=O)Cc2ccncc2)ncn1 ; Cl] HCl |
| 121 | 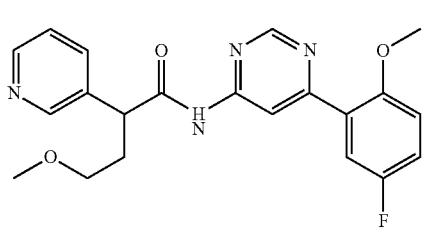 [SMILES: COCCC(C(=O)Nc1cc(-c2cc(F)ccc2OC)ncn1)c1cccnc1] |
| 122 | 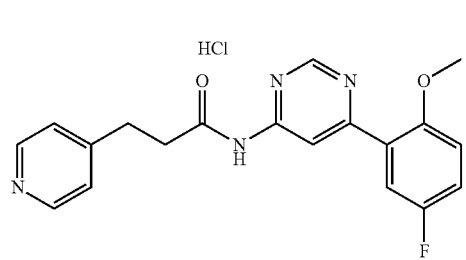 [SMILES: Cl ; COc1ccc(F)cc1-c1cc(NC(=O)CCc2ccncc2)ncn1] HCl |
| 123 | 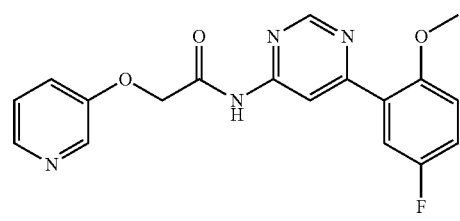 [SMILES: COc1ccc(F)cc1-c1cc(NC(=O)COc2cccnc2)ncn1] |
| 124 | 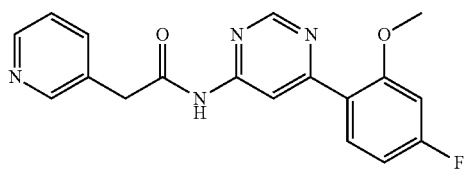 [SMILES: COc1cc(F)ccc1-c1cc(NC(=O)Cc2cccnc2)ncn1] |
| 125 | 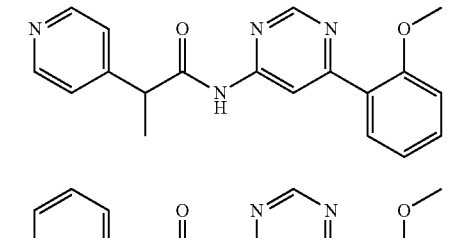 |
| 126 | 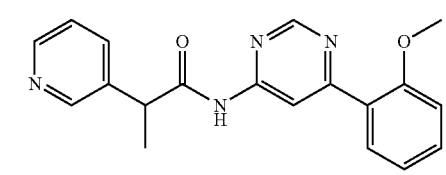 [SMILES: COc1ccccc1-c1cc(NC(=O)C(C)c2cccnc2)ncn1] |

| | |
|---|---|
| 127 | 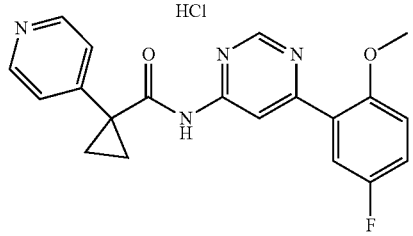 [SMILES: Cl ; COc1ccc(F)cc1-c1cc(NC(=O)C2(c3ccncc3)CC2)ncn1] |
| 128 | 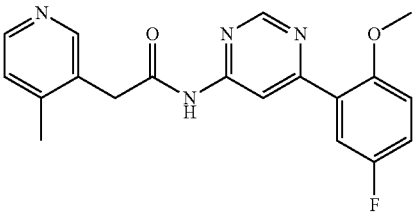 [SMILES: COc1ccc(F)cc1-c1cc(NC(=O)Cc2cnccc2C)ncn1] |
| 129 | 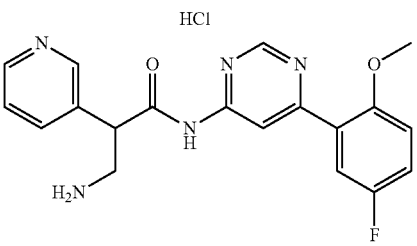 [SMILES: Cl ; COc1ccc(F)cc1-c1cc(NC(=O)C(CN)c2cccnc2)ncn1] |
| 130 | 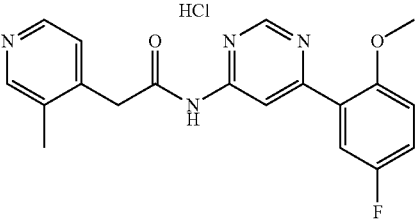 [SMILES: Cl ; COc1ccc(F)cc1-c1cc(NC(=O)Cc2ccncc2C)ncn1] |
| 131 | 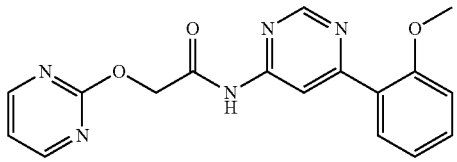 [SMILES: COc1ccccc1-c1cc(NC(=O)COc2ncccn2)ncn1] |
| 132 | 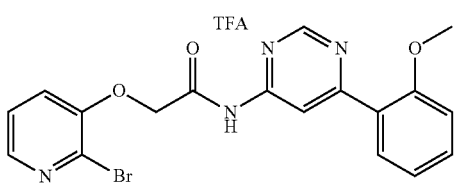 [SMILES: COc1ccccc1-c1cc(NC(=O)COc2cccnc2Br)ncn1] |
| 133 | 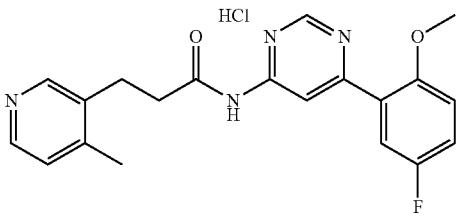 [SMILES: COc1ccc(F)cc1-c1cc(NC(=O)CCc2cnccc2C)ncn1 ; Cl] |
| 134 | 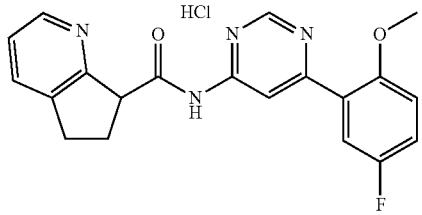 [SMILES: Cl ; COc1ccc(F)cc1-c1cc(NC(=O)C2CCc3cccnc32)ncn1] |
| 135 | 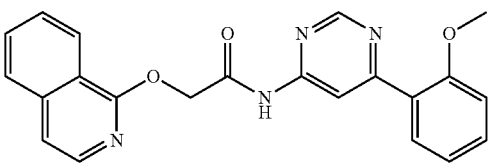 [SMILES: COc1ccccc1-c1cc(NC(=O)COc2nccc3ccccc23)ncn1] |
| 136 | 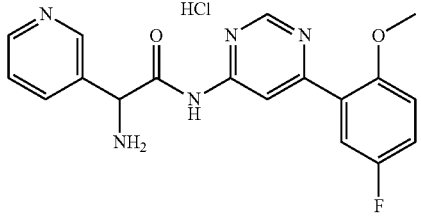 [SMILES: Cl ; COc1ccc(F)cc1-c1cc(NC(=O)C(N)c2cccnc2)ncn1] |
| 137 | 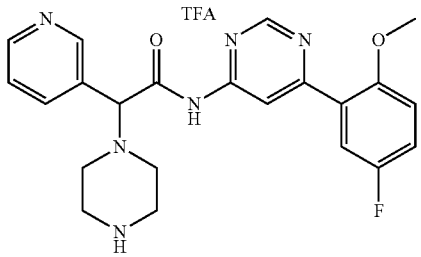 [SMILES: COc1ccc(F)cc1-c1cc(NC(=O)C(c2cccnc2)N2CCNCC2)ncn1 ; "TFA"] |
| 138 | 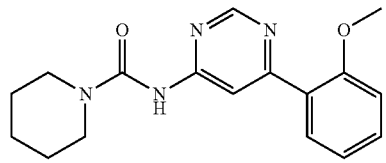 [SMILES: COc1ccccc1-c1cc(NC(=O)N2CCCCC2)ncn1] |
| 139 | 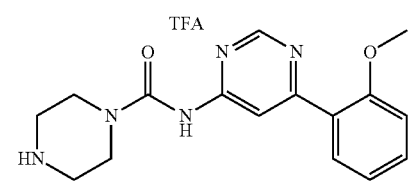 [SMILES: COc1ccccc1-c1cc(NC(=O)N2CCNCC2)ncn1] |
| 140 | 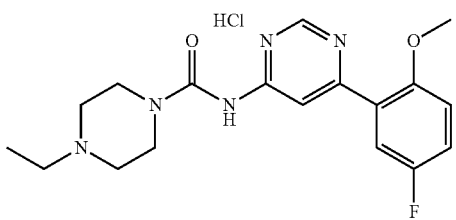 [SMILES: CCN1CCN(C(=O)Nc2cc(-c3cc(F)ccc3OC)ncn2)CC1 ; Cl] |

| 141 | 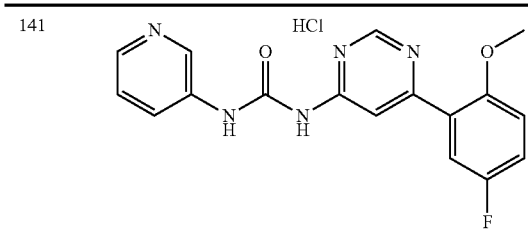 |
|---|---|
| 142 | 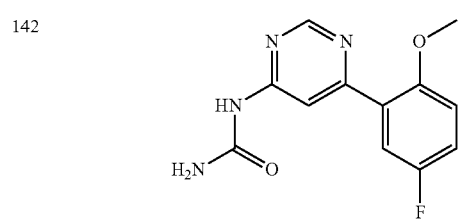 |
| 143 | 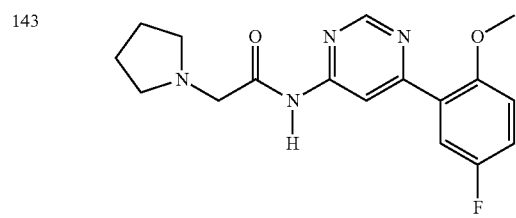 |
| 144 | 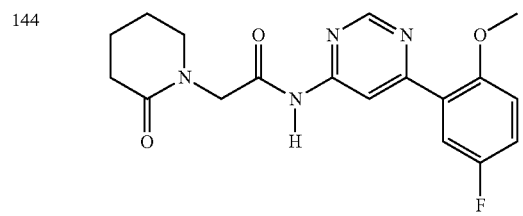 |
| 145 | 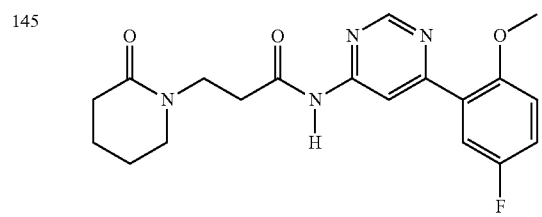 |
| 146 | 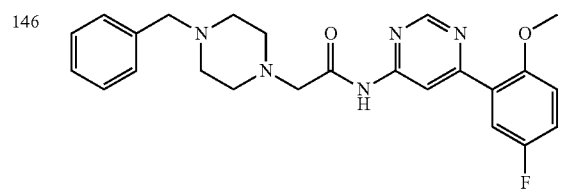 |
| 147 | 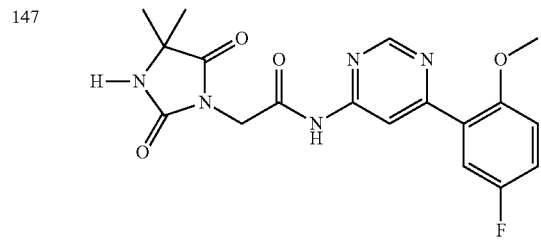 |
| 148 | 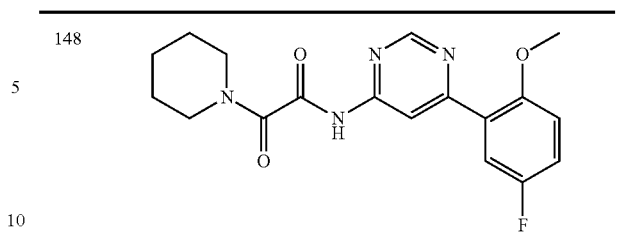 |
|---|---|
| 149 | 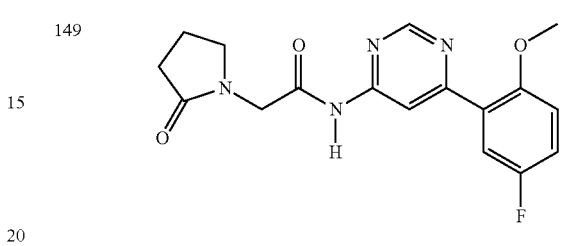 |
| 150 | 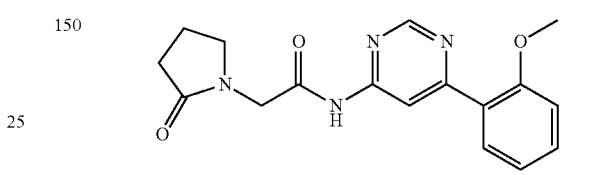 |
| 151 | 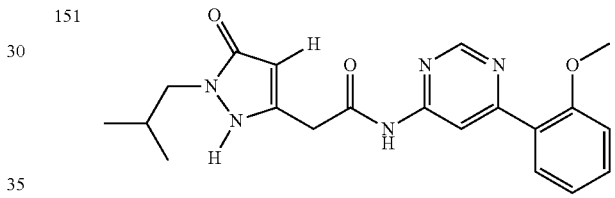 |
| 152 | 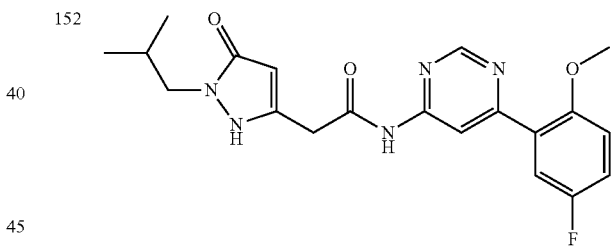 |
| 153 | 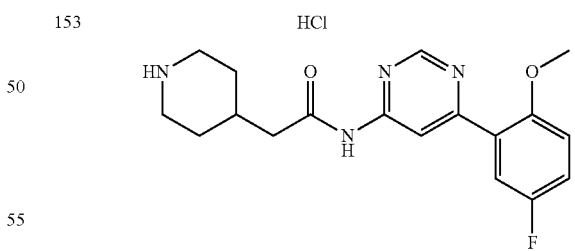 |
| 154 | 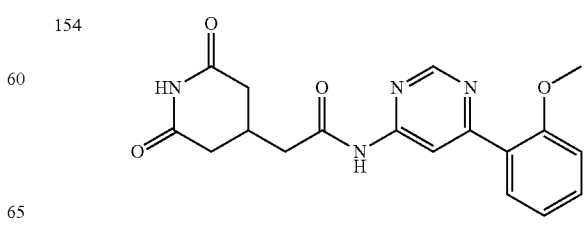 |

155 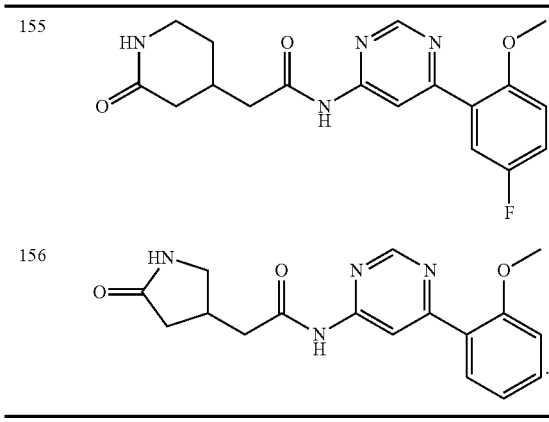

156

29. The compound as defined in claim 1 and selected from the group consisting of Example compounds 1A to 21A and 23A to 34A:

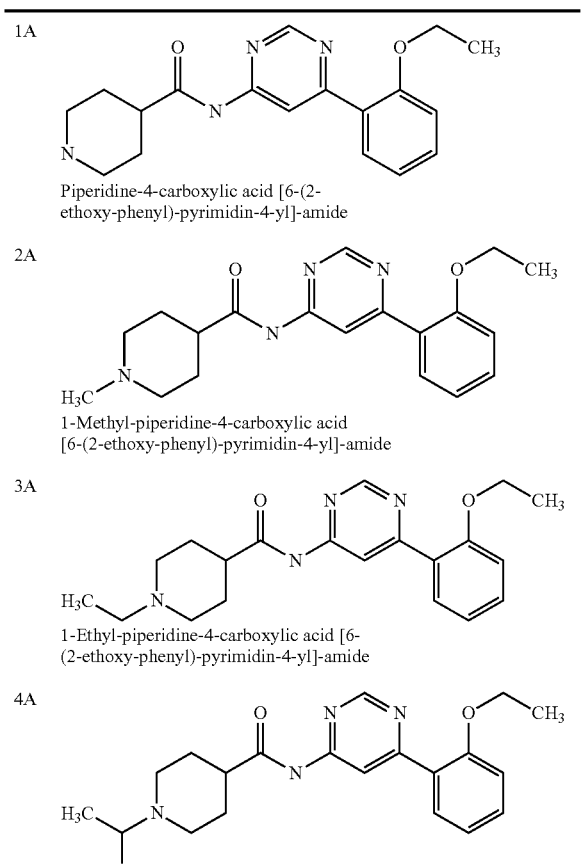

1A Piperidine-4-carboxylic acid [6-(2-ethoxy-phenyl)-pyrimidin-4-yl]-amide 2A 1-Methyl-piperidine-4-carboxylic acid [6-(2-ethoxy-phenyl)-pyrimidin-4-yl]-amide 3A 1-Ethyl-piperidine-4-carboxylic acid [6-(2-ethoxy-phenyl)-pyrimidin-4-yl]-amide 4A 1-Isopropyl-piperidine-4-carboxylic acid [6-(2-ethoxy-phenyl)-pyrimidin-4-yl]-amide 5A 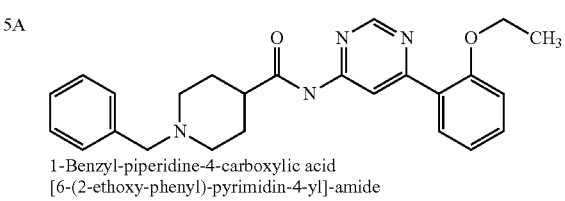
1-Benzyl-piperidine-4-carboxylic acid [6-(2-ethoxy-phenyl)-pyrimidin-4-yl]-amide 6A 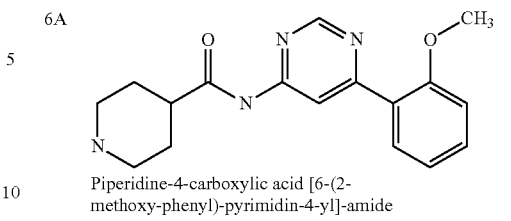
Piperidine-4-carboxylic acid [6-(2-methoxy-phenyl)-pyrimidin-4-yl]-amide 7A 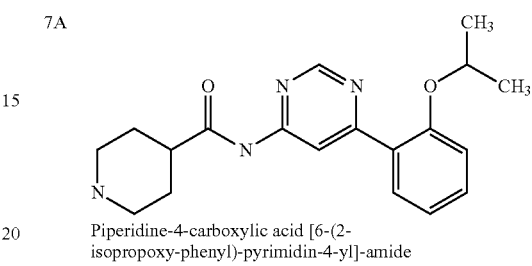
Piperidine-4-carboxylic acid [6-(2-isopropoxy-phenyl)-pyrimidin-4-yl]-amide 8A 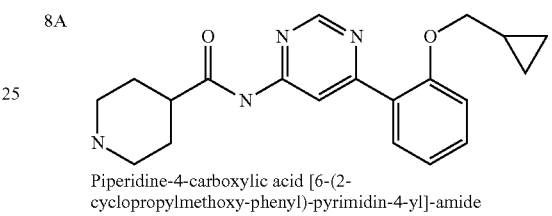
Piperidine-4-carboxylic acid [6-(2-cyclopropylmethoxy-phenyl)-pyrimidin-4-yl]-amide 9A 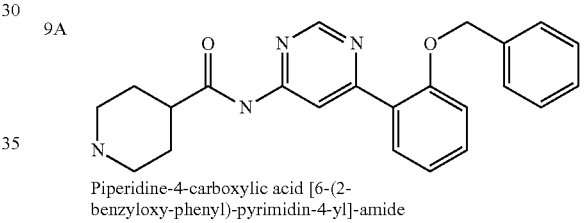
Piperidine-4-carboxylic acid [6-(2-benzyloxy-phenyl)-pyrimidin-4-yl]-amide 10A 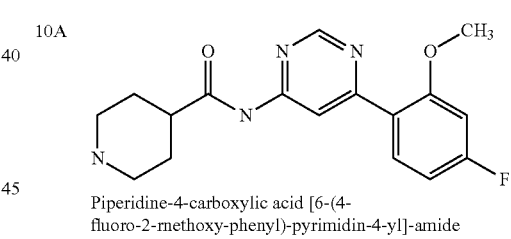
Piperidine-4-carboxylic acid [6-(4-fluoro-2-methoxy-phenyl)-pyrimidin-4-yl]-amide 11A 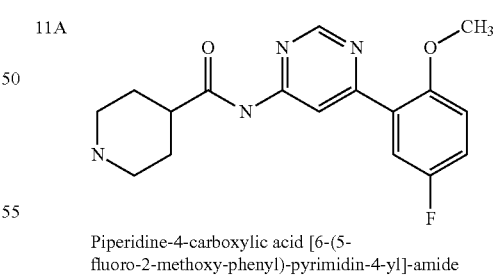
Piperidine-4-carboxylic acid [6-(5-fluoro-2-methoxy-phenyl)-pyrimidin-4-yl]-amide 12A 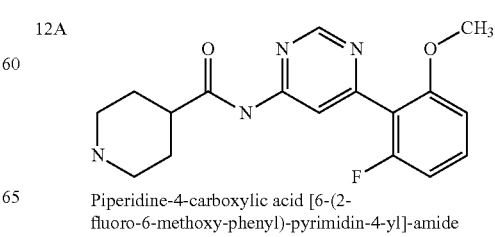
Piperidine-4-carboxylic acid [6-(2-fluoro-6-methoxy-phenyl)-pyrimidin-4-yl]-amide 13A 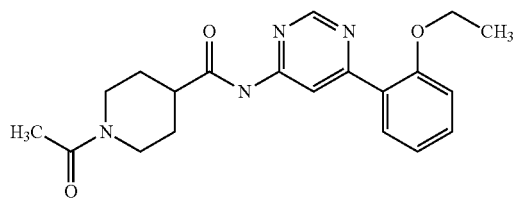 [SMILES: CCOc1ccccc1-c1cc(NC(=O)C2CCN(C(C)=O)CC2)ncn1]
1-Acetyl-piperidine-4-carboxylic acid [6-(2-ethoxy-phenyl)-pyrimidin-4-yl]-amide 14A 
Piperidine-4-carboxylic acid [6-(2-methoxy-phenyl)-pyrimidin-4-yl]-amide hydrochloride 15A 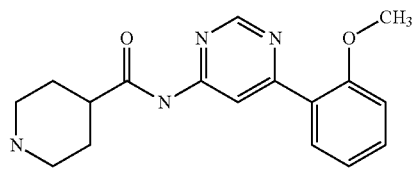 [SMILES: COc1ccccc1-c1cc(NC(=O)C2CCNCC2)ncn1]
Piperidine-4-carboxylic acid [6-(2-methoxy-phenyl)-pyrimidin-4-yl]-amide mesylate 16A 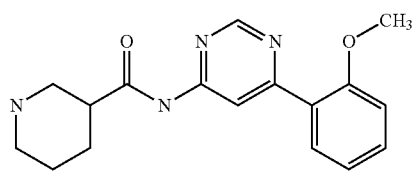 [SMILES: COc1ccccc1-c1cc(NC(=O)C2CCCNC2)ncn1]
Piperidine-3-carboxylic acid [6-(2-methoxy-phenyl)-pyrimidin-4-yl]-amide 17A 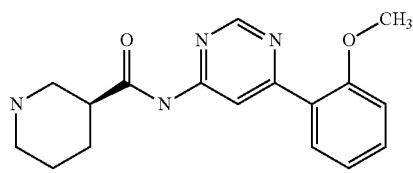 [SMILES: COc1ccccc1-c1cc(NC(=O)[C@H]2CCCNC2)ncn1]
(S)-Piperidine-3-carboxylic acid [6-(2-methoxy-phenyl)-pyrimidin-4-yl]-amide 18A 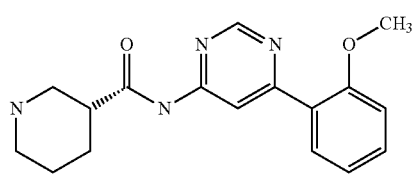
(R)-Piperidine-3-carboxylic acid [6-(2-methoxy-phenyl)-pyrimidin-4-yl]-amide 19A 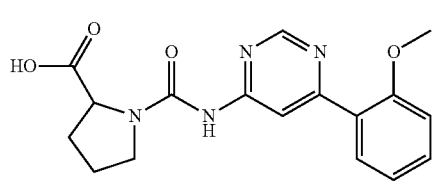 [SMILES: COc1ccccc1-c1cc(NC(=O)N2CCCC2C(=O)O)ncn1]
1-[6-(2-Methoxy-phenyl)-pyrimidin-4-ylcarbamoyl]-pyrrolidine-2-carboxylic acid 20A 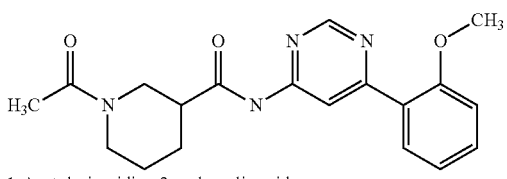
1-Acetyl-piperidine-3-carboxylic acid [6-(2-methoxy-phenyl)-pyrimidin-4-yl]-amide 21A 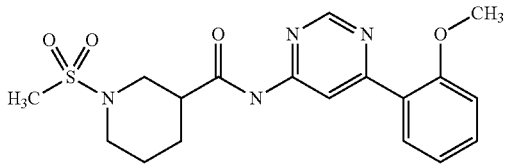
1-Methanesulfonyl-piperidine-3-carboxylic acid [6-(2-methoxy-phenyl)-pyrimidin-4-yl]-amide 23A 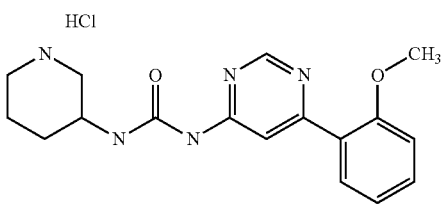 [SMILES: Cl ; COc1ccccc1-c1cc(NC(=O)NC2CCCNC2)ncn1]
1-[6-(2-Methoxy-phenyl)-pyrimidin-4-yl]-3-piperidin-3-yl-urea hydrochloride 24A 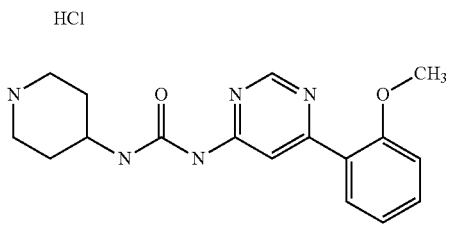 [SMILES: Cl ; COc1ccccc1-c1cc(NC(=O)NC2CCNCC2)ncn1]
1-[6-(2-Methoxy-phenyl)-pyrimidin-4-yl]-3-piperidin-4-yl-urea hydrochloride 25A 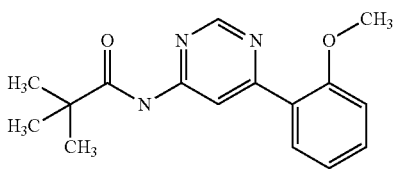 [SMILES: COc1ccccc1-c1cc(NC(=O)C(C)(C)C)ncn1]
N-[6-(2-Methoxy-phenyl)-pyrimidin-4-yl]-2,2-dimethyl-propionamide 26A 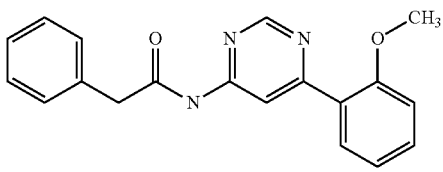 [SMILES: COc1ccccc1-c1cc(NC(=O)Cc2ccccc2)ncn1]
N-[6-(2-Methoxy-phenyl)-pyrimidin-4-yl]-2-phenyl-acetamide 27A 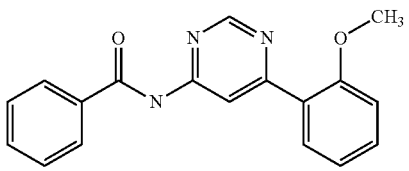 [SMILES: COc1ccccc1-c1cc(NC(=O)c2ccccc2)ncn1]
N-[6-(2-Methoxy-phenyl)-pyrimidin-4-yl]-benzamide

| | |
|---|---|
| 28A | 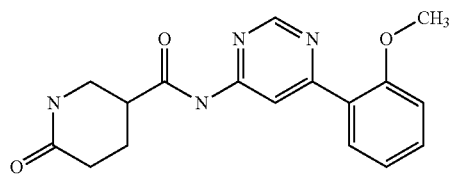 [SMILES: COc1ccccc1-c1cc(NC(=O)C2CCC(=O)NC2)ncn1]
6-Oxo-piperidine-3-carboxylic acid [6-(2-methoxy-phenyl)-pyrimidin-4-yl]-amide |
| 29A | 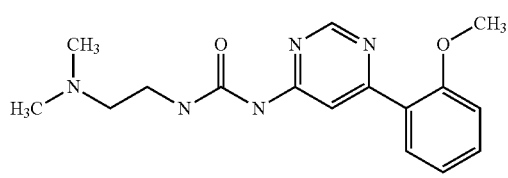
1-(2-Dimethylamino-ethyl)-3-[6-(2-methoxy-phenyl)-pyrimidin-4-yl]-urea |
| 30A | 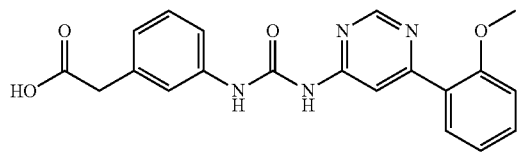 [SMILES: COc1ccccc1-c1cc(NC(=O)Nc2cccc(CC(=O)O)c2)ncn1]
(3-{3-[6-(2-methoxy-phenyl)-pyrimidin-4-yl]-ureido}-phenyl)-acetic acid |
| 31A | 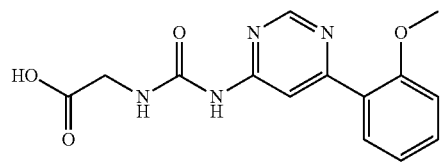 [SMILES: COc1ccccc1-c1cc(NC(=O)NCC(=O)O)ncn1]
{3-[6-(2-methoxy-phenyl)-pyrimidin-4-yl]-ureido}-acetic acid |
| 32A | 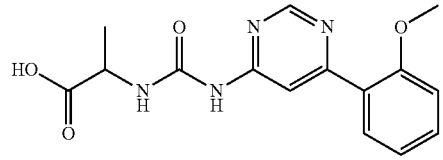 [SMILES: COc1ccccc1-c1cc(NC(=O)NC(C)C(=O)O)ncn1]
2-{3-[6-(2-methoxy-phenyl)-pyrimidin-4-yl]-ureido}-propionic acid |
| 33A | 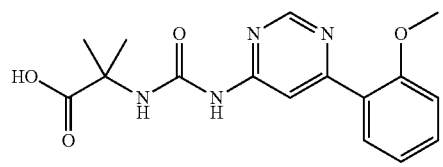 [SMILES: COc1ccccc1-c1cc(NC(=O)NC(C)(C)C(=O)O)ncn1]
2-{3-[6-(2-methoxy-phenyl)-pyrimidin-4-yl]-ureido}-2-methyl-propionic acid |
| 34A | 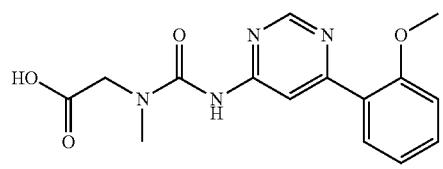 [SMILES: COc1ccccc1-c1cc(NC(=O)N(C)CC(=O)O)ncn1]
{3-[6-(2-methoxy-phenyl)-pyrimidin-4-yl]-1-methyl-ureido}-acetic acid. |

\* \* \* \* \*

UNITED STATES PATENT AND TRADEMARK OFFICE
CERTIFICATE OF CORRECTION

| | |
|---|---|
| PATENT NO. | : 8,716,296 B2 |
| APPLICATION NO. | : 12/226286 |
| DATED | : May 6, 2014 |
| INVENTOR(S) | : Hans Allgeier et al. |

It is certified that error appears in the above-identified patent and that said Letters Patent is hereby corrected as shown below:

In the Specification

Column 10,
Line 44, "-($C_{1-8}$alkyl)" should be -- -($C_{1-6}$alkyl) --.

Column 14,
Line 7, "$C_{1-4}$alkyl" (second occurrence) should be -- $C_{1-4}$haloalkyl --.

Column 16,
Line 44, "$R^7$" should be -- $R^6$ and $R^7$ --.

Column 76,
Line 11, "-$NR^{10}R^{10}$" should be -- -$NR^{10}R^{20}$ --.

Column 103,
Line 57, "it 13.5 min" should be -- rt 13.5 min --.

Column 104,
Line 22, "CH-N" should be -- C$\underline{H}$-N --.
Line 38, "$CH_2$-Ch-$CH_2$" should be -- $CH_2$-C$\underline{H_2}$-$CH_2$ --.

Column 114,
Line 54, "it 19.4" should be -- rt 19.4 --.

Column 125,
Line 1, "it 14.3 min" should be -- rt 14.3 min --.
Line 14, "it 16.5 min" should be -- rt 16.5 min --.

Signed and Sealed this
Twenty-seventh Day of January, 2015

Michelle K. Lee
*Deputy Director of the United States Patent and Trademark Office*

Column 127,
Line 12, "it 10.35" should be -- rt 10.35 --.
Line 33, "it 10.1 min" should be -- rt 10.1 min --.

Column 141,
Line 9, "-NCHCH$_3$" should be -- -NCH$_2$CH$_3$ --.

Column 142,
Line 5, "-OCH$_2$CH$_3$" should be -- -OCH$_2$CH$_3$ --.
Line 7, "-OCH$_2$CH$_3$" should be -- -OCH$_2$CH$_3$ --.
Line 67, "OCH$_2$CH$_3$" should be -- OCH$_2$CH$_3$ --.

Column 143,
Line 2, "OCH$_2$CH$_3$" should be -- OCH$_2$CH$_3$ --.

Column 149,
Line 62, "purity =" should be -- purity λ = --.

Column 151,
Line 1, "purity =" should be -- purity λ = --.

Column 153,
Line 31, "OCH$_2$CH$_3$" should be -- OCH$_2$CH$_3$ --.
Line 33, "OCH$_2$CH$_3$" should be -- OCH$_2$CH$_3$ --.

Column 155,
Line 2, "CH$_3$SO$_3$H" should be -- CH$_3$SO$_3$H --.

In the Claims

Column 193,
Line 10, "alkyl)R$^{12}$" should be -- alkyl)R$^{21}$ --.
Line 14, "-SR$^{22}$ -SR$^{22}$, -SO$_2$R$^2$" should be -- -SR$^{22}$ -SOR$^{22}$, -SO$_2$R$^{22}$ --.
Line 16, "R$^2$" (two occurrences) should be -- R$^{22}$ --.

Column 194,
Line 1, "SO$_2$R$^3$" should be -- SO$_2$R$^{33}$ --.

Column 195,
Line 6, "C$_{4-6}$haloalkyl" should be -- C$_{1-6}$haloalkyl --.
Line 23, "-C(O)OC$_{11}$alkyl" should be -- -C(O)OC$_{1-6}$alkyl --.
Line 54, delete "C$_{1-4}$ally-O-".

CERTIFICATE OF CORRECTION (continued)
U.S. Pat. No. 8,716,296 B2

Column 196,
Line 3, "$C_{1-16}$alkenyloxy, $C_{1-6}$" should be -- $C_{1-6}$alkenyloxy, $C_{3-6}$ --.
Line 16, "$C_{1-6}$alkyl" should be -- $C_{1-4}$alkyl --.

Column 197,
Line 37, "C-alkyl" should be -- $C_{1-4}$alkyl --.
Line 48, after "OR$^{22}$", insert a -- , --.
Line 48, after "-SOR$^{22}$", insert a -- , --.
Line 48, "-C(O)R$^2$" should be -- -C(O)R$^{22}$ --.
Line 49, "alkyl-O-R$^2$" should be -- alkyl-O-R$^{22}$ --.
Line 52, after "NR$^{11}$R$^{12}$" (first occurrence), insert a -- , --.
Line 53, after "NR$^{11}$R$^{12}$", insert a -- , --.

Column 198,
Line 10, "C-alkyl" should be -- $C_{1-4}$alkyl --.

Column 201,
Line 34, "R$^2$" should be -- R$^{20}$ --.